(12) United States Patent
Zhang et al.

(10) Patent No.: US 11,179,391 B2
(45) Date of Patent: Nov. 23, 2021

(54) COMPOUND WITH KINASE INHIBITORY ACTIVITY AND PREPARATION METHOD AND USE THEREOF

(71) Applicant: Fuyao Zhang, Shanghai (CN)

(72) Inventors: Fuyao Zhang, Shanghai (CN); Xianjie Chen, Shanghai (CN); Weijun Fang, Shanghai (CN); Hua Sun, Shanghai (CN)

(73) Assignee: Fuyao Zhang, Shanghai (CN)

( * ) Notice: Subject to any disclaimer, the term of this patent is extended or adjusted under 35 U.S.C. 154(b) by 0 days.

(21) Appl. No.: 16/610,708

(22) PCT Filed: May 7, 2018

(86) PCT No.: PCT/CN2018/085848
§ 371 (c)(1),
(2) Date: Nov. 4, 2019

(87) PCT Pub. No.: WO2018/202202
PCT Pub. Date: Nov. 8, 2018

(65) Prior Publication Data
US 2020/0155550 A1    May 21, 2020

(30) Foreign Application Priority Data
May 5, 2017 (CN) .......................... 201710315240.4

(51) Int. Cl.
| C07D 401/14 | (2006.01) |
| A61K 31/506 | (2006.01) |
| A61P 35/00 | (2006.01) |
| A61K 31/551 | (2006.01) |
| A61K 45/06 | (2006.01) |

(52) U.S. Cl.
CPC .......... A61K 31/506 (2013.01); A61K 31/551 (2013.01); A61K 45/06 (2013.01); A61P 35/00 (2018.01); C07D 401/14 (2013.01)

(58) Field of Classification Search
CPC ............................ C07D 401/14; C07D 405/14
See application file for complete search history.

(56) References Cited

U.S. PATENT DOCUMENTS

| 2010/0160340 A1 | 6/2010 | Coates |
| 2018/0000819 A1 | 1/2018 | Wu |
| 2019/0071427 A1 | 3/2019 | Zheng |

FOREIGN PATENT DOCUMENTS

| CN | 104910137 A | 9/2015 |
| CN | 105294655 A | 2/2016 |
| CN | 106083823 A | 11/2016 |
| CN | 107793399 A | 3/2018 |
| CN | 108794452 A | 11/2018 |
| WO | 2008032157 A2 | 3/2008 |
| WO | 2011101409 A1 | 8/2011 |
| WO | 2011130232 A1 | 10/2011 |
| WO | 2014183520 A1 | 11/2014 |
| WO | 2015066452 A3 | 6/2015 |
| WO | 2016014904 A1 | 1/2016 |
| WO | 2016015604 A1 | 2/2016 |
| WO | 2016015605 A1 | 2/2016 |
| WO | 2016173505 A1 | 11/2016 |
| WO | 2016173557 A1 | 11/2016 |
| WO | 2017177836 A1 | 3/2017 |
| WO | 2018045957 A1 | 3/2018 |

OTHER PUBLICATIONS

Banker et al. "Modern Pharmaceutics", 3rd Ed. p. 596 (1996).*
"Burger's Medicinal Chemistry", edited by Manfred E.Wolf, 5th Ed. Part 1, pp. 975-977 (1995).*
Bauer, Journal of Validation Technology, p. 15-23 (2008).*
International Search Report and Written Opinion of PCT/CN2018/085848 dated Aug. 6, 2018.
Extended European Search Report issued in the counterpart European application No. 18794759.3 dated Feb. 26, 2020.

(Continued)

*Primary Examiner* — Emily A Bernhardt
(74) *Attorney, Agent, or Firm* — MH2 Technology Law Group, LLP

(57) ABSTRACT

The present invention provides a compound as shown in general formulas (I) or (II) and a pharmaceutically acceptable salt, an isomer or a mixture form thereof, a solvate, a polymorph, a stable isotope derivative, or a prodrug of the same. The compound of the present invention has CDK kinase inhibitory activity and can be used in treating a disease related to CDK kinase, such as a cancer.

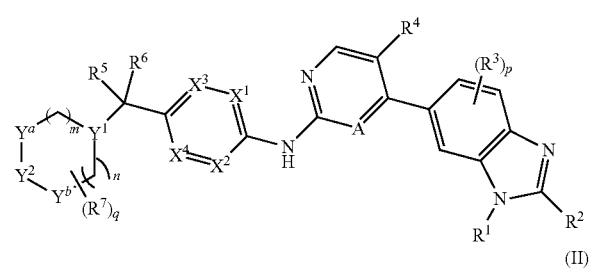

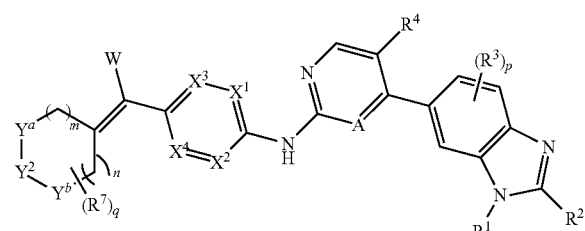

4 Claims, 2 Drawing Sheets

(56) References Cited

OTHER PUBLICATIONS

Chinese First Office Action in corresponding Chinese Application No. 201710315240.4 dated Jul. 27, 2020, 32 pages.
Chinese Second Office Action in corresponding Chinese Application No. 201710315240.4 dated Jan. 18, 2021, 19 pages.
European Office Action in corresponding European Application No. 18794759.3 dated Nov. 13, 2020, 5 pages.

* cited by examiner

COMPOUND WITH KINASE INHIBITORY ACTIVITY AND PREPARATION METHOD AND USE THEREOF

CROSS-REFERENCE TO RELATED APPLICATIONS

This application is a national stage entry from International Application No. PCT/CN2018/085848, filed on May 7, 2018, published as International Publication No. WO 2018/202202 A1 on Aug. 11, 2018, and claims priority under 35 U.S.C. § 119 from Chinese patent application No. 201710315240.4, filed on May 5, 2017, the entire contents of all of which are incorporated herein by reference.

FIELD OF THE INVENTION

The present invention relates to a compound with kinase inhibitory activity, a preparation method, and a use thereof.

BACKGROUND OF THE INVENTION

Abnormal cell cycle regulation is a prominent feature of cancerous lesion. Cyclin-dependent kinases (CDKs) play essential roles in the cell cycle regulation. The cyclin-dependent kinases are a family of protein serine/threonine enzymes. Cyclin could bind to CDKs to form a complex, which phosphorylates or dephosphorylates pRB to efficiently regulate the GI-S phase of the cell cycle. Cell repair or cancerization will be promoted when an exception occurs. The current CDKs include CDK1-13, and cyclins can be divided into cyclin A-L. Different CDKs bind to different cyclins and play different roles in the cell cycle regulation, CDK inhibitors have emerged as a novel treatment strategy for the treatment of cancer and other related diseases by re-controlling of the cell cycle.

The major pharmaceutical companies have developed a variety of CDK inhibitors, such as Alvocidib (flavopiridol), Riviciclib (P276-00), Seliciclib (roscovitine), Dinaciclib (BAY-1000394), Milciclib (PHA-848125), Palbociclib (PD-0332991), Ribociclib (LEE-011), Abemaciclib (LY-2835219). Among them, Palbociclib (PD-0332991, Trade name: Ibrance®, Pfizer Inc.) as the first CDK4/6 inhibitor was approved by FDA on Feb. 3, 2015. It is used for treating estrogen receptor (ER)-positive, human epidermal growth factor receptor 2 (HER2)-negative advanced or metastatic breast cancer of postmenopausal women who have not received systemic treatment in combination with letrozole. Similarly, Ribociclib (LEE-011, Trade name: Kisqali®, Novartis) as a second CDK4/6 inhibitor was approved by the FDA on Mar. 15, 2017, in combination with an aromatase inhibitor for the treatment of hormone receptor-positive (HR+), human epidermal growth factor receptor 2-negative (HER2-) advanced or metastatic breast cancer of postmenopausal women. The successful marketing of these drugs also demonstrates the reliability of CDK targets and the potential advantages for the treatment of related diseases such as cancer.

Recently, the development of highly selective CDK inhibitors has become one of the hotspots in the new drugs R&D. The published patents of selective CDK4/6 inhibitors include WO2016173505A1, US20160340A1, WO2011130232A1, WO2011101409A1, WO2008032157A2, WO2014183520A1, WO2016014904A1, etc.

In order to further develop new drugs for the treatment of cancer-related diseases and to meet the huge market demand for CDK-mediated diseases drugs, we urgently need to develop a new generation of CDK inhibitors with high efficiency, low toxicity, and clinical application value.

SUMMARY OF THE INVENTION

The present invention aims to provide a novel class of compounds with kinase inhibitory activity, a preparation method, and a use thereof.

In a first aspect, the present invention provides a compound represented by general formula (I) or (II), a pharmaceutically acceptable salt thereof, an isomer thereof or a mixture of isomers, a solvate thereof, a polymorph thereof, a stable isotope derivative thereof or a prodrug thereof;

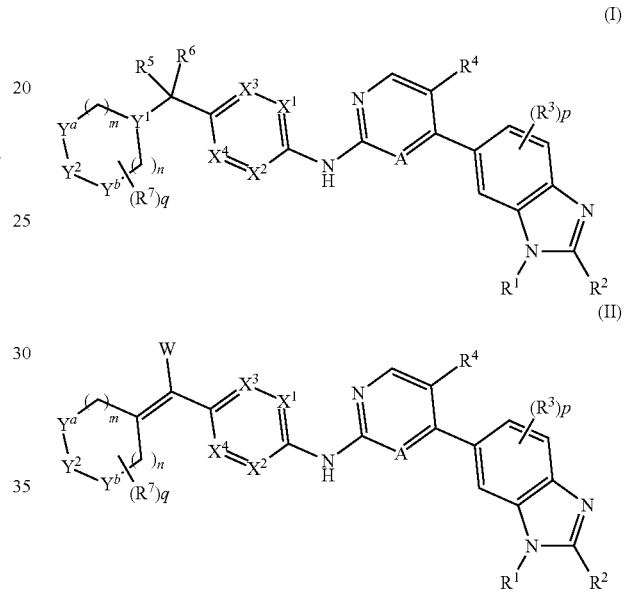

wherein, $R^1$ and $R^2$ are each independently selected from hydrogen, deuterium, substituted or unsubstituted alkyl, substituted or unsubstituted haloalkyl, substituted or unsubstituted alkoxy, substituted or unsubstituted cycloalkyl, or substituted or unsubstituted heterocycloalkyl;

$R^3$ and $R^4$ are each independently selected from hydrogen, deuterium, halogen, hydroxyl, cyano, amino, substituted or unsubstituted alkyl, substituted or unsubstituted alkoxy, substituted or unsubstituted cycloalkyl, or substituted or unsubstituted heterocycloalkyl;

A is selected from $CR^8$ or N, and $R^8$ is selected from hydrogen, deuterium, halogen, hydroxyl, cyano, amino, alkenyl, alkynyl, substituted or unsubstituted alkyl, substituted or unsubstituted alkoxy, substituted or unsubstituted cycloalkyl, or substituted or unsubstituted heterocycloalkyl;

$X^1$, $X^2$, $X^3$, and $X^4$ are each independently selected from $CR^9$ or N, and $R^9$ is selected from hydrogen, deuterium, halogen, hydroxyl, cyano, amino, alkenyl, alkynyl, substituted or unsubstituted alkyl, substituted or unsubstituted alkoxy, substituted or unsubstituted cycloalkyl, substituted or unsubstituted heterocycloalkyl, substituted or unsubstituted aryl, or substituted or unsubstituted heteroaryl;

in $R^5$ and $R^6$,

1) $R^5 \neq R^6$, and $R^5$ and $R^6$ are each independently selected from hydrogen, deuterium, halogen, hydroxyl, mercapto, cyano, substituted or unsubstituted alkyl, substituted or unsubstituted haloalkyl, substituted or unsubstituted heterocycloalkyl, substituted or unsubstituted alkoxy, substituted or unsubstituted alkylmercapto, substituted or unsubstituted cycloalkyl, substituted or unsubstituted aryl, substituted or unsubstituted heteroaryl, —OR$^{10}$, —SR$^{10}$, —NR$^{10}$R$^{10a}$, —CONR$^{10}$R$^{10a}$, —SO$_2$NR$^{10}$R$^{10a}$, —C(O)$_t$R$^{11}$, —S(=O)$_t$R$^{11}$, —OC(=O)R$^{11}$, —C≡CR$^{11}$ or —CR$^{11}$=CR$^{11}$R$^{11a}$, or R$^5$ and R$^6$ together with the carbon atom to which they are attached form C$_{3-7}$ monocycloalkyl and bicycloalkyl, C$_{5-12}$ spirobicyclic group or C$_{5-12}$ bridged heterobicyclic group, or R$^5$ and R$^6$ together with the carbon atom to which they are attached form a cyclic moiety containing 1-3 heteroatoms, wherein the heteroatoms are selected from N, O, S, P or B;

alternatively,

2) R$^5$ and R$^6$ are combined to form a substituted or unsubstituted exocyclic double bond

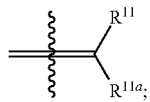

W is selected from hydrogen, deuterium, halogen, cyano, substituted or unsubstituted alkyl, substituted or unsubstituted alkoxy, substituted or unsubstituted alkylmercapto, substituted or unsubstituted cycloalkyl, substituted or unsubstituted aryl, substituted or unsubstituted heteroaryl, —OR$^{10}$, —SR$^{10}$, —NR$^{10}$R$^{10a}$, —SO$_2$NR$^{10}$R$^{10a}$, —C(O)$_t$R$^{11}$, —S(O)$_t$R$^{11}$, —OC(O)R$^{11}$, —C≡CR$^{11}$ or —CR$^{11}$=CR$^{11}$R$^{11a}$;

Y$^1$ is selected from N or CR$^a$;

Y$^a$ and Y$^b$ are each independently selected from —CR$^{11}$R$^{11a}$—, —N(R$^{10}$), —C(=O)—, —S(=O)$_t$ or —O—;

Y$^2$ is selected from —CR$^a$R$^b$, —NR$^b$, —C(=O), —S(=O)$_t$, —S— or —O—; alternatively, Y$^1$ and Y$^a$, Y$^1$ and Y$^b$, Y$^2$ and Y$^a$, or Y$^2$ and Y$^b$ form a C=C or C=N double bond;

R$^7$ is selected from hydrogen, deuterium, halogen, hydroxyl, cyano, oxo, substituted or unsubstituted alkyl, substituted or unsubstituted alkoxy, substituted or unsubstituted alkylmercapto, substituted or unsubstituted cycloalkyl, substituted or unsubstituted heterocycloalkyl, substituted or unsubstituted aryl, or substituted or unsubstituted heteroaryl, —OR$^{10}$, —SR$^{10}$, —NR$^{10}$R$^{10a}$, —SO$_2$NR$^{10}$R$^{10a}$, —C(O)$_t$R$^{11}$, —S(O)$_t$R$^{11}$, —OC(O)R$^{11}$, —C≡CR$^{11}$, —CR$^{11}$=CR$^{11}$R$^{11a}$ or —B(OR$^{10}$)$_2$, or a plurality of R$^7$ together with the carbon atoms or heteroatoms to which they are attached form a cyclic moiety containing 0-3 heteroatoms, wherein the heteroatoms are selected from N, O, S, P or B;

p is the number of substituents R$^3$ and selected from 0, 1, 2 or 3;

m and n are each independently selected from 0, 1, 2, 3 or 4;

q is the number of substituents R$^7$ and selected from 0, 1, 2, 3 or 4;

t is 1 or 2;

R$^{10}$ is selected from hydrogen, deuterium, substituted or unsubstituted alkyl, substituted or unsubstituted alkoxy, substituted or unsubstituted alkylmercapto, substituted or unsubstituted cycloalkyl, substituted or unsubstituted heterocycloalkyl, substituted or unsubstituted aryl, or substituted or unsubstituted heteroaryl;

R$^{10a}$ is selected from hydrogen, deuterium, halogen, hydroxyl, amino, substituted or unsubstituted alkyl, substituted or unsubstituted alkoxy, substituted or unsubstituted alkylmercapto, substituted or unsubstituted cycloalkyl, substituted or unsubstituted heterocycloalkyl, substituted or unsubstituted aryl, or substituted or unsubstituted heteroaryl;

alternatively, R$^{10}$ and R$^{10a}$ together with the nitrogen atom to which they are attached form a cyclic moiety containing 1-3 heteroatoms, wherein the heteroatoms are selected from N, O, S, P or B;

R$^{11}$ and R$^{11a}$ are each independently selected from hydrogen, deuterium, halogen, hydroxyl, amino, substituted or unsubstituted alkyl, substituted or unsubstituted alkoxy, substituted or unsubstituted alkylmercapto, substituted or unsubstituted cycloalkyl, substituted or unsubstituted heterocycloalkyl, substituted or unsubstituted aryl, or substituted or unsubstituted heteroaryl; alternatively, R$^{11}$ and R$^{11a}$ together with the carbon atom to which they are attached form a cyclic moiety containing 0-3 heteroatoms, wherein the heteroatoms are selected from N, O, S, P or B;

R$^a$ and R$^b$ are each independently selected from hydrogen, deuterium, oxo, halogen, hydroxyl, cyano, amino, substituted or unsubstituted alkyl, substituted or unsubstituted alkoxy, substituted or unsubstituted alkylmercapto, substituted or unsubstituted cycloalkyl, substituted or unsubstituted heterocycloalkyl, substituted or unsubstituted aryl, substituted or unsubstituted heteroaryl, —OR$^{10}$, —SR$^{10}$, —NR$^{10}$R$^{10a}$, —SO$_2$NR$^{10}$R$^{10a}$, —C(O)$_t$R$^{11}$, —S(O)$_t$R$^{11}$, —OC(O)R$^{11}$, —C≡CR$^{11}$ or —CR$^{11}$=CR$^{11}$R$^{11a}$; alternatively, R$^a$ and R$^b$ together with the carbon atom to which they are attached form monocycloalkyl and bicycloalkyl, C$_5$-12 spirobicyclic group or C$_5$-12 bridged heterobicyclic group containing 0-3 heteroatoms, wherein the heteroatoms are selected from N, O, S, P or B.

In a preferred embodiment of the present invention, R$^1$ is methyl, difluoromethyl, ethyl, propyl, isopropyl, cyclopropyl, cyclobutyl, isobutyl, tert-butyl, cyclopentyl or cyclohexyl; and/or, R$^2$ is H, D, F, Cl, CF$_3$, CHF$_2$ or CH$_3$.

In a preferred embodiment of the present invention, A is preferably N or CR$^8$, and R$^8$ is preferably H, D, F, Cl, NH$_2$, CN, OCH$_3$ or CH$_3$.

In a preferred embodiment of the present invention, R$^3$ and R$^4$ are each independently H, D, F, Cl, CN, NH$_2$, OCH$_3$, CH$_3$, ethyl, isopropyl, or cyclopropyl.

In a preferred embodiment of the present invention, X$^1$, X$^2$, X$^3$, and X$^4$ are preferably selected from any one of the following situations: (1) X$^1$=N, and X$^2$, X$^3$ and X$^4$=CR$^9$; (2) X$^1$ and X$^3$=N, and X$^2$ and X$^4$ are CR$^9$; or X$^2$ and X$^4$=N, and X$^1$ and X$^3$ are CR$^9$; (3) X$^1$ and X$^2$=N, and X$^3$ and X$^4$ are CR$^9$; or X$^3$ and X$^4$=N, and X$^1$ and X$^2$ are CR$^9$; (4) X$^1$ and X$^4$=N, and X$^2$ and X$^3$ are CR$^9$; or X$^1$ and X$^4$=N, and X$^2$ and X$^3$ are CR$^9$; and R$^9$ is preferably hydrogen, deuterium, halogen, hydroxyl, cyano, amino, substituted or unsubstituted alkyl, substituted or unsubstituted alkoxy, substituted or unsubstituted cycloalkyl, or substituted or unsubstituted heterocycloalkyl.

In a preferred embodiment of the present invention, the compound represented by general formula (I) or (II) is shown as follows:

(I-1)

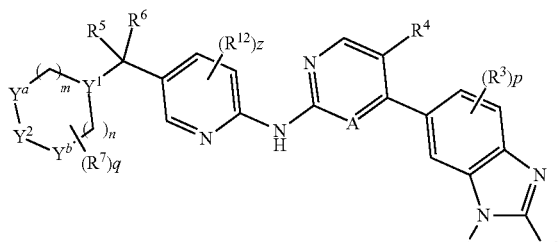

(II-1)

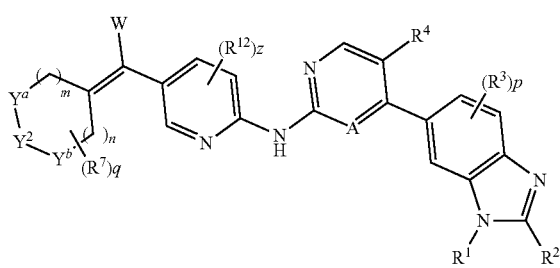

wherein z is the number of substituents $R^{12}$ and is 0, 1, 2 or 3; the definitions of $R^1$, $R^2$, $R^3$, $R^4$, $R^5$, $R^6$, $R^7$, y, $Y^2$, $Y^a$, $Y^b$, W, m, n, p, and q are defined as above;

each $R^{12}$ is independently selected from hydrogen, deuterium, halogen, hydroxyl, cyano, amino, alkenyl, alkynyl, substituted or unsubstituted alkyl, substituted or unsubstituted alkoxy, substituted or unsubstituted cycloalkyl, substituted or unsubstituted heterocycloalkyl, substituted or unsubstituted aryl, or substituted or unsubstituted heteroaryl.

In a preferred embodiment of the present invention,

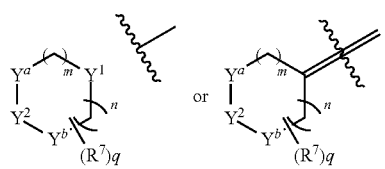

is selected from any one of the following moieties:

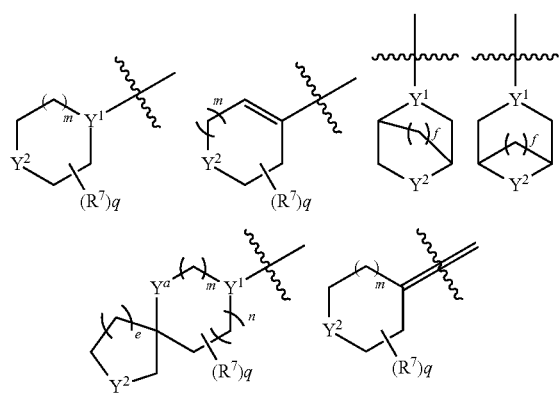

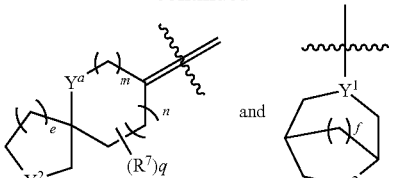

wherein the definitions of $R^7$, $Y^1$, $Y^2$, $Y^a$, m, n, and q are defined as above, and e and f are each independently 0, 1, 2, or 3.

In some aspects of the present invention, the compound represented by the general formula (I) or (II) is shown as follows:

(I-2)

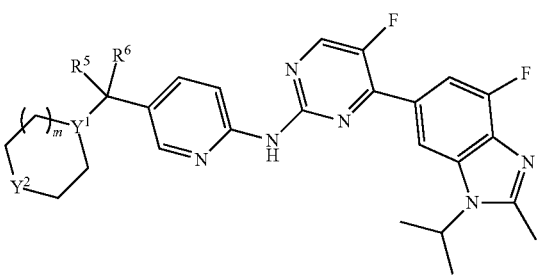

(I-3)

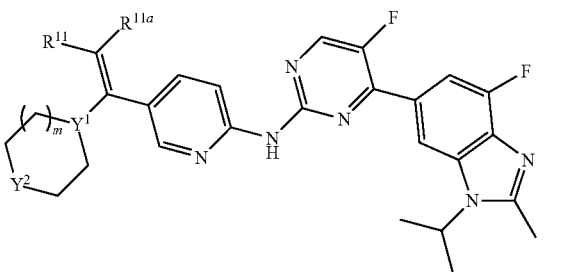

(II-2)

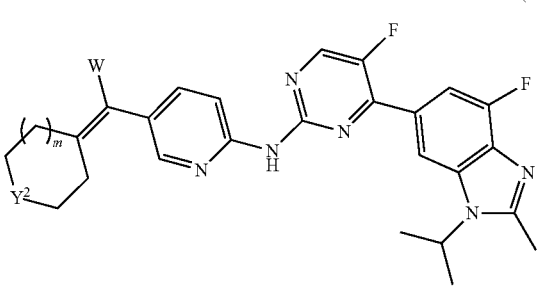

wherein,
$R^5$ and $R^6$ are each independently hydrogen, $C_{1-3}$ alkyl, hydroxyl, amino, halogen, $C_{1-3}$ alkoxy, —OC(O)$R^{20}$ or $C_{1-3}$ alkyl substituted by hydroxyl, and $R^5 \neq R^6$;
$R^{20}$ is $C_{1-3}$ alkyl;
$R^{11}$ and $R^{11a}$ are each independently H or $C_{1-3}$ alkyl;
m is 0 or 1;
$Y^1$ is N or $CR^{21}$;
$R^{21}$ is hydrogen or halogen;
$Y^2$ is $CR^{22}R^{23}$ or $NR^{24}$;
$R^{22}$ and $R^{23}$ are each independently hydrogen, $C_{1-5}$ alkyl or —$NR^{25}R^{26}$; or $R^{22}$ and $R^{23}$ together with the carbon atom to which they are attached form a 5- to 7-membered cycloalkyl containing 0-3 heteroatoms, wherein the heteroatoms are optionally selected from N, O or S;

$R^{24}$ is hydrogen, $C_{1-5}$ alkyl, $C_{3-5}$ cycloalkyl, $C_{1-5}$ haloalkyl or $C_{1-3}$ alkyl substituted by $R^{27}$;

$R^{27}$ is hydroxyl or $C_{1-3}$ alkoxy;

$R^{25}$ and $R^{26}$ are each independently hydrogen, $C_{1-5}$ alkyl or $C_{3-5}$ cycloalkyl; or $R^{25}$ and $R^{26}$ together with the nitrogen atom to which they are attached form a 5- to 7-membered cycloalkyl containing 1-3 heteroatoms, wherein the heteroatoms are optionally selected from N, O or S;

W is hydrogen or $C_{1-3}$ alkyl.

In some aspects of the present invention, the $C_{1-3}$ alkyl is each independently methyl, ethyl, propyl, or isopropyl.

In some aspects of the present invention, the $C_{1-5}$ alkyl is each independently methyl, ethyl, propyl, isopropyl, n-butyl, isobutyl, tert-butyl or n-pentyl.

In some aspects of the present invention, the $C_{1-3}$ alkoxy is each independently methoxy, ethoxy, n-propoxy or isopropoxy.

In some aspects of the present invention, the halogen is each independently selected from fluorine, chlorine, bromine, or iodine.

In some aspects of the present invention, the $C_{3-5}$ cycloalkyl can be cyclopropyl, cyclobutyl, or cyclopentyl.

In some aspects of the present invention, the $C_{1-5}$ haloalkyl can be selected from methyl, ethyl, n-propyl, or isopropyl substituted by halogen, and the halogen can be fluorine, chlorine, bromine or iodine (e.g., fluorine). The number of halogens can be one or more than one.

In some aspects of the present invention, $R^5$ can be hydrogen, methyl, ethyl, isopropyl, hydroxyl, amino, fluorine, methoxy, —OC(O)CH$_3$ or —CH$_2$OH.

In some aspects of the present invention, $R^5$ can be hydrogen, methyl, ethyl, hydroxyl, amino, or —CH$_2$OH.

In some aspects of the present invention, $R^6$ can be hydrogen, methyl, ethyl, isopropyl, hydroxyl, amino, fluorine, methoxy, —OC(O)CH$_3$ or —CH$_2$OH.

In some aspects of the present invention, $R^6$ can be selected from hydrogen, methyl, ethyl, hydroxyl, amino, or —CH$_2$OH.

In some aspects of the present invention, at least one of $R^5$ and $R^6$ is hydrogen.

In some embodiments of the present invention, one of $R^5$ and $R^6$ is hydrogen, and the other is methyl.

In some aspects of the present invention, $R^{11}$ can be hydrogen.

In some aspects of the present invention, $R^{11a}$ can be hydrogen.

In some aspects of the present invention, m can be 0.

In some aspects of the present invention, $Y^1$ can be N, CH or CF, and can also be CH.

In some aspects of the present invention, $Y^2$ can be

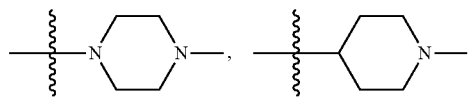

or NR$^{24}$ and R$^{24}$ can be hydrogen, methyl, ethyl, isopropyl, cyclopropyl,

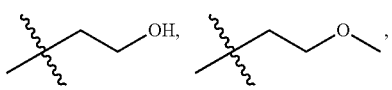

-continued

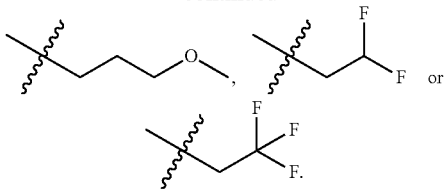

The $Y^2$ can also be NR$^{24}$, and the $R^{24}$ can be methyl, ethyl, isopropyl, cyclopropyl, or

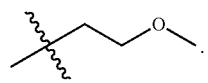 [SMILES: *CCOC]

$Y^2$ is preferably NCH$_2$CH$_3$.

In some aspects of the present invention, the W can be hydrogen, methyl, or ethyl, and can also be hydrogen.

In a preferred embodiment of the present invention, the compound represented by the general formula (I) or (II) is optionally selected from any one of the following compounds:

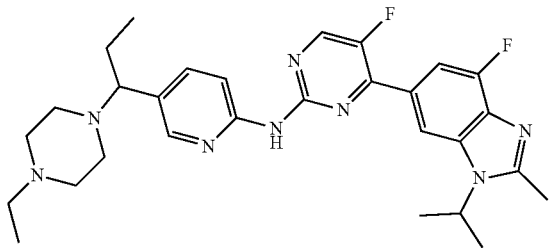

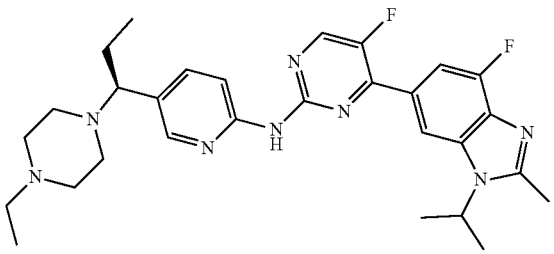

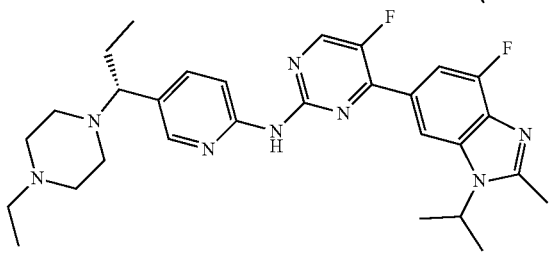

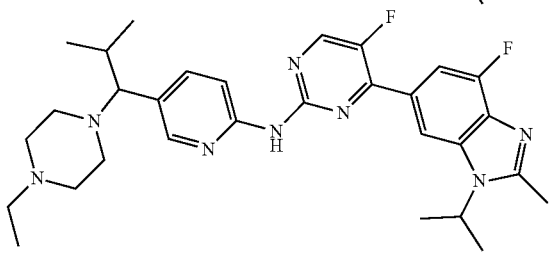

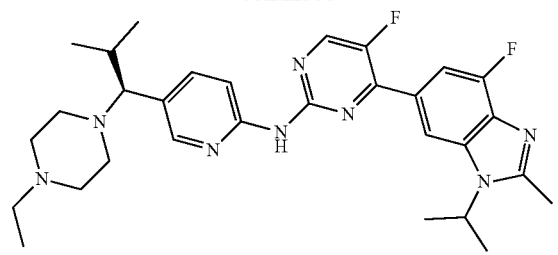
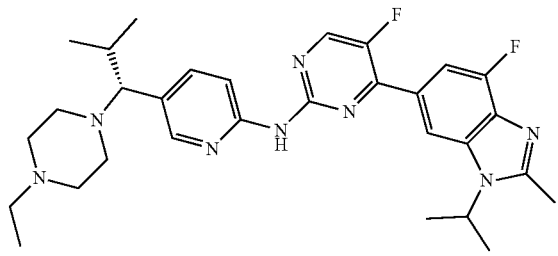
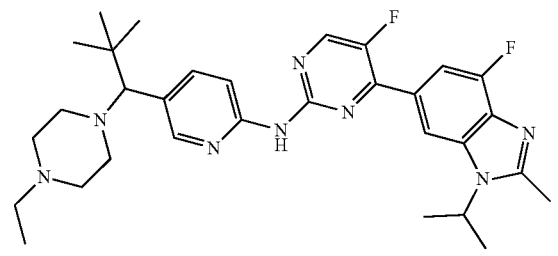
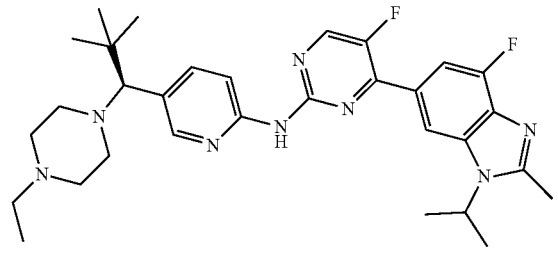
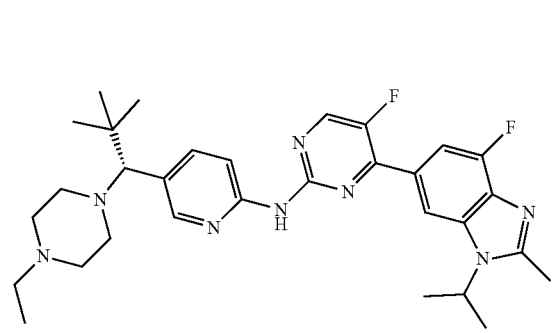
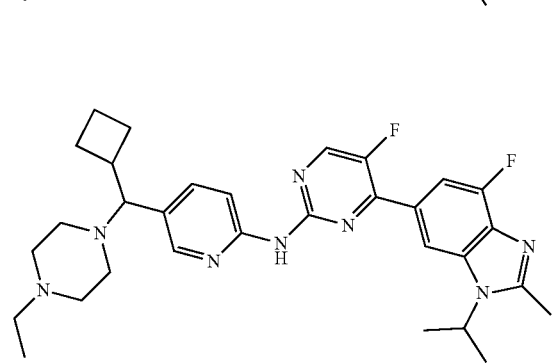
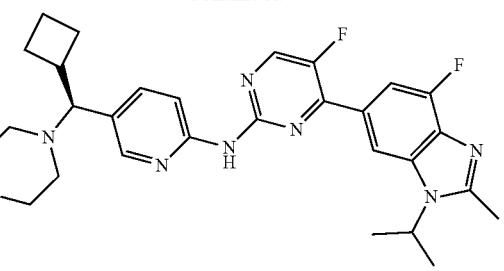
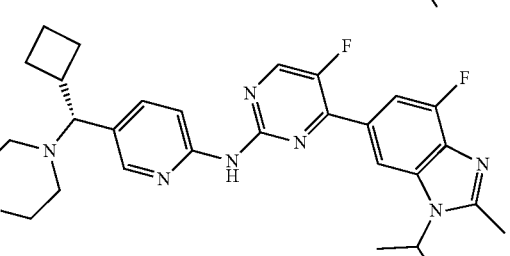
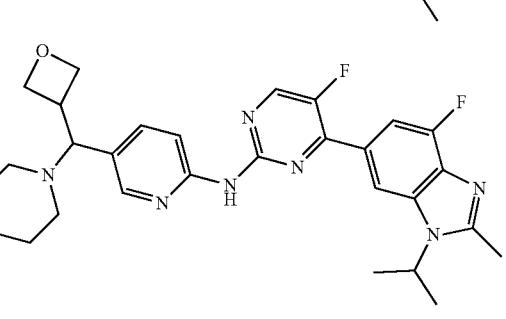
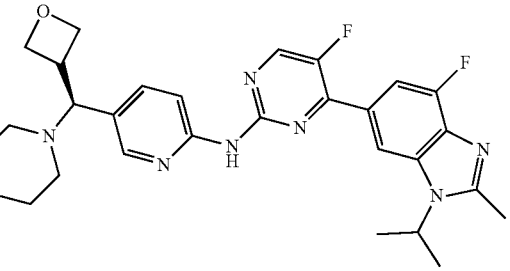
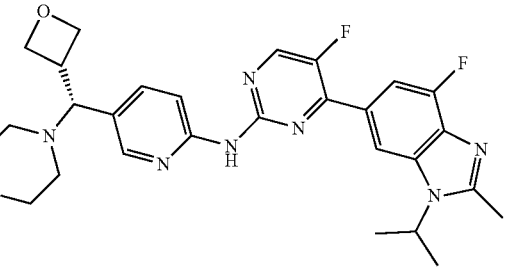
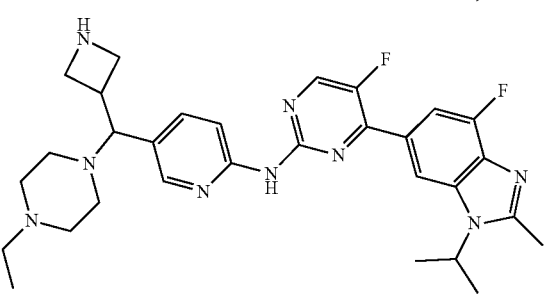

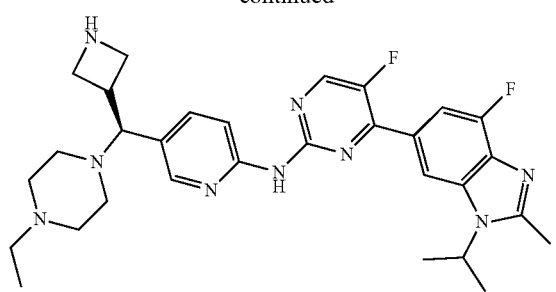
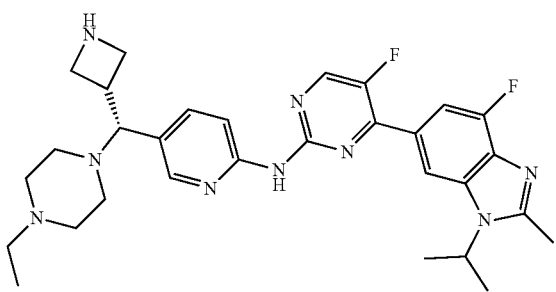
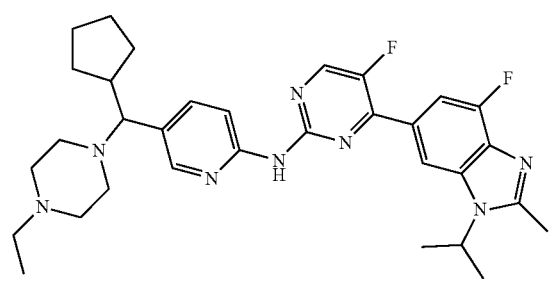
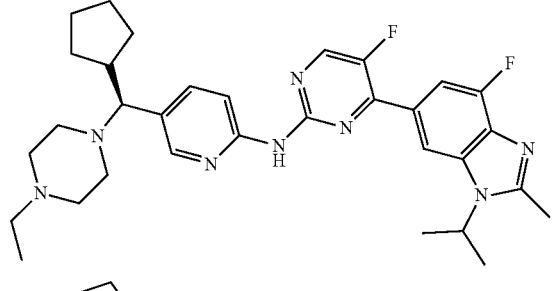
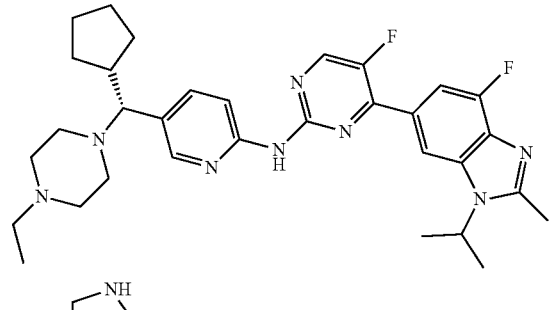
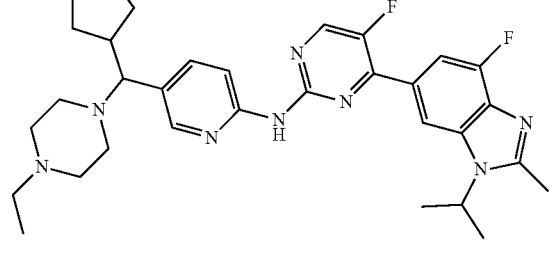
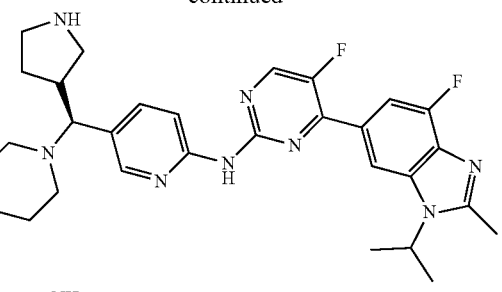
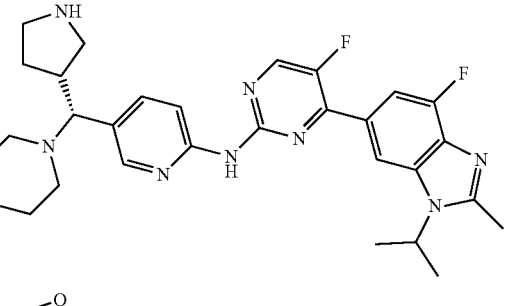
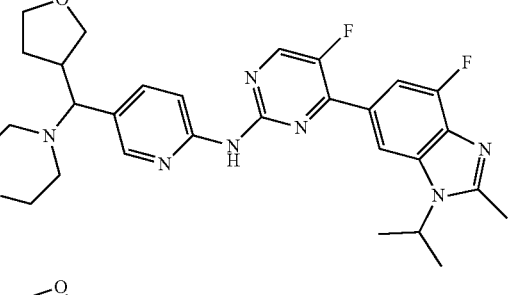
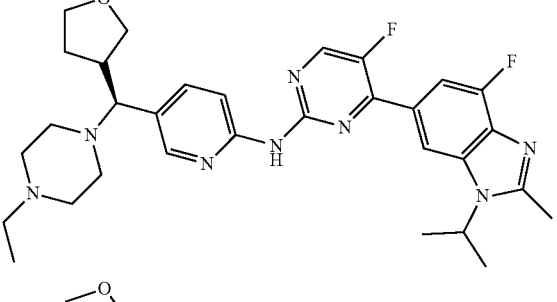
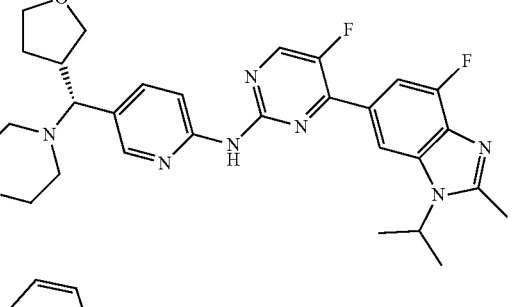
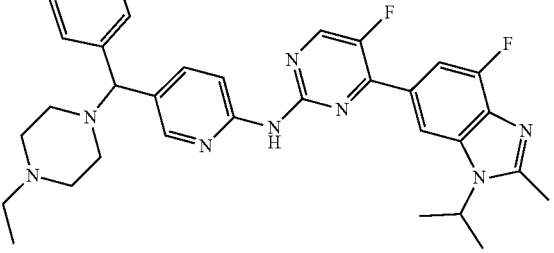

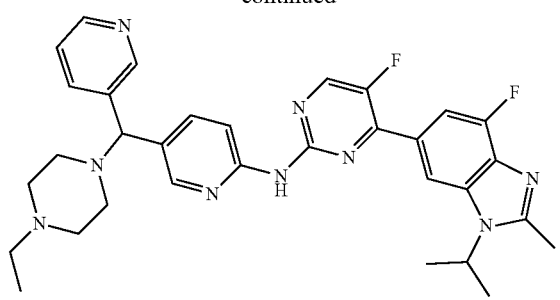
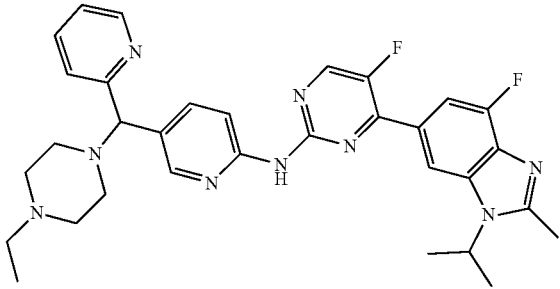
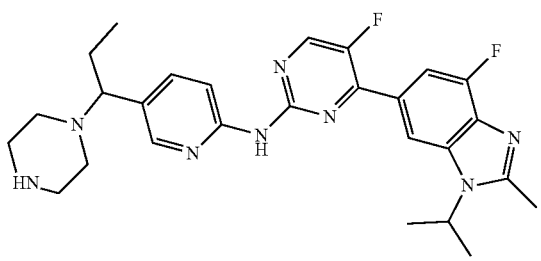
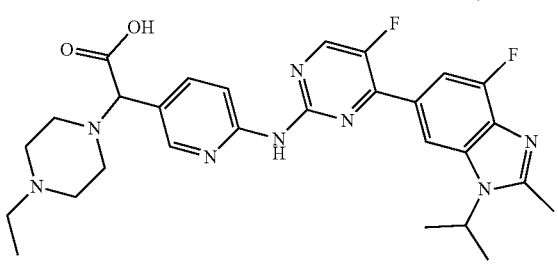
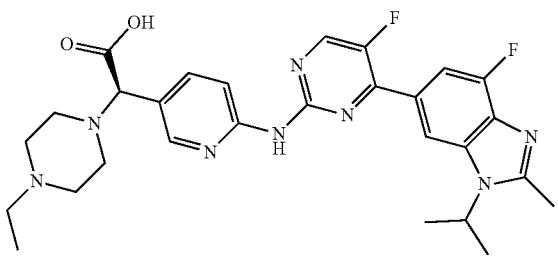
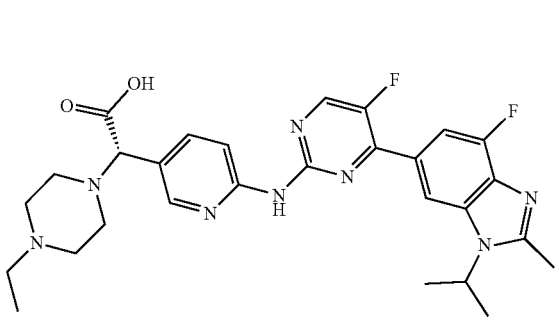
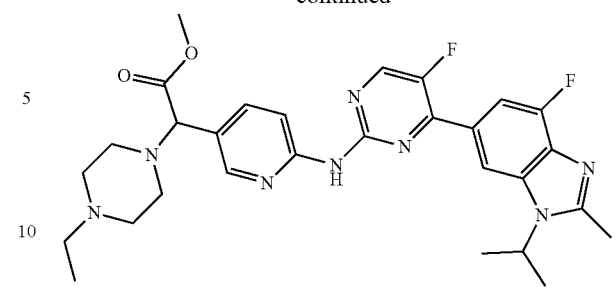
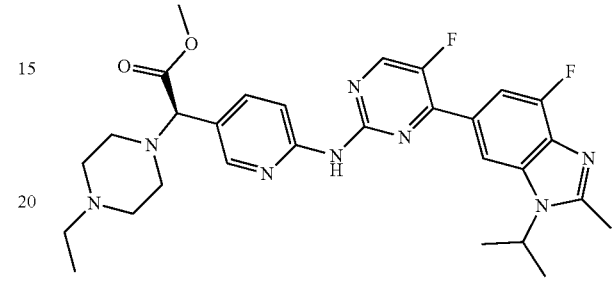
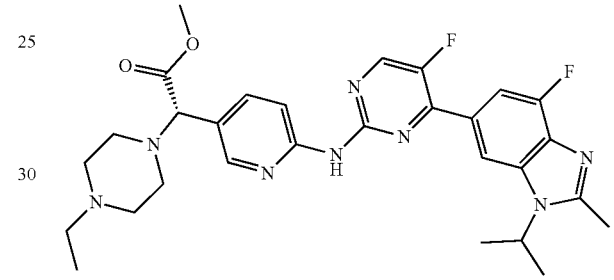
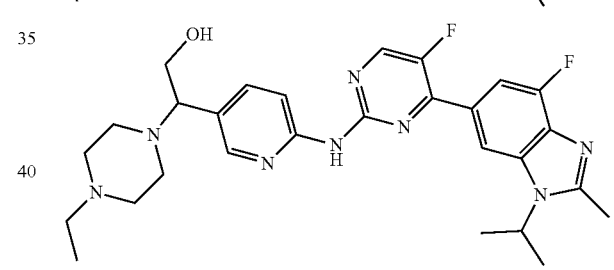
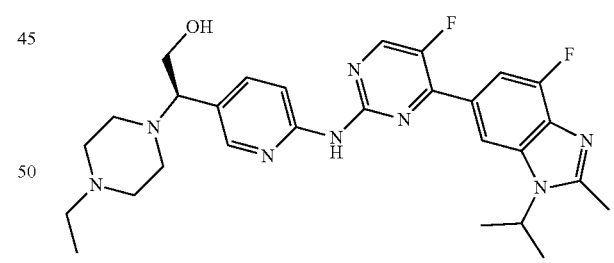
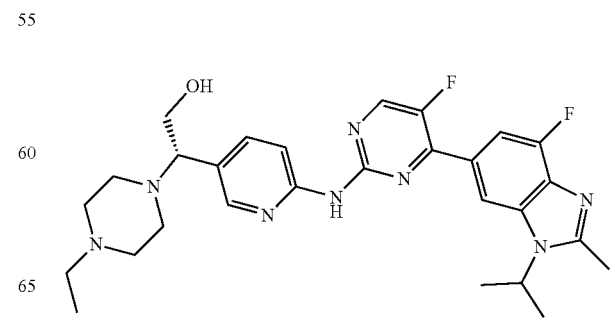

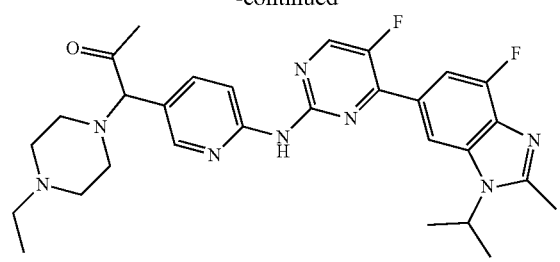
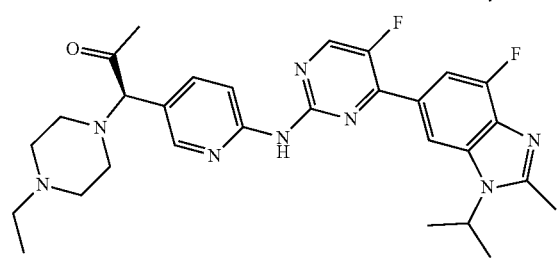
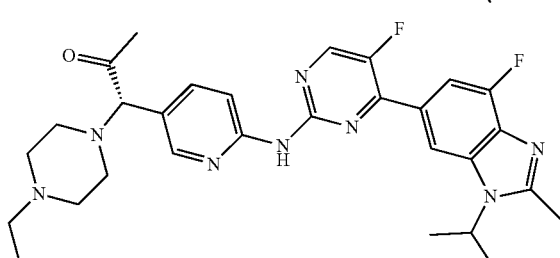
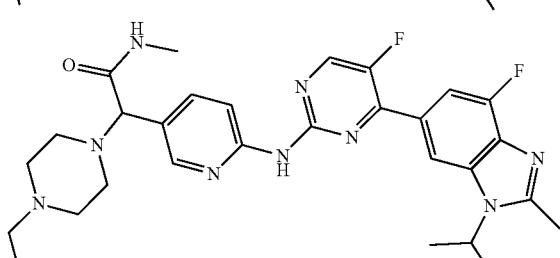
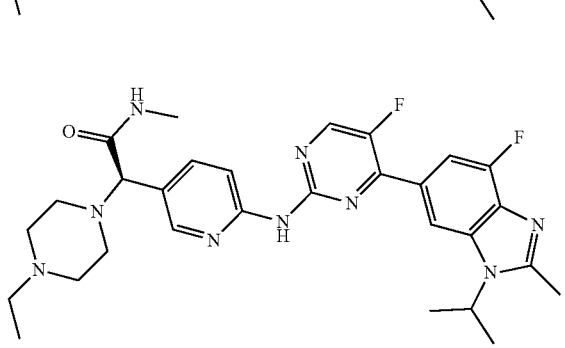
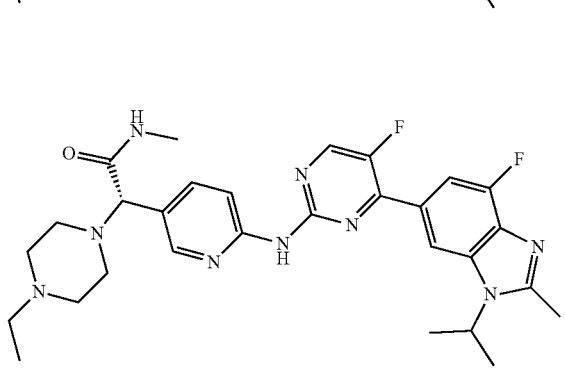
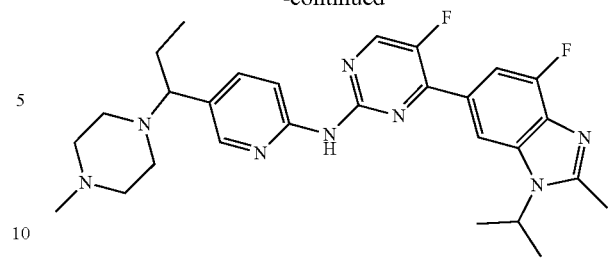
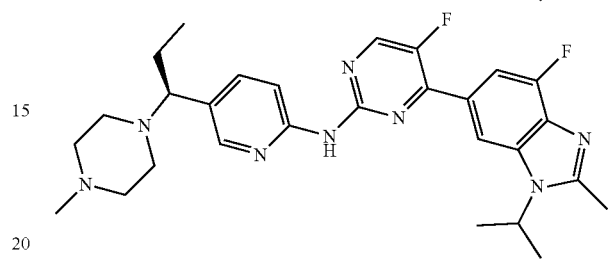
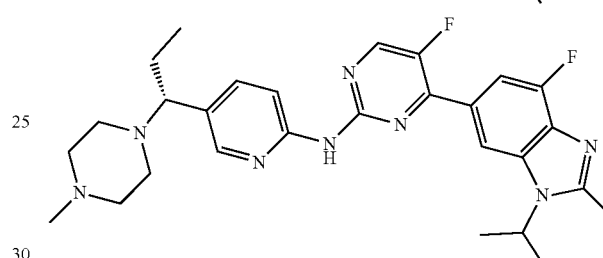
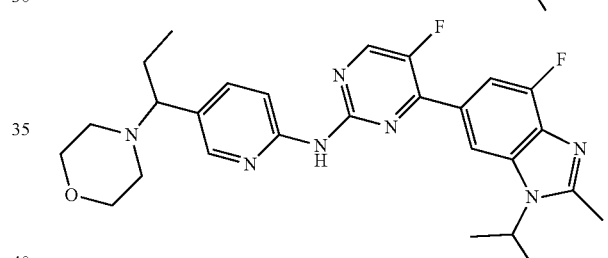
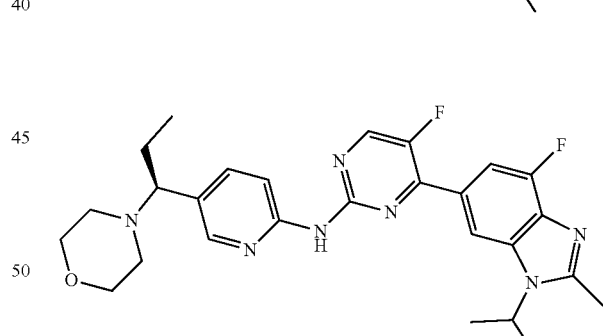
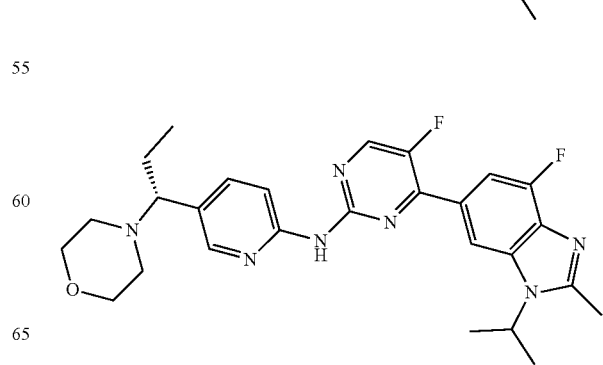

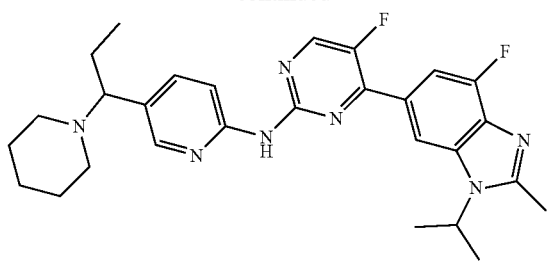
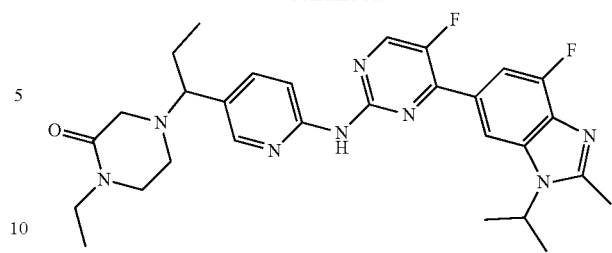
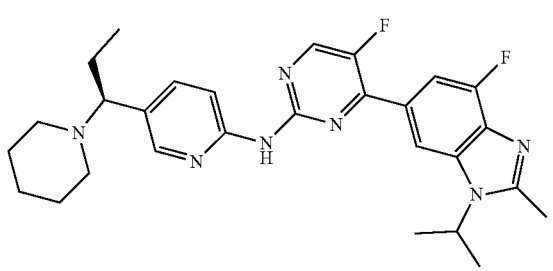
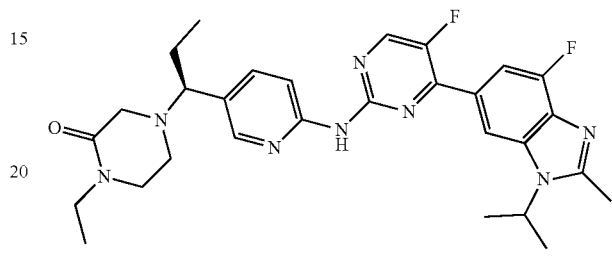
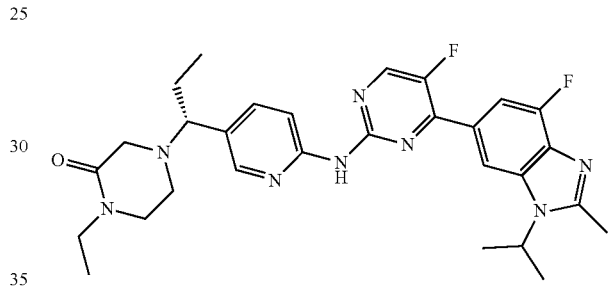
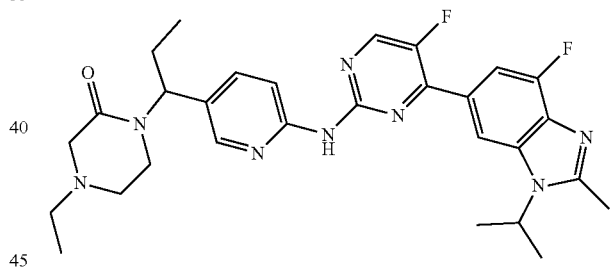
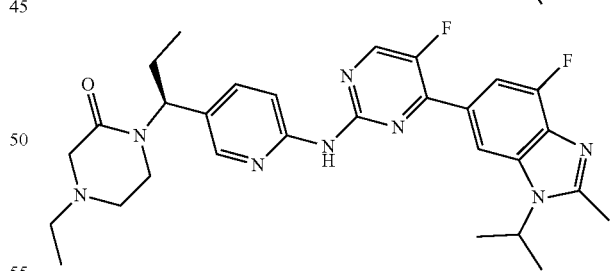
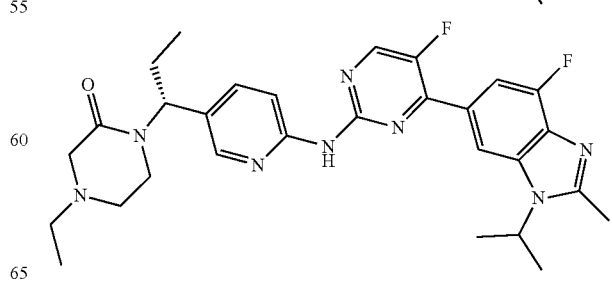

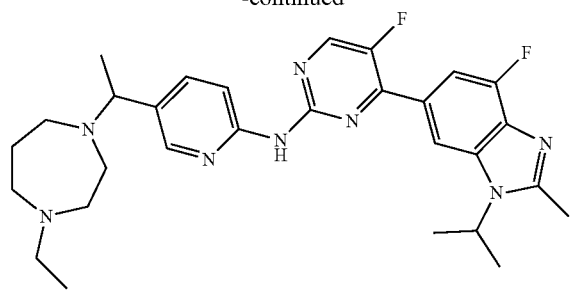
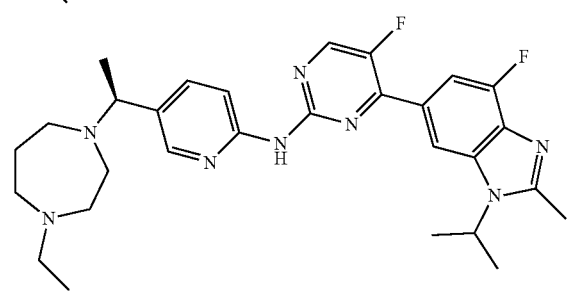
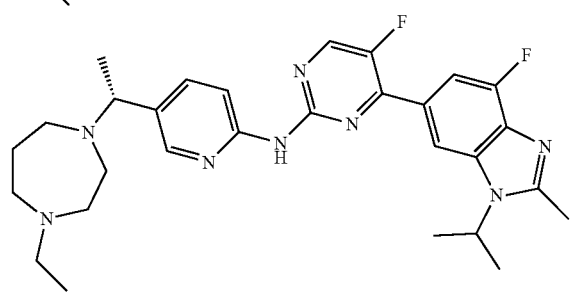
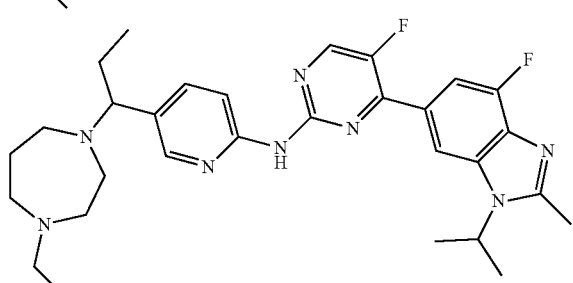
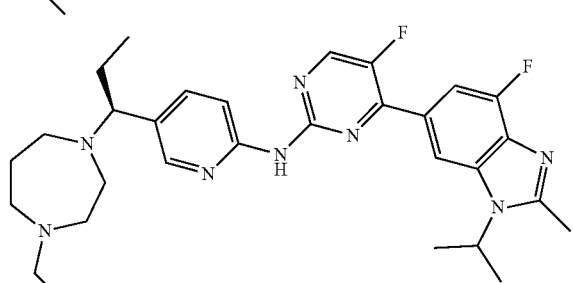
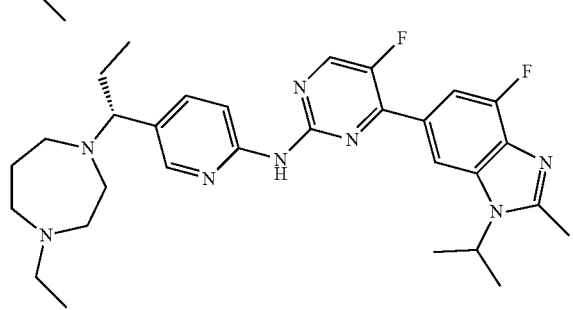
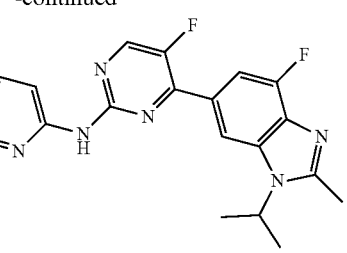
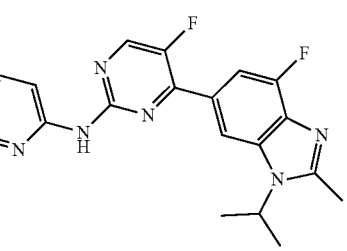
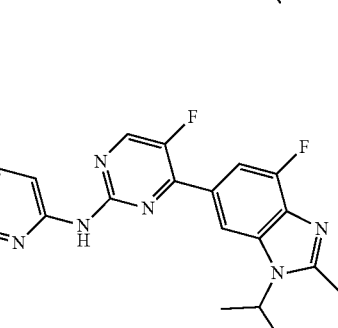
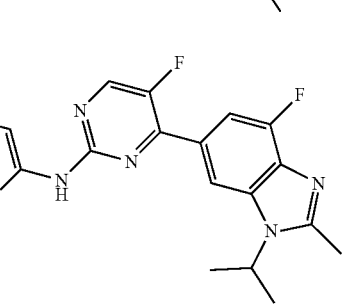
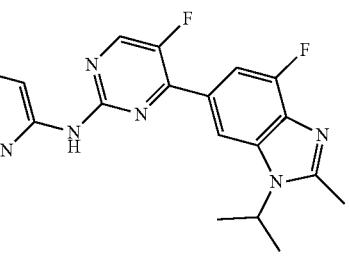
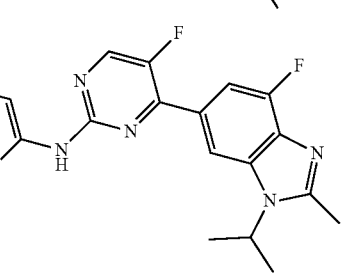

21
-continued
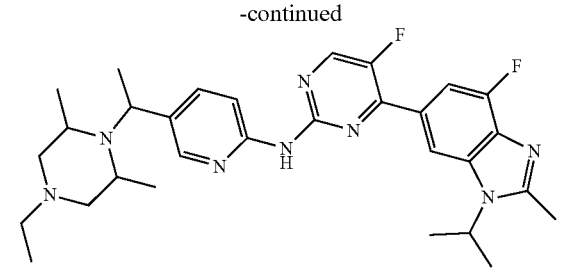
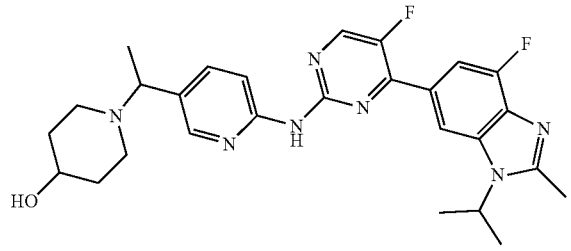
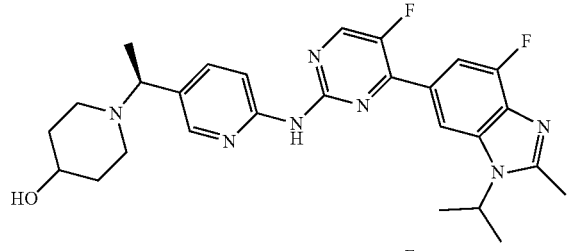
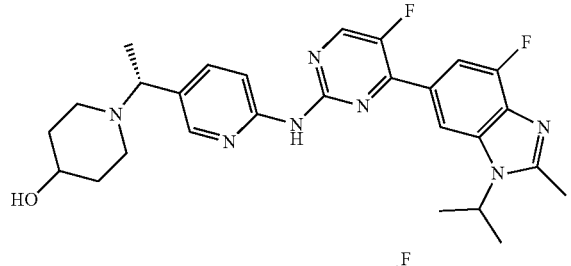
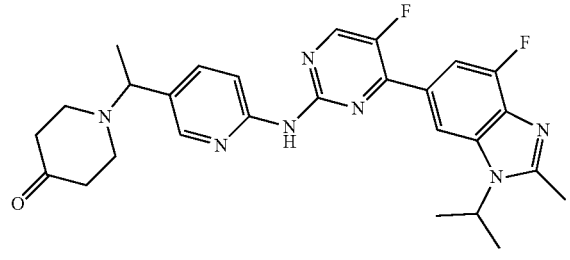
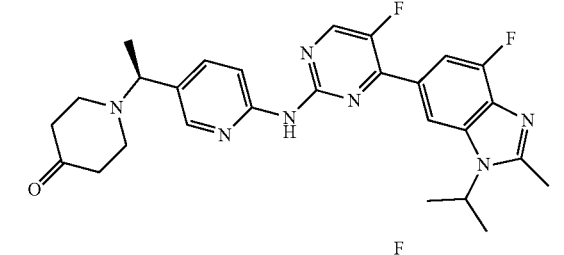
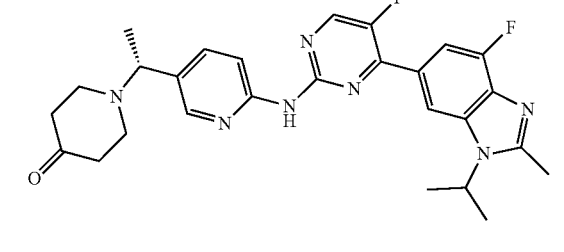
22
-continued
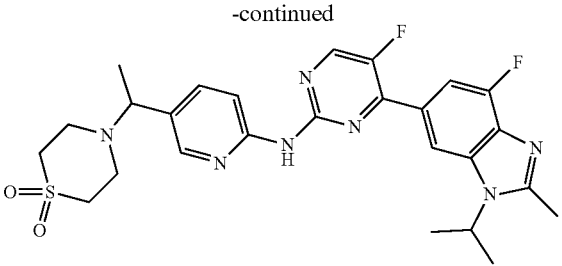
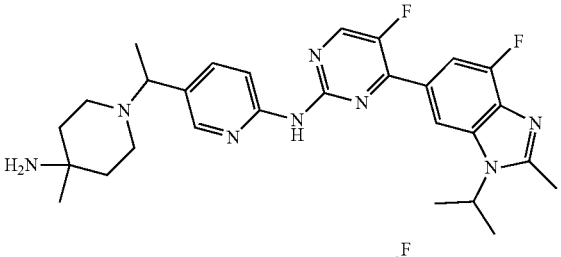
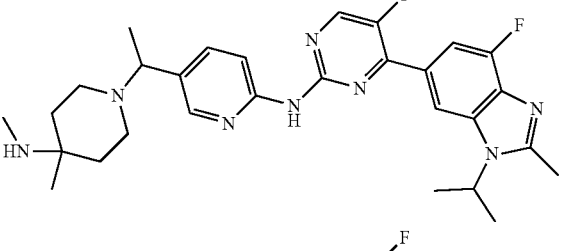
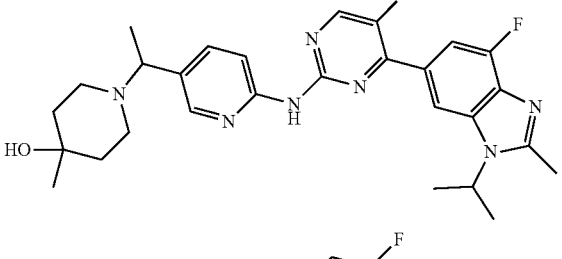
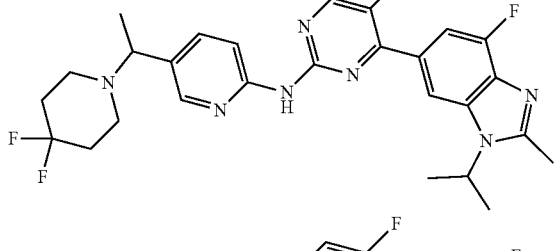
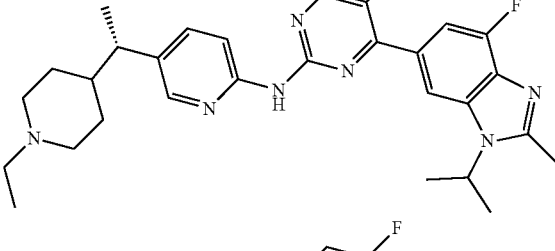
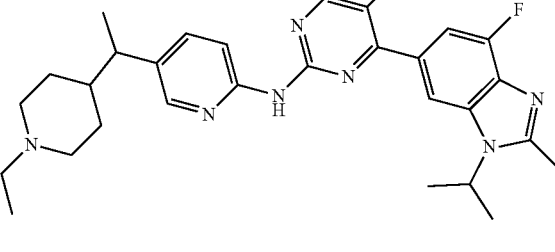

23
-continued
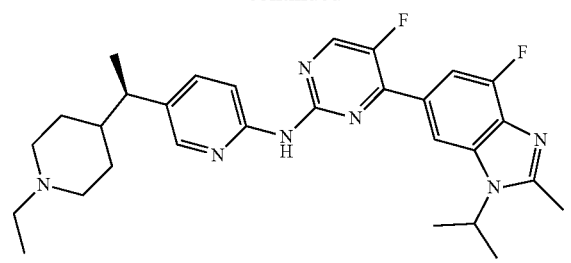
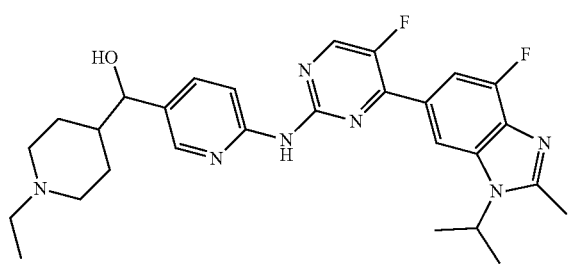
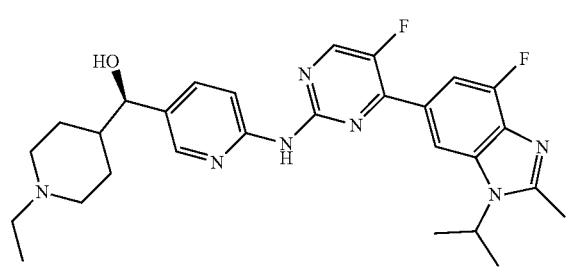
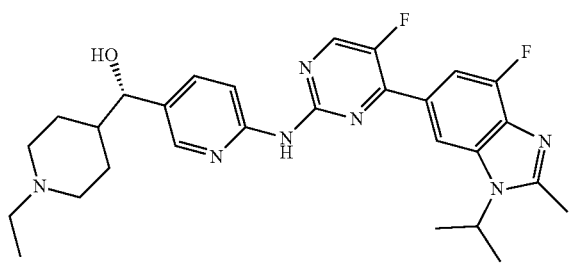
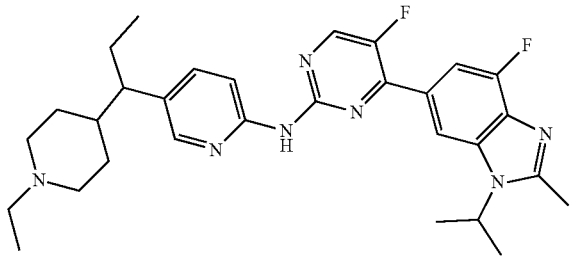
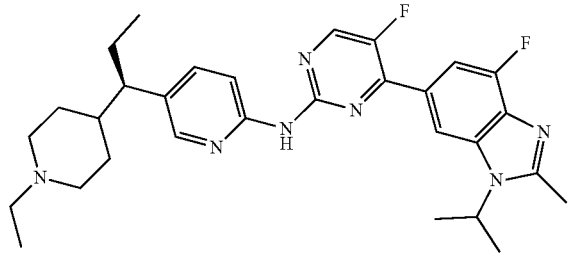
24
-continued
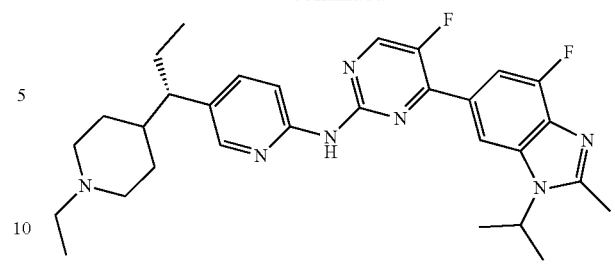
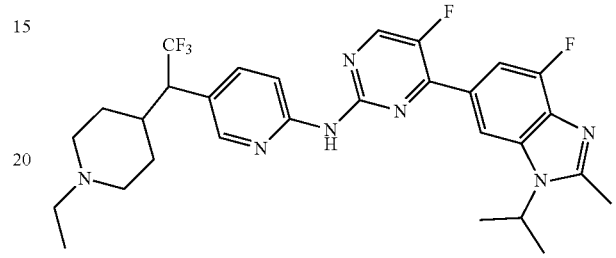
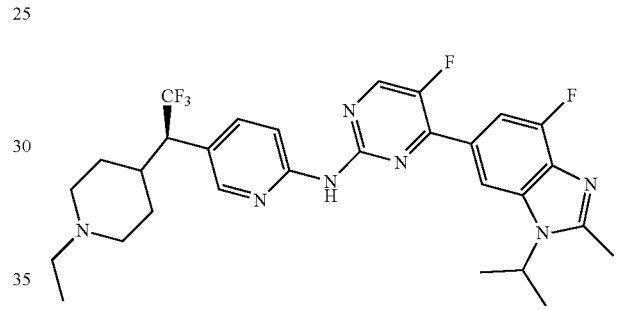
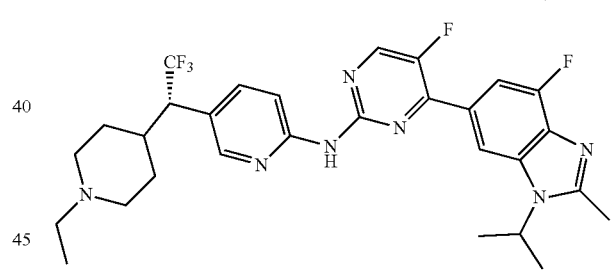
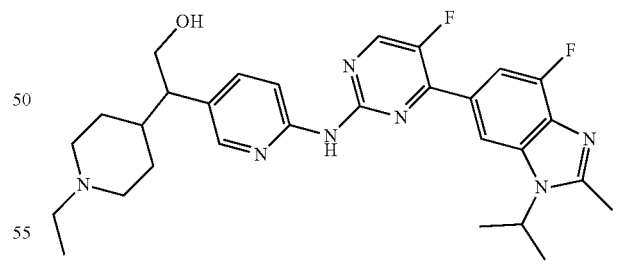
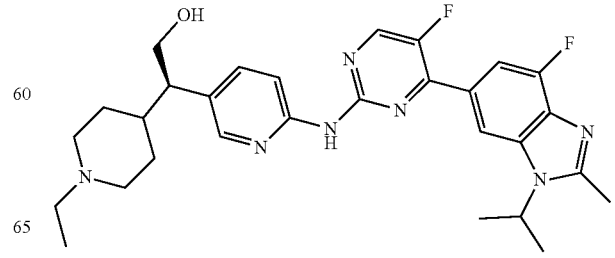

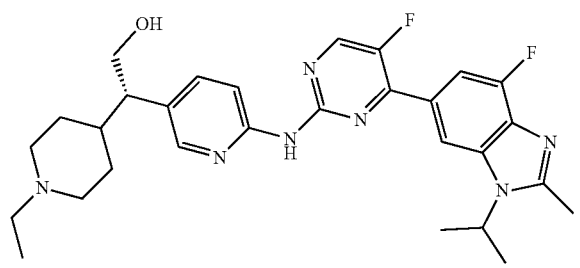
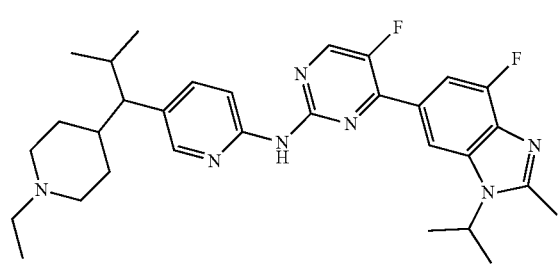
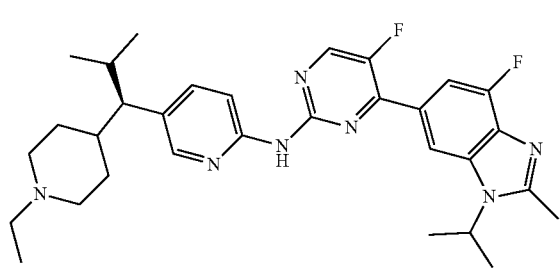
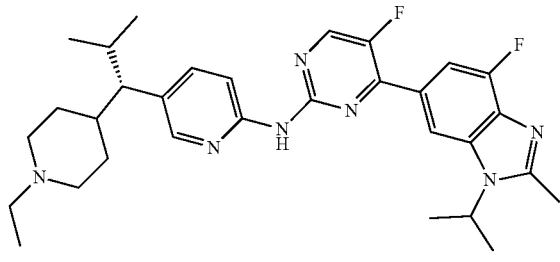
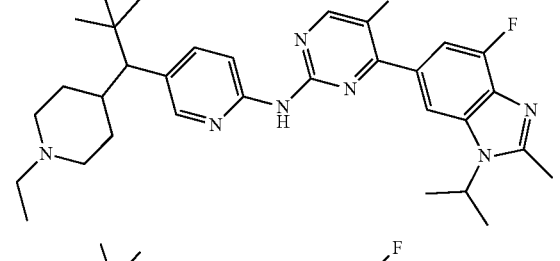
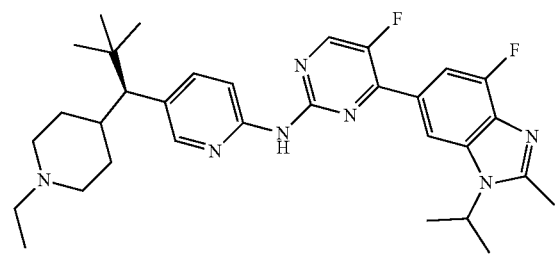
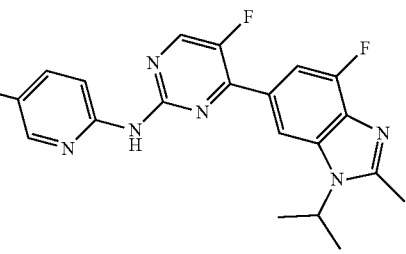
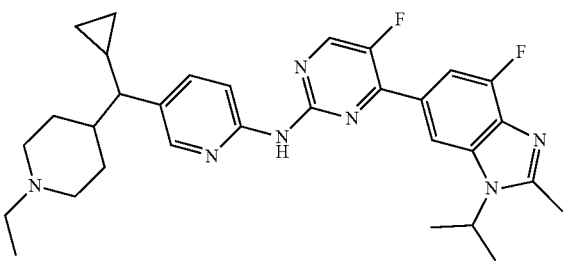
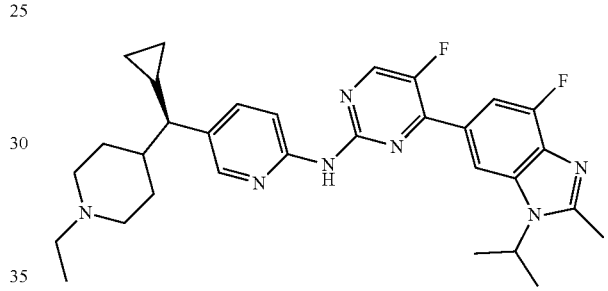
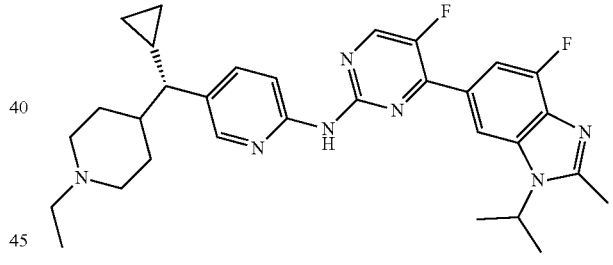
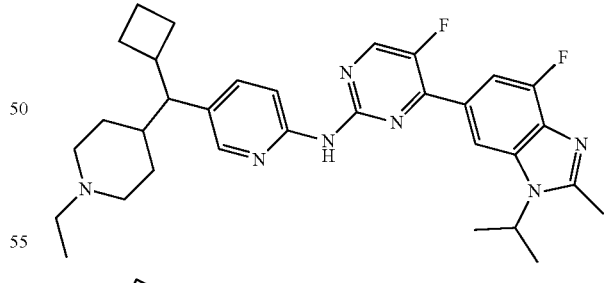
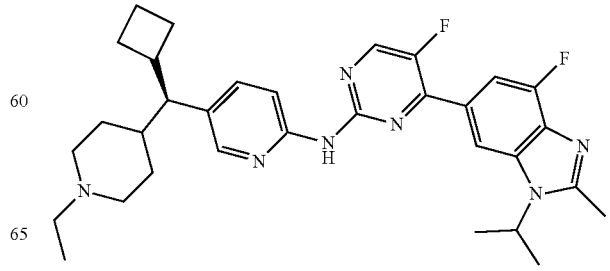

-continued
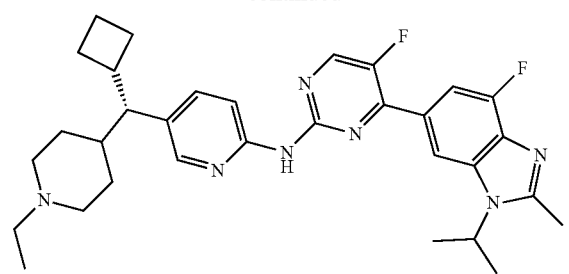
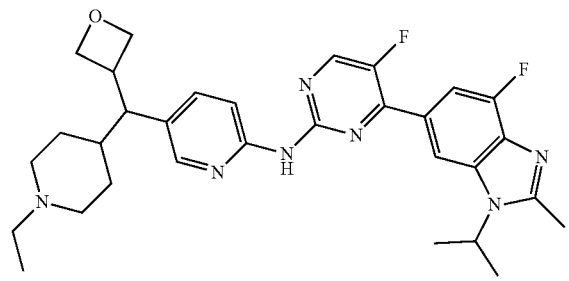
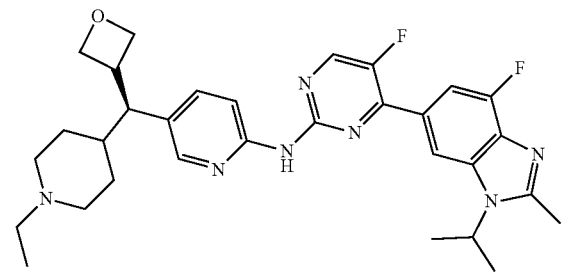
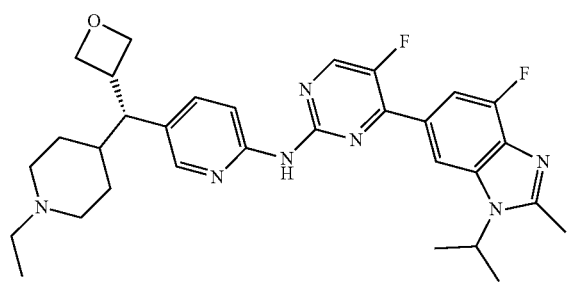
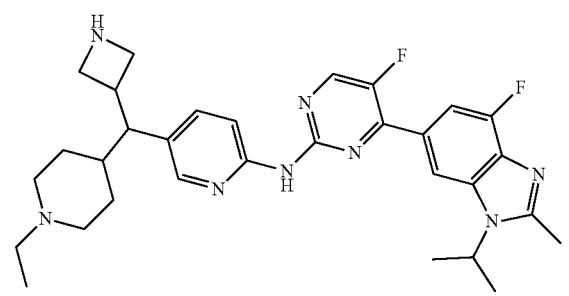
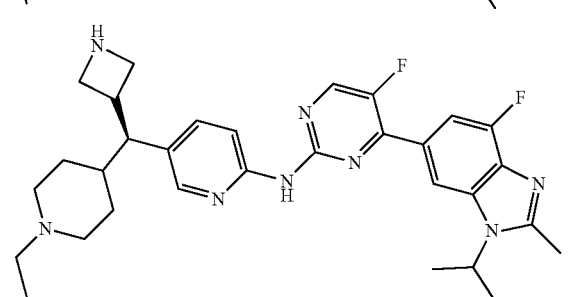
-continued
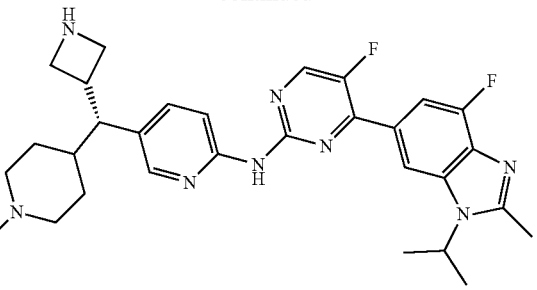
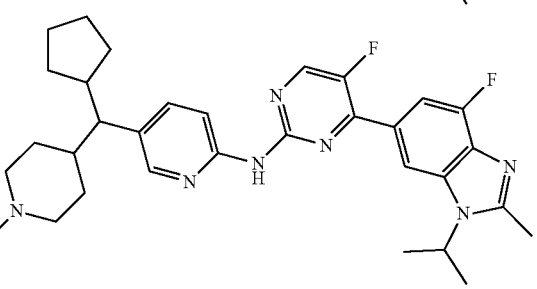
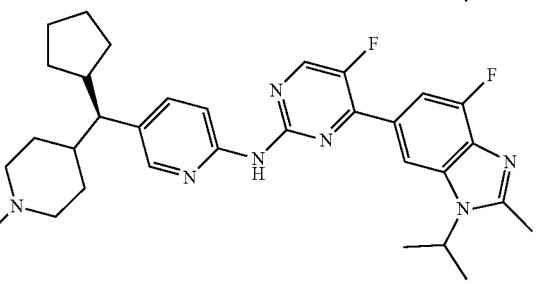
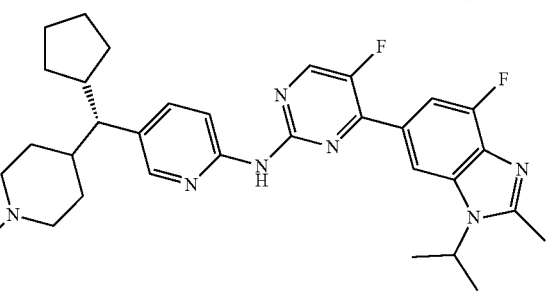
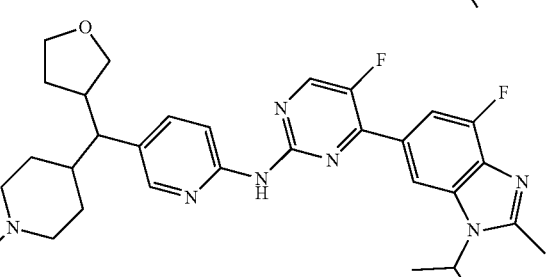
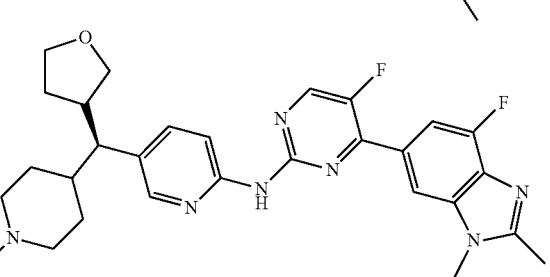

29
-continued
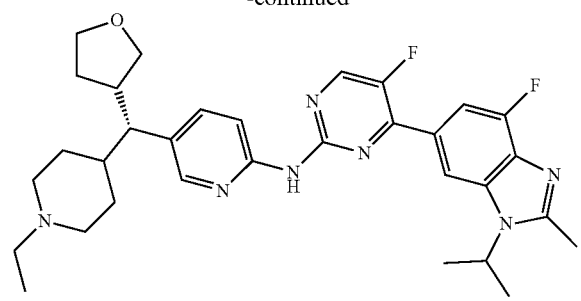
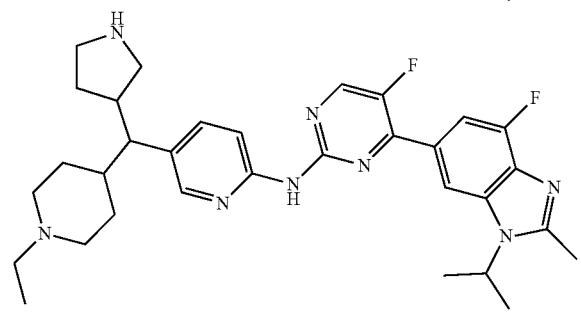
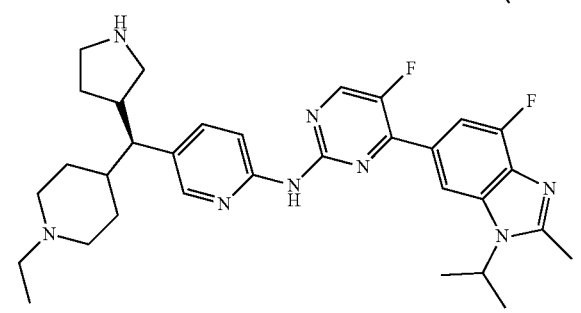
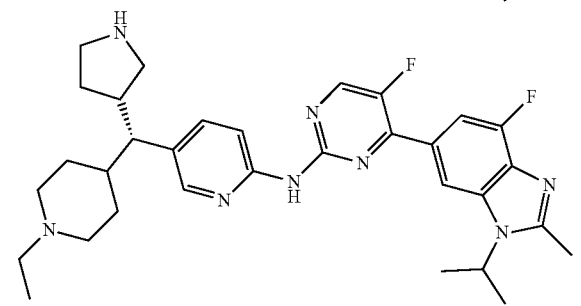
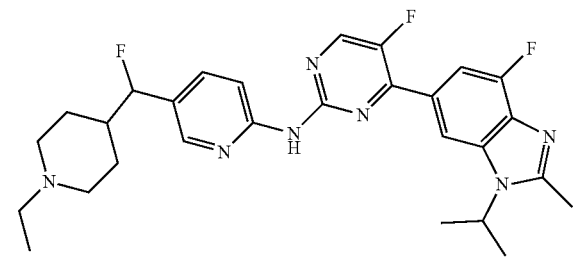
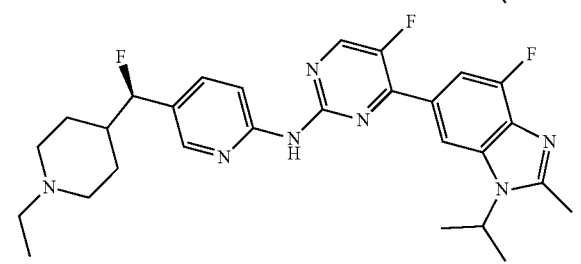
30
-continued
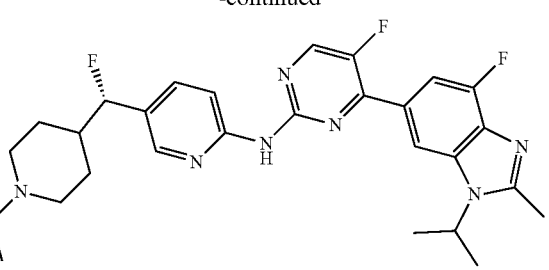
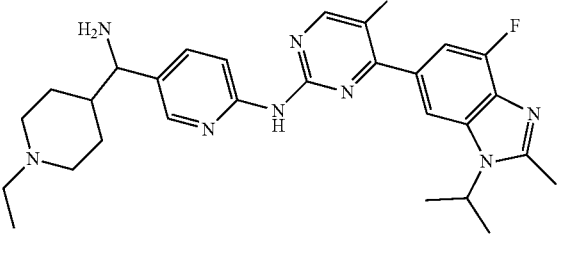
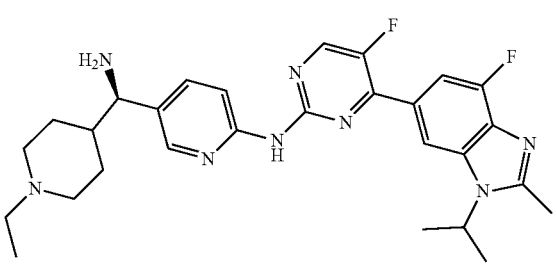
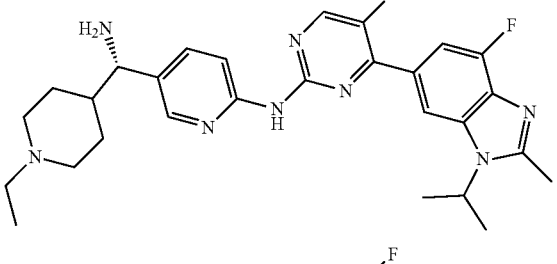
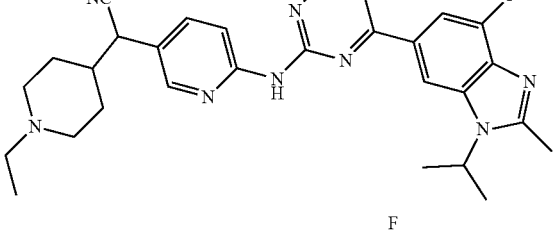
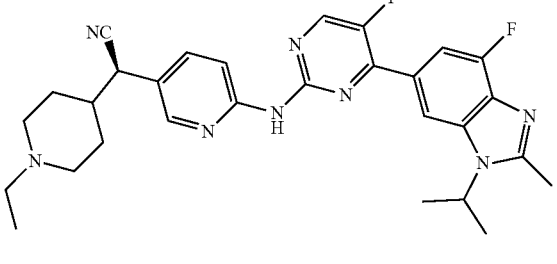

31
-continued
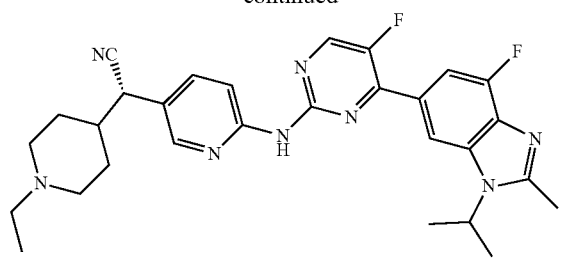
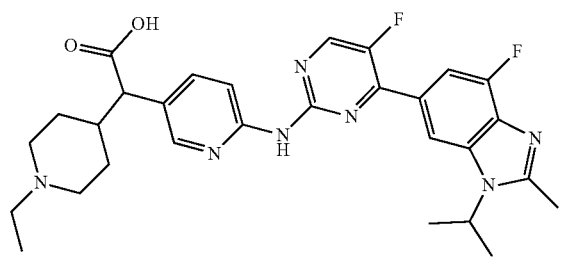
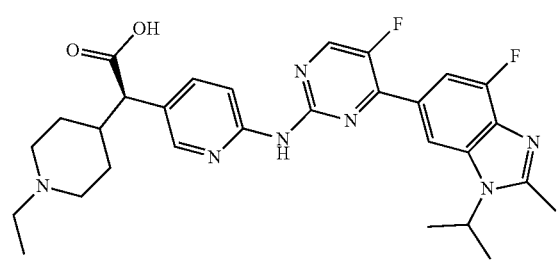
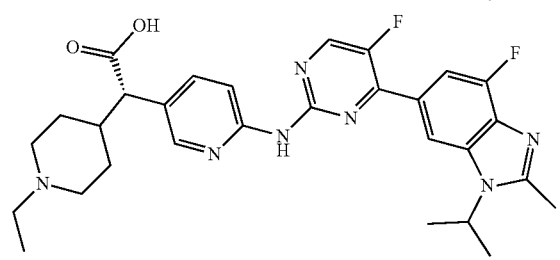
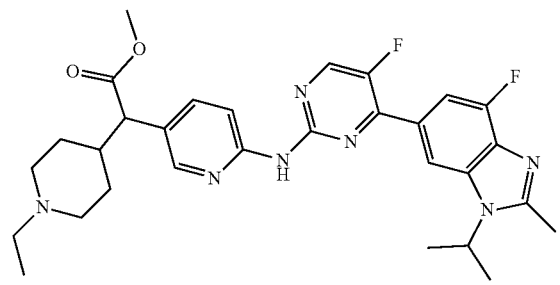
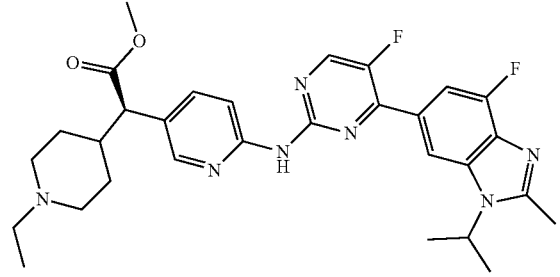
32
-continued
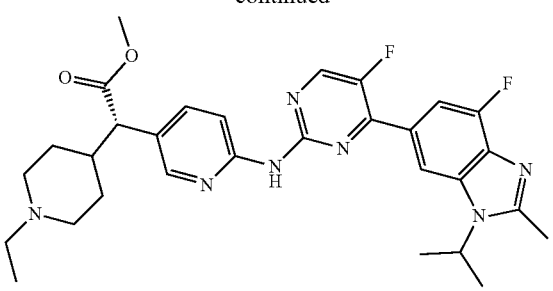
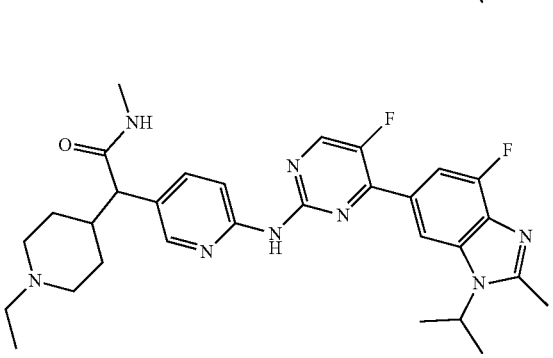
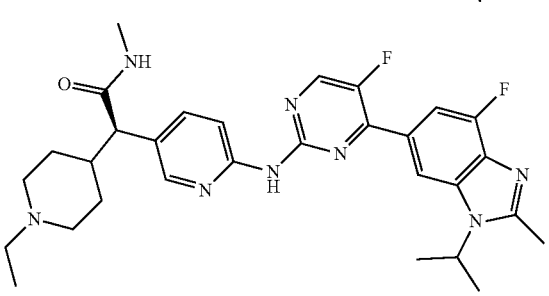
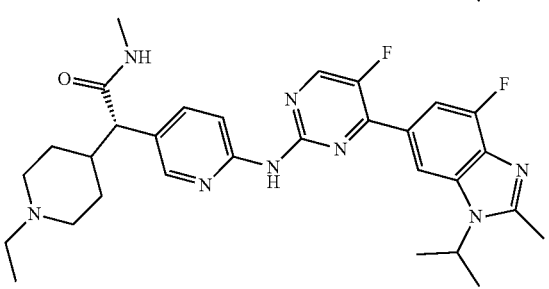
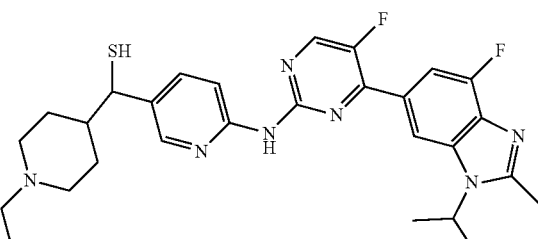
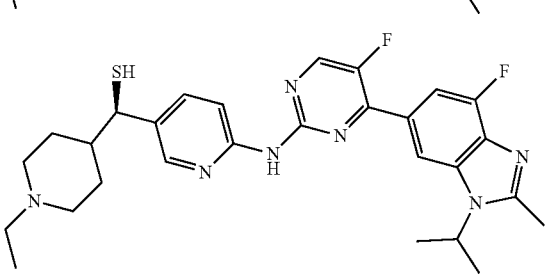

33
-continued
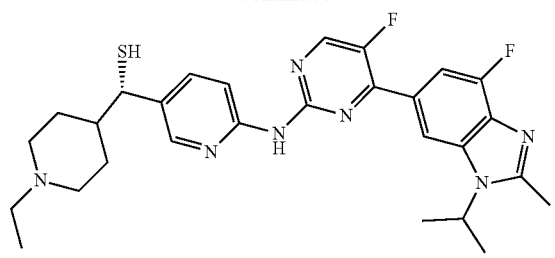
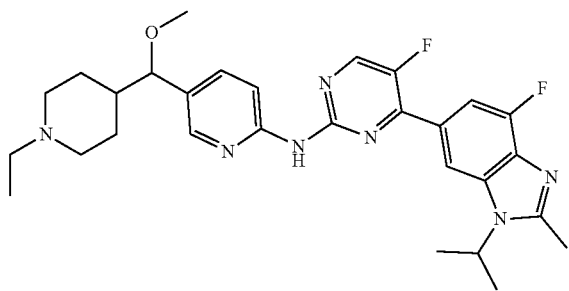
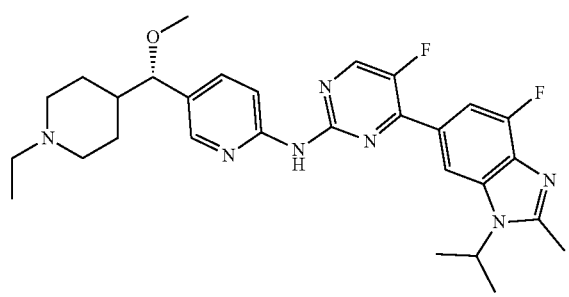
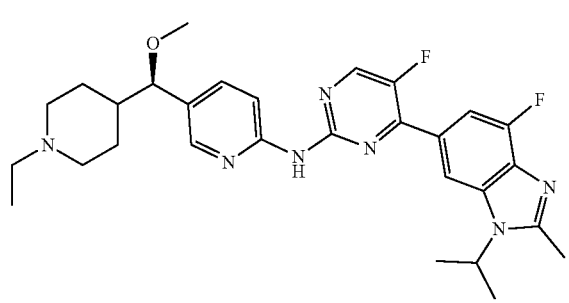
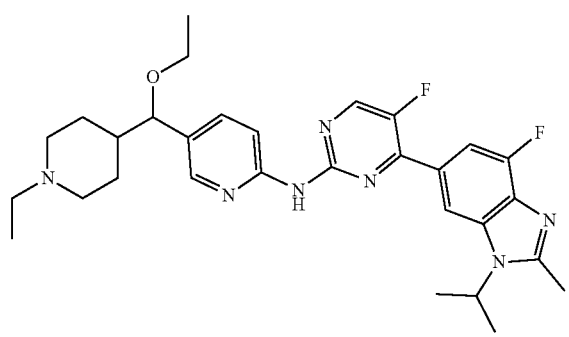
34
-continued
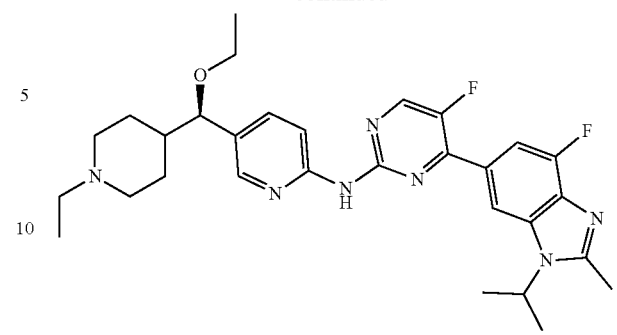
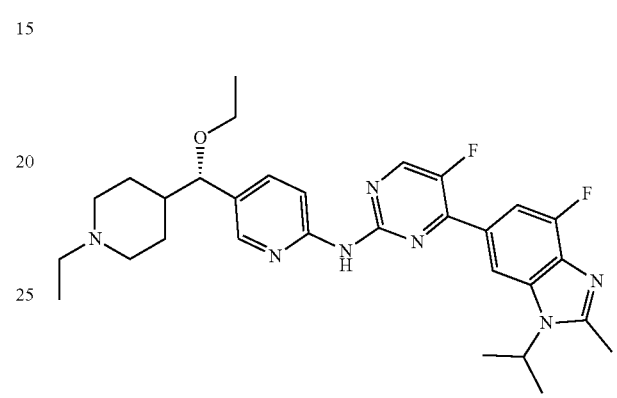
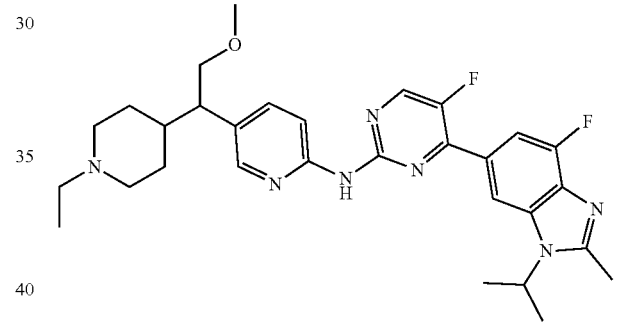
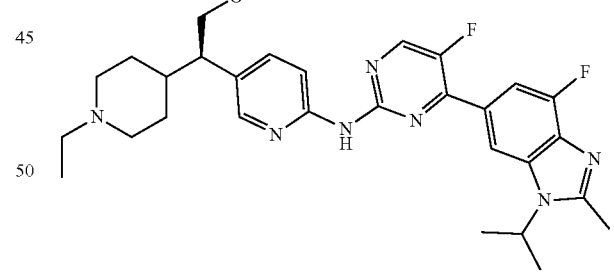
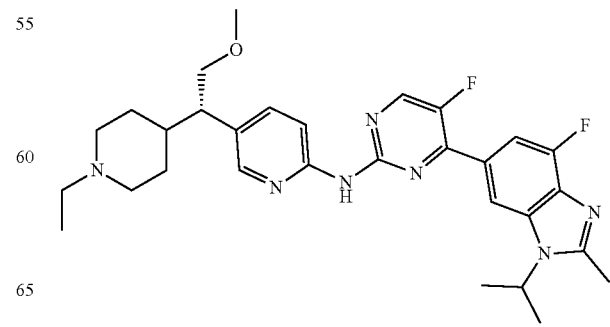

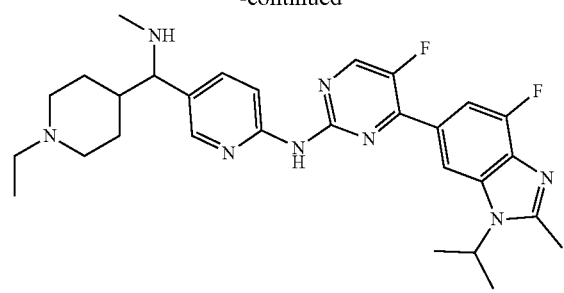
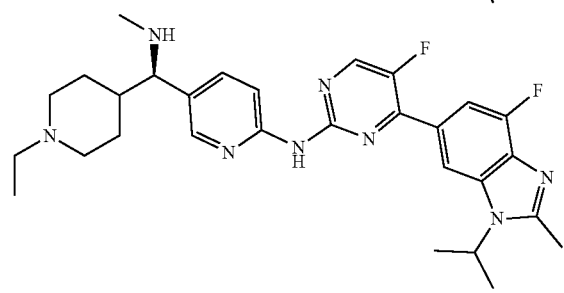
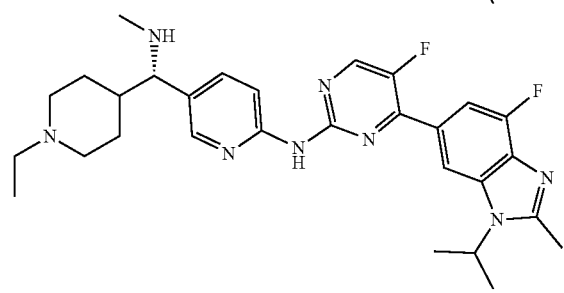
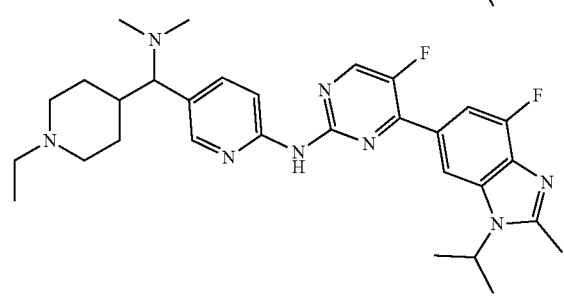
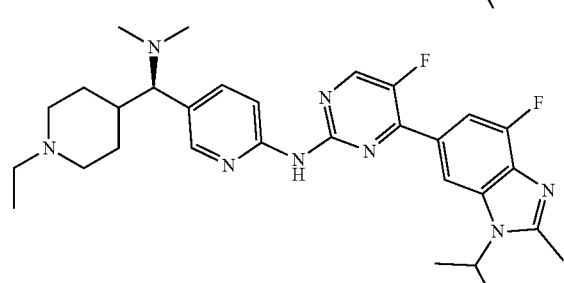
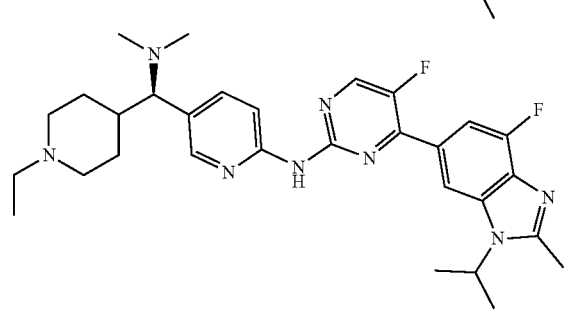
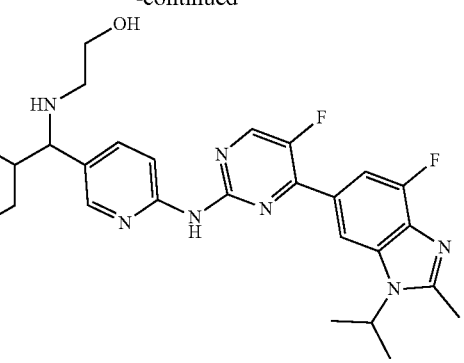
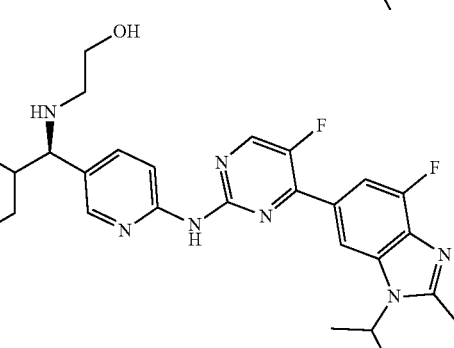
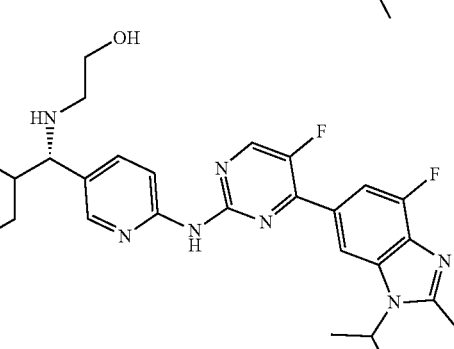
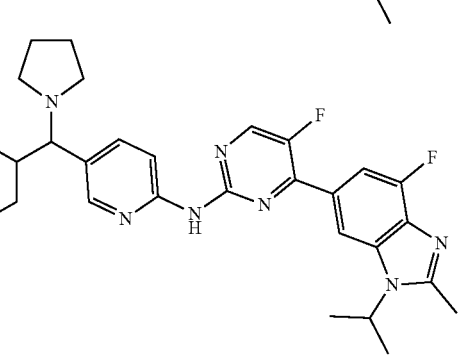
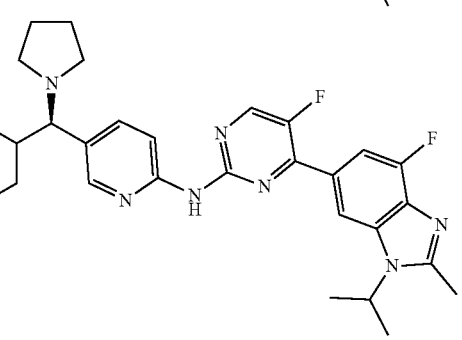

37
-continued
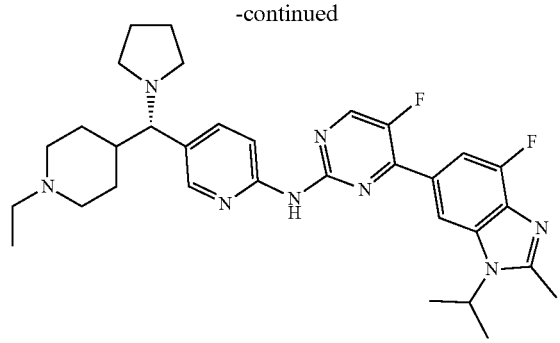
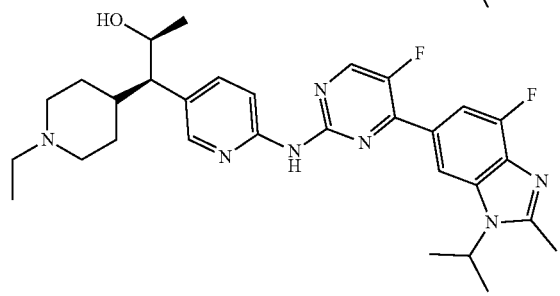
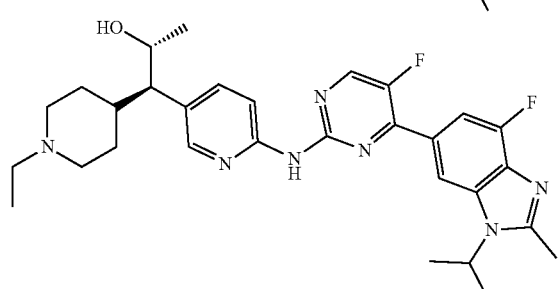
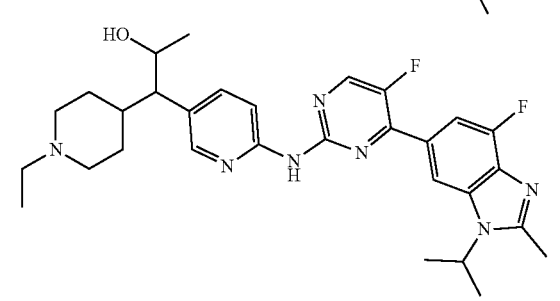
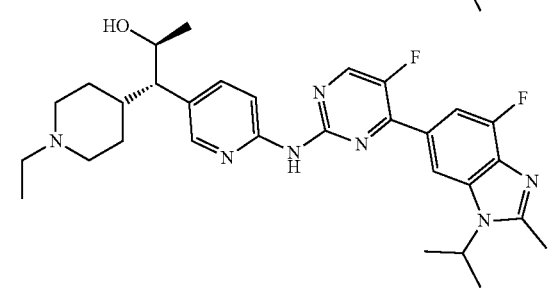
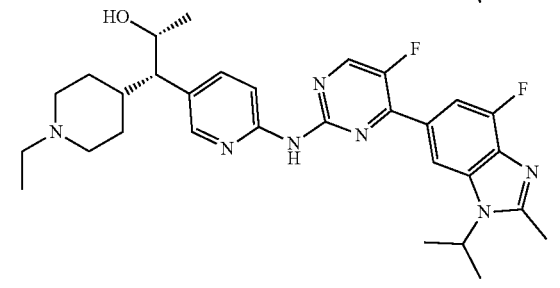
38
-continued
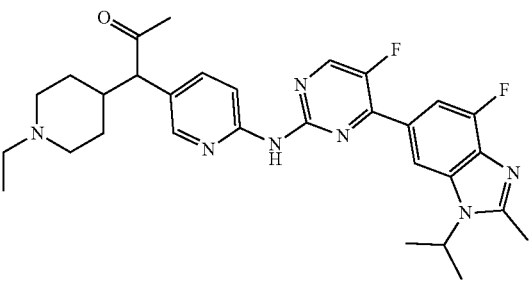
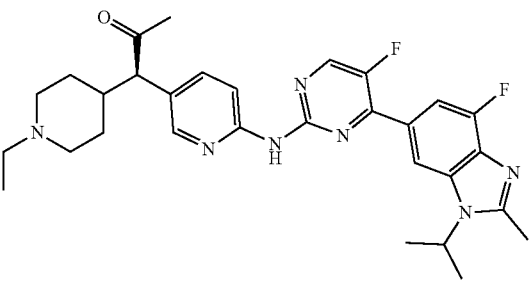
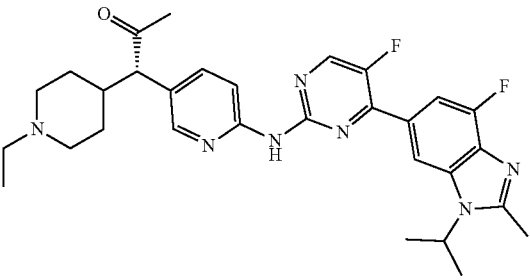
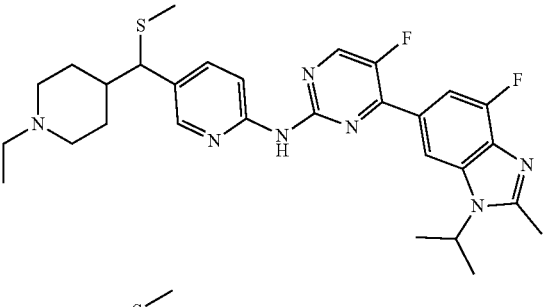
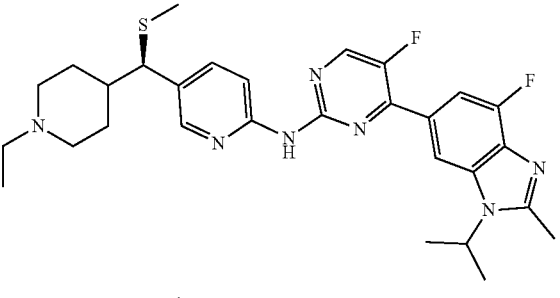
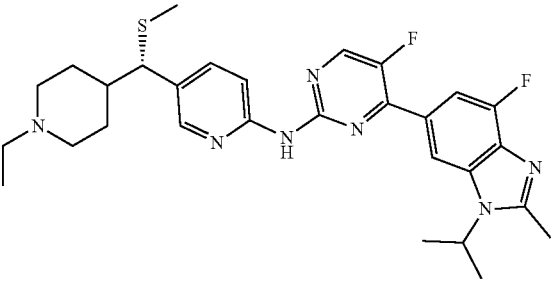

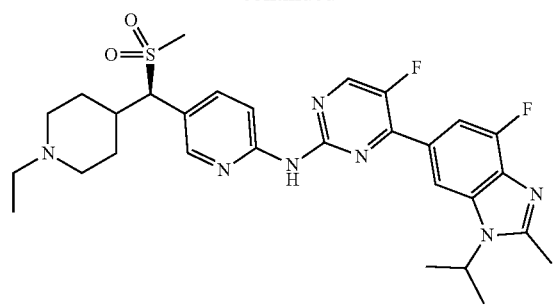
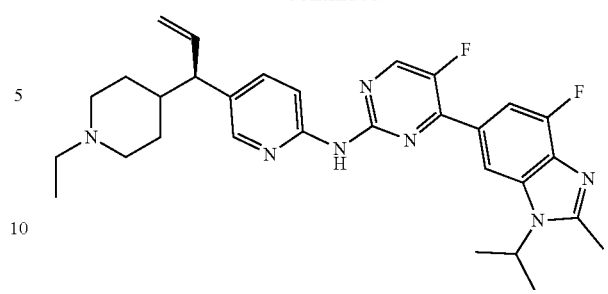
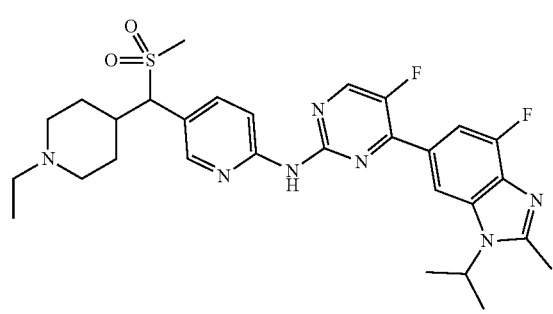
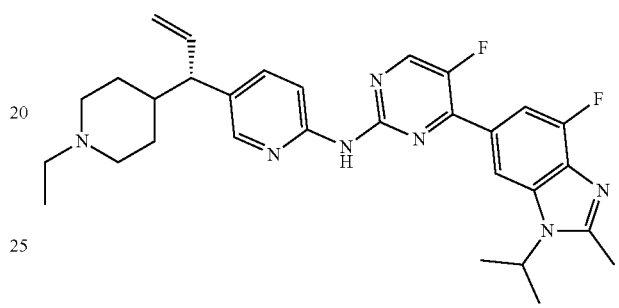
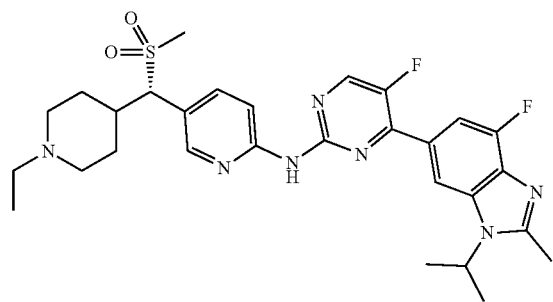
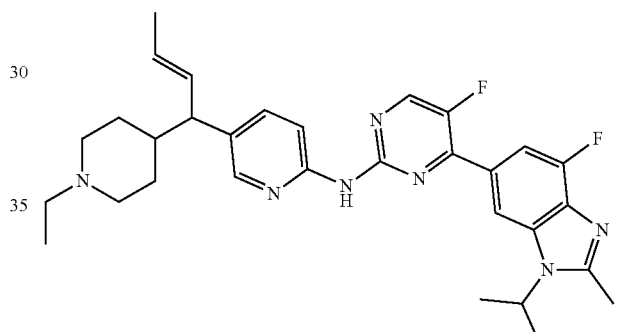
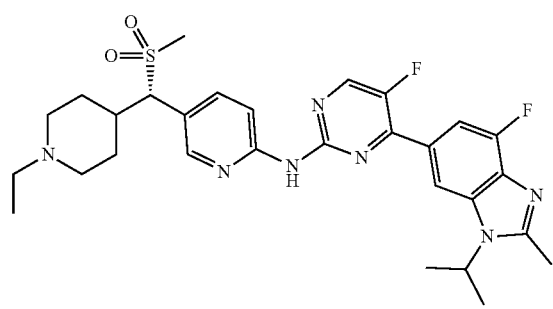
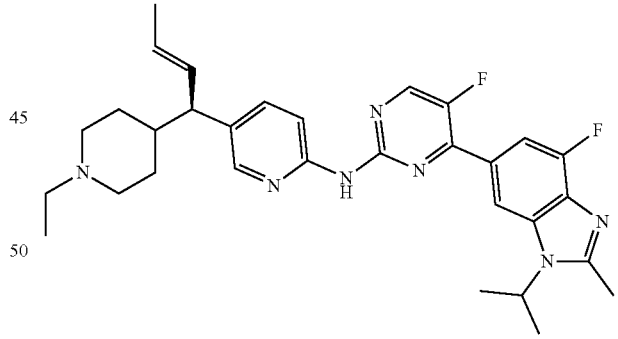
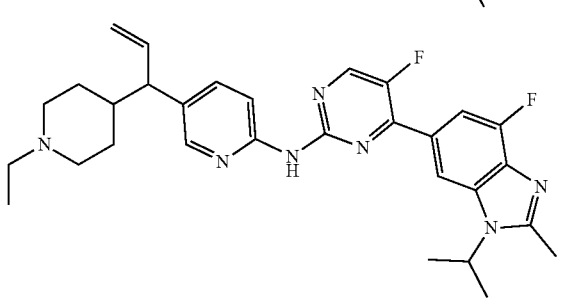
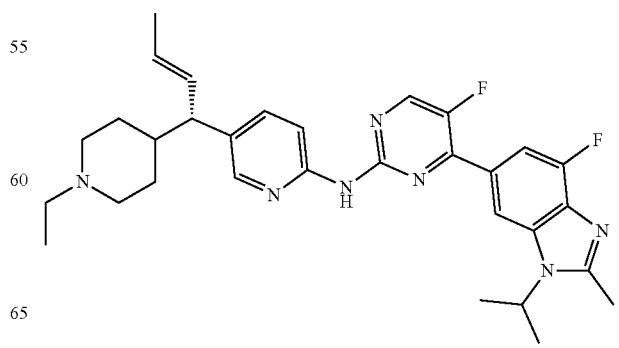

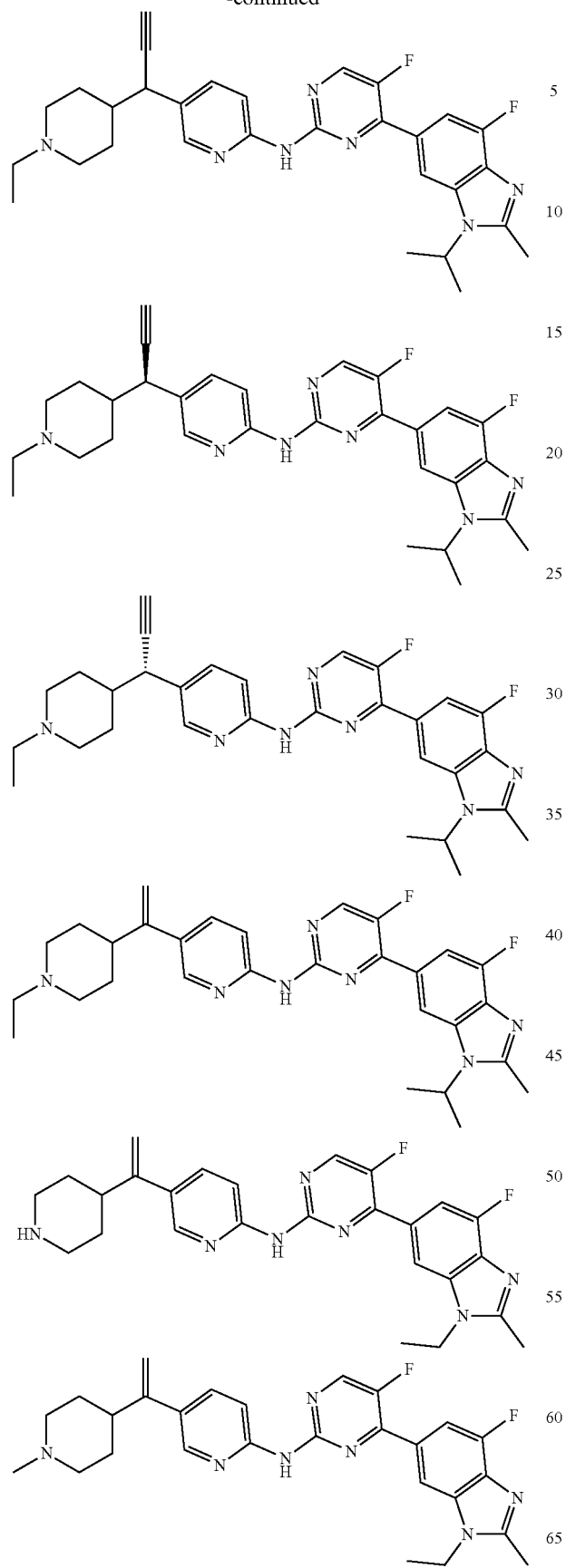

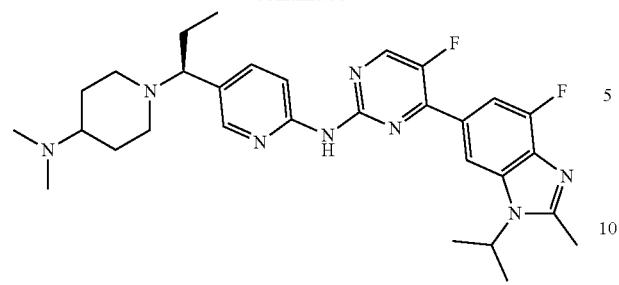
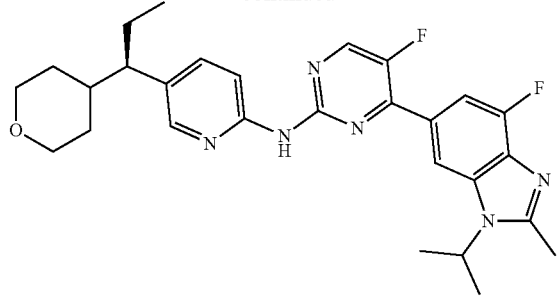
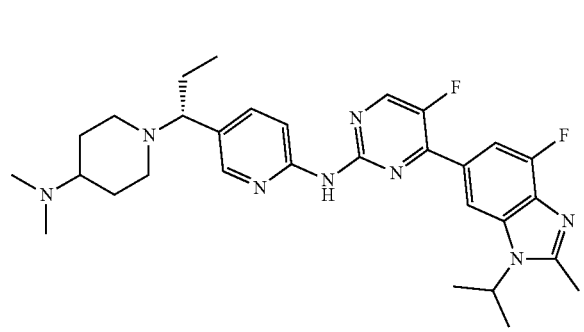
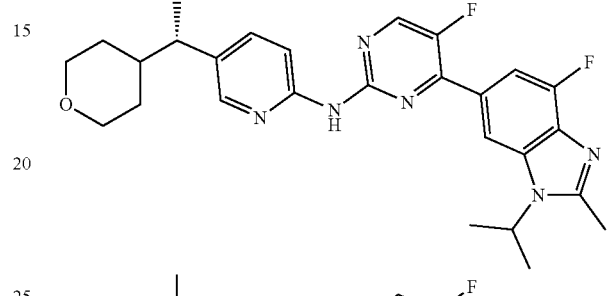
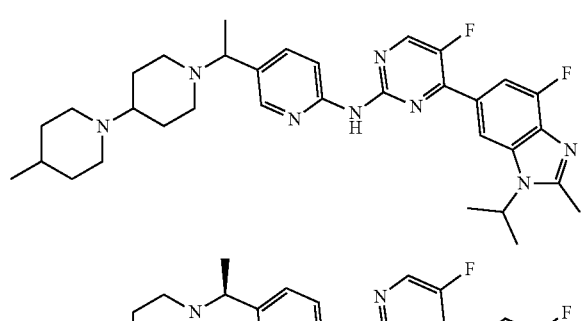
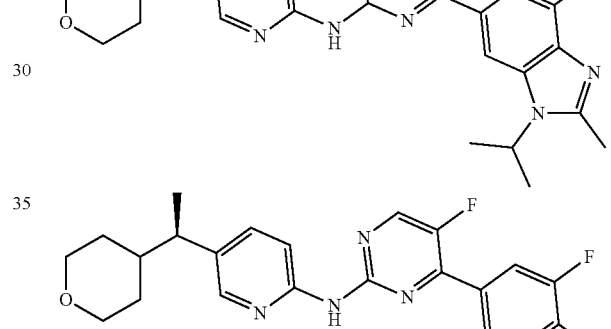
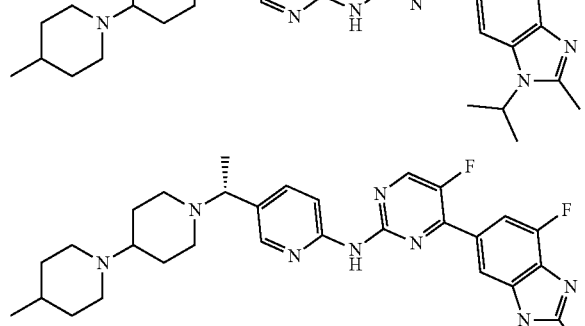
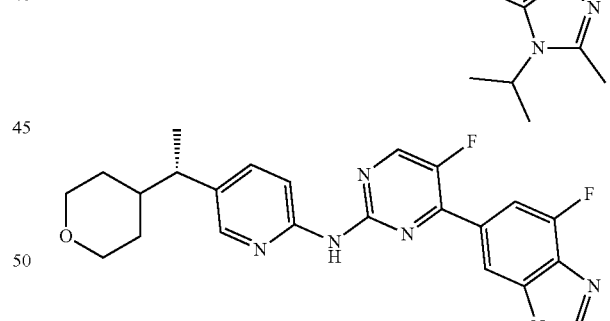
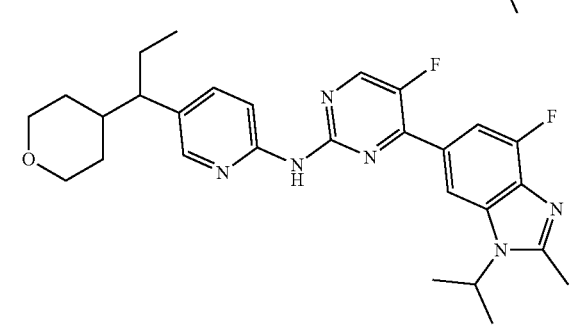
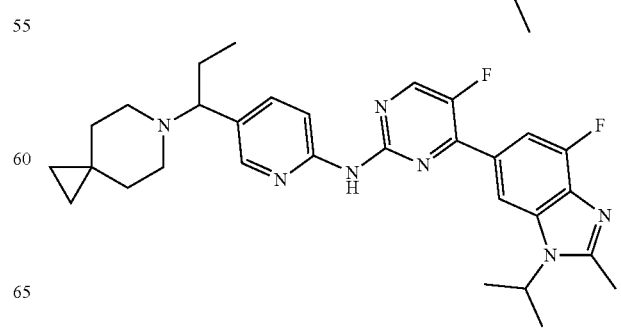

45
-continued
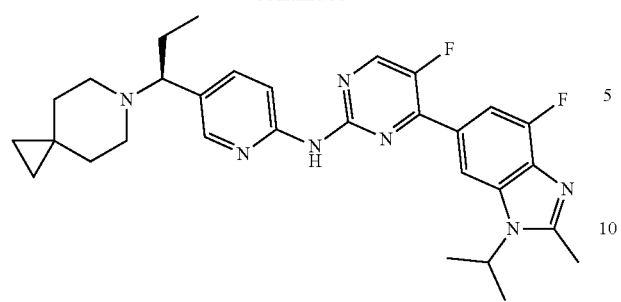
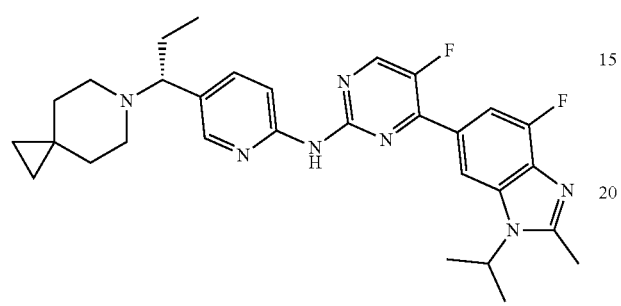
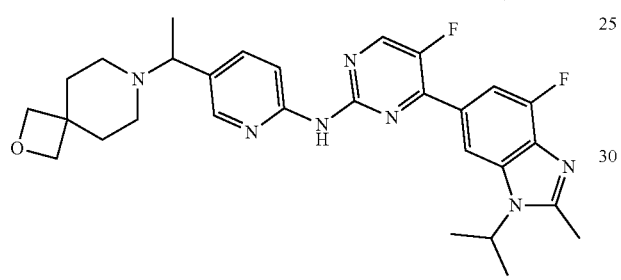
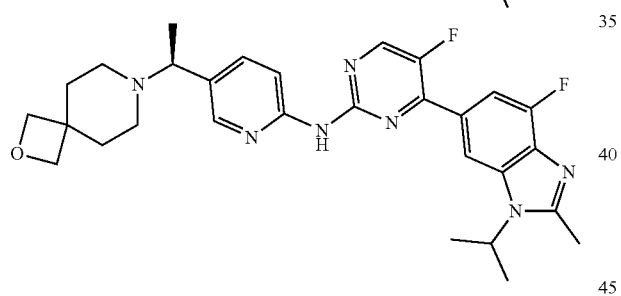
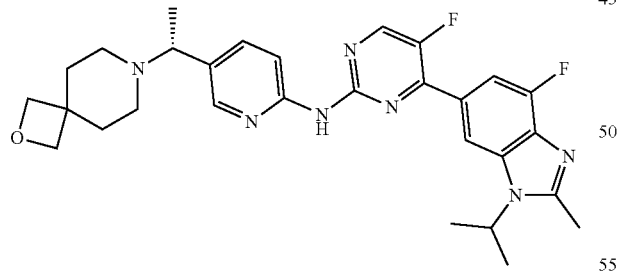
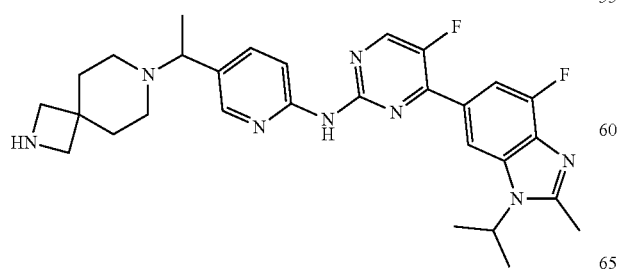
46
-continued
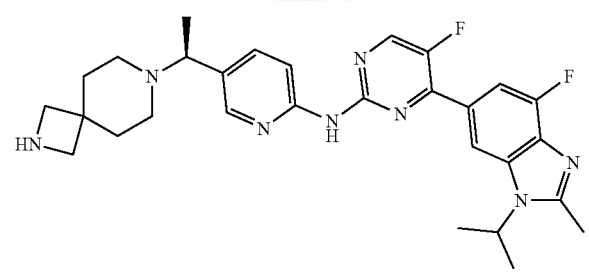
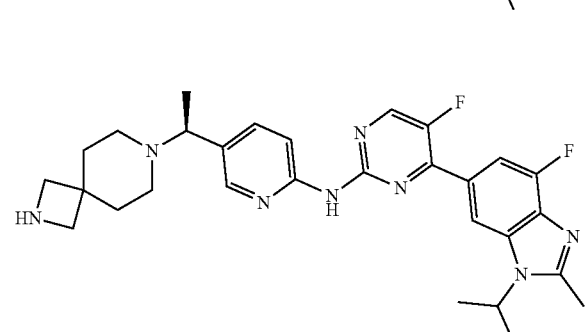
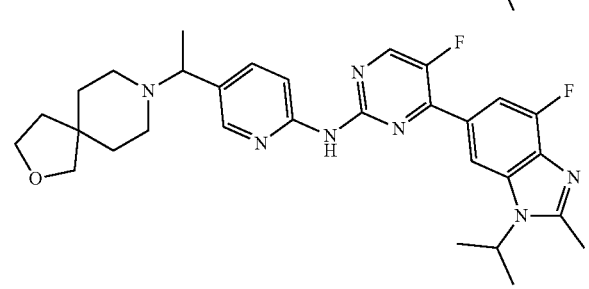
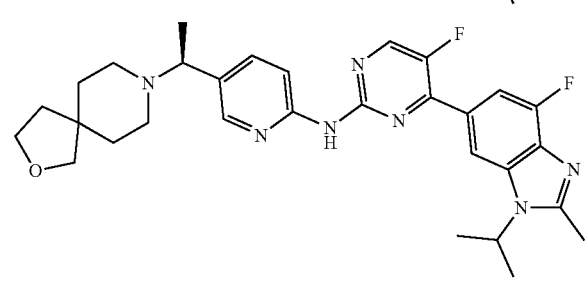
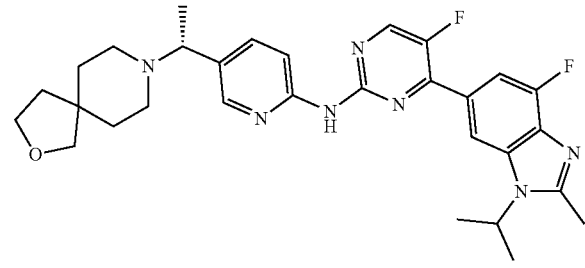
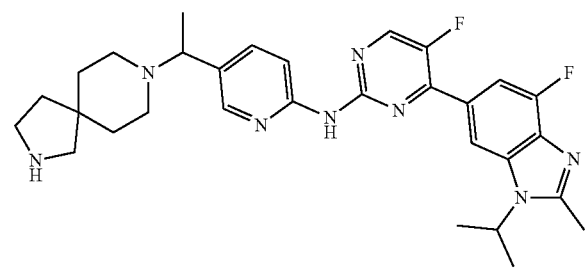

47
-continued
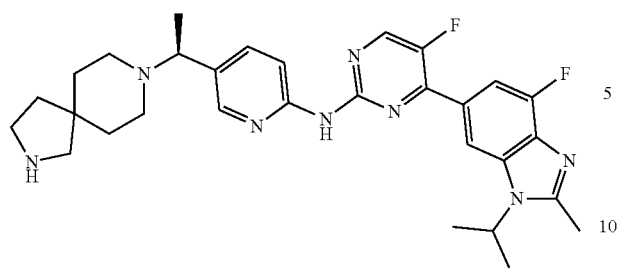
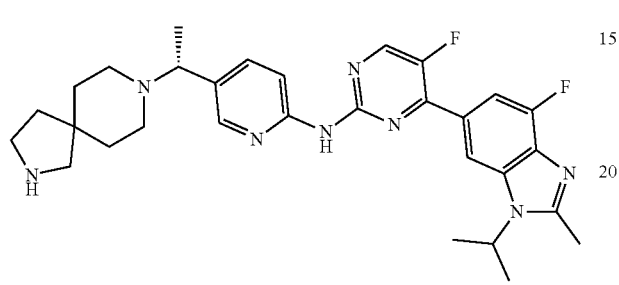
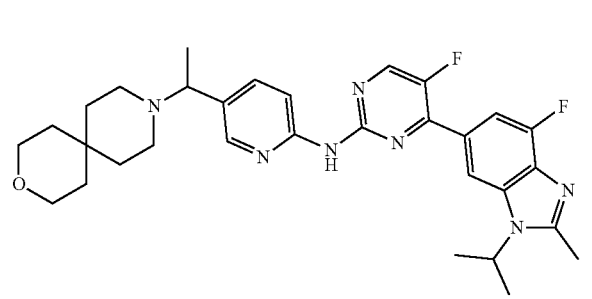
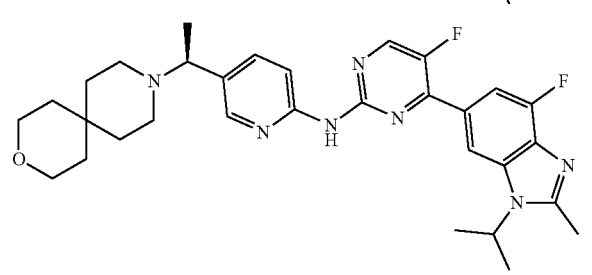
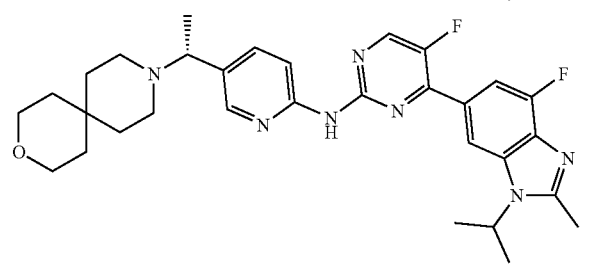
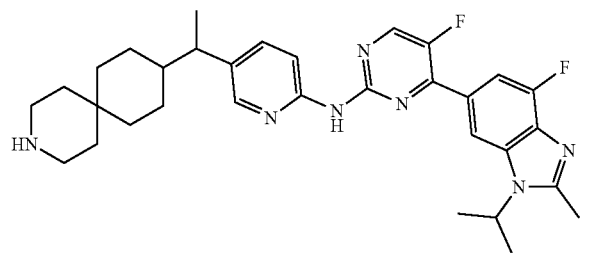
48
-continued
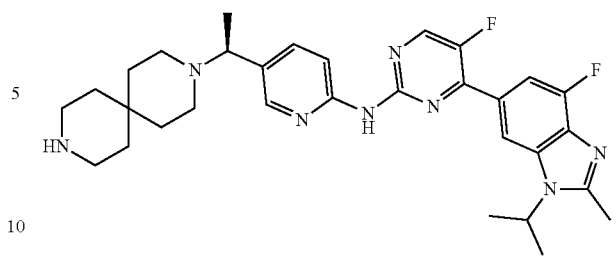
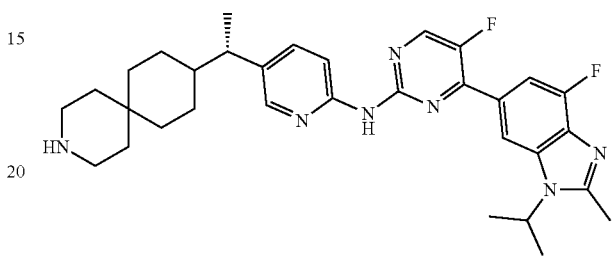
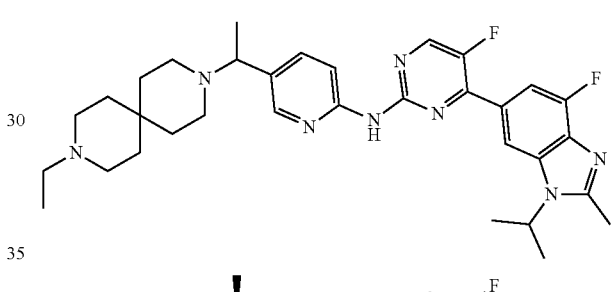
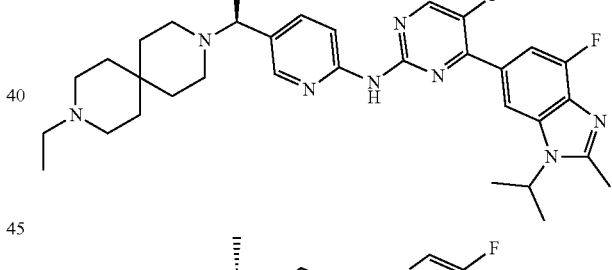
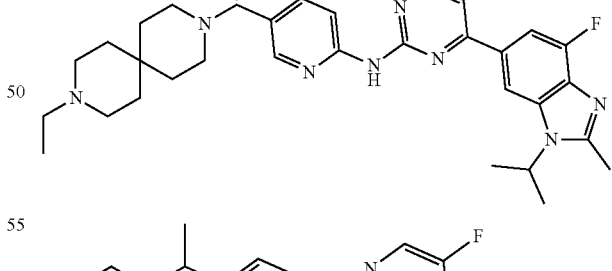
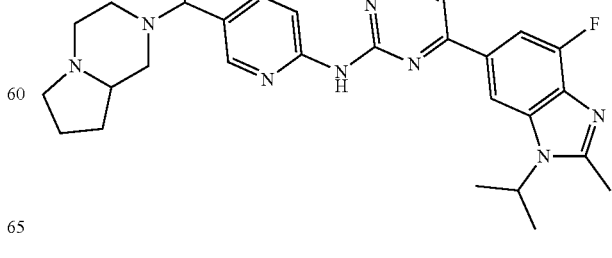

49
-continued
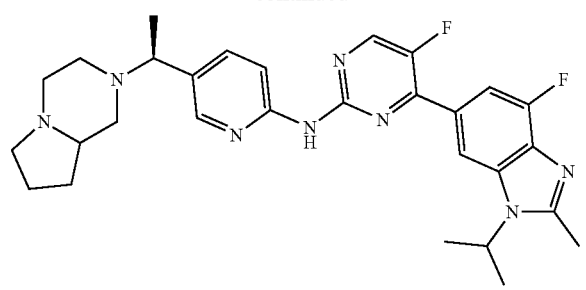
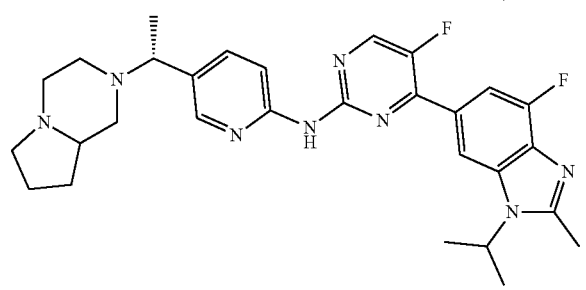
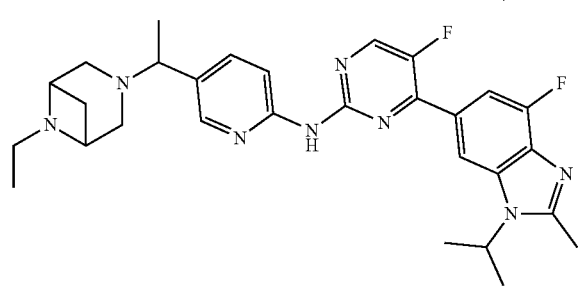
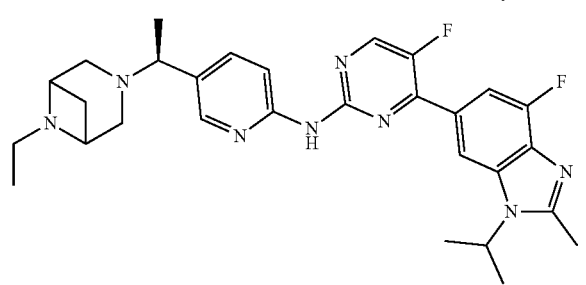
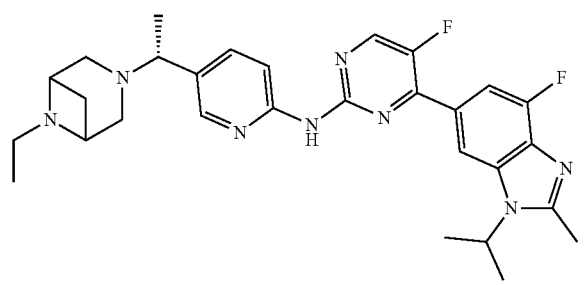
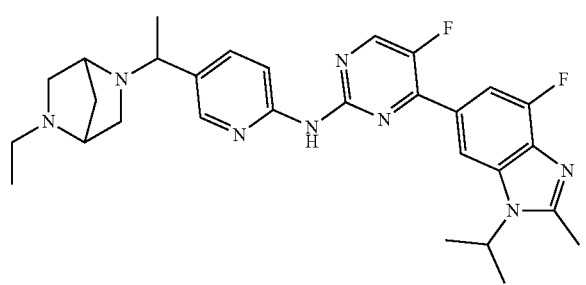
50
-continued
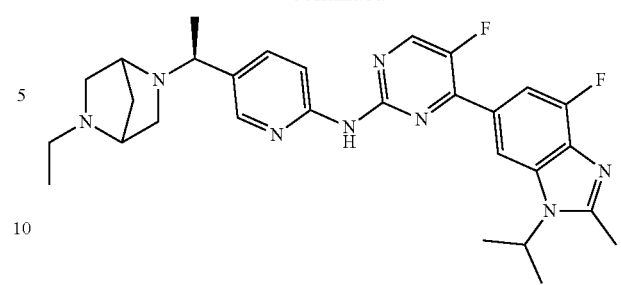
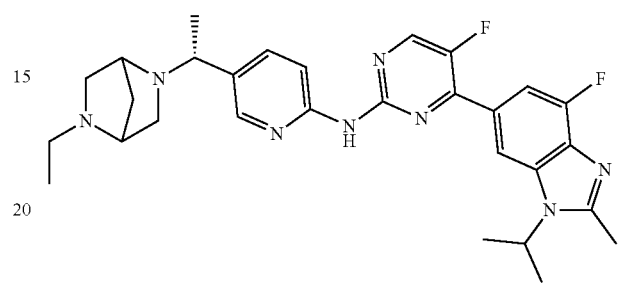
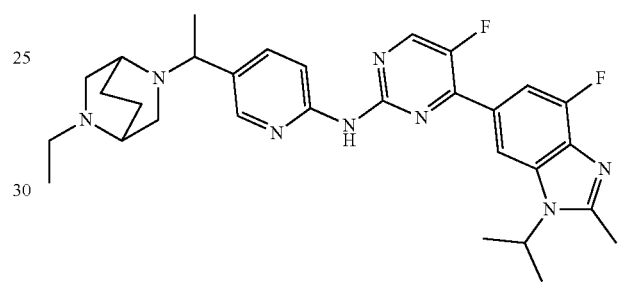
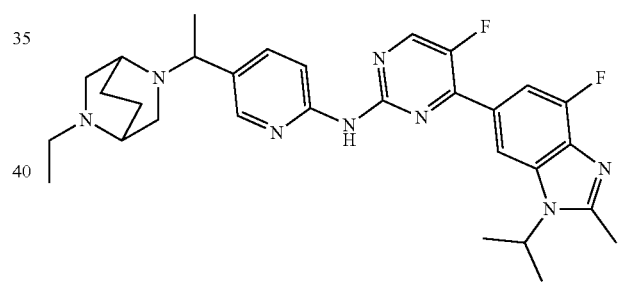
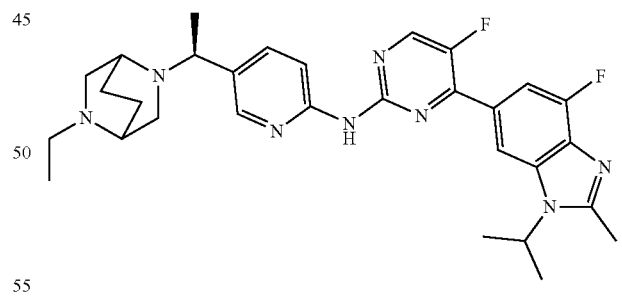
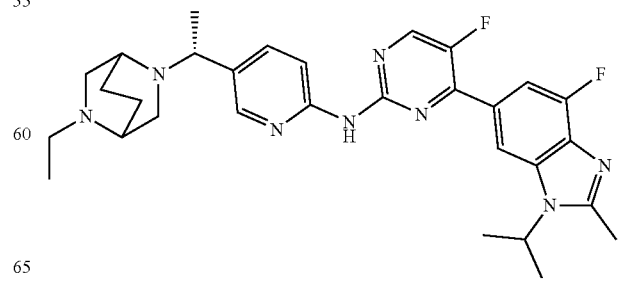

51
-continued
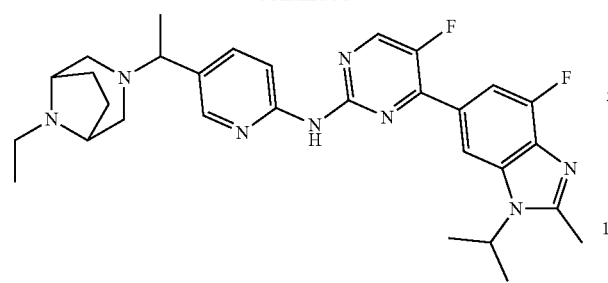
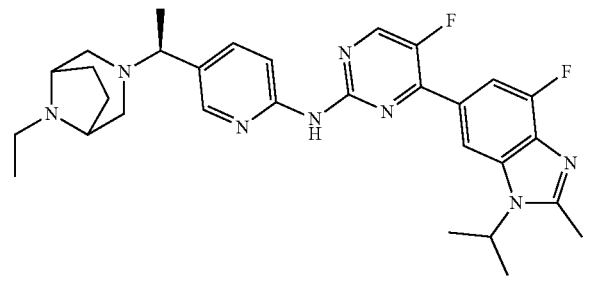
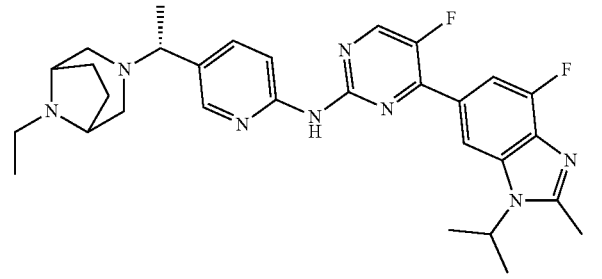
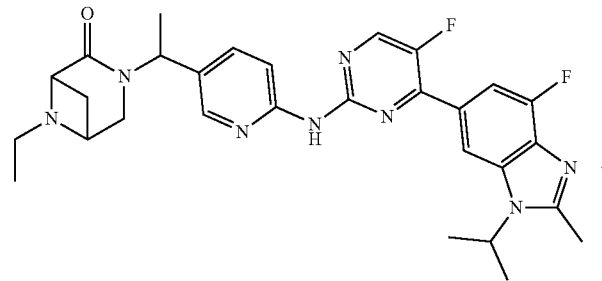
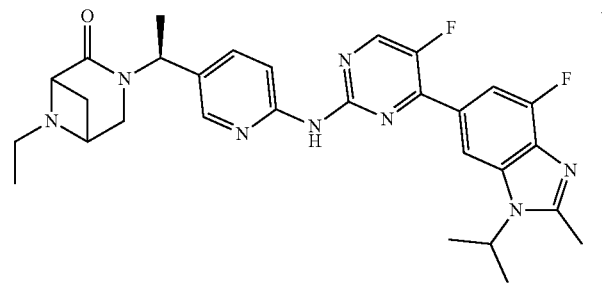
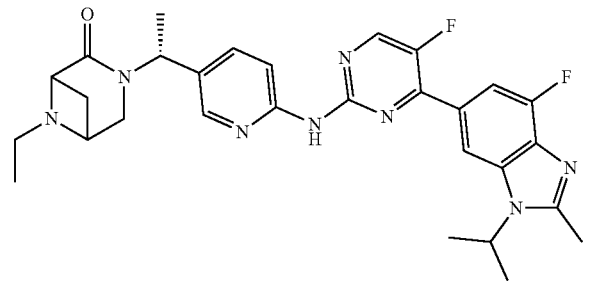
52
-continued
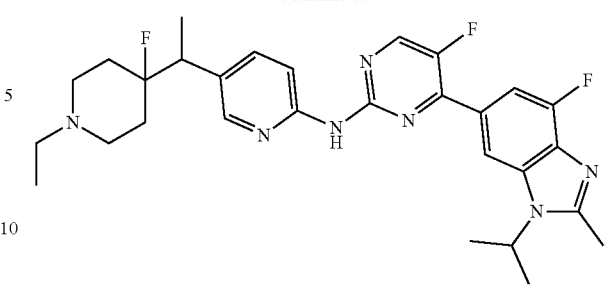
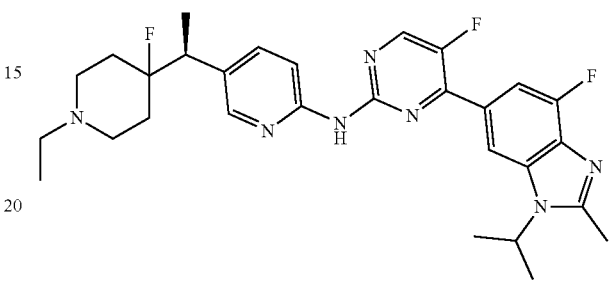
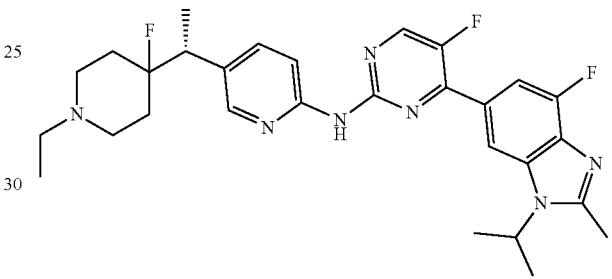
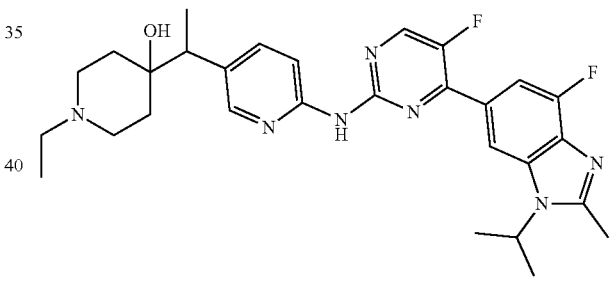
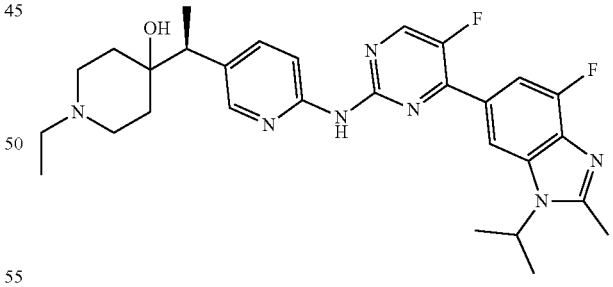
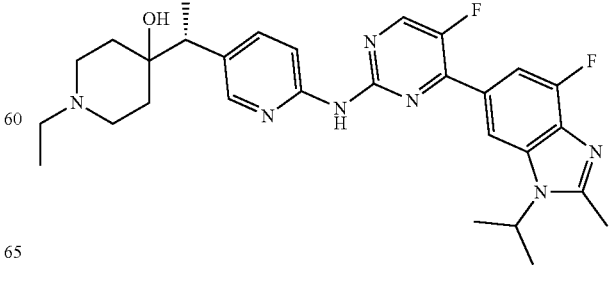

53
-continued
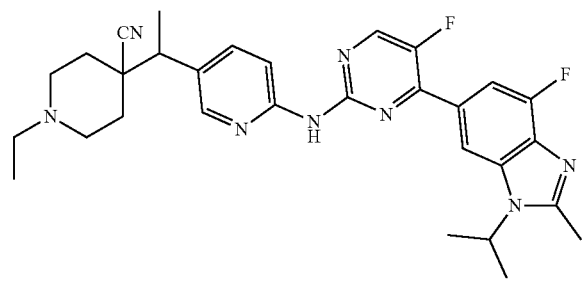
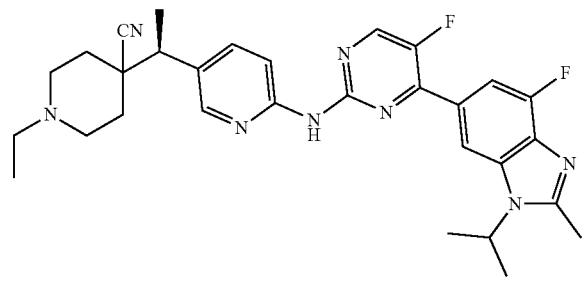
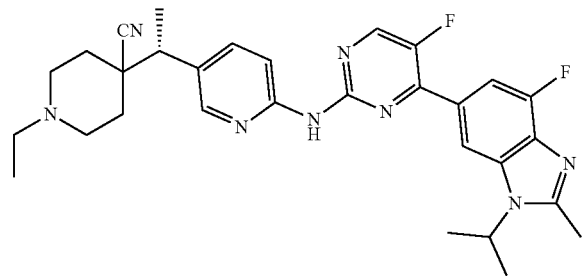
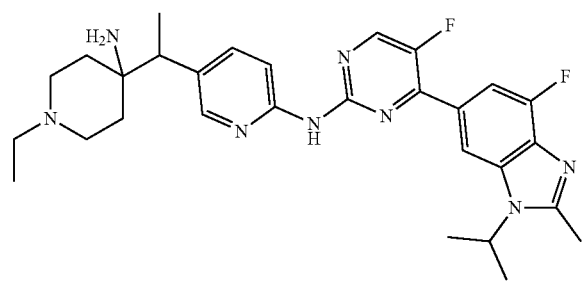
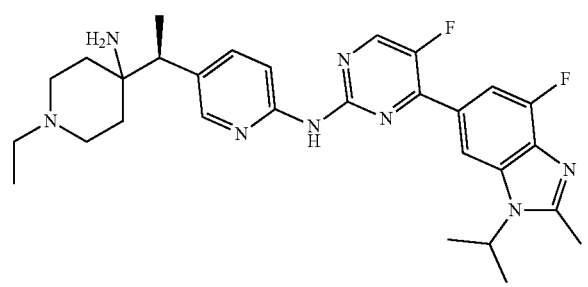
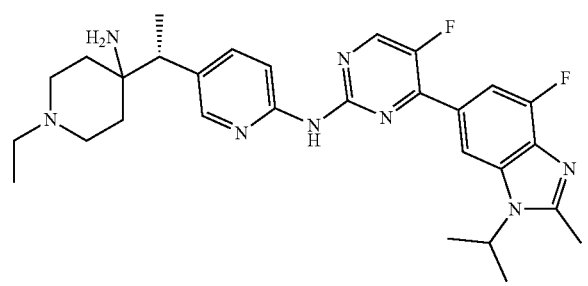
54
-continued
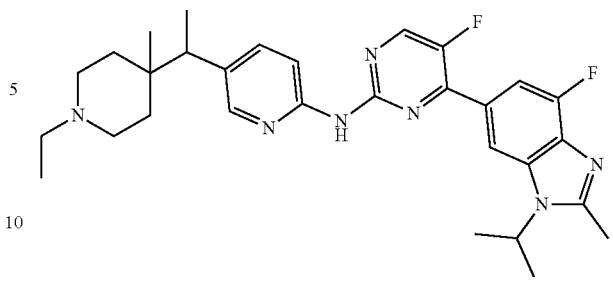
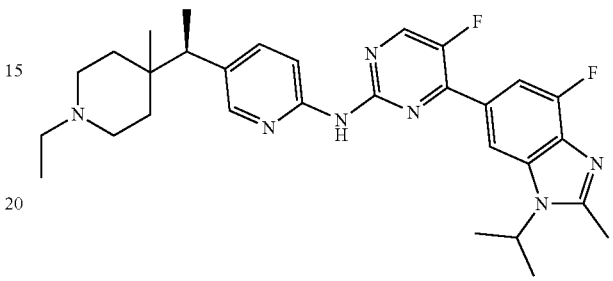
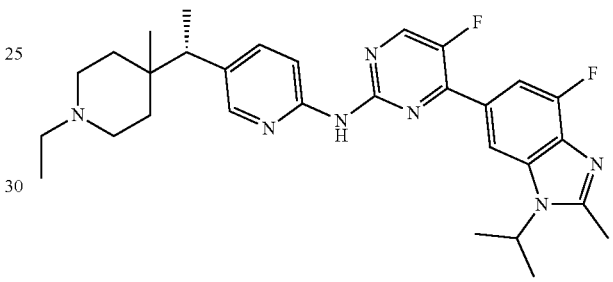
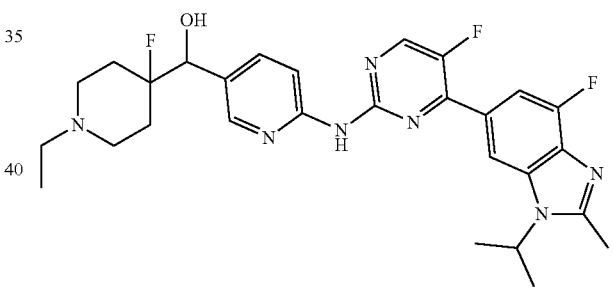
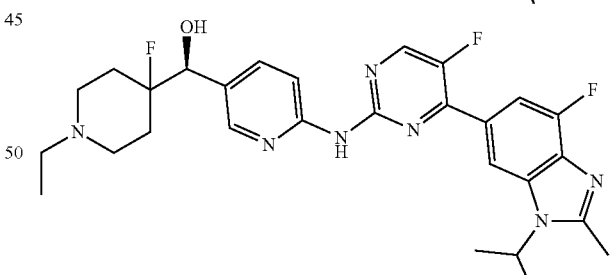
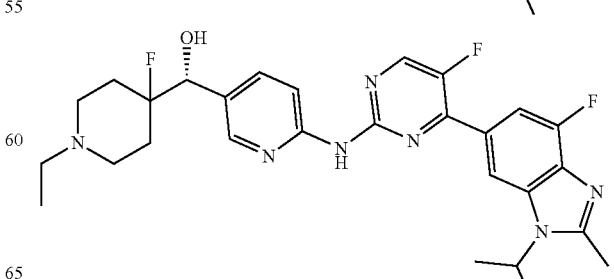

55
-continued
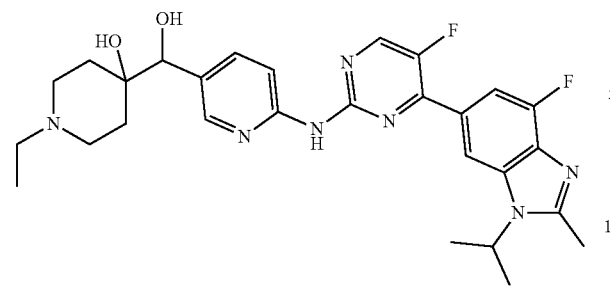
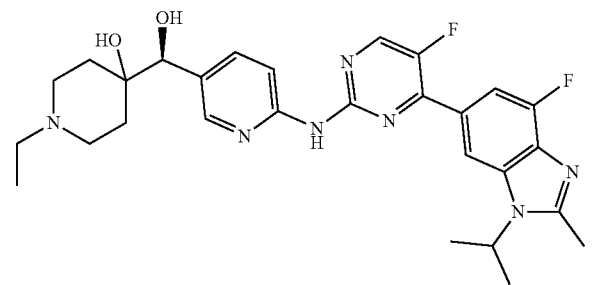
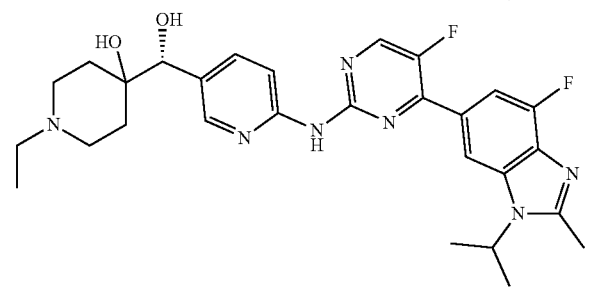
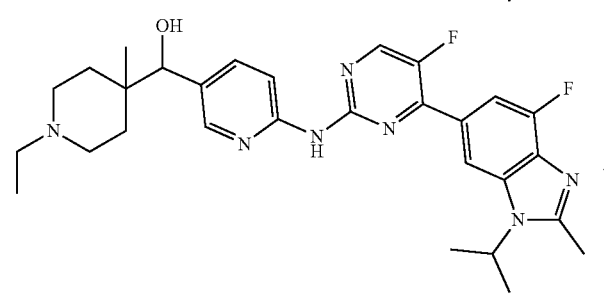
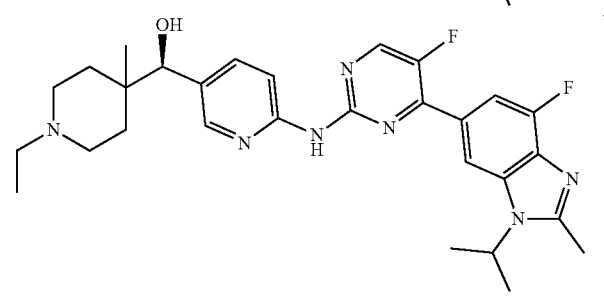
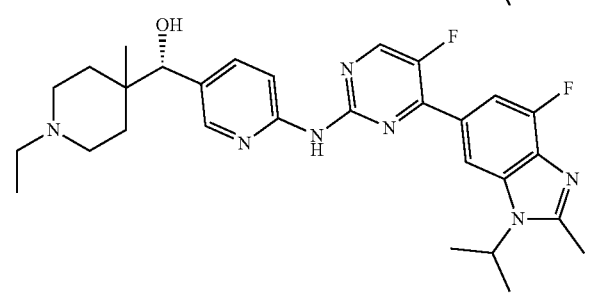
56
-continued
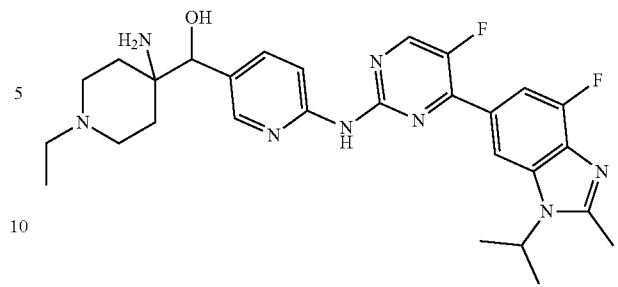
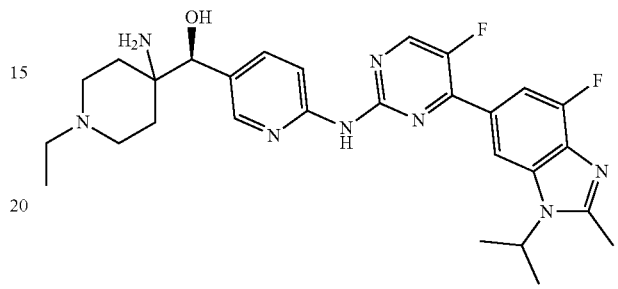
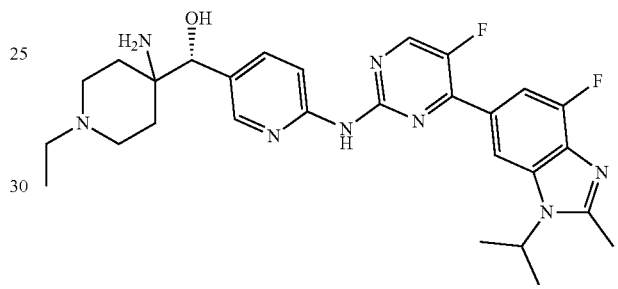
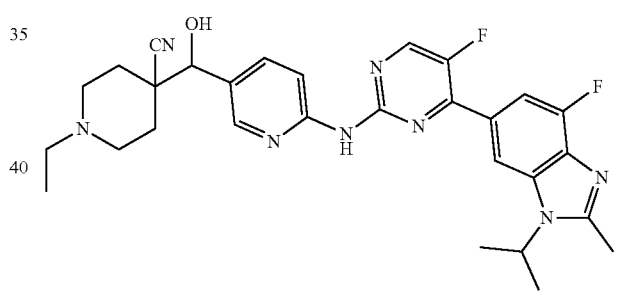
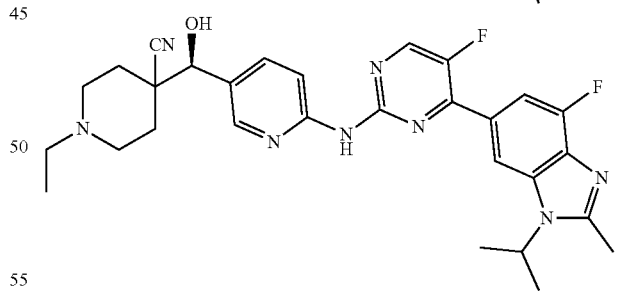
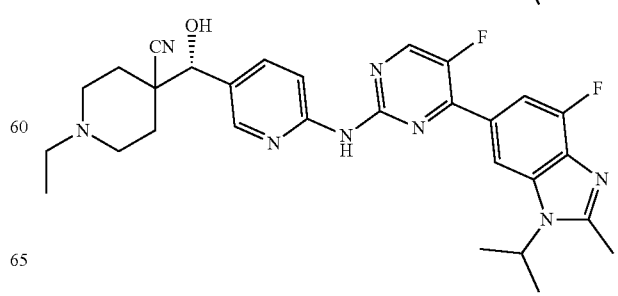

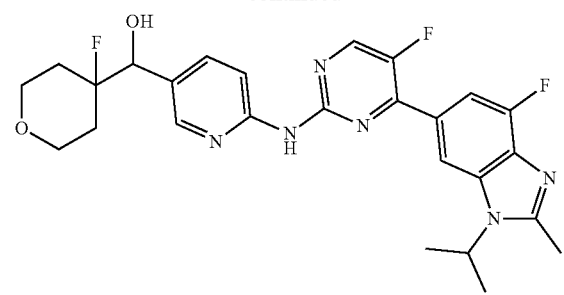
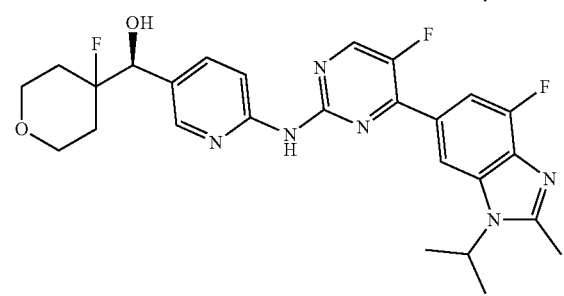
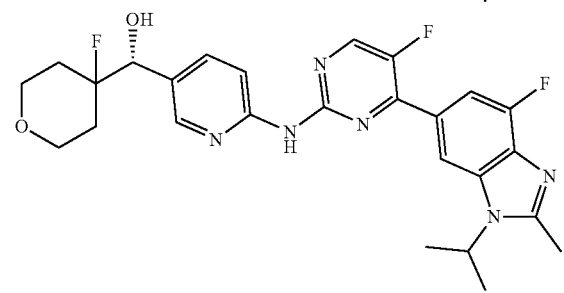
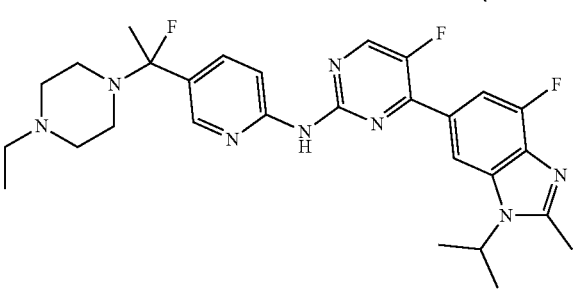
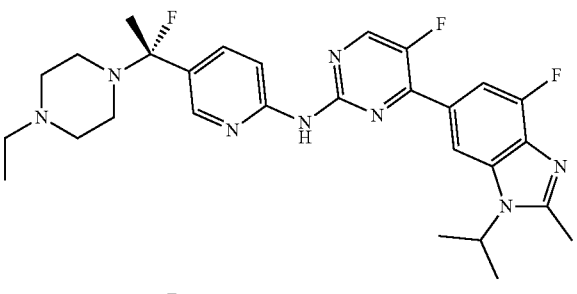
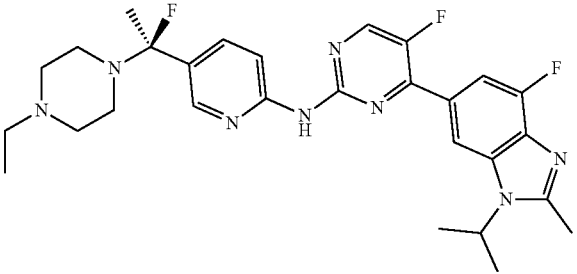
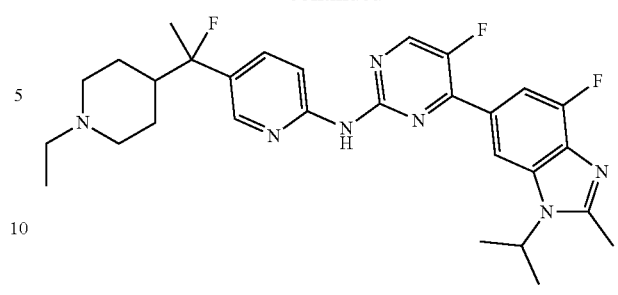
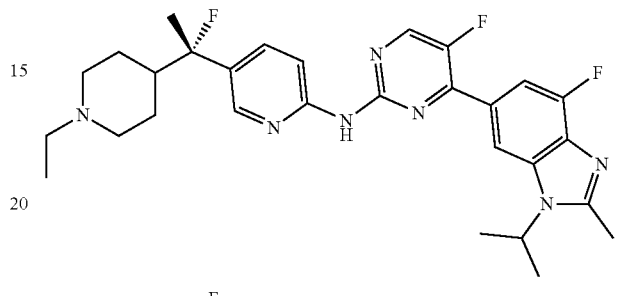
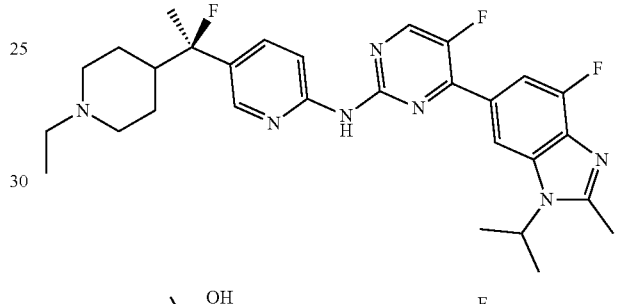
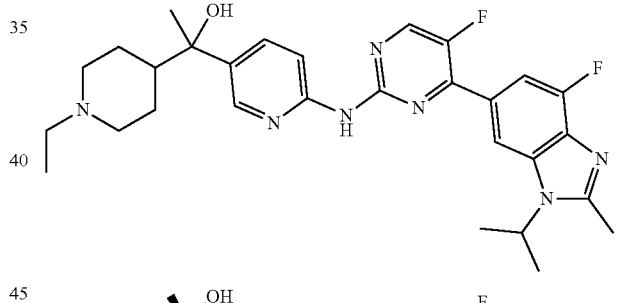
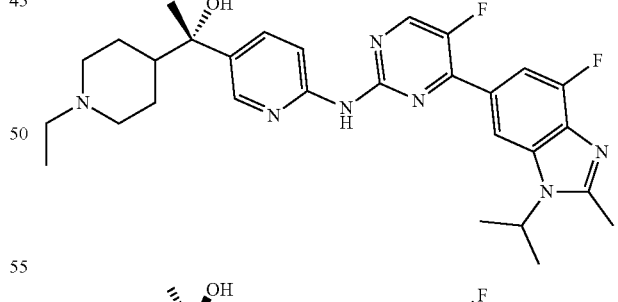
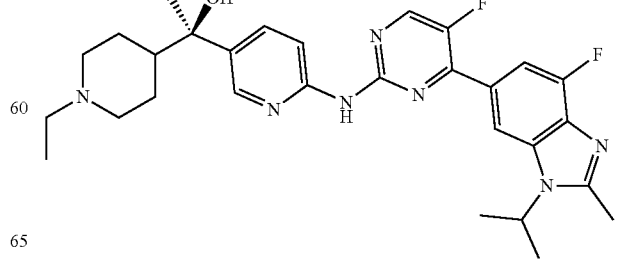

-continued
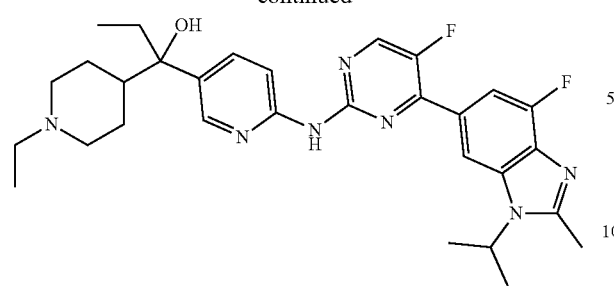 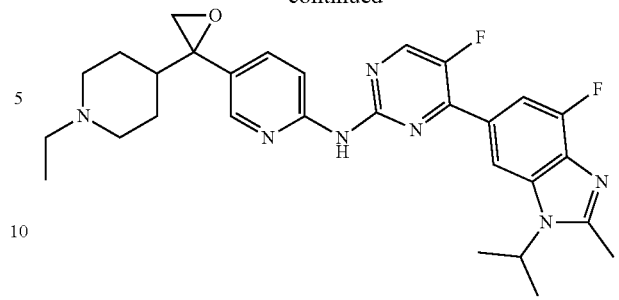
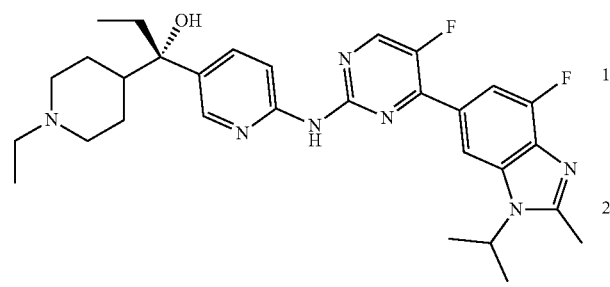 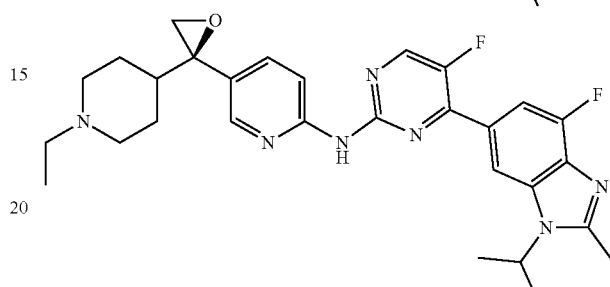
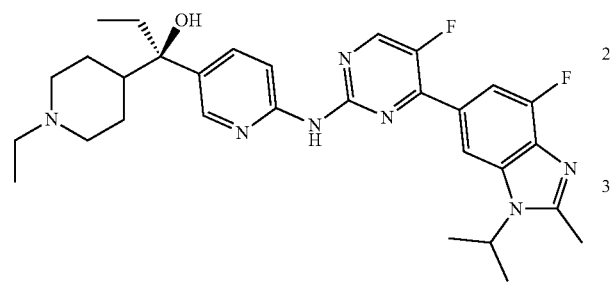 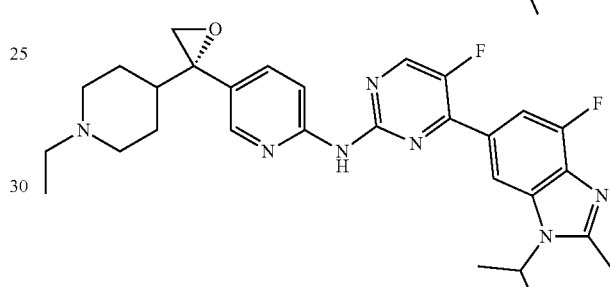
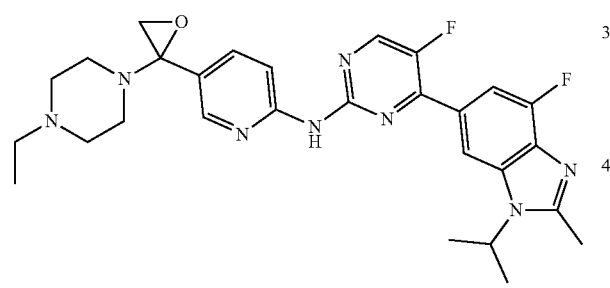 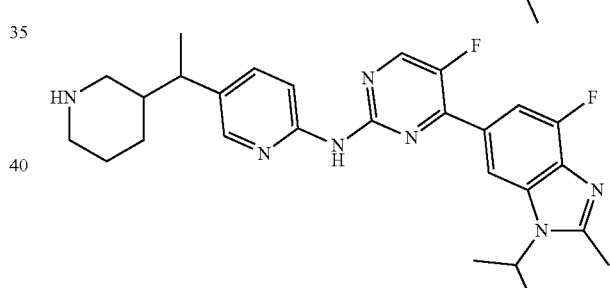
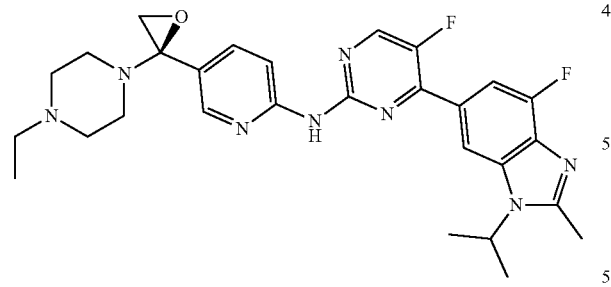 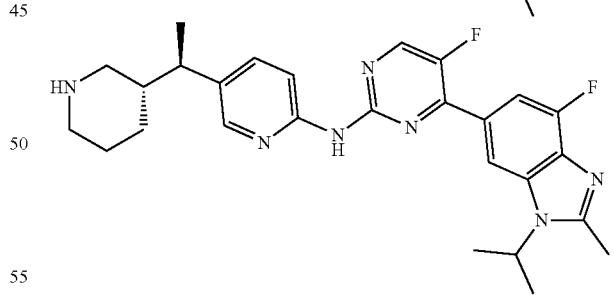
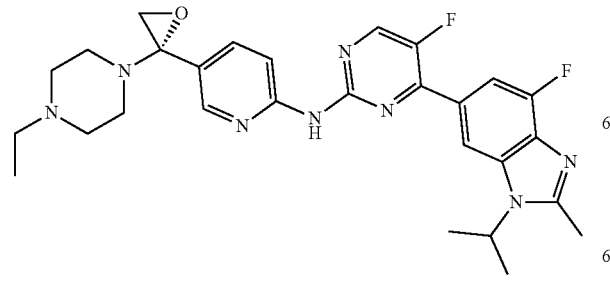 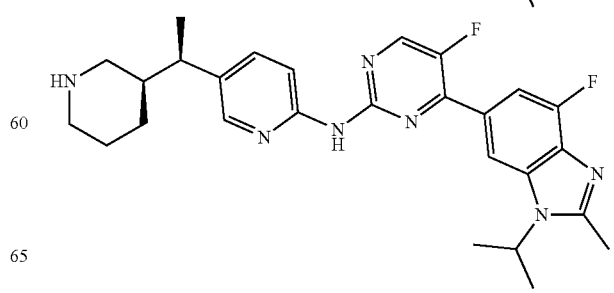

61
-continued
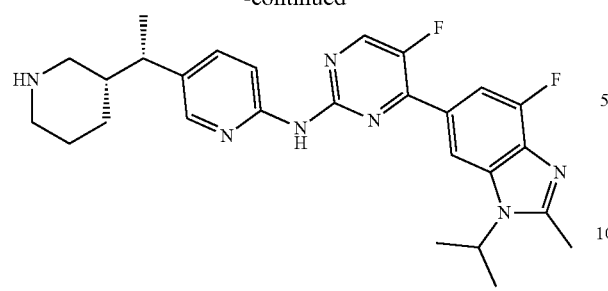
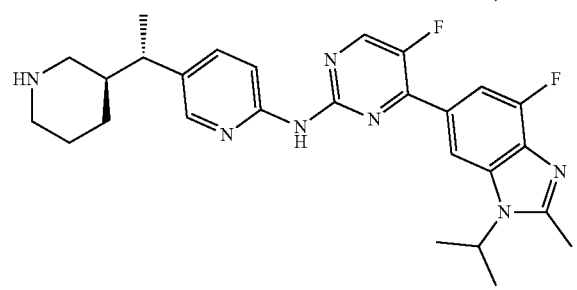
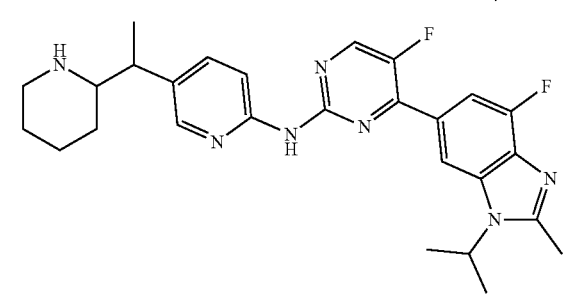
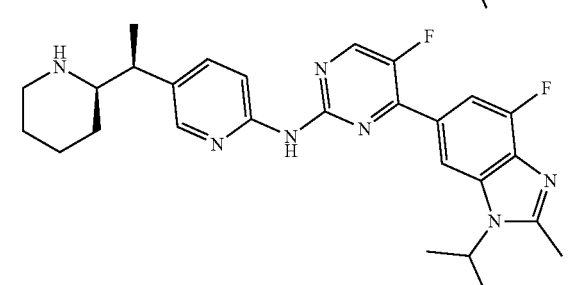
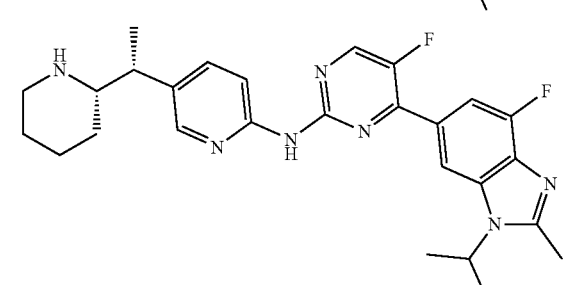
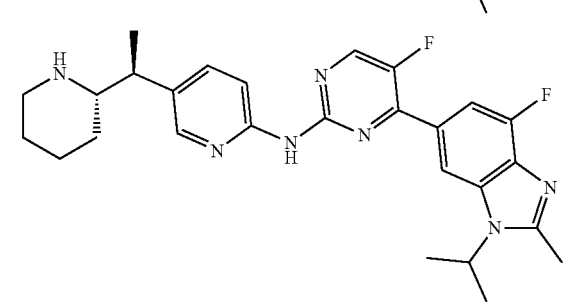
62
-continued
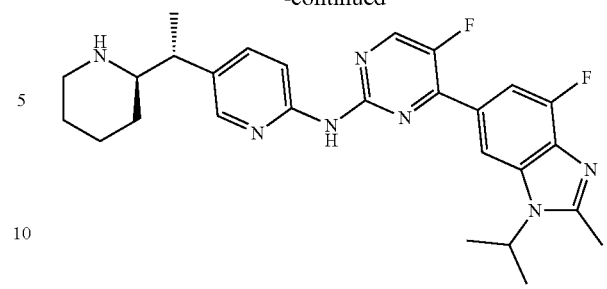
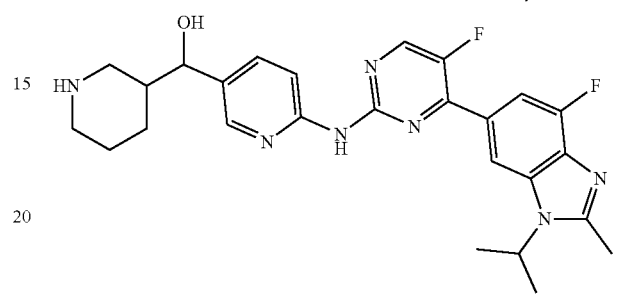
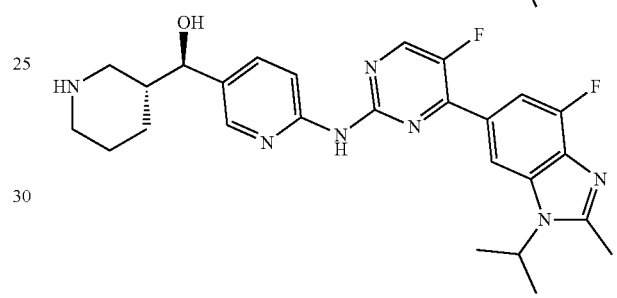
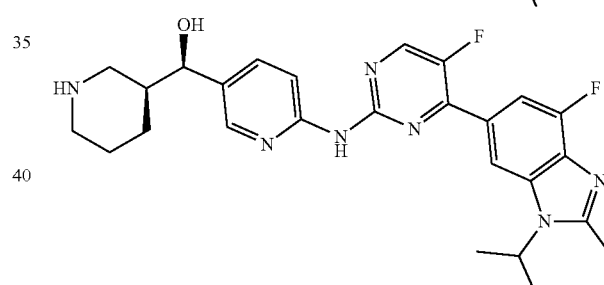
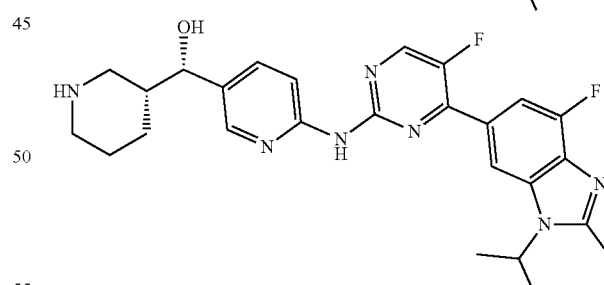
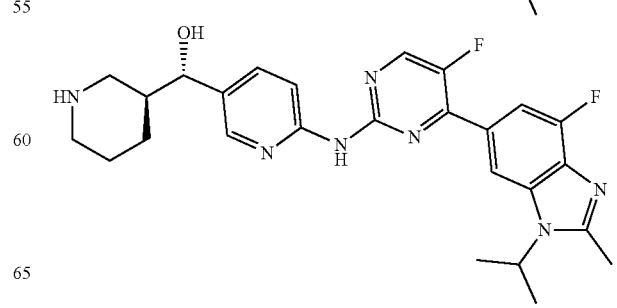

63
-continued
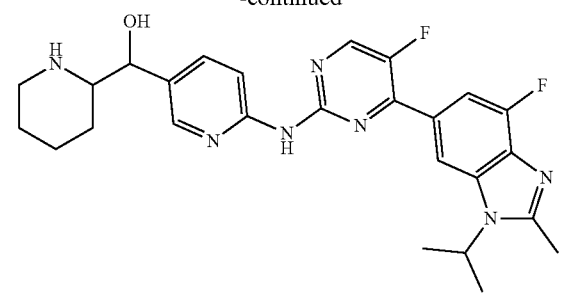
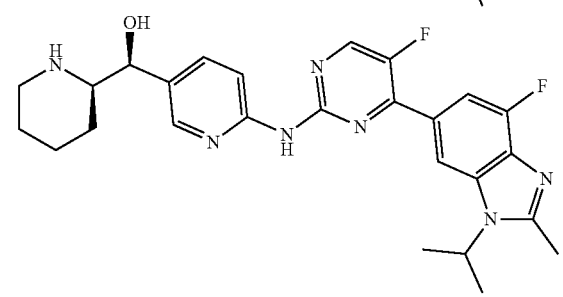
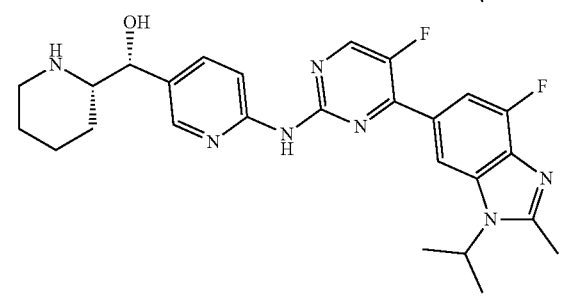
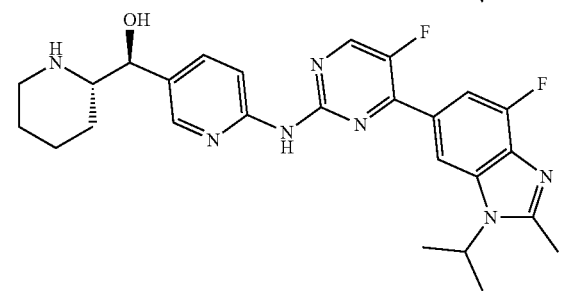
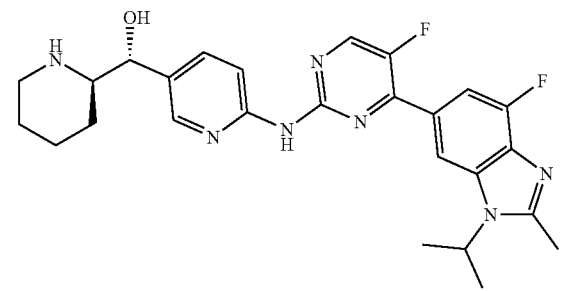
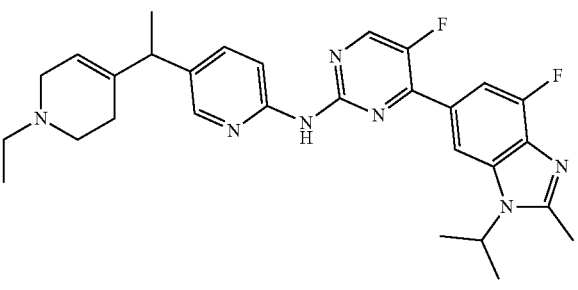
64
-continued
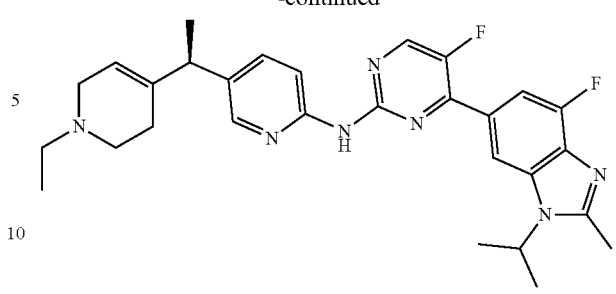
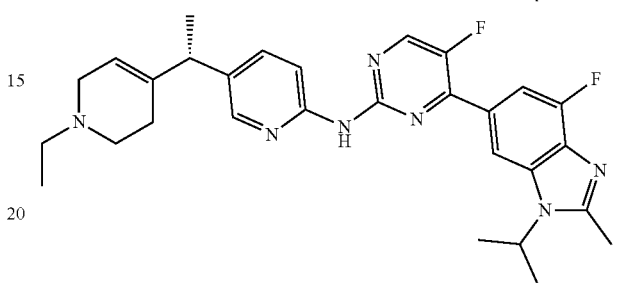
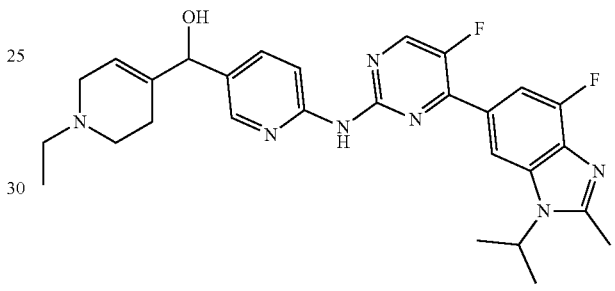
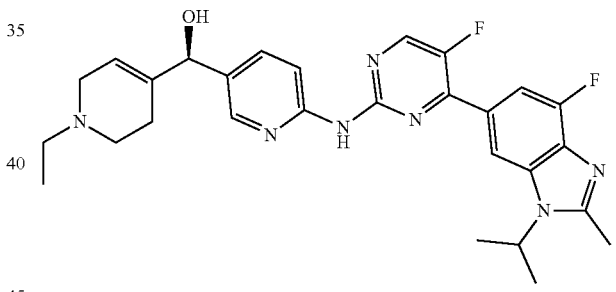
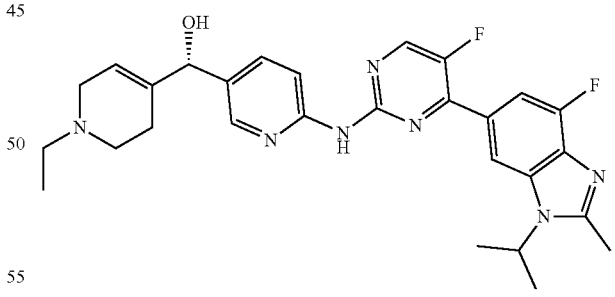
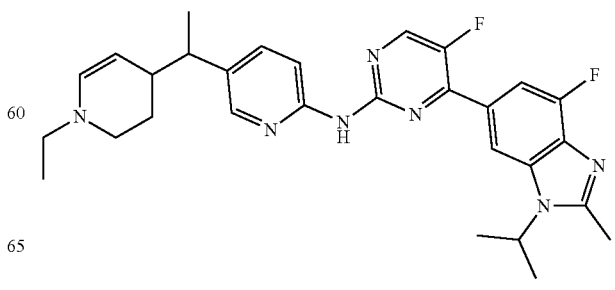

65
-continued
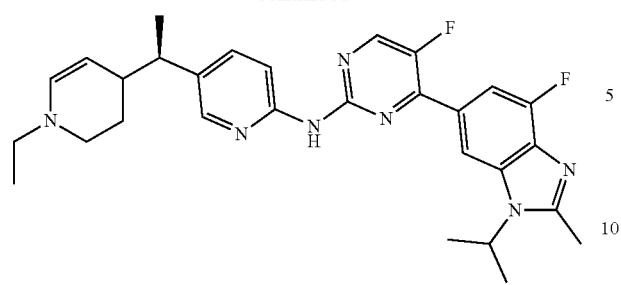
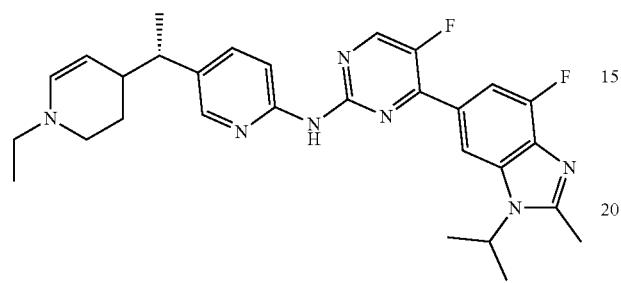
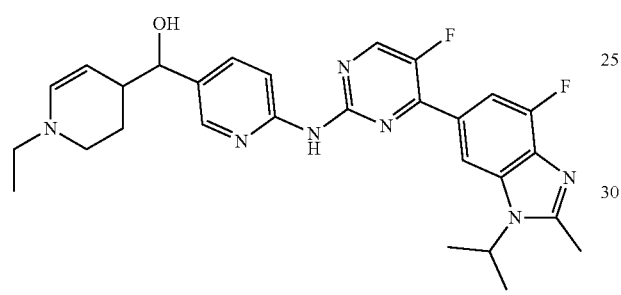
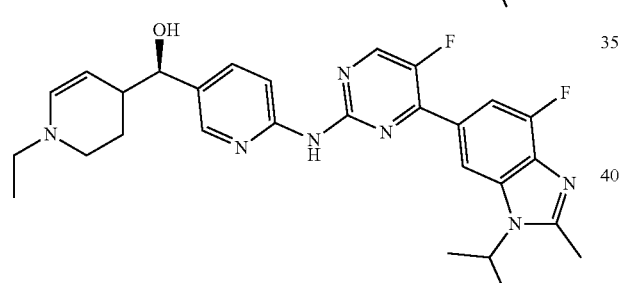
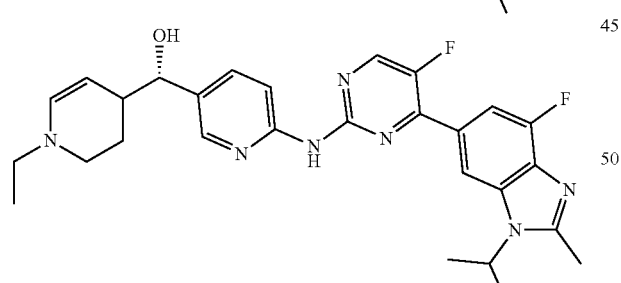
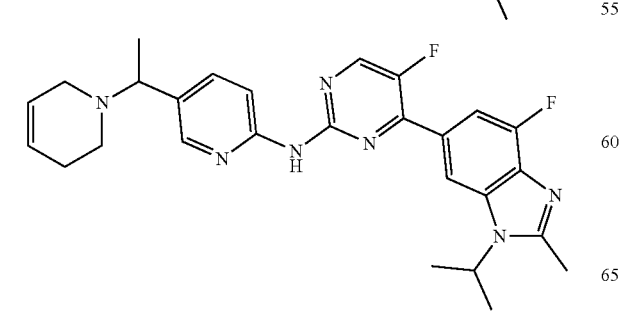
66
-continued
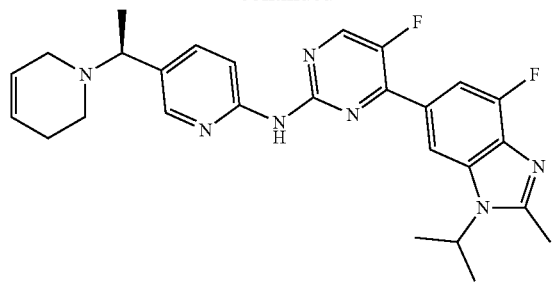
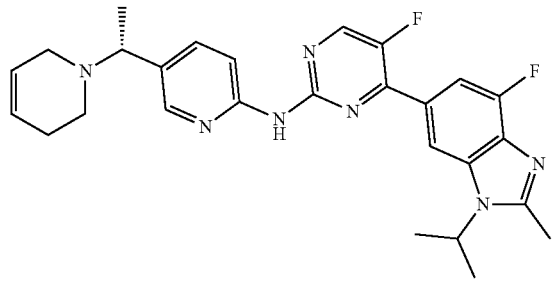
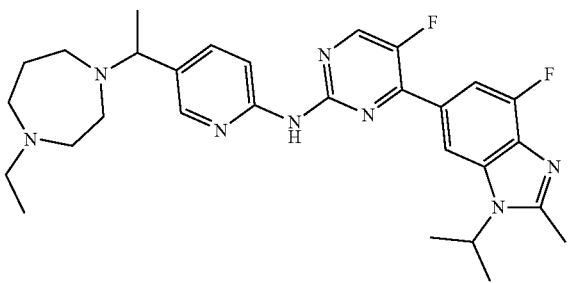
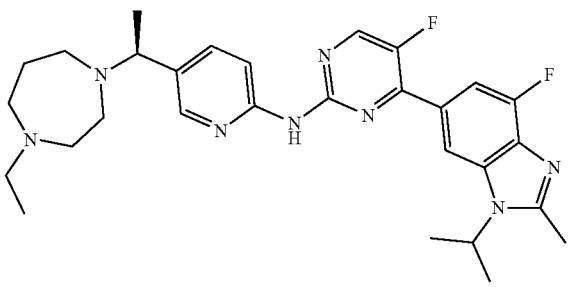
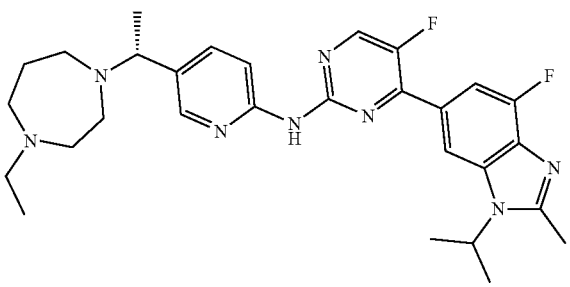
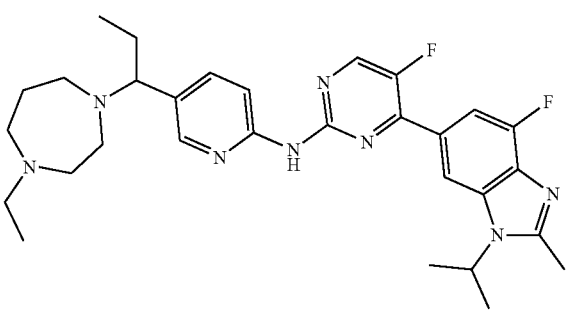

67
-continued
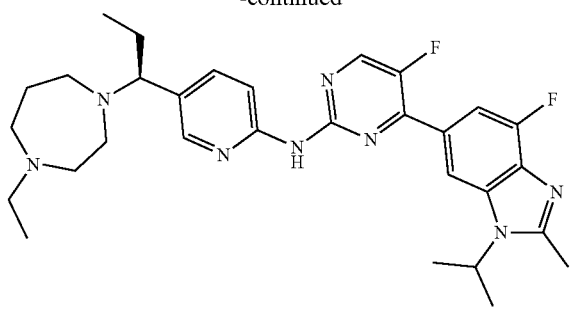
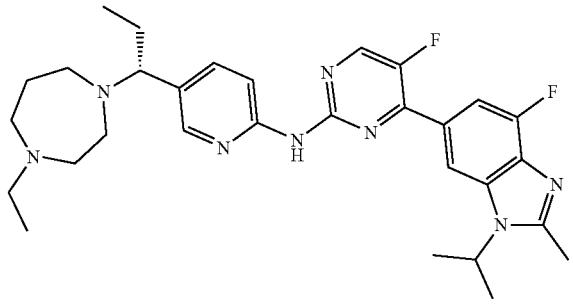
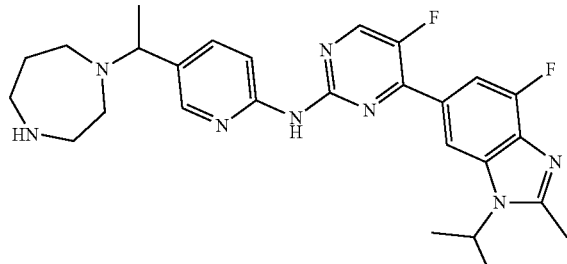
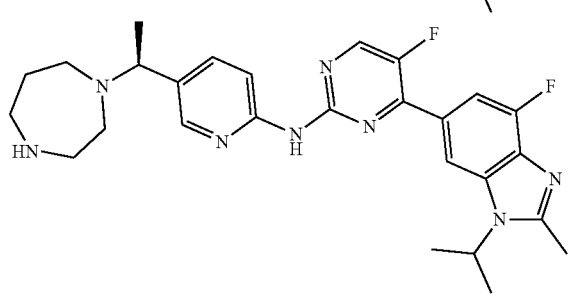
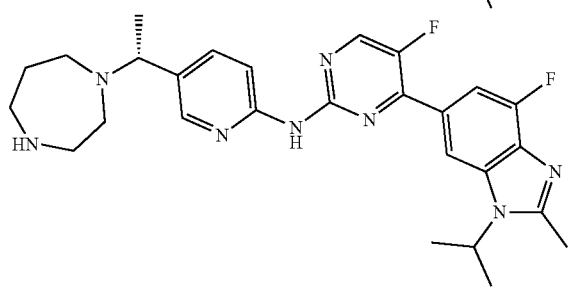
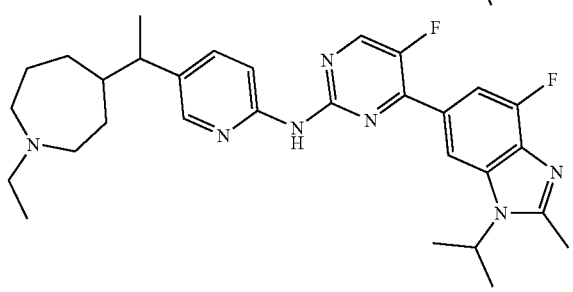
68
-continued
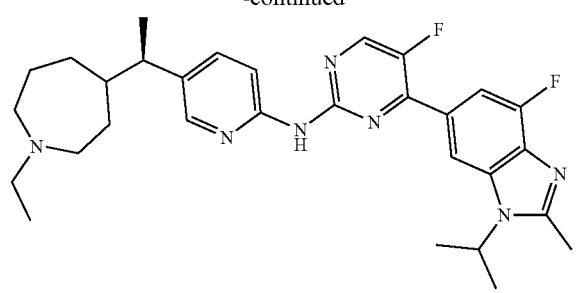
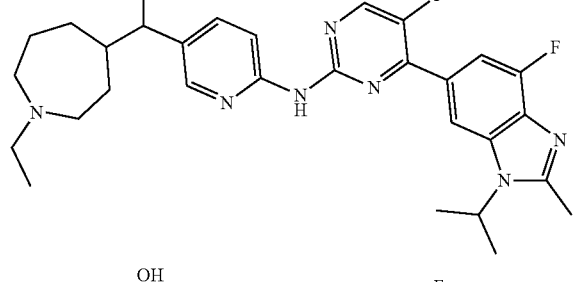
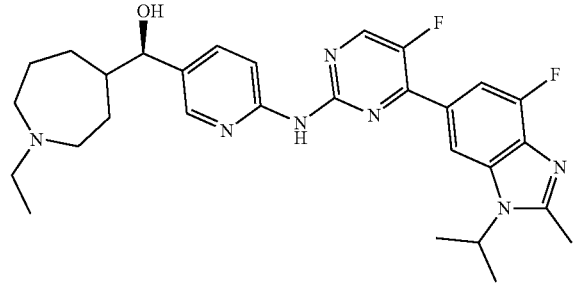
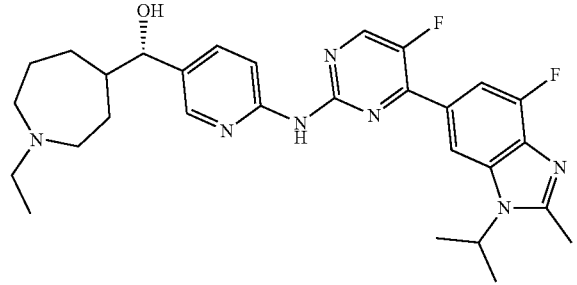
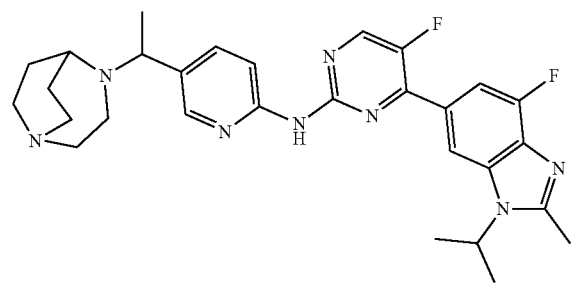

69
-continued
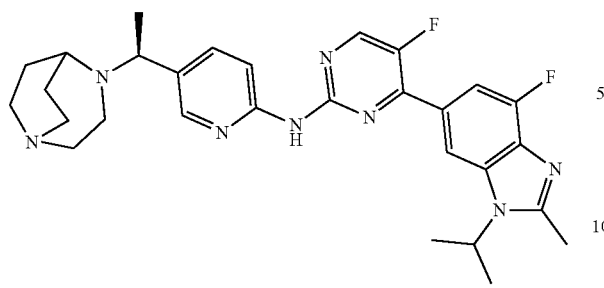
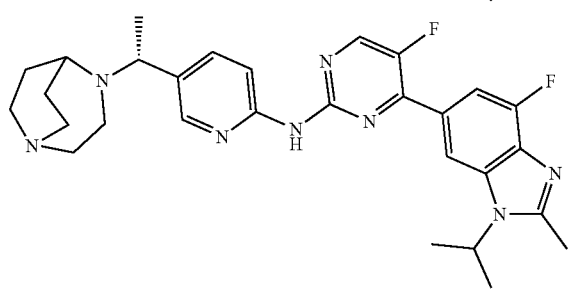
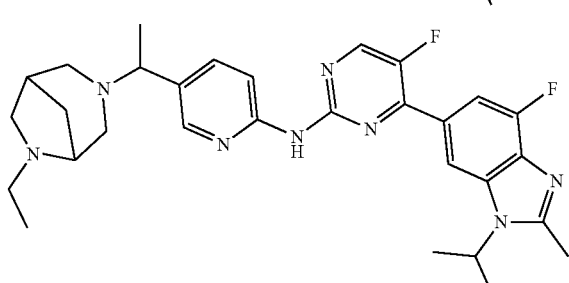
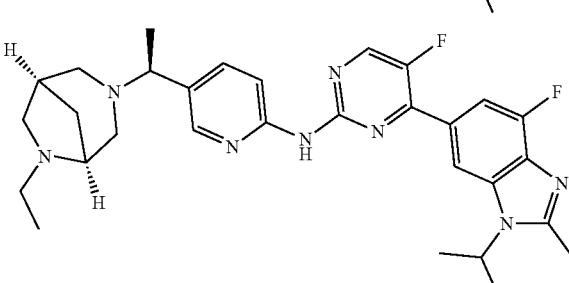
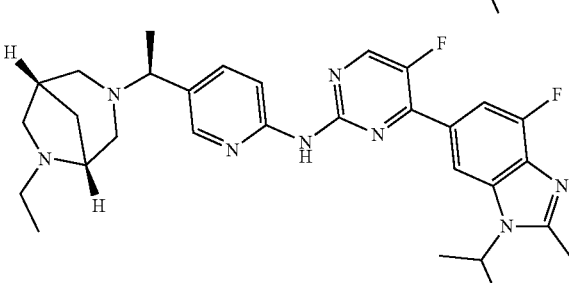
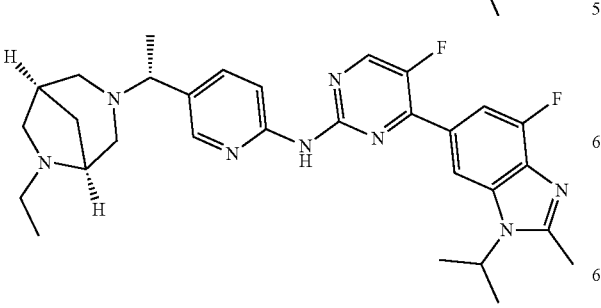
70
-continued
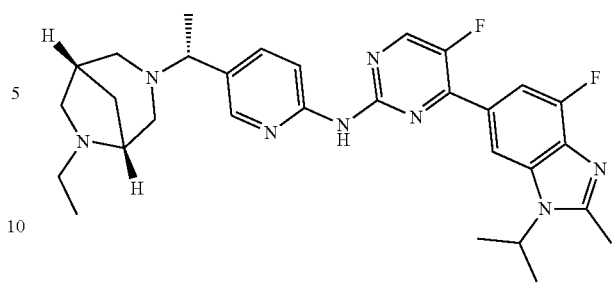
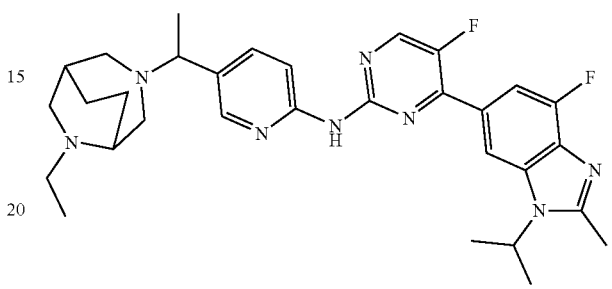
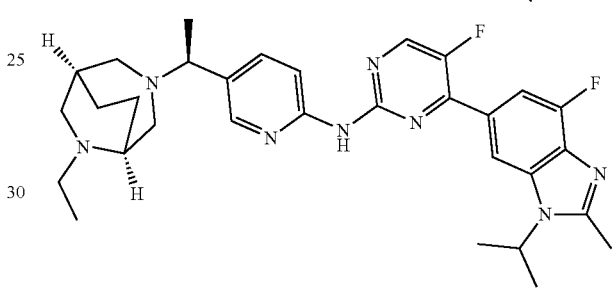
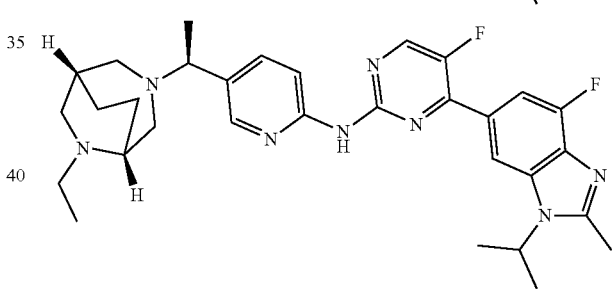
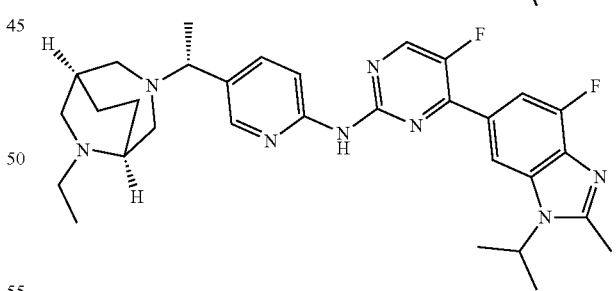
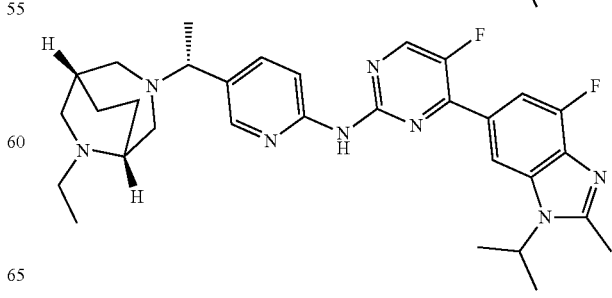

71
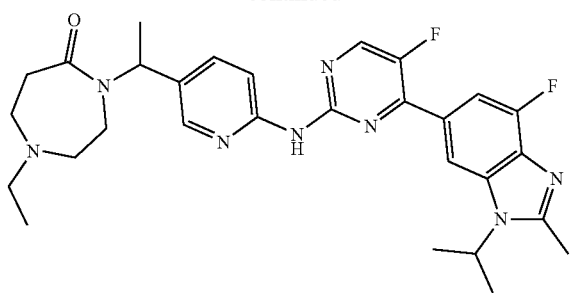
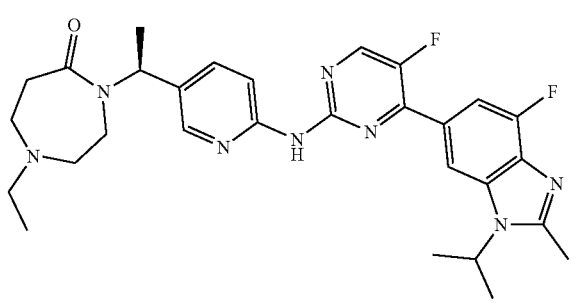
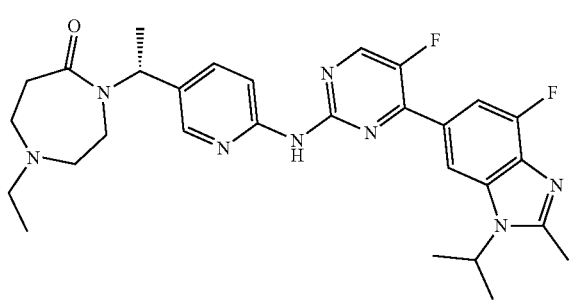
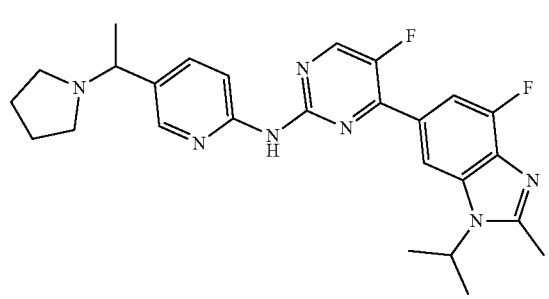
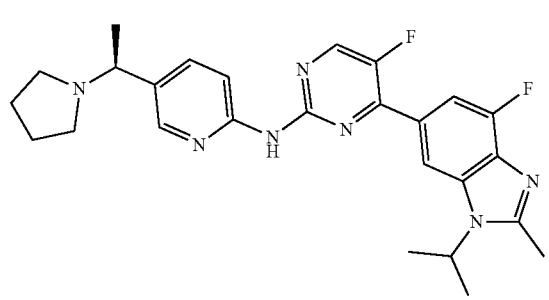
72
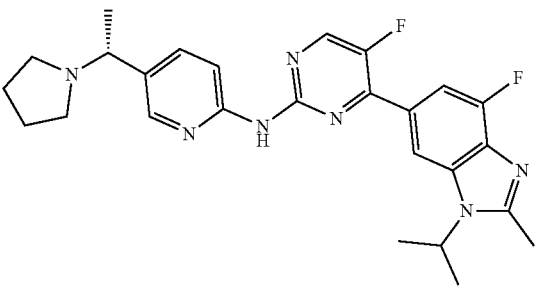
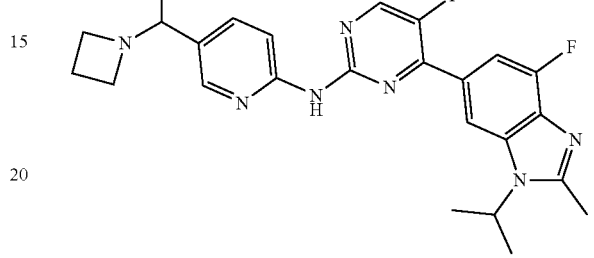
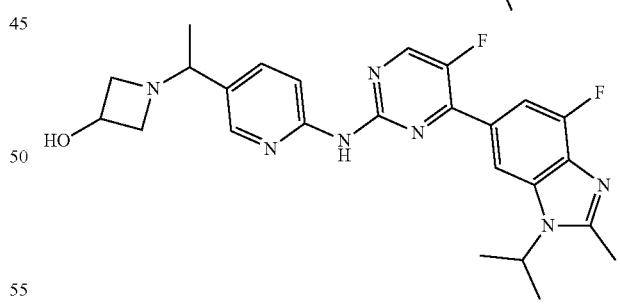
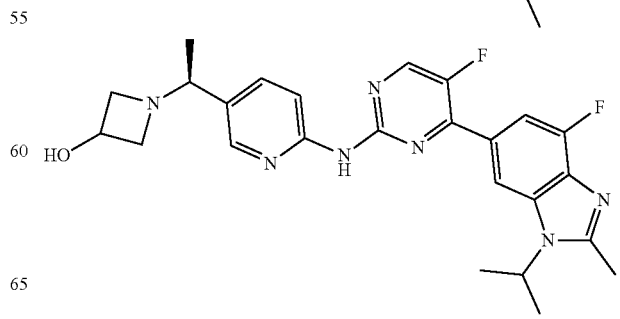

73
-continued
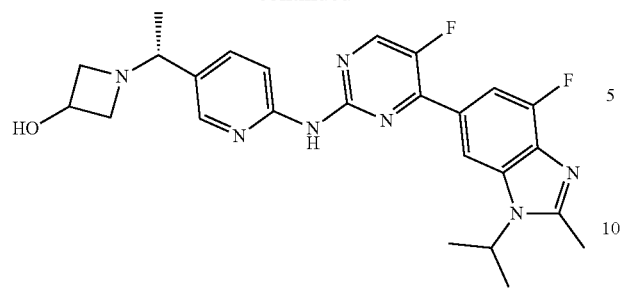
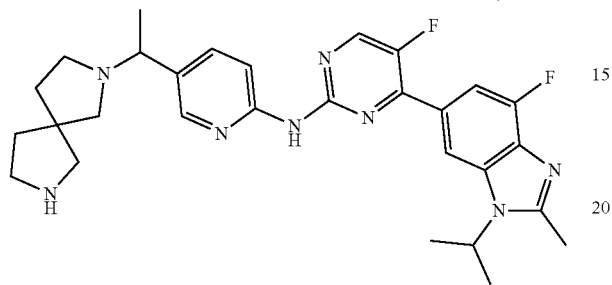
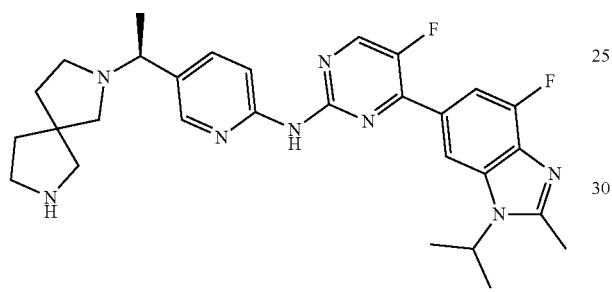
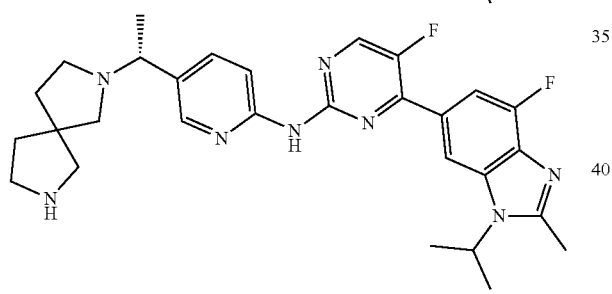
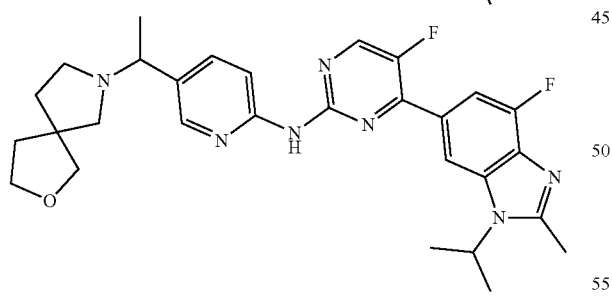
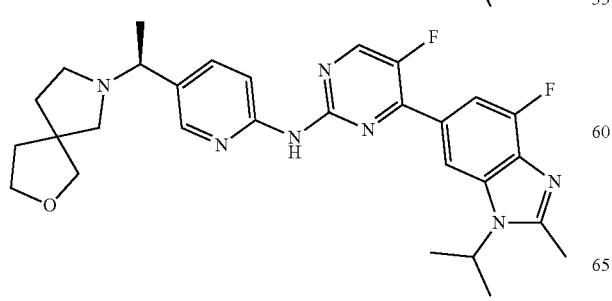
74
-continued
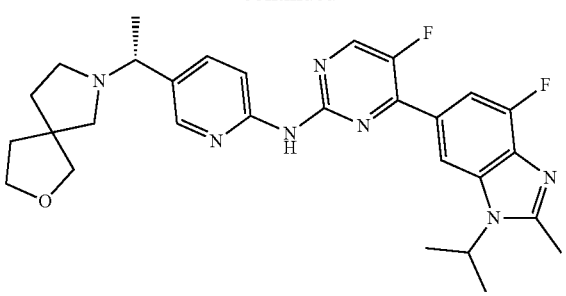
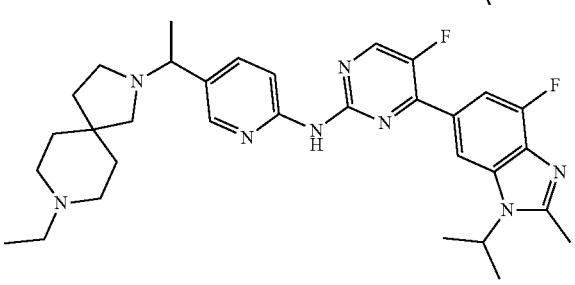
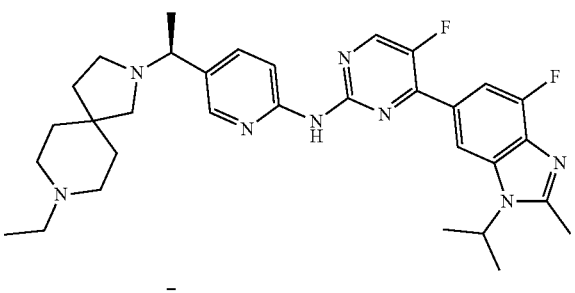
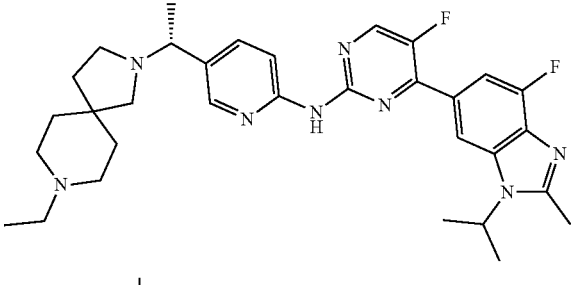
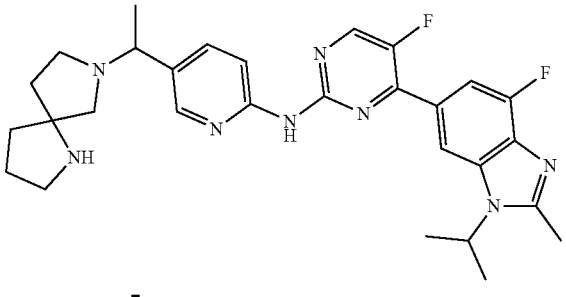
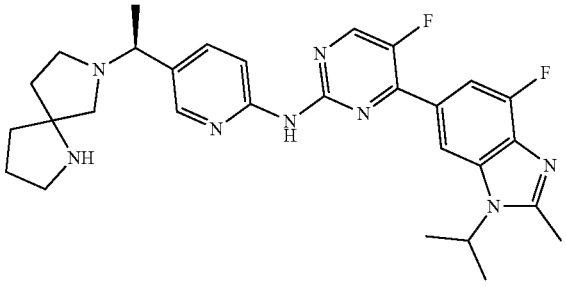

75
-continued
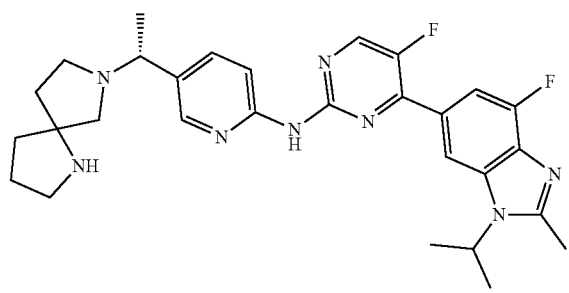
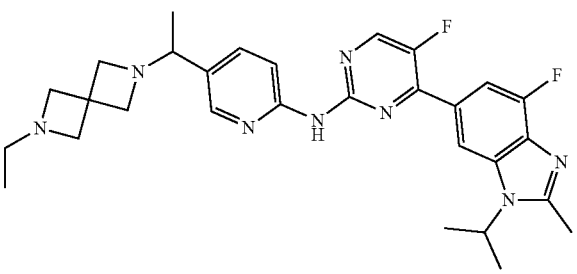
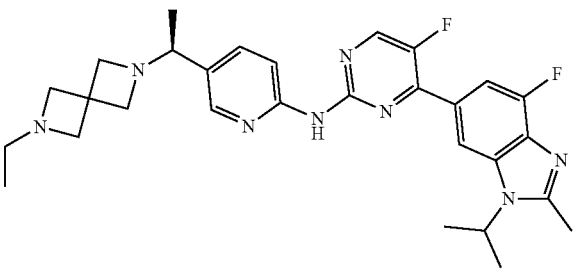
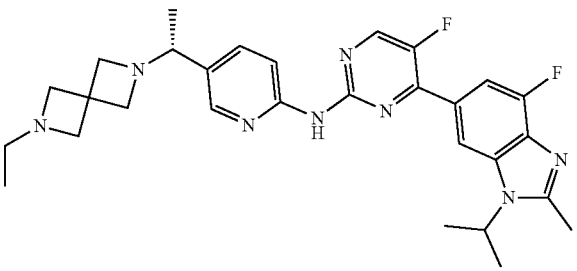
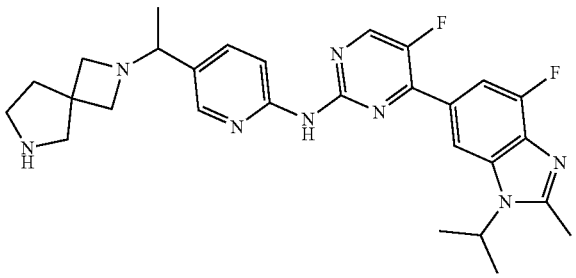
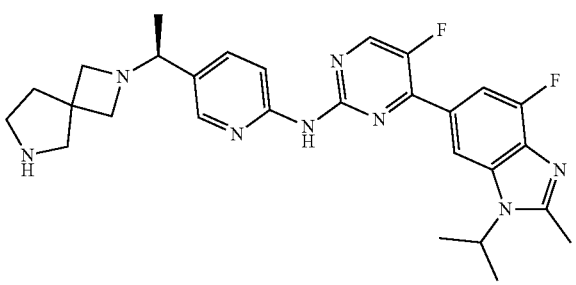
76
-continued
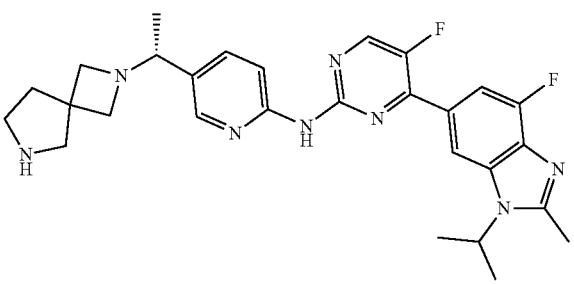
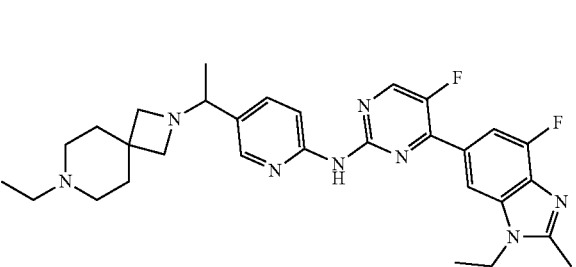
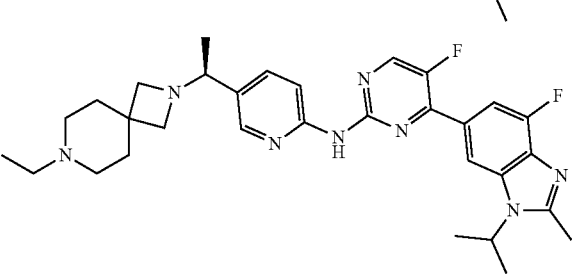
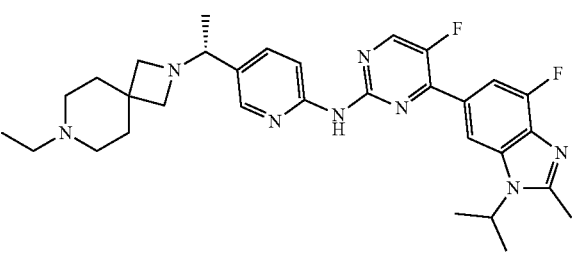
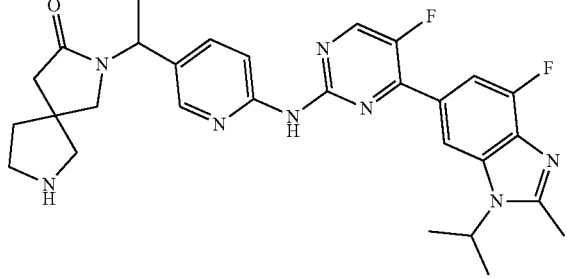
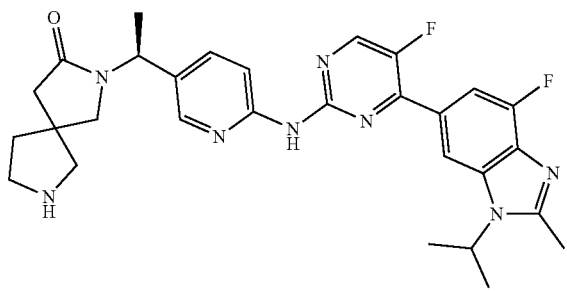

77
-continued
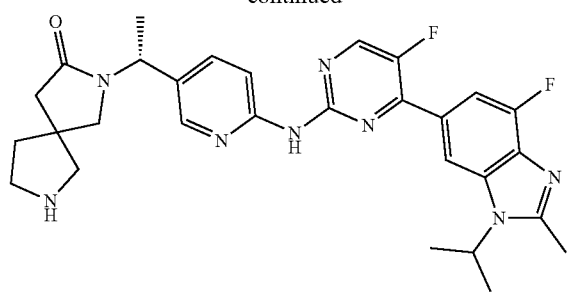
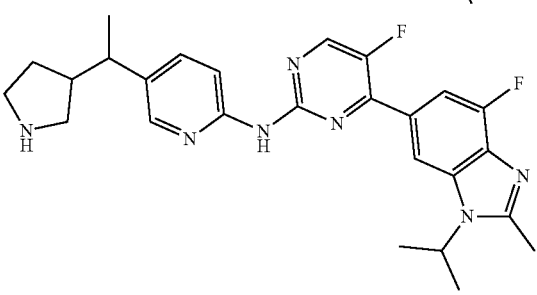
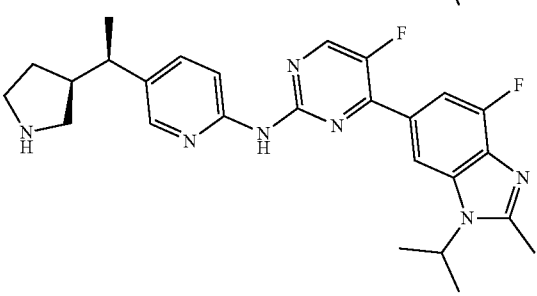
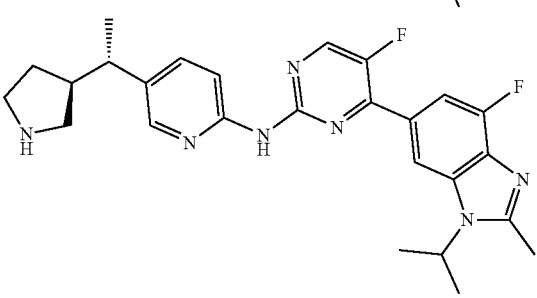
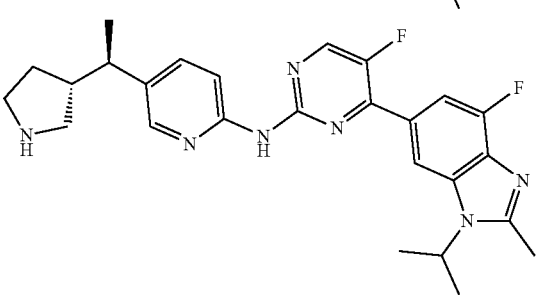
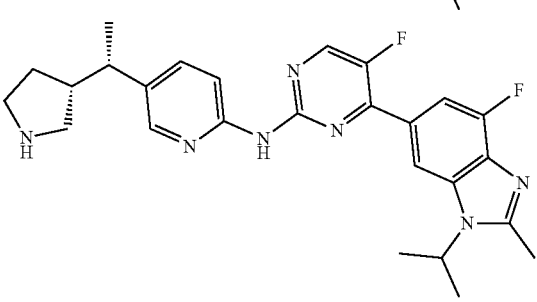
78
-continued
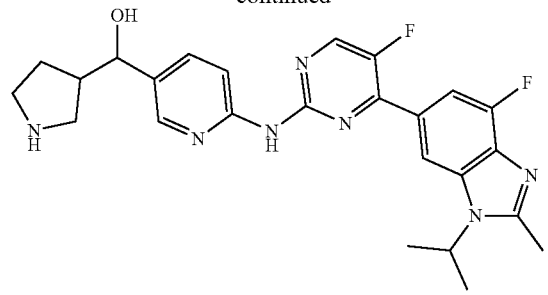
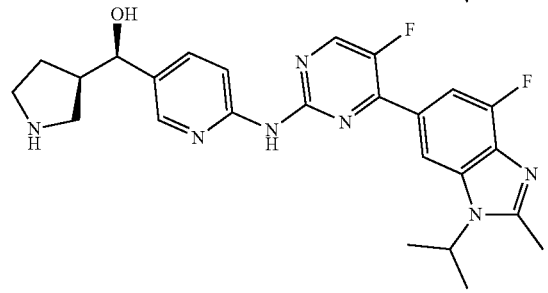
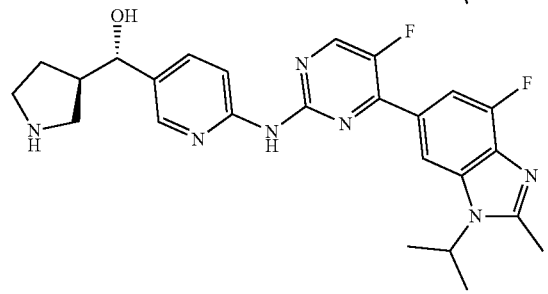
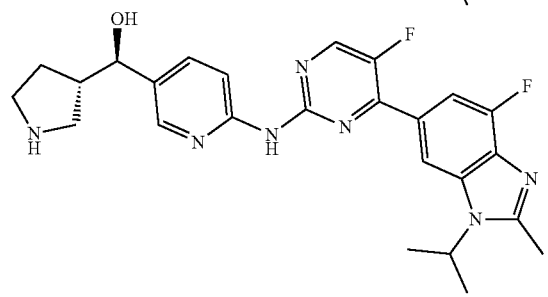
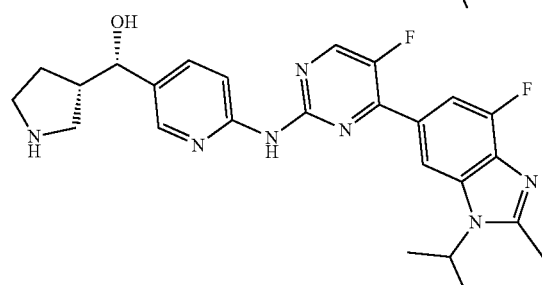
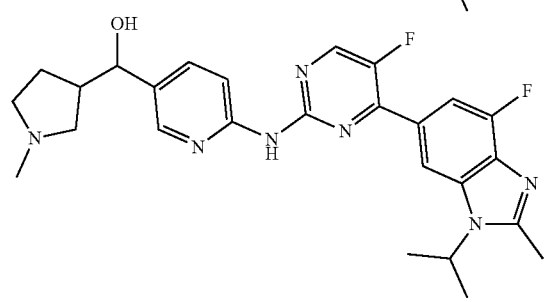

| 79 -continued | 80 -continued |
|---|---|
| 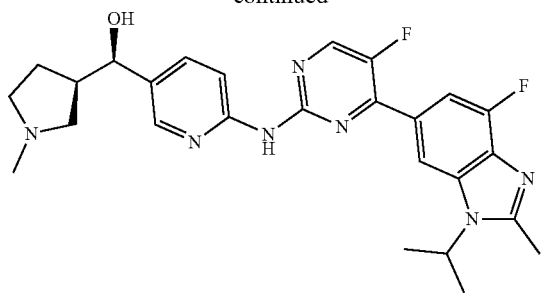 | 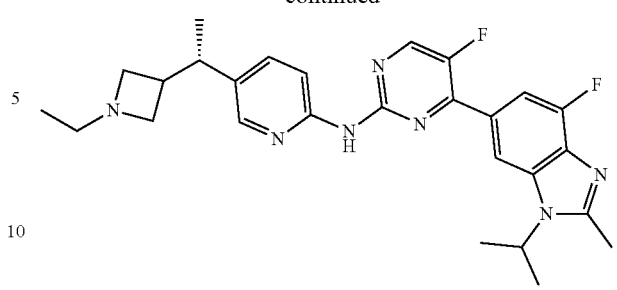 |
| 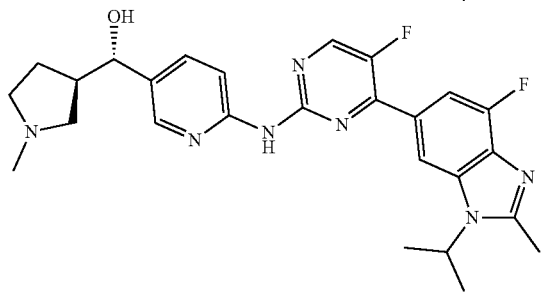 | 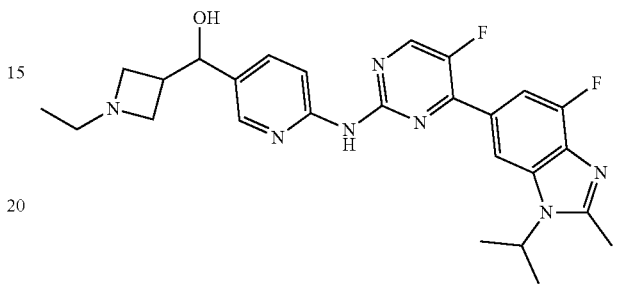 |
| 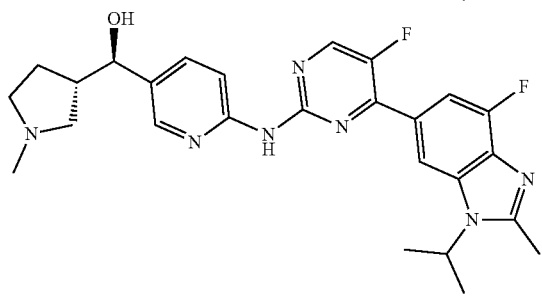 | 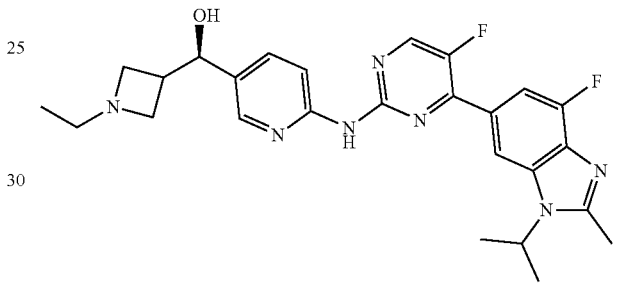 |
| 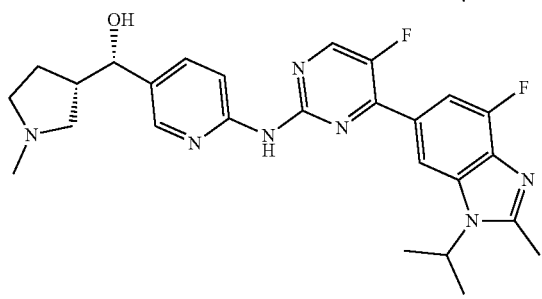 | 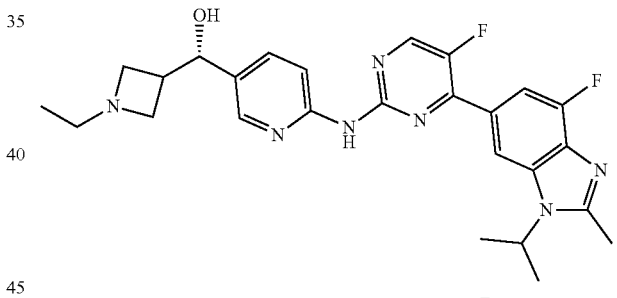 |
| 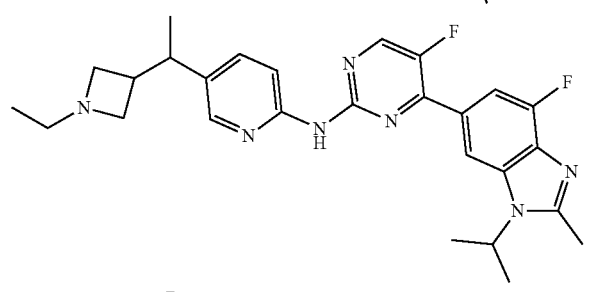 | 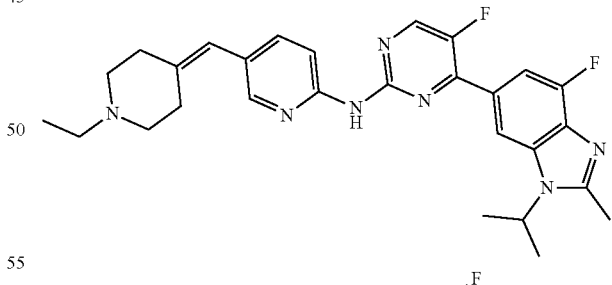 |
| 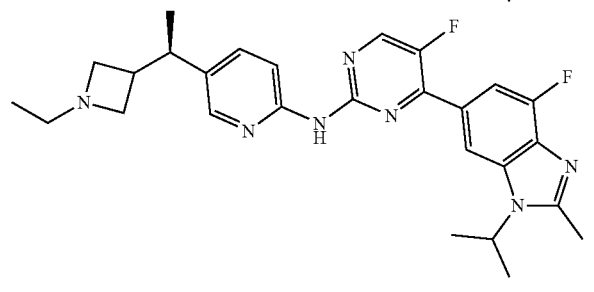 | 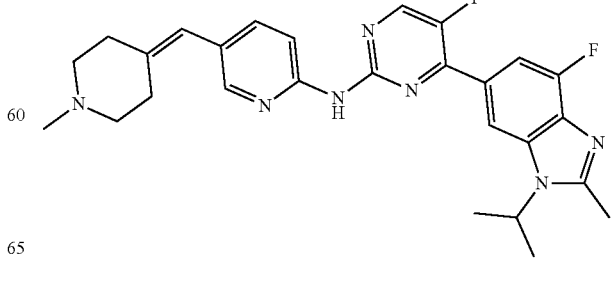 |

81
-continued
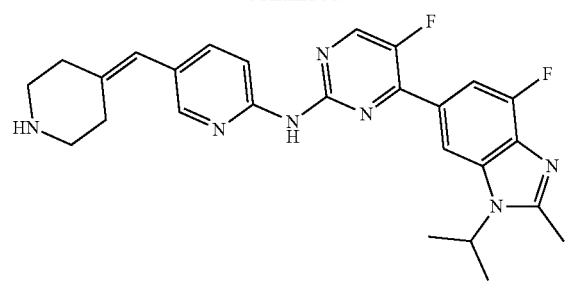
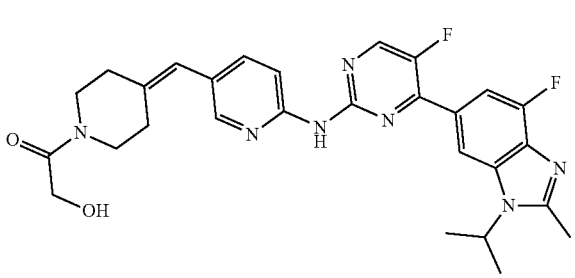
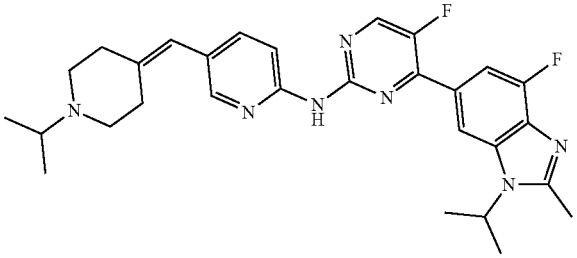
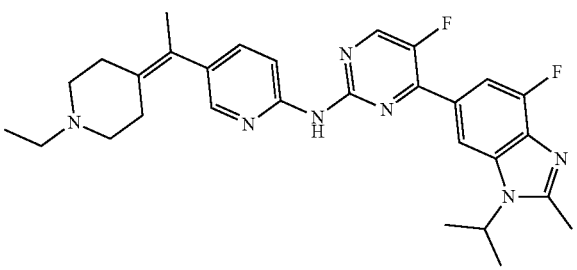
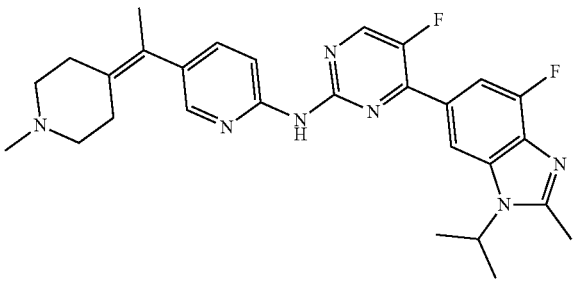
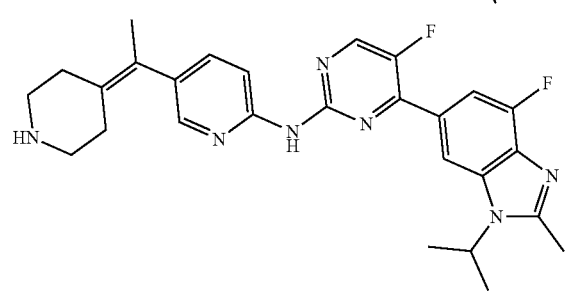
82
-continued
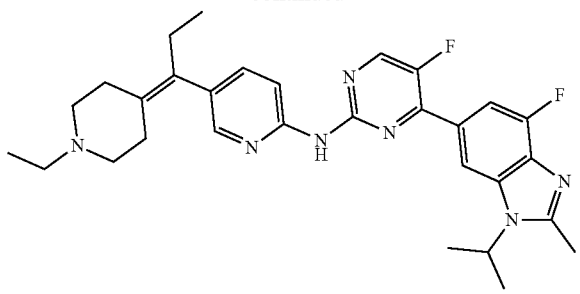
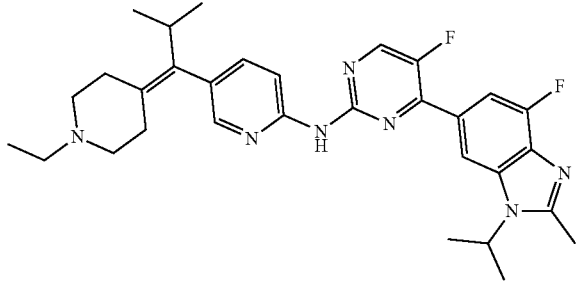
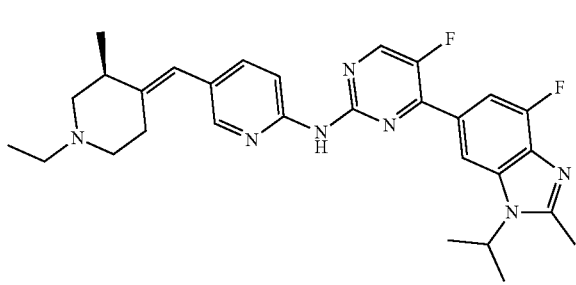
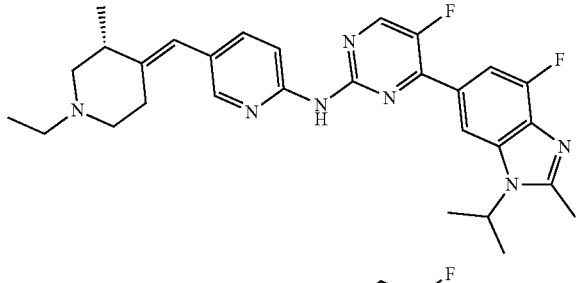
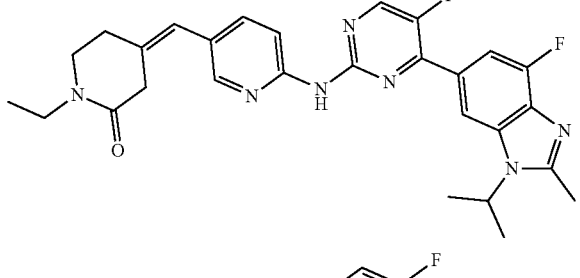
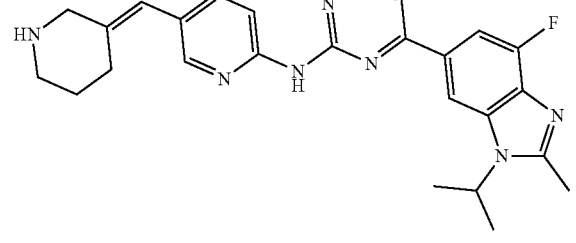

83
-continued
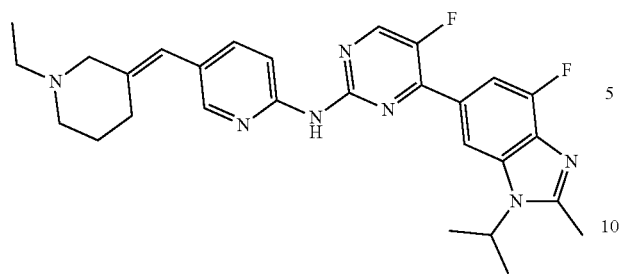
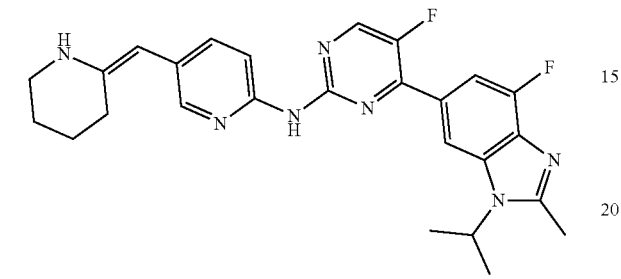
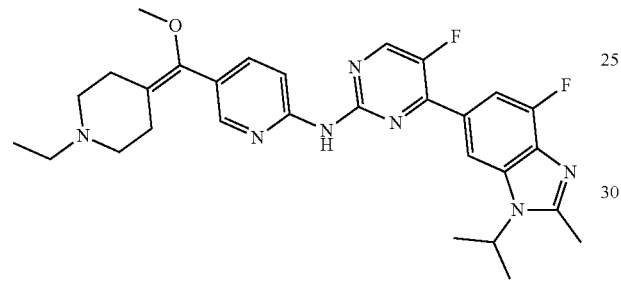
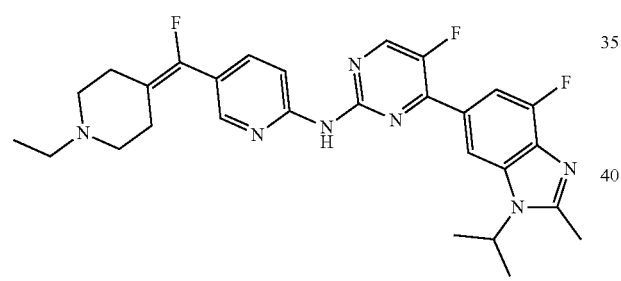
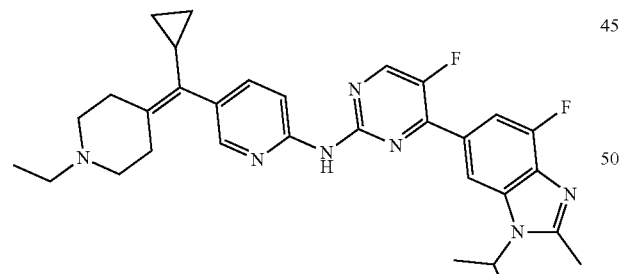
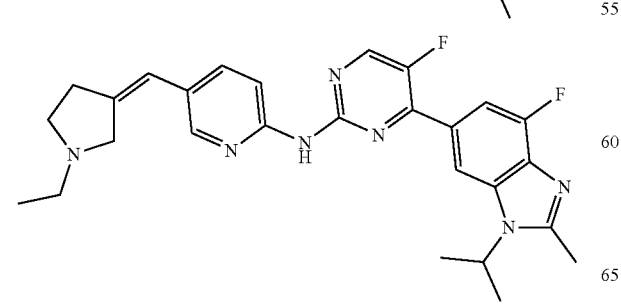
84
-continued
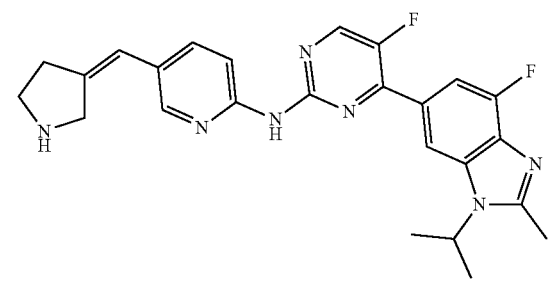
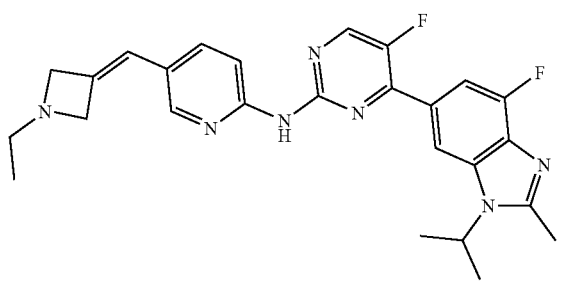
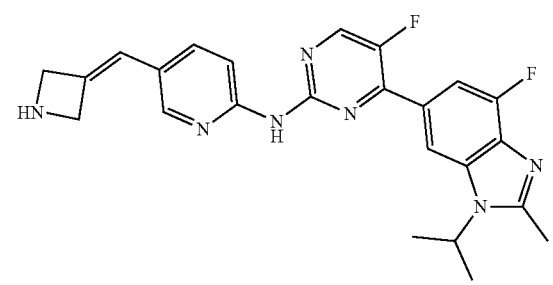
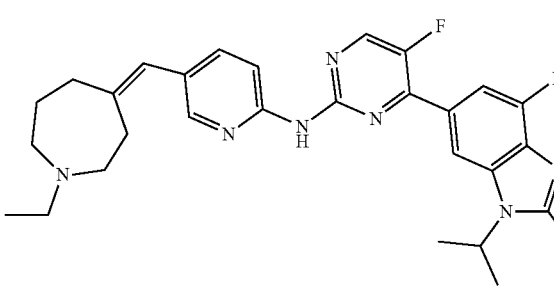
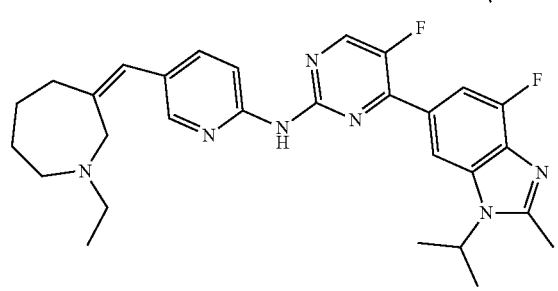
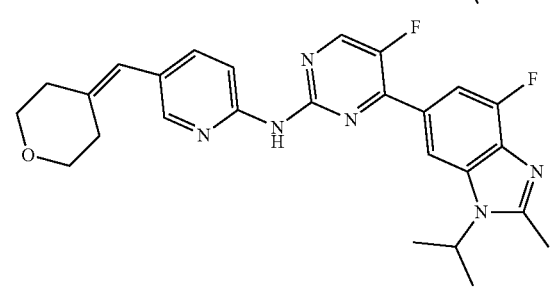

85
-continued
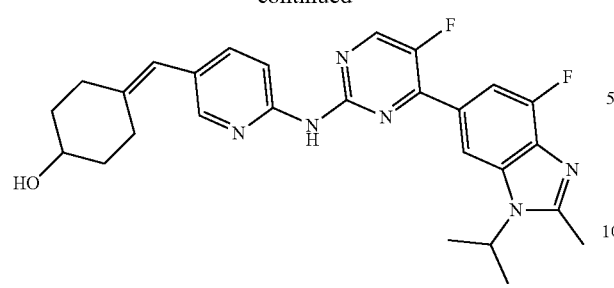
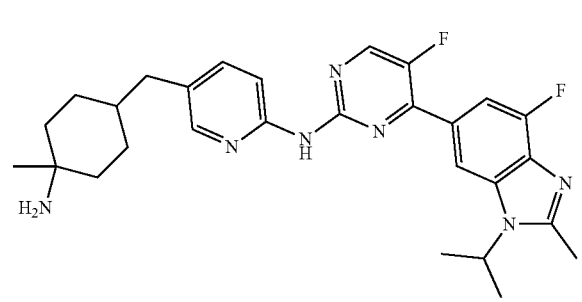
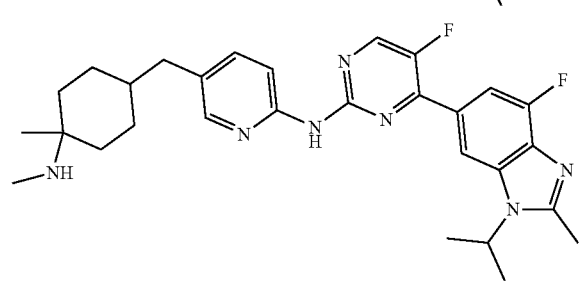
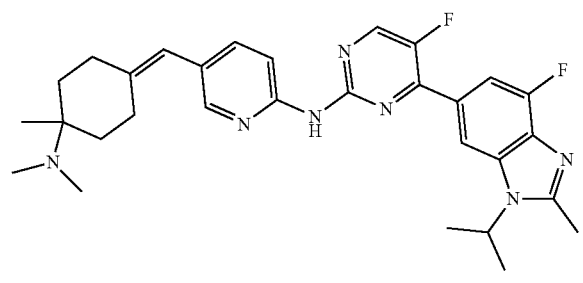
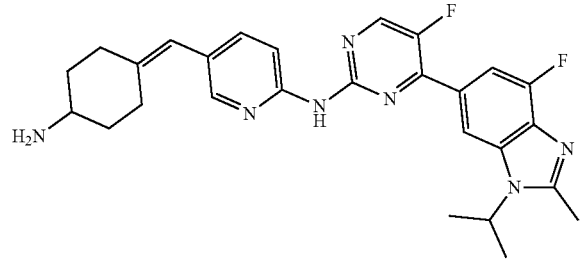
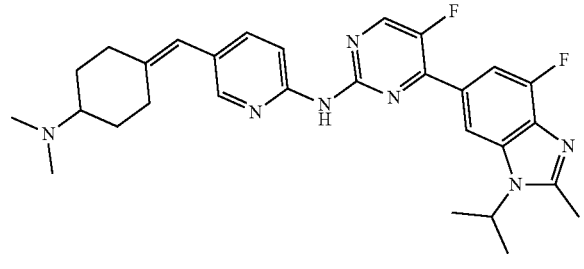
86
-continued
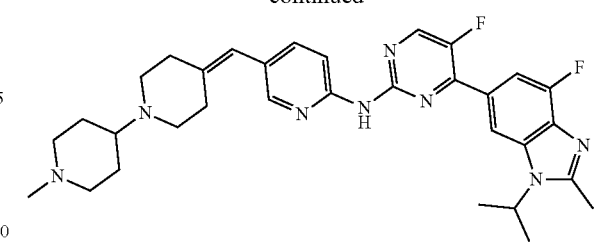
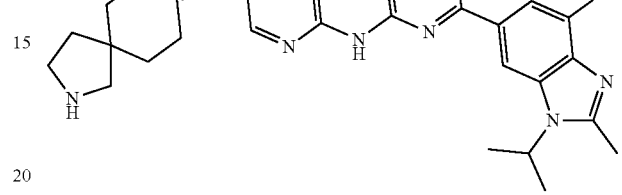
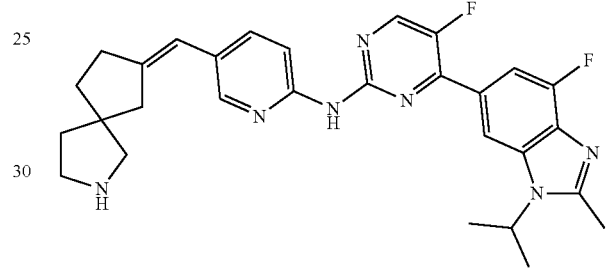
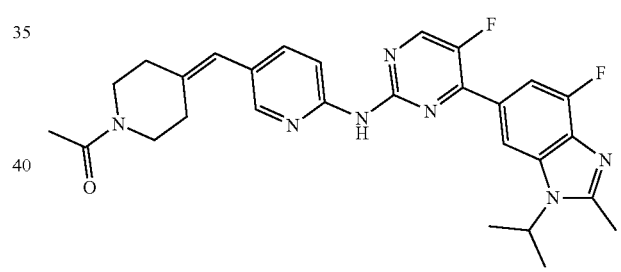
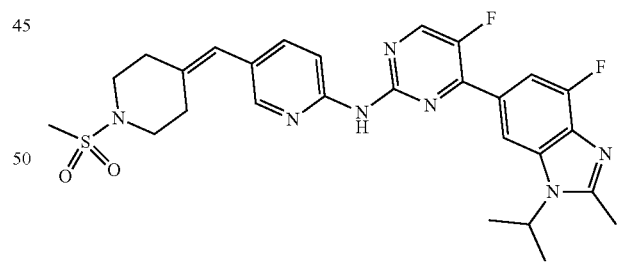
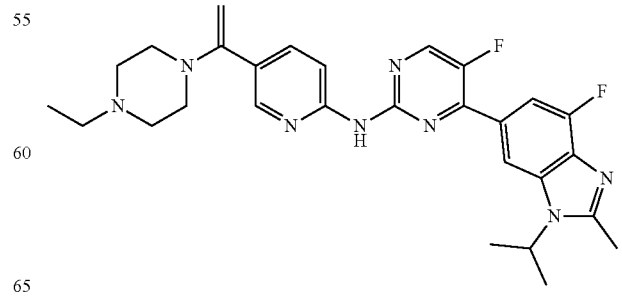

87
-continued
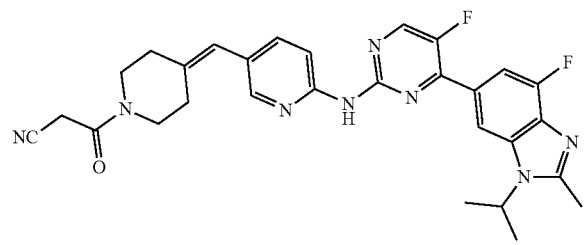
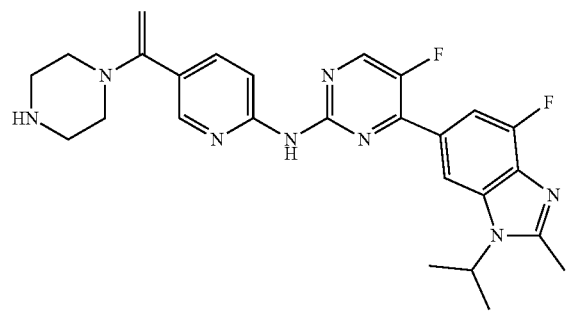
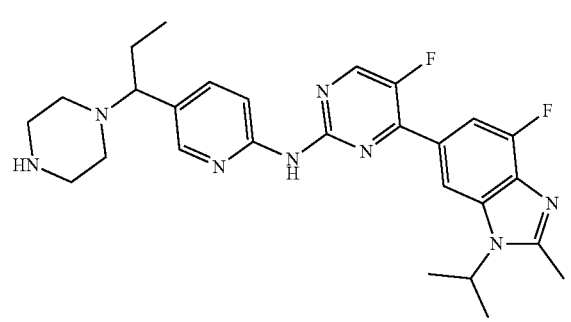
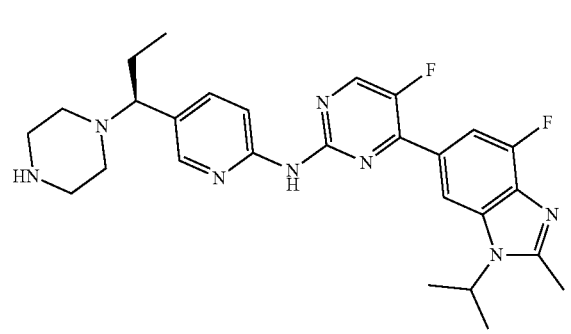
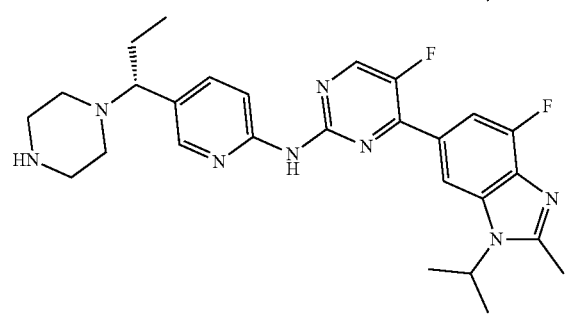
88
-continued
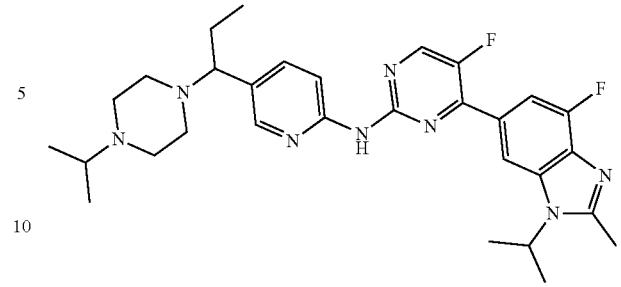
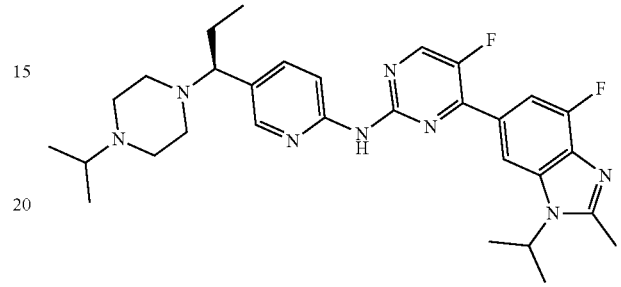
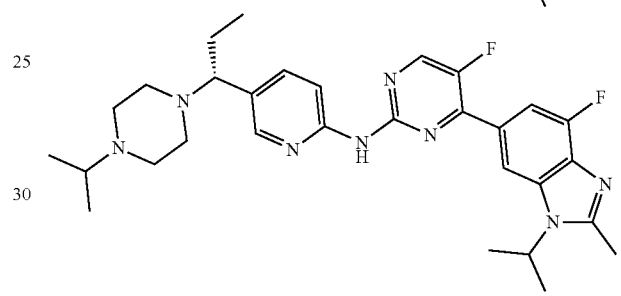
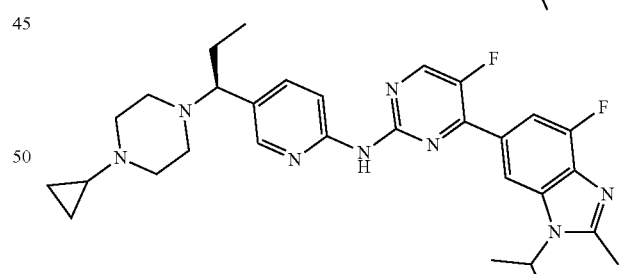
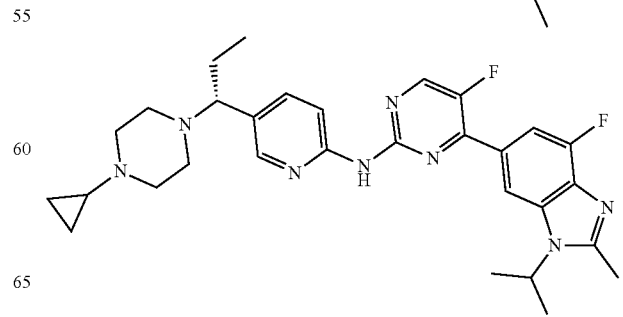

89
-continued
90
-continued
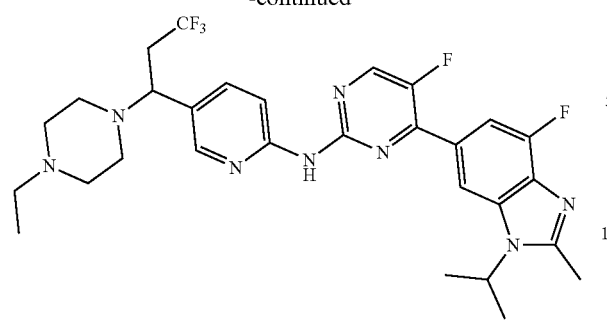
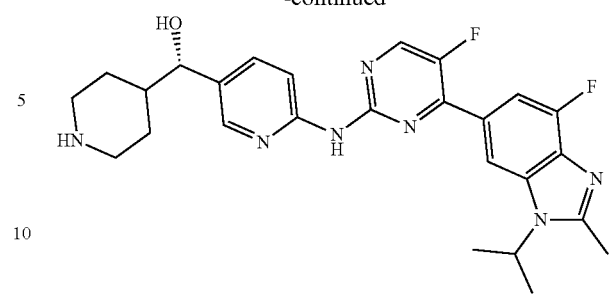

91
-continued
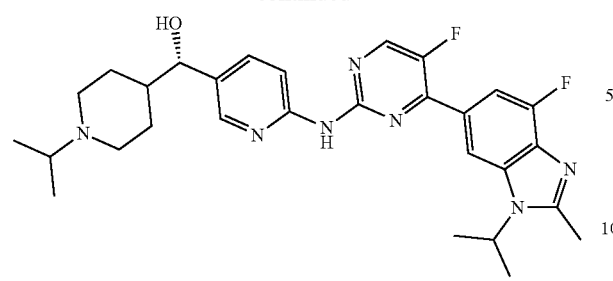
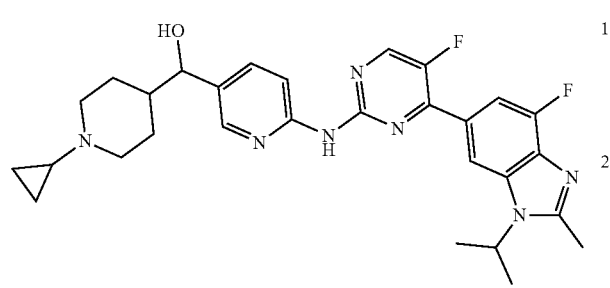
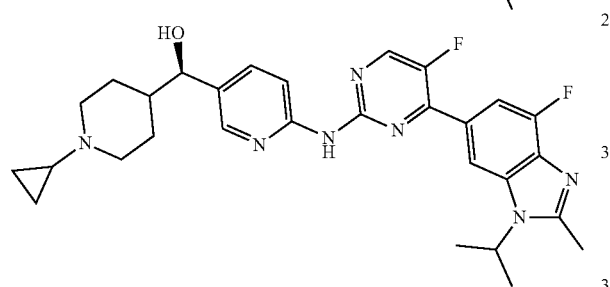
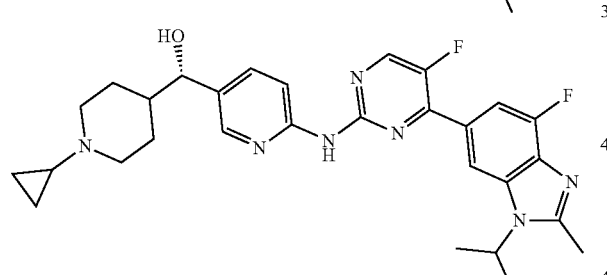
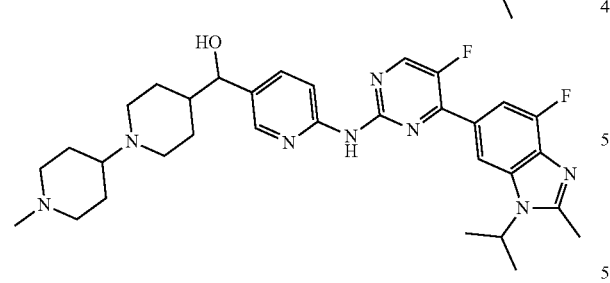
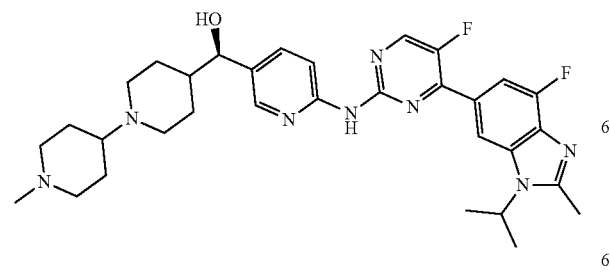
92
-continued
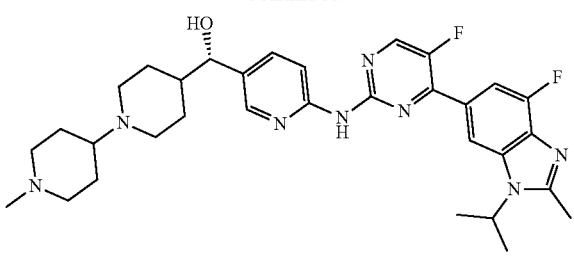
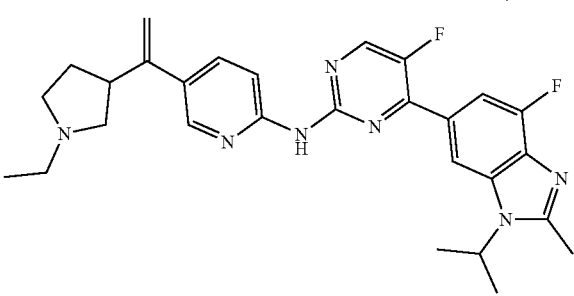
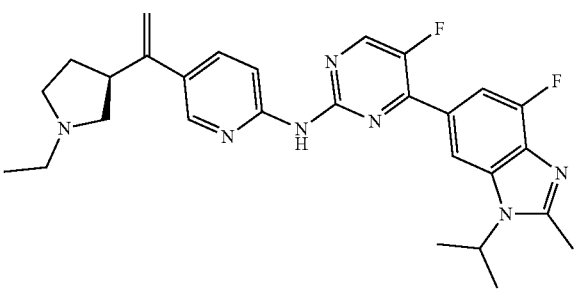
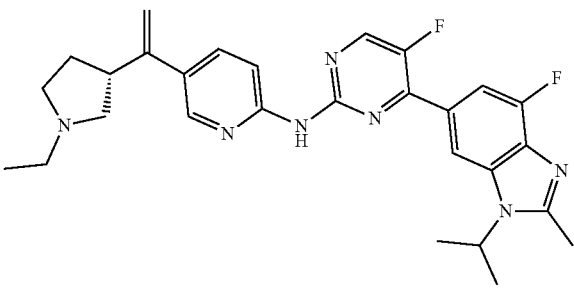
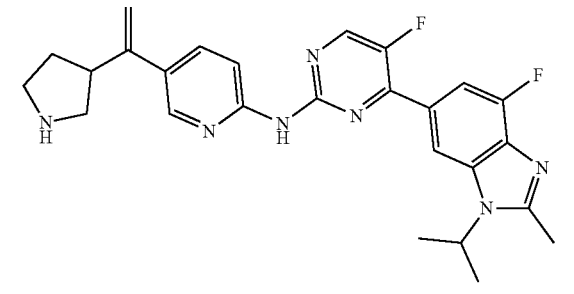
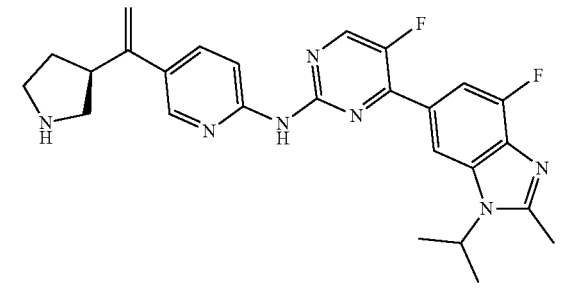

-continued
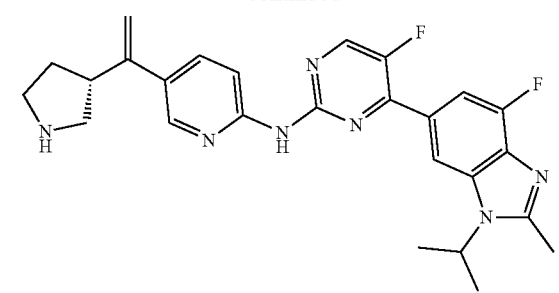
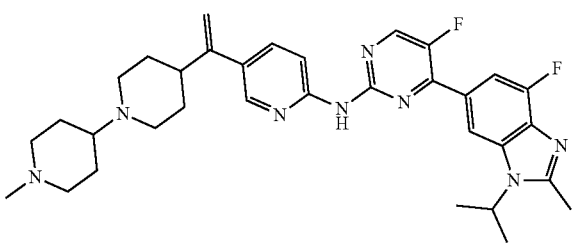
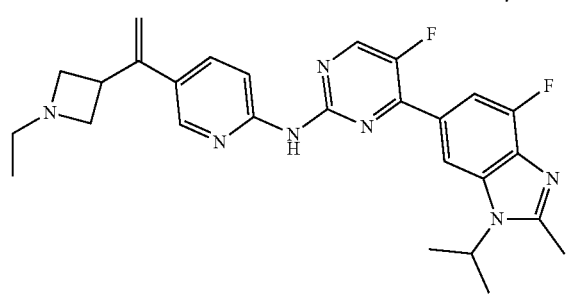
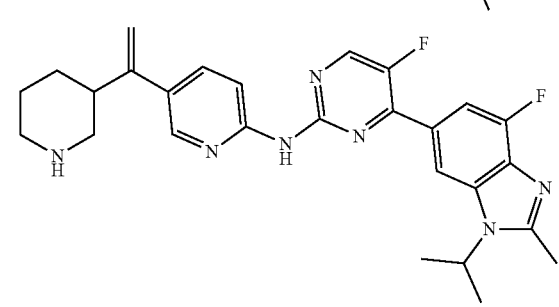
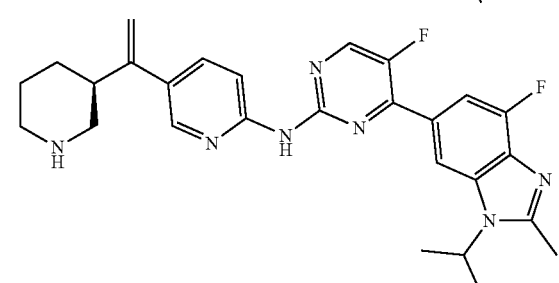
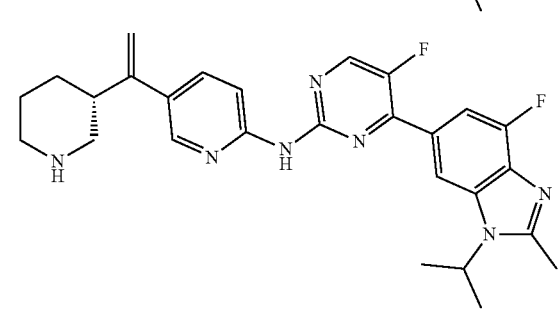
-continued
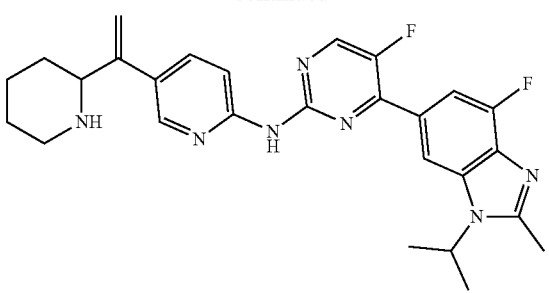
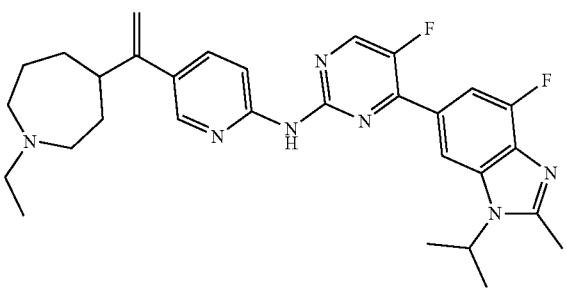
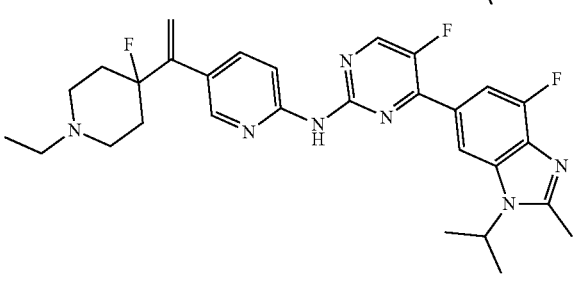
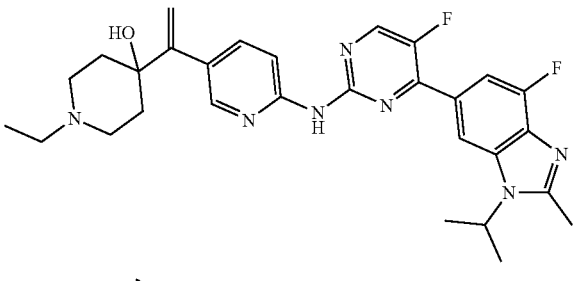
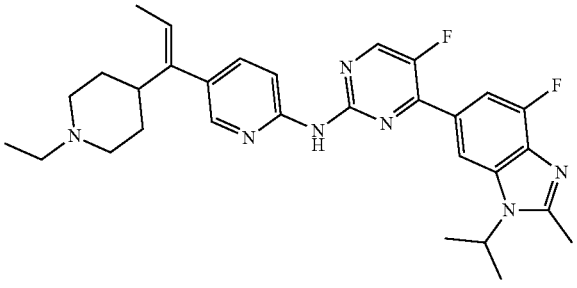
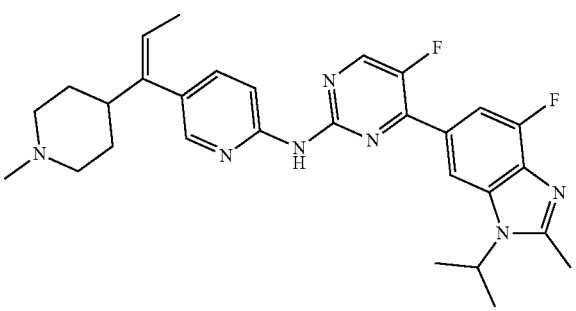

95
-continued
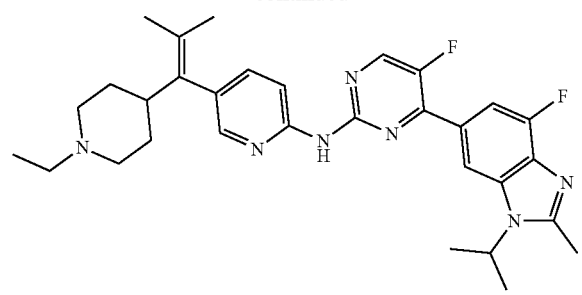
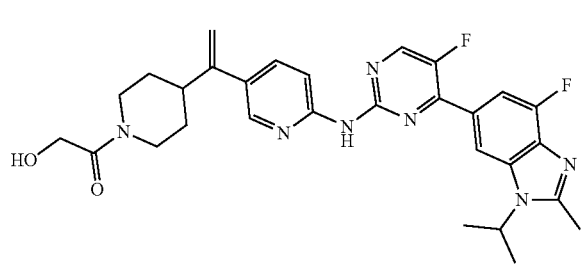
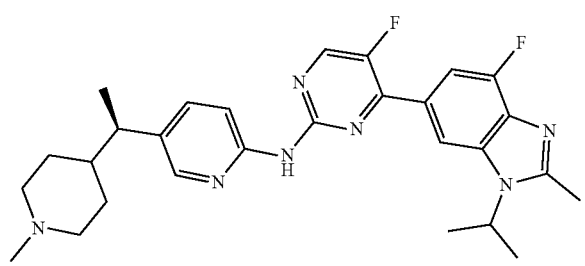
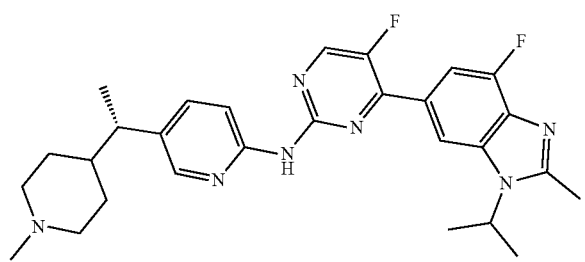
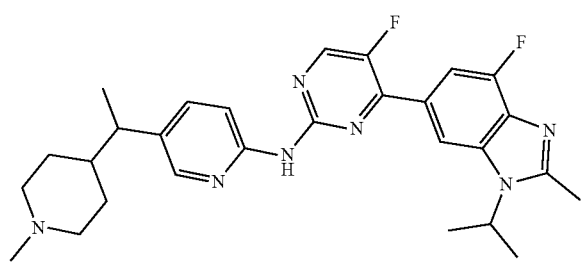
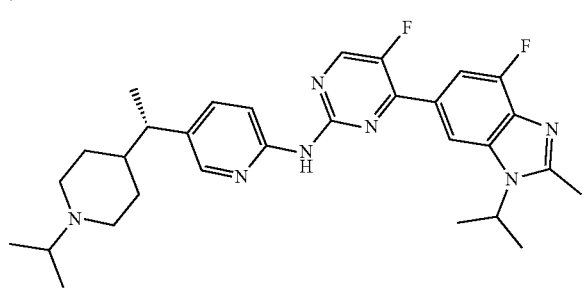
96
-continued
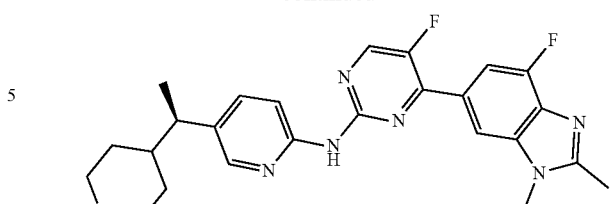
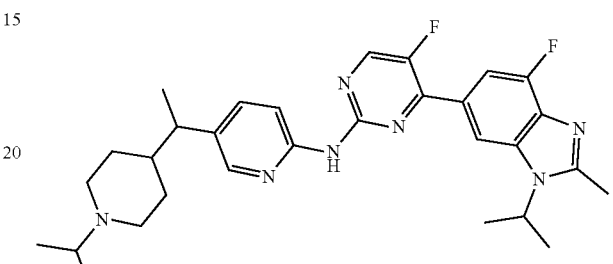
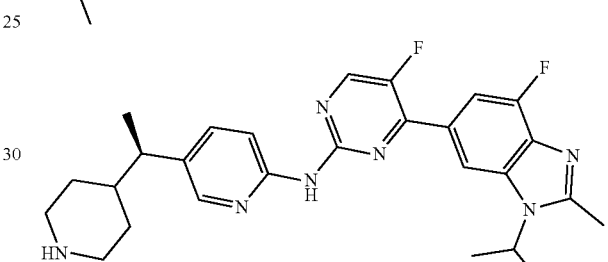
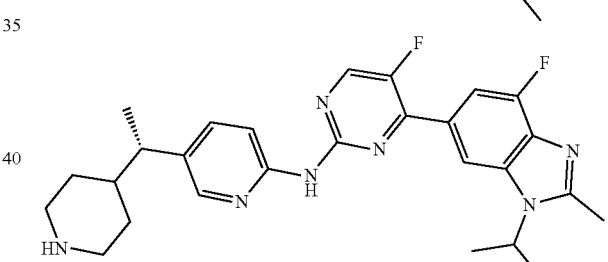
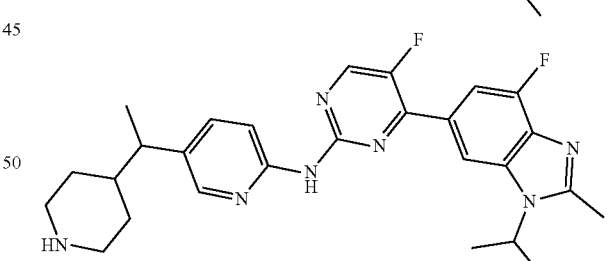
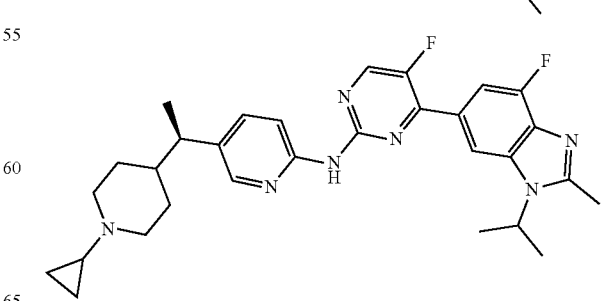

97
-continued
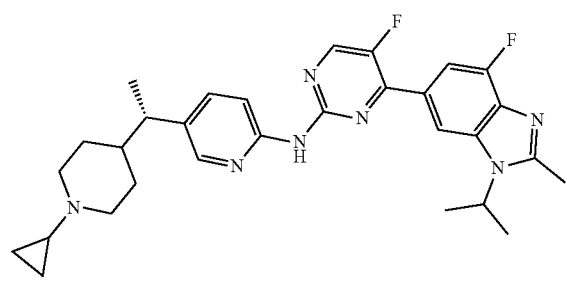
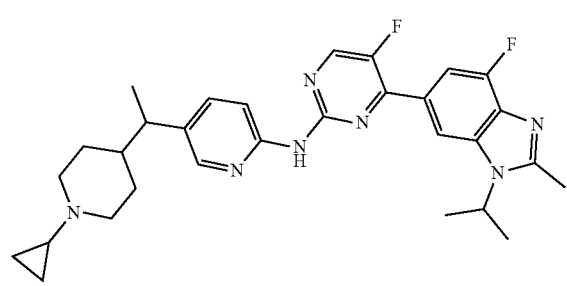
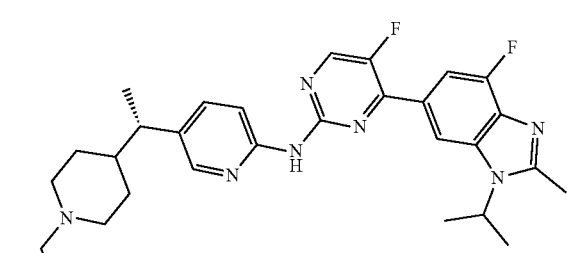
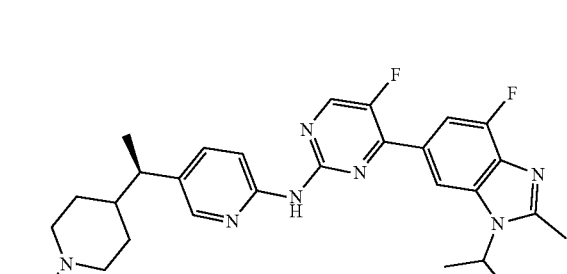
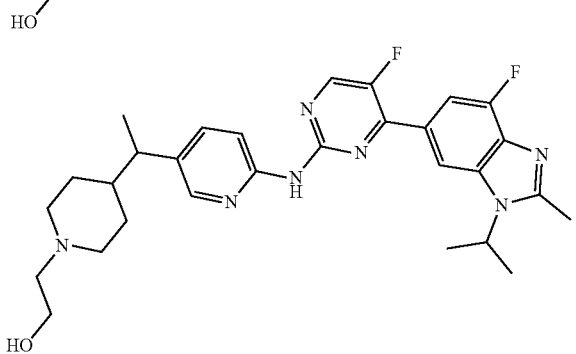
98
-continued
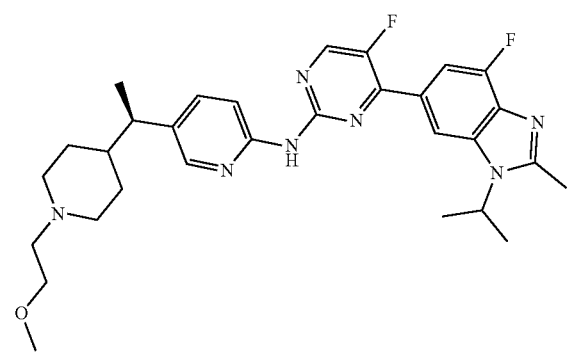
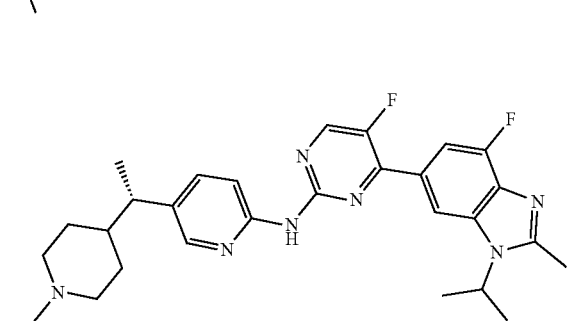
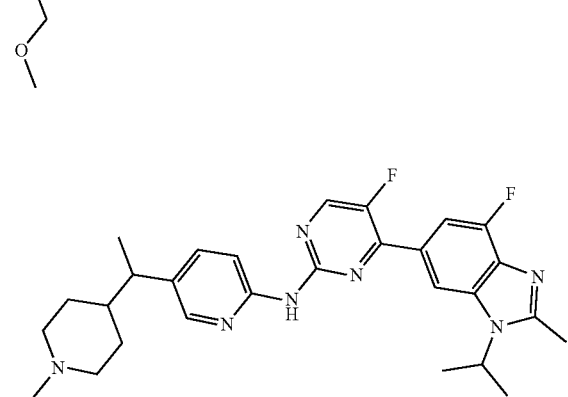
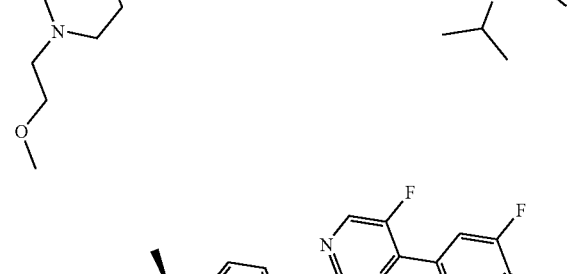
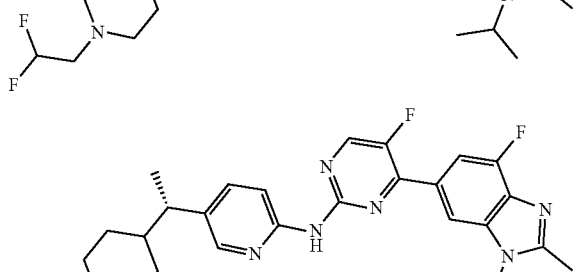

99
-continued
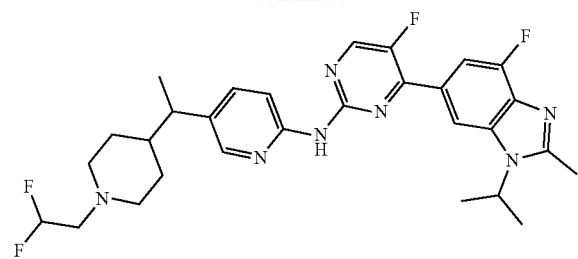
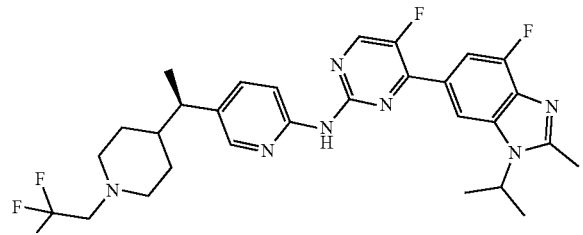
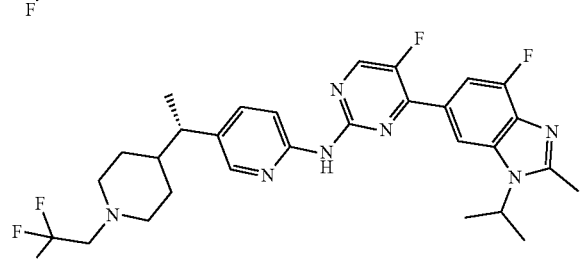
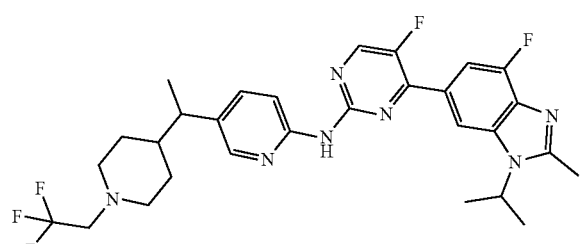
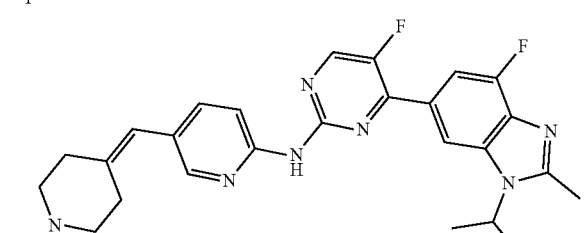
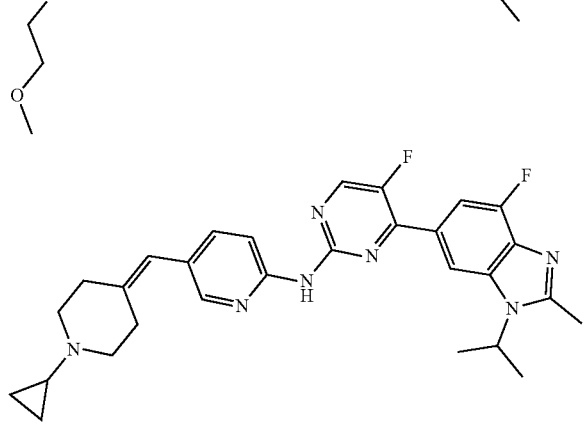
100
-continued
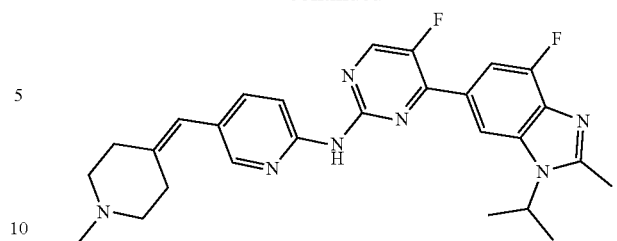
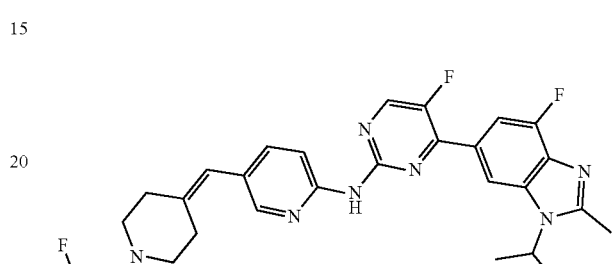
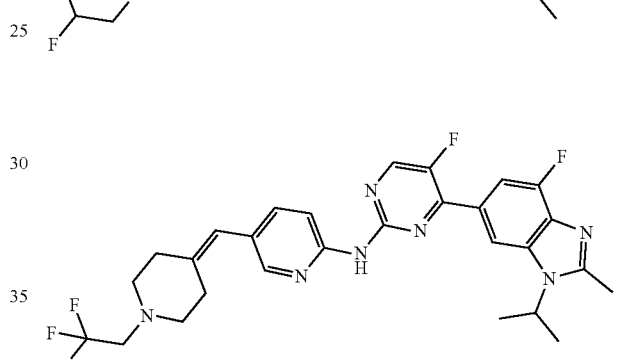
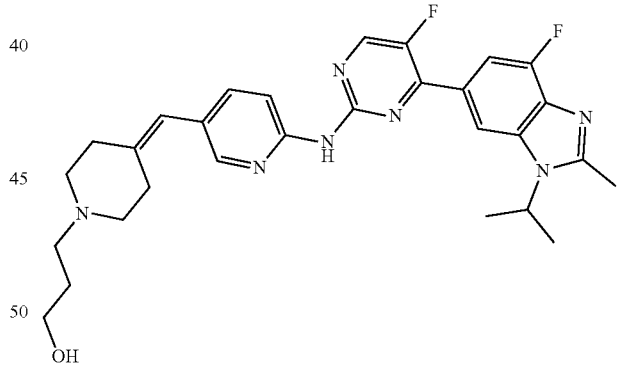
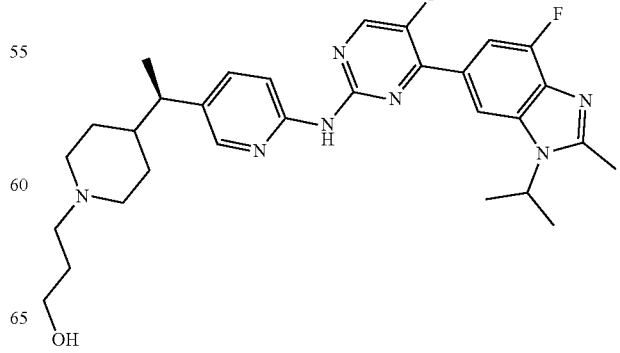
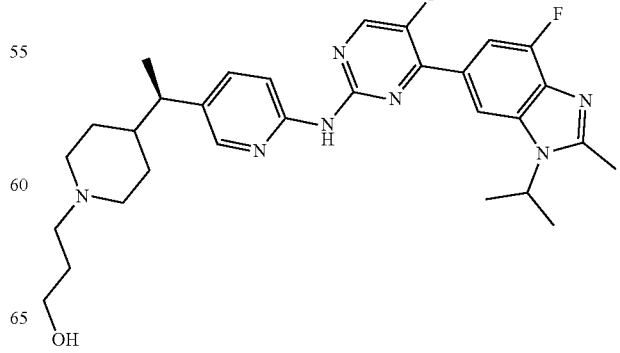

101
-continued
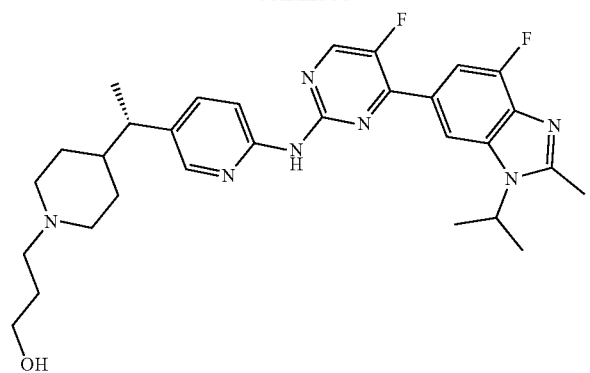
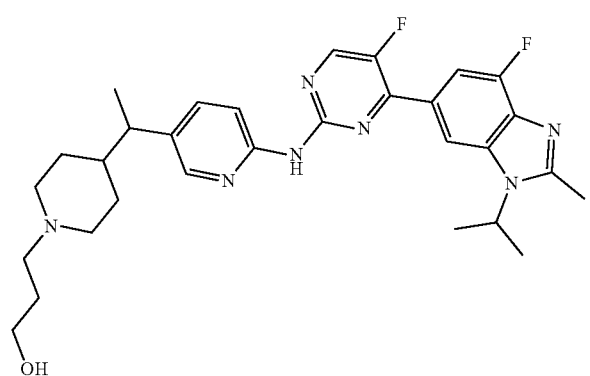
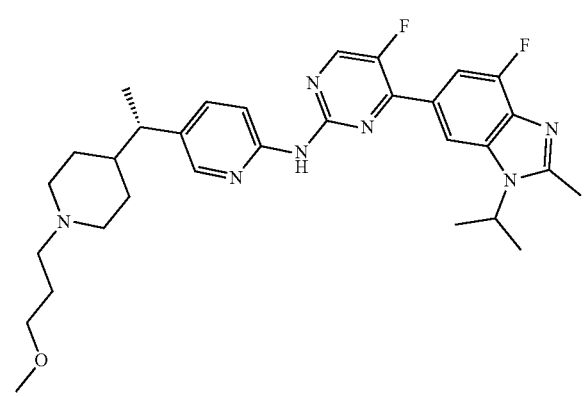
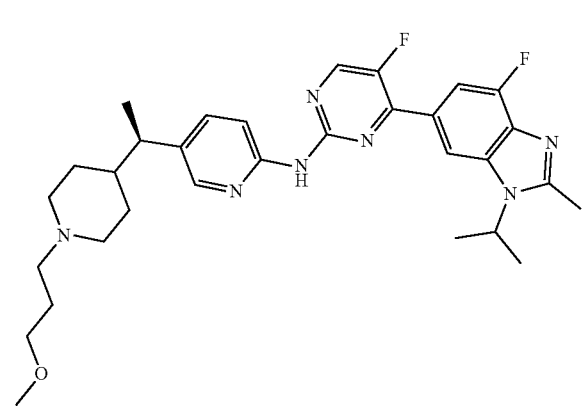
102
-continued
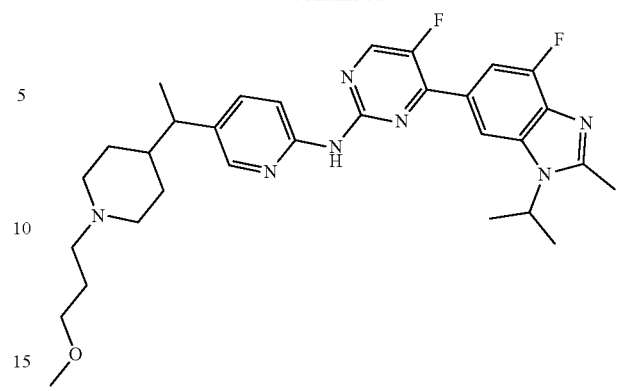
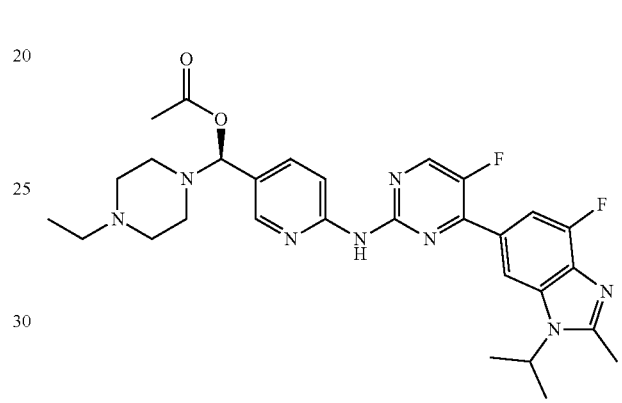
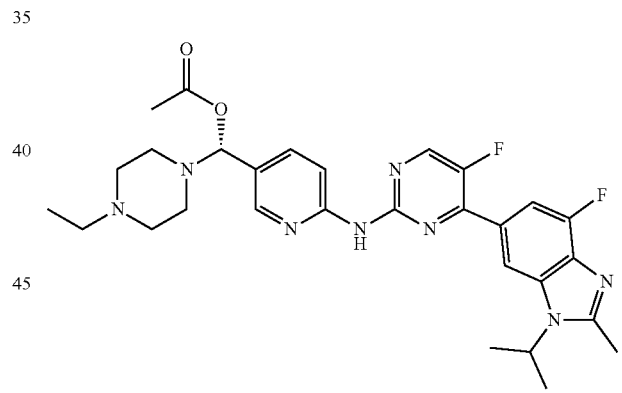
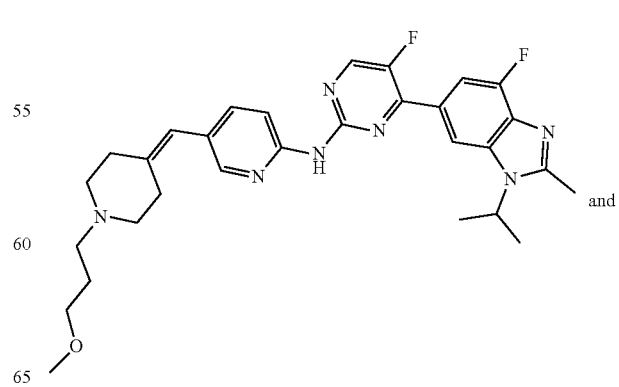
and -continued

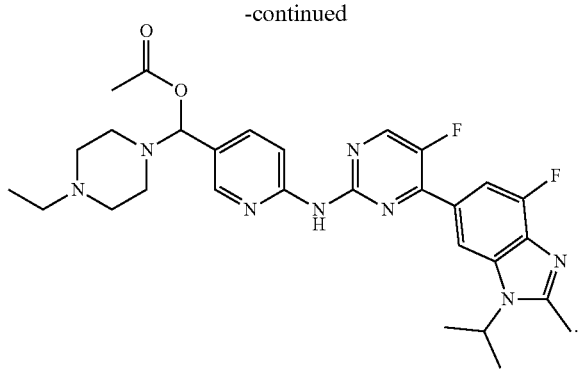

In the present invention, the compound represented by the general formula (I) can be preferably obtained from racemic compound 101 under the following chiral separation conditions.

Compound 101

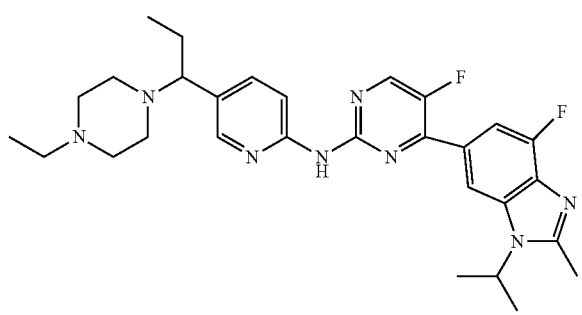

The chiral separation method can comprise the following conditions:
chiral column is Chiralpak AD-H 10 mm×250 mm, 5 μm;
column temperature is 40° C.;
mobile phase A is 0.1% DEA in hexane, and the percentage is the volume percentage; mobile phase B is ethanol;
gradient is mobile phase A/mobile phase B=50/50, and the ratio is volume percent;
flow rate is 6.0 mL/min;
detection wavelength is UV 210 nm;
the compound represented by the general formula (I) is collected at RT for 15 minutes or 20 minutes.

In the present invention, the compound represented by the general formula (I) can be preferably obtained from racemic compound 102 under the following chiral separation conditions.

Compound 102

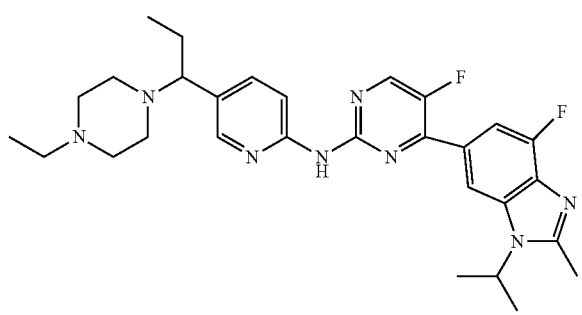

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 16 minutes or 22 minutes.

In the present invention, the compound represented by the general formula (I) can be preferably obtained from racemic compound 103 under the following chiral separation conditions.

Compound 103

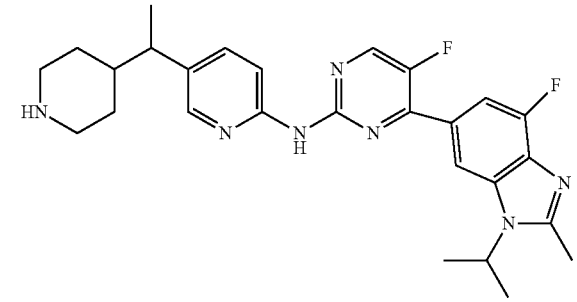

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 13 minutes or 19 minutes.

In the present invention, the compound represented by the general formula (I) can be preferably obtained from racemic compound 104 under the following chiral separation conditions.

Compound 104

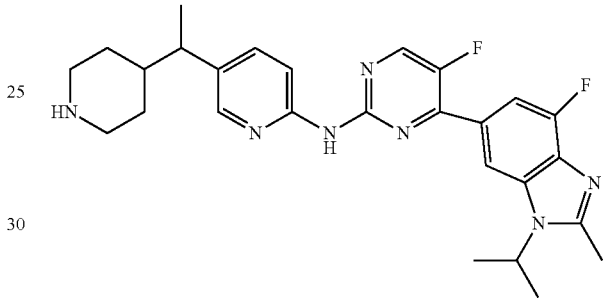

The chiral separation method can comprise the following conditions:
chiral column is Chiralpak AD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume percent;
flow rate is 3.0 mL/min;
detection wavelength is UV 210 nm;
the compound represented by the general formula (I) is collected separately at RT for 30 minutes or 36 minutes.

In the present invention, the compound represented by the general formula (I) can be preferably obtained from racemic compound 105 under the following chiral separation conditions.

Compound 105

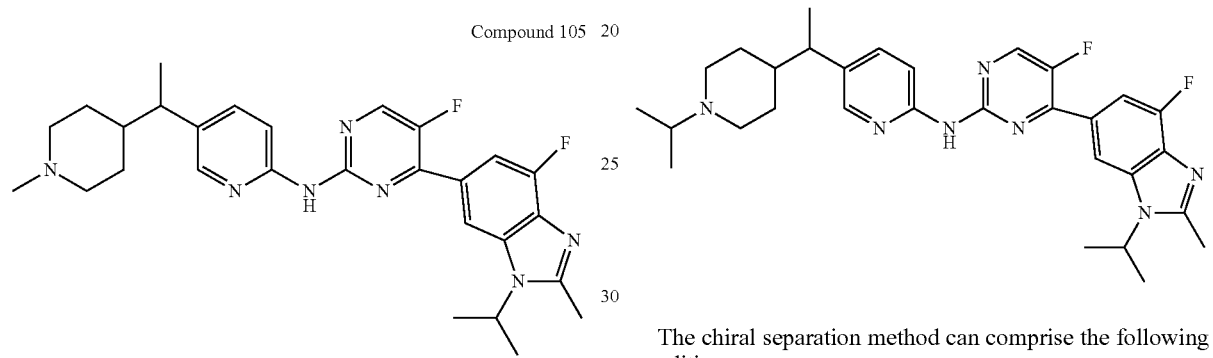

The chiral separation method can comprise the following conditions:
chiral column is Chiralpak AS-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 14.5 minutes or 18 minutes.

In the present invention, the compound represented by the general formula (I) can be preferably obtained from racemic compound 106 under the following chiral separation conditions.

Compound 106

The chiral separation method can comprise the following conditions:
chiral column is Chiralpak AD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume percent;
flow rate is 3.0 mL/min;
detection wavelength is UV 210 nm;
the compound represented by the general formula (I) is collected separately at RT for 23 minutes or 29 minutes.

In the present invention, the compound represented by the general formula (I) can be preferably obtained from racemic compound 107 under the following chiral separation conditions.

Compound 107

The chiral separation method can comprise the following conditions:
chiral column is Chiralpak AS-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 17.5 minutes or 24 minutes.

In the present invention, the compound represented by the general formula (I) can be preferably obtained from racemic compound 108 under the following chiral separation conditions.

Compound 108

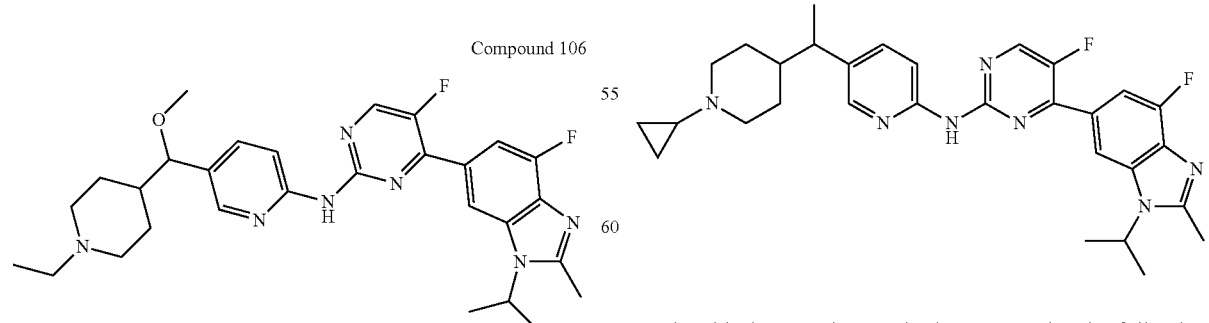

The chiral separation method can comprise the following conditions:
chiral column is Chiralpak AS-H 10 mm×250 mm, 5 µm;
column temperature is 40° C.;

mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 18.4 minutes or 25 minutes.

In the present invention, the compound represented by the general formula (I) can be preferably obtained from racemic compound 109 under the following chiral separation conditions.

Compound 109

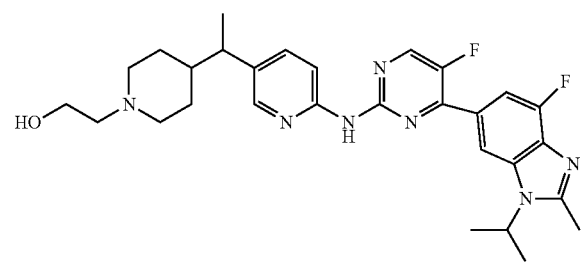

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 14.6 minutes or 18.4 minutes.

In the present invention, the compound represented by the general formula (I) can be preferably obtained from racemic compound 110 under the following chiral separation conditions.

Compound 110

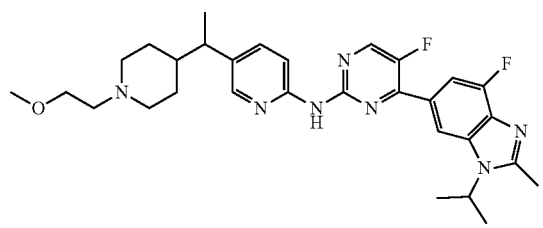

chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;

flow rate is 3.0 mL/min;
detection wavelength is UV 300 nm;
the compound represented by the general formula (I) is collected separately at RT for 15.7 minutes or 21.3 minutes.

In the present invention, the compound represented by the general formula (I) can be preferably obtained from racemic compound 111 under the following chiral separation conditions.

Compound 111

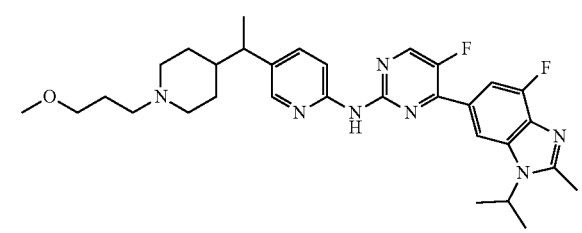

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 14.9 minutes or 19.7 minutes.

In the present invention, the compound represented by the general formula (I) can be preferably obtained from racemic compound 112 under the following chiral separation conditions.

Compound 112

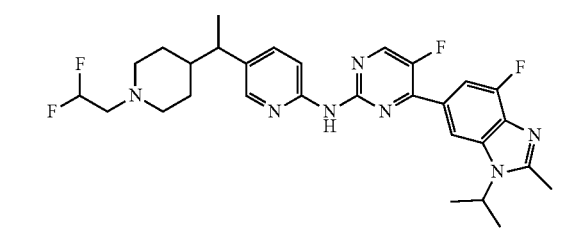

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) is collected separately at RT for 18.3 minutes or 24.8 minutes.

In the present invention, the compound preferably represented by the general formula (I) can be obtained from racemic compound 113 under the following chiral separation conditions.

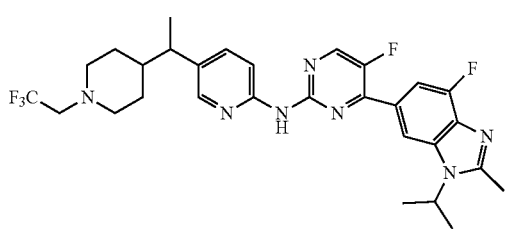

Compound 113

The chiral separation method can comprise the following conditions:
chiral column is Chiralpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=80/20, and the ratio is volume percent;
flow rate is 3.0 mL/min;
detection wavelength is UV 300 nm;
the compound represented by the general formula (I) was collected separately at RT for 19.7 minutes or 25.1 minutes.

Even if other chiral resolution and purification methods are employed, it will fall within the scope of the present invention to obtain a single chiral compound at a corresponding retention time under the chiral separation methods described in the present invention.

In a second aspect, the invention also provides a process for preparing the compound represented by the general formula (I), which comprises the following steps:

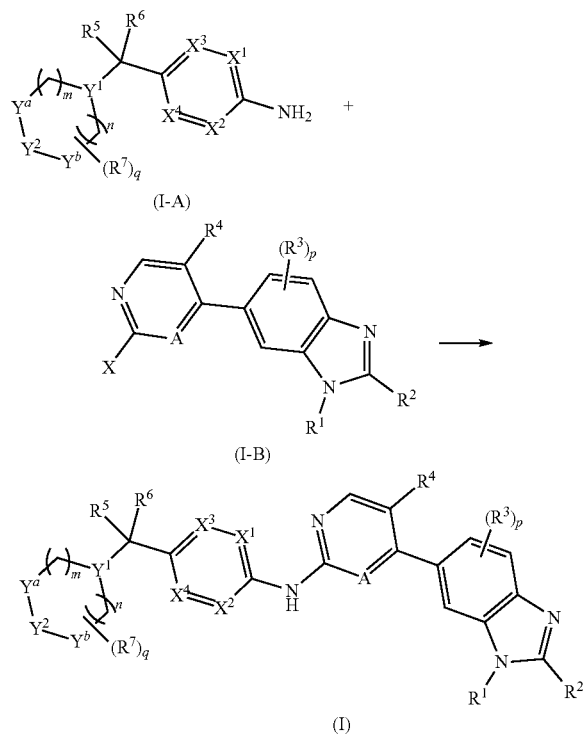

coupling the compound represented by the general formula (I-A) with the compound represented by the general formula (I-B) under basic and catalyst conditions to obtain the compound represented by the general formula (I);

wherein X is halogen; the definitions of $R^1$, $R^2$, $R^3$, $R^4$, $R^5$, $R^6$, $R^7$, $X^1$, $X^2$, $X^3$, $X^4$, $Y^1$, $Y^2$, $Y^a$, $Y^b$, A, m, m, p and q are defined as above.

The invention also provides a process for preparing the compound represented by the general formula (II), which comprises the following steps:

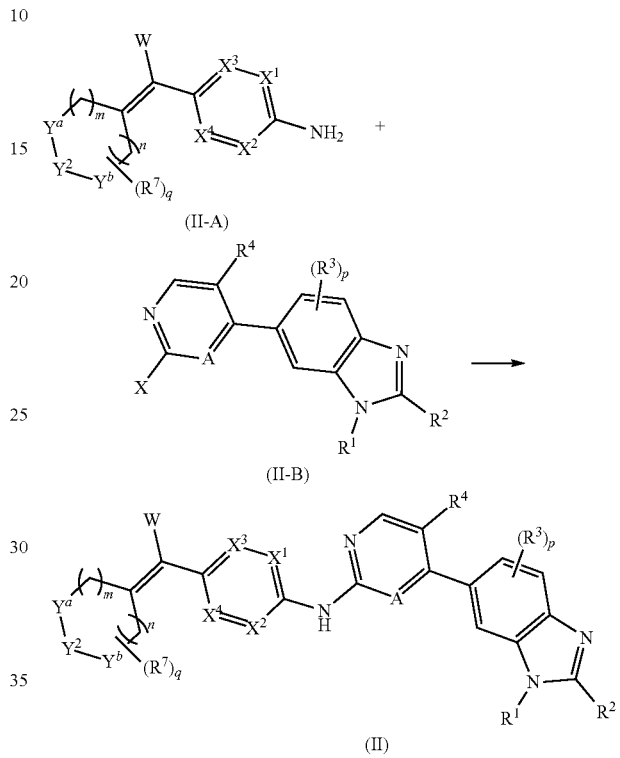

coupling the compound represented by the general formula (II-A) with the compound represented by the general formula (II-B) under basic and catalyst conditions to obtain the compound represented by the general formula (II);

wherein X is halogen; the definitions of $R^1$, $R^2$, $R^3$, $R^4$, $R^7$, $X^1$, $X^2$, $X^3$, $X^4$, $Y^2$, $Y^a$, $Y^b$, W, A, m, m, p, and q are defined as above.

In the coupling reaction, the reagents that provide basic conditions include organic bases and inorganic bases, and the organic bases include, but are not limited to, lithium hexamethyldisilazane, sodium hexamethyldisilazane, potassium hexamethyldisilazane, lithium diisopropylamide, n-butyllithium, sec-butyllithium, triethylamine, pyridine, 2,6-dimethylpyridine, N, N-diisopropylethylamine, potassium tert-butoxide, sodium tert-butoxide, lithium tert-butoxide, tetrabutylammonium fluoride or N-methylmorpholine, etc. The inorganic bases include, but are not limited to, potassium carbonate, sodium carbonate, sodium bicarbonate, sodium hydroxide, potassium hydroxide, lithium hydroxide, cesium fluoride, cesium carbonate, lithium carbonate, potassium phosphate, sodium hydride or potassium hydride, etc.

In the coupling reaction, the catalyst includes, but is not limited to, triphenylphosphine, 4,5-bis(diphenylphosphino)-9,9-dimethylxanthene, tris(dibenzylideneacetone)dipalladium, 2, 2'-bis(diphenylphosphino)-1,1'-binaphthyl, 2-(dicyclohexylphosphino)biphenyl, 1 1'-bis(diphenylphosphino)ferrocene palladium(II) dichloride, bis (triphenylphosphine)palladium(II) dichloride, palladium dichloride, palladium acetate, cuprous iodide, palladium on carbon (Pd/C), rhodium on carbon (Rh/C) or Raney nickel, and etc.

In a third aspect, the present invention also provides a pharmaceutical composition comprising a therapeutically effective amount of the compound represented by the general formula (I) or (II), the pharmaceutically acceptable salt thereof, the isomer thereof or the mixture form of the isomers, the solvate thereof, the polymorph thereof, the stable isotope derivative thereof or the prodrug thereof, and a pharmaceutically acceptable carrier, diluent or excipient.

In a fourth aspect, the present invention also provides a use of the compound represented by the general formula (I) or (II), the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing CDK inhibitors.

In some aspects of the present invention, the CDK can be one or more than one of CDK1, CDK2, CDK4, CDK5, CDK6, CDK7, CDK8, CDK9, CDK10, CDK11, CDK12, and CDK13.

In some aspects of the present invention, the CDK can be one or more than one of CDK1, CDK2, CDK4, CDK6, CDK7, and CDK9.

In some aspects of the present invention, the CDK can be CDK4 and/or CDK6.

In a fifth aspect, the present invention also provides a use of the compound represented by the general formula (I) or (II), the pharmaceutically acceptable salt thereof, the isomer thereof or the mixture forms of the isomers, the solvate thereof, the polymorph thereof, the stable isotope derivative thereof or the prodrug thereof, or the pharmaceutical composition for manufacturing a medicament for inhibiting or treating abnormal cell proliferation, infection, inflammatory diseases, autoimmune diseases, cardiovascular diseases or neurodegenerative diseases related to CDK mediation.

In a sixth aspect, the present invention also provides a use of the compound represented by the general formula (I) or (II), the pharmaceutically acceptable salt thereof, the isomer thereof or the mixture forms of the isomers, the solvate thereof, the polymorph thereof, the stable isotope derivative thereof or the prodrug thereof, or the pharmaceutical composition for manufacturing a medicament preventing, relieving and/or treating abnormal cell proliferation, infection (e.g., virus infections such as HIV, HBV, etc.), inflammatory diseases (e.g., rheumatoid arthritis, etc.), autoimmune diseases (e.g., psoriasis, lupus erythematosus, diabetes, etc.), cardiovascular diseases (e.g., stroke, myocardial infarction, atherosclerosis, etc.) or neurodegenerative diseases (e.g., Alzheimer's disease, Parkinson's disease, etc.), wherein the abnormal cell proliferative disease can be a cancer.

In a seventh aspect, the present invention also provides a method for inhibiting CDK activity, which comprises administering a therapeutically effective amount of the compound represented by the general formula (I) or (II), the pharmaceutically acceptable salt thereof, the isomer or the mixture forms of the isomers, the solvate, the polymorph thereof, the stable isotope derivative thereof or the prodrug thereof, or the pharmaceutical composition.

In an eighth aspect, the invention also provides a use of the compound represented by the general formula (I) or (II), the pharmaceutically acceptable salt thereof, isomer or the mixture forms of the isomers, the solvate thereof, the polymorph thereof, the stable isotope derivative thereof or the prodrug thereof, or the pharmaceutical composition for manufacturing a medicament for treating a cancer, wherein the cancer includes breast cancer, ovarian cancer, prostate cancer, melanoma, brain tumor (e.g., glioma), nasopharyngeal carcinoma, esophageal cancer, gastric cancer, liver cancer, pancreatic cancer, colorectal cancer (e.g., colon cancer, rectal cancer, etc.), lung cancer (e.g., small cell lung cancer, non-small cell lung cancer, squamous cell carcinoma, undifferentiated carcinoma, etc.), renal carcinoma, skin cancer, glioblastoma, neuroblastoma, sarcoma, liposarcoma, osteochondroma, osteocarcinoma, osteosarcoma, seminoma, testicular tumor, uterine tumor (e.g., cervical cancer, endometrial cancer, etc.), head and neck tumor (e.g., laryngeal cancer, pharyngeal cancer, tongue cancer, etc.), multiple myeloma, malignant lymphoma (e.g., reticulum cell sarcoma, hedgerow lymphosarcoma, Hodgkin's lymphoma, mantle cell lymphoma, etc.), polycythemia vera, leukemia (e.g., acute granulocytic leukemia, chronic granulocytic leukemia, acute lymphoblastic leukemia, chronic lymphoblastic leukemia, etc.), thyroid tumor, ureteral tumor, bladder tumor, gallbladder cancer, cholangiocarcinoma, chorionic epithelial cancer or pediatric tumor (e.g., neuroblastoma, embryonic testicular cancer, retinoblastoma, etc.).

In a ninth aspect, the invention also provides a use of the compound represented by the general formula (I) or (II), the pharmaceutically acceptable salt thereof, the isomer or the mixture forms of the isomers, the solvate thereof, the polymorph thereof, the stable isotope derivative thereof or the prodrug thereof, or the pharmaceutical composition for manufacturing a medicament for treating a cancer, wherein the compound represented by the general formula (I) or (II), the pharmaceutically acceptable salt thereof, the isomer thereof or the mixture form of the isomers, the solvate thereof, the polymorph thereof, the stable isotope derivative thereof, the prodrug thereof, or the pharmaceutical composition can be used in combination with one or more than one other anti-cancer agents which are selected from the group consisting of alkylating agents (e.g., cyclophosphamide, chlormethine hydrochloride, dibromomannitol, carmustine, dacarbazine, melphalan, etc.), platinum complexes (e.g., cisplatin, carboplatin, etc.), metabolic antagonists (e.g., methotrexate, 5-fluorouracil, capecitabine, pemetrexed, etc.), alkaloids (e.g., docetaxel, paclitaxel, vinblastine, irinotecan, etc.), antibody drugs (e.g., trastuzumab, partrozumab, bevacizumab, etc.), hormonal anticancer agents (e.g., leuprorelin, dutasteride, dexamethasone, etc.), proteasome inhibitors (e.g., boraxzomib, ixazomib, lenalidomide, etc.), CDK inhibitors (e.g., palbociclib, ribociclib, etc.), VEGFR or EGFR inhibitors (e.g., alfatinib, imatinib, gefitinib, erlotinib, etc.), m-TOR inhibitors (e.g., everolimus, sirolimus, etc.), PI3K inhibitors (e.g., idelalisib, etc.), B-Raf inhibitors (e.g., sorafenib, vemurafenib, rivarofini, etc.), PARP inhibitors (e.g., olaparib, niraparib, etc.), c-Met kinase inhibitors (e.g., crizotinib, etc.), ALK inhibitors (e.g., ceritinib, alectinib, etc.), AKT inhibitors (e.g., perifosine, etc.), ABL inhibitors, FLT3 inhibitors, PD-1 monoclonal antibodies (e.g., Opdivo, Keytruda, etc.) or PD-L monoclonal antibodies (Atezolizumab), and etc.

DETAILED DESCRIPTION OF THE INVENTION

Unless otherwise stated to the contrary, the terms used in the specification and claims have the following definitions.

The term "oxo" refers to "═O".

The term "alkyl" refers to a saturated aliphatic hydrocarbon group, including linear or branched groups of 1 to 20 carbon atoms, preferably 1 to 10 carbon atoms, more preferably 1 to 8 carbon atoms, and non-limiting examples include, but are not limited to, methyl, ethyl, n-propyl, n-butyl, isobutyl, tert-butyl, sec-butyl, n-pentyl, 2-methylbutyl, 3-methylbutyl, 1, 1-dimethylpropyl, 1, 2-dimethylpropyl, 2, 2-dimethylpropyl, 1-ethylpropyl, n-hexyl, 2-methylpentyl, 3-methylpentyl, 4-methylpentyl, 1, 1-dimethylbutyl, 1, 2-dimethylbutyl, 2, 2-dimethylbutyl, 1, 3-dimethylbutyl, 2, 3-dimethylbutyl, 3, 3-dimethylbutyl, 1, 1, 2-trimethylpropyl, 1-ethyl-2-methylpropyl, n-heptyl, 2-methylhexyl, 3-methylhexyl, 4-methylhexyl, 5-methylhexyl, 2, 2-dimethylpentyl, 2, 3-dimethylpentyl, 2,3-dimethylpentyl, 2, 4-dimethylpentyl, 3, 3-dimethylpentyl, 3, 4-dimethylpentyl, 2-ethylpentyl, 3-ethylpentyl, octyl, nonyl, decyl, undecyl, dodecyl, and various isomers thereof, and the like. The alkyl can be substituted or unsubstituted and can be substituted at any available junction, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkyloxy, heterocycloalkyloxy, cycloalkylmercapto, heterocycloalkylmercapto, oxo, amino, haloalkyl, hydroxyalkyl, carboxyl or carboxylate group, etc. When "alkyl" and its prefix are used herein, both linear and branched saturated carbon bonds are included.

The term "cycloalkyl" refers to a saturated or partially unsaturated monocyclic or polycyclic group comprising from 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include, but are not limited to, cyclopropyl, cyclobutyl, cyclopentyl, cyclopentenyl, cyclohexyl, cyclohexenyl, cyclohexadiene, cycloheptyl, cyclooctyl, and the like. Non-limiting examples of polycyclic cycloalkyl include, but are not limited to, spirocycloalkyl, fused cycloalkyl and bridged cycloalkyl. Cycloalkyl can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkoxy, heterocycloalkoxy, cycloalkoxy, cycloalkoxy, cycloalkoxy, cycloalkylmercapto, heterocycloalkylmercapto, oxo, amino, haloalkyl, hydroxyalkyl, carboxyl or carboxylate group, and the like.

The term "haloalkyl" refers to an alkyl can be substituted by one or more than one the same or different halogen atoms, wherein the definition of the alkyl is as defined in the present invention.

The term "alkenyl" refers to an alkyl as defined in the present invention consisting of at least two carbon atoms and at least one carbon-carbon double bond, preferably $C_2$-$C_{10}$ alkenyl, more preferably $C_2$-$C_6$ alkenyl, most preferably $C_2$-$C_4$ alkenyl, such as vinyl, propenyl, 1-propenyl, and the like. The alkenyl group can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkoxy, heterocycloalkoxy, cycloalkoxy, cycloalkoxy, cycloalkoxy, cycloalkylmercapto, heterocycloalkylmercapto, oxo, amino, haloalkyl, hydroxyalkyl, carboxyl or carboxylate group, and the like.

The term "alkynyl" refers to an alkyl as defined in the present invention consisting of at least two carbon atoms and at least one carbon-carbon triple bond, preferably $C_2$-$C_{10}$ alkynyl, more preferably $C_2$-$C_6$ alkynyl, most preferably $C_2$-$C_4$ alkynyl, such as ethynyl, 1-propynyl, 2-propynyl, and the like. The alkynyl group can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkoxy, heterocycloalkoxy, cycloalkoxy, cycloalkoxy, cycloalkoxy, cycloalkylmercapto, heterocycloalkylmercapto, oxo, amino, haloalkyl, hydroxyalkyl, carboxyl or carboxylate group, and the like.

The term "heterocycloalkyl" refers to a saturated or partially unsaturated monocyclic or polycyclic hydrocarbon group comprising from 3 to 20 ring atoms, wherein one or more than one ring atoms are selected from heteroatoms of N, O, $S(O)_m$, $P(O)_m$ (wherein m is an integer from 0 to 2), but excluding ring moiety of —O—O, —O—S— or —S—S— and the remaining ring atoms are carbon. Preferably 3 to 12 ring atoms containing 1 to 4 heteroatoms, and non-limiting examples of monocyclic heterocycloalkyl include pyrrolyl, piperidinyl, piperazinyl, morpholinyl, tetrahydrofuranyl, pyranyl, and the like. Polycyclic heterocycloalkyl include spiro heterocycloalkyl, fused heterocycloalkyl and bridged heterocycloalkyl. Heterocycloalkyl can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkyloxy, heterocycloalkyloxy, cycloalkylmercapto, heterocycloalkylmercapto, oxo, amino, haloalkyl, hydroxyalkyl, carboxyl or carboxylate group, and the like.

The term "alkoxy" refers to —O-(alkyl) and —O-(cycloalkyl), wherein the definitions of the alkyl and the cycloalkyl are as described in the description. Non-limiting examples include, but are not limited to, methoxy, ethoxy, propoxy, butoxy, cyclopropoxy, cyclobutoxy, cyclopentyloxy, cyclohexyloxy, and the like. The alkoxy group can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkyloxy, heterocycloalkyloxy, cycloalkylmercapto, heterocycloalkylmercapto, oxo, amino, haloalkyl, hydroxyalkyl, carboxyl or carboxylate group, and the like.

The term "alkylmercapto" refers to —S-(alkyl) and —S-(cycloalkyl), wherein the definitions of the alkyl and the cycloalkyl are as described in the description. Non-limiting examples include, but are not limited to, methylmercapto, ethylmercapto, propylmercapto, butylmercapto, cyclopropylmercapto, cyclobutylmercapto, cyclopentylmercapto, cyclohexylmercapto, and the like. Alkylmercapto can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkoxy, heterocycloalkoxy, cycloalkylmercapto, heterocycloalkylmercapto, oxo, amino, haloalkyl, hydroxyalkyl, carboxyl or carboxylate group, and the like.

The term "aryl" refers to any stable conjugated hydrocarbon ring system group of 6 to 18 carbon atoms, preferably 6 to 10 carbon atoms, which can be monocyclic, bicyclic, tricyclic or more cyclic aromatic groups, such as phenyl, naphthyl, anthracene and the like. The aryl ring can be fused to a ring of heteroaryl, heterocycloalkyl or cycloalkyl. The aryl can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkyloxy, heterocycloalkyloxy, heterocycloalkyloxy, cycloalkylmercapto, heterocycloalkylmercapto, oxo, amino, haloalkyl, hydroxyalkyl, carboxyl or carboxylate group, and the like.

The term "heteroaryl" refers to an aromatic ring system in which at least one carbon atom in the ring is replaced by a heteroatom selected from N, O or S, preferably a 5- to 7-membered monocyclic moiety or a 7- to 12-membered bicyclic moiety, more preferably a 5- to 6-membered heteroaryl, such as pyrrolyl, imidazolyl, pyridyl, pyrimidinyl, thiazolyl, thienyl, pyrazinyl, triazolyl, tetrazolyl, oxazolyl, indazolyl, and the like. The heteroaryl ring can be fused to a ring of aryl, heterocycloalkyl or cycloalkyl. The heteroaryl can be substituted or unsubstituted, and the substituent is preferably one or more than one groups, independently selected from alkyl, halogen, hydroxyl, mercapto, cyano, alkenyl, alkynyl, alkoxy, alkylmercapto, alkylamino, nitro, cycloalkyl, heterocycloalkyl, aryl, heteroaryl, cycloalkyloxy, heterocycloalkyloxy, heterocycloalkyloxy, cycloalkylmercapto, heterocycloalkylmercapto, oxo, amino, haloalkyl, hydroxyalkyl, carboxyl or carboxylate group, and the like.

The term "hydroxyl" refers to —OH.

The term "halogen" refers to fluorine, chlorine, bromine or iodine.

The term "nitro" refers to —$NO_2$.

The term "amino" refers to —$NH_2$.

The term "cyano" refers to —CN.

The term "carboxylic acid" refers to —C(O)OH.

The term "mercapto" refers to —SH.

The term "carboxylate group" refers to —C(O)O-alkyl, —C(O)O-aryl, or —C(O)O-cycloalkyl, wherein the definitions of alkyl, the aryl, and the cycloalkyl are as defined above.

The term "substituted" means that one or more than one hydrogen or deuterium atoms in the group, preferably 1 to 5 hydrogens or deuterium atoms, are independently substituted by a corresponding number of substituents.

The term "pharmaceutically acceptable salt" refers to a salt that can retain the biological effectiveness of the free base without other toxic and side effects, and can be an acidic salt, a basic salt or an amphoteric salt. Non-limiting examples include, but are not limited to, acidic salts including hydrochloride, hydrobromide, sulfate, pyrosulfate, bisulfate, sulfite, bisulfite, phosphate, monohydrogen phosphate, dihydrogen phosphate, metaphosphate, pyrophosphate, nitrate, acetate, propionate, caprate, octanoate, formate, acrylate, isobutyrate, hexanoate, heptanoate, oxalate, malonate, succinate, suberate, benzoate, methyl benzoate, phthalate, maleate, methanesulfonate, p-toluenesulfonate, benzenesulfonate, (D, L)-tartrate, citrate, maleate, (D, L-)malate, fumarate, stearate, oleate, cinnamate, laurate, glutamate, aspartate, triflate, mandelate, ascorbate, salicylate, and the like. When the compound of the present invention contains acidic groups, pharmaceutically acceptable salts thereof can further include alkali metal salts (e.g., sodium salt or potassium salt), alkaline earth metal salts (e.g., calcium salt or magnesium salt), organic base salts (e.g., alkyl aromatics, amino acids, etc.).

The term "solvate" refers to an aggregate (or associated complex) formed by one or more than one solvent molecules with a compound of the present invention. Solvents of the formed solvate include, but are not limited to, water, dimethyl sulfoxide, methanol, ethanol, isopropanol, acetic acid, and the like.

The term "polymorph" refers to different solid crystalline phases generated by the presence of two or more different molecular arrangements in the solid-state of the compound of the present invention, which may exist as a single crystal form or a mixture of polycrystal forms.

The term "stable isotope derivative" refers to an isotope substituted derivative obtained by replacing any hydrogen atom of the compound of the present invention with 1 to 5 deuterium atoms, or an isotope substituted derivative obtained by replacing any carbon atom of the compound of the present invention with 1 to 3 $C^{14}$ atoms, or an isotope derivative obtained by replacing any oxygen atom with 1 to 3 $O^{18}$ atoms of the compound of the present invention.

The term "prodrug" refers to a compound that can be converted to a bioactive compound of the present invention under physiological conditions (e.g., in vivo) or by solvent decomposition and can be understood to be a pharmaceutically acceptable metabolic precursor. The prodrugs can be inactive or less active substances than active parent compounds but they can be rapidly converted in vivo to produce the parent compounds of the present invention, which can improve their solubility in animals as well as metabolic characteristics. The prodrug includes, for example, amino protecting groups, carboxyl protecting groups, phospholipids, and the like.

The term "pharmaceutical composition" refers to a mixture of one or more than one compounds described herein or pharmaceutically acceptable salts or prodrugs thereof and other chemical components, as well as other components such as physiologically acceptable carriers and excipients. The purpose of the pharmaceutical composition is to promote the administration of the organism and to facilitate the absorption of the active ingredient and exert biological activity.

The term "isomer" refers to a stereoisomer comprising an enantiomer, a diastereomer and cis/trans isomer is one of the diastereomers. The isomers of the present compounds can be their enantiomers, diastereomers, and any mixture thereof, including the formation and presence of free or salt forms.

The term "effective amount" or "therapeutically effective amount" refers to a sufficient amount of a drug or agent that is non-toxic but that achieves the desired effect. The determination of the effective amount varies from person to person, depending on the age and general condition of the recipient, and also on the particular active substance. The appropriate effective amount in a case can be determined by the skilled person in the art according to routine tests.

Abbreviations for any protecting groups, amino acids, and other compounds are commonly used and recognized abbreviations, unless otherwise specified, or refer to IUPAC-IUBC Commission on Biochemical Nomenclature (See Biochem. 1972, 11, 942-944).

EXAMPLES

Figure 1:
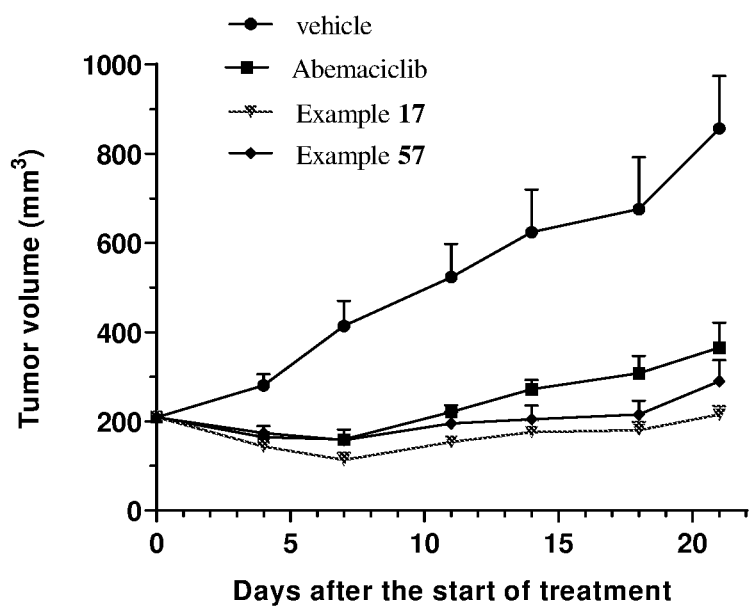
FIG. 1 shows the inhibitory effects on tumor volumes in MCF-7 cancer cells of vehicle, examples 17, 57 and Abemaciclib.

The following examples further describe the present invention, but these examples should not limit the scope of the present invention.

In the examples of the invention, the experimental methods without specifying specific conditions are generally in accordance with conventional methods and conditions, or in accordance with the conditions recommended by the manufacturers of raw materials or commodities. The reagents without specific sources are conventional reagents purchased from the market.

All compounds of the present invention can be determined by nuclear magnetic resonance (NMR) or mass spectrometry (MS). The NMR shift (δ) is recorded in units of 10-6 (ppm). The NMR measuring instrument is Bruker AVANCE-400 spectrometer. The deuterated solvents tested are deuterated chloroform ($CDCl_3$), deuterated methanol (MeOD) or deuterated dimethyl sulfoxide (DMSO-$d_6$), and the internal standard is tetramethylsilane (TMS).

Low-resolution mass spectrometry (MS) is determined by Agilent 6120 quadruple LCMS mass spectrometer.

The HPLC purity is determined by Agilent HPLC Agilent 1260/1220 chromatograph (Agilent Zorb Ax BonusRP 3.5μ m×4.6 mm×150 mm or Boston pHlex ODS 4.6 mm×150 mm×3 μm).

The compounds of the present invention and their intermediates can be isolated and purified by conventional preparative HPLC, silica gel plate, column chromatography, or flash column chromatography.

The thin-layer chromatography silica gel plate uses Yantai Huanghai, Yantai Xinnuo Chemical Industry HSGF254, or Qingdao GF254 silica gel plate. The silica gel plate used for thin-layer chromatography (TLC) is 2.5×5 cm, 0.2 mm-0.25 mm, and the thin layer chromatography separation (Prep-TLC) used for purifying products is 1 mm or 0.4 mm-0.5 mm, 20×20 cm.

Column chromatography (silica gel column chromatography) is generally used in sizes of 100-200 mesh or 200-300 mesh or 300-400 mesh.

The flash separator is Agela Technologies MP200, and the column is generally Flash column silica-CS (12 g-330 g).

The preparative HPLC (Prep-HPLC) is Gilson GX-281, and the column model is Welch Ultimate XB-C18 21.2 mm×250 mm×10 μm.

The chiral columns are CHIRALCEL OD-H, OJ-H or CHIRALPAK AD-H, AS-H 4.6 mm×250 mm×5 μm, and the preparation column types are CHIRALCEL OD-H, OJ-H or CHIRALPAK AD-H, AS-H 10 mm×250 mm×5 μm.

The known starting materials of the present invention can be synthesized by methods known in the art, or purchased from suppliers such as Sigma-Aldrich, ACROS, Alaf, TCI, J&K Scientific, energy-chemical, Accela ChemBio, Macklin, Siyanbio chemical companies and the like.

Anhydrous solvents such as anhydrous tetrahydrofuran, anhydrous dichloromethane or anhydrous N, N-dimethylacetamide are commercially available from the above chemical companies.

Unless otherwise specified in the examples, the reaction is generally carried out under a nitrogen or argon atmosphere. The nitrogen or argon atmosphere refers to that the reaction flask is connected to a balloon of nitrogen or argon having a volume of about 1 L and subjected to three pumping displacements.

The hydrogen atmosphere means that the reaction flask is connected to a hydrogen balloon having a volume of about 1 L and subjected to three pumping displacements.

The pressurized hydrogenation reaction uses a pressure-resistant sealed glass reaction vessel and is connected to a hydrogen pressure gauge.

In the examples, unless otherwise specified, the reaction temperature is room temperature, and the temperature is 15-25° C.

The reactions in the examples are generally monitored by LCMS or TLC, wherein the LCMS is as described above. The developing solvent system used for TLC is generally: dichloromethane and methanol, petroleum ether and ethyl acetate, dichloromethane and ethyl acetate, petroleum ether and dichloromethane, ethyl acetate and methanol, etc. The volume ratio of the solvent is adjusted according to the polarity of the compound, and a small amount (0.1%-10%) of base (e.g. triethylamine or 37% ammonia water, etc.) or acid (e.g. acetic acid, etc.) can also be added for adjustment.

The compounds can be purified by Prep-TLC, column chromatography or Agela preparation system. The elution solvent system is generally dichloromethane and methanol, petroleum ether and ethyl acetate, dichloromethane and ethyl acetate, petroleum ether and dichloromethane, ethyl acetate and methanol, etc. The volume ratio of the solvent is adjusted according to the polarity of the compound. A small amount (0.1%-10%) of base (e.g. triethylamine or 37% ammonia water, etc.) or acid (e.g. acetic acid, etc.) can also be added for adjustment.

The following abbreviations are used throughout the present invention:

DIPEA: N, N-diisopropylethylamine
DMF: N, N-dimethylformamide
NMP: N-methylpyrrolidone
THF: tetrahydrofuran
DCM: dichloromethane
MeOH: methanol
PE: petroleum ether
EA: ethyl acetate
HCl: hydrochloric acid
$K_2CO_3$: potassium carbonate
$Cu_2O$: cuprous oxide
DMEDA: N,N'-dimethylethylenediamine
$NaBH_4$: sodium borohydride
TBSCl: tert-butyldimethylchlorosilane
TFA: trifluoroacetic acid
$(Boc)_2O$: di-tert-butyl dicarbonate
$Na_2S_2O_3$: sodium thiosulfate
$NaHCO_3$: sodium bicarbonate
AIBN: azobisisobutyronitrile
NBS: N-bromosuccinimide
NaOH: sodium hydroxide
NaH: sodium hydride
$NaBH(OAc)_3$: sodium triacetoxyborohydride
Dess-martin oxidant: (1,1,1-triacetoxy)-1,1-dihydro-1,2-phenyliodo-3(1H)-one
n-BuLi: n-butyllithium
$NH_3.H_2O$: Ammonia
DEA: diethylamine
Hexane: n-hexane
$CDCl_3$: Deuterated chloroform
$H_2$: hydrogen
$H_2O$: water
$Pd_2(dba)_3$: tris(dibenzylideneacetone)dipalladium CyJohnPhos: 2-(dicyclohexylphosphino) biphenyl XantPhos: 4,5-bis-diphenylphosphino-9,9-dimethyl-oxazepine LiHMDS: bistrimethylsilylamine lithium RT: retention time SFC: Supercritical Fluid Chromatography TLC: Thin layer chromatography Prep-TLC: preparative thin-layer chromatography Prep-HPLC: preparative high-performance liquid chromatography Example 1

N-(5-(1-(4-ethylpiperazin-1-yl)propyl)pyridin-2-yl)-5-fluoro-4-(4-fluoro-1-isopropyl-2-methyl-1H-benzo[d]imidazol-6-yl)pyrimidin-2-amine

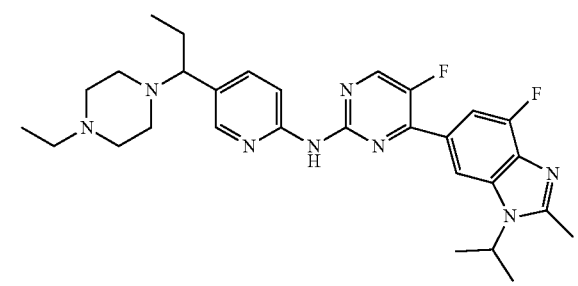

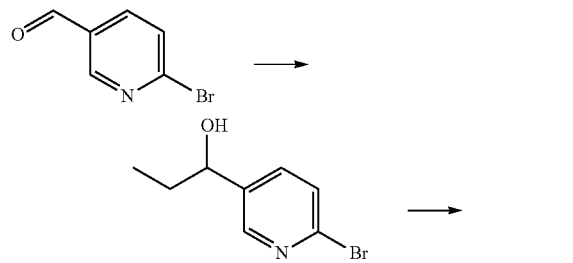

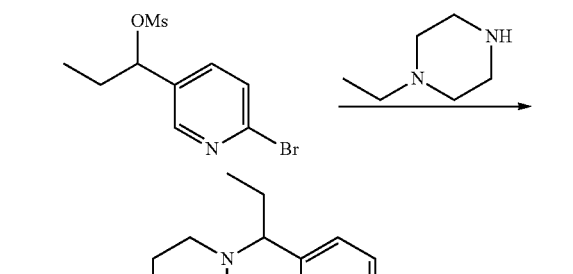

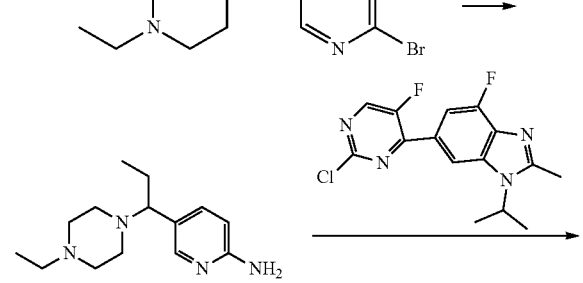

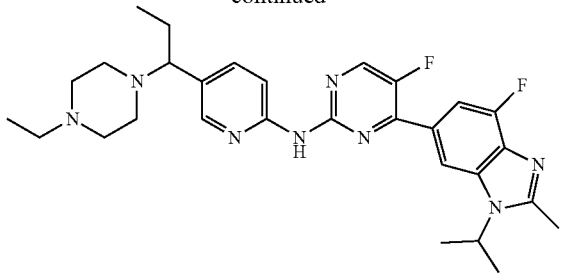

Step 1) 1-(6-bromopyridin-3-yl) propan-1-ol

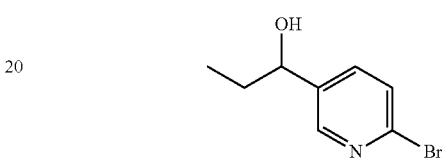

Ethyl magnesium bromide solution (2.0 M in THF, 16 mL) was added dropwise to a solution of 2-bromo-5-aldehyde pyridine (5.0 g, 26.9 mmol) in dry THF (50 mL) cooled in an ice-water bath under nitrogen atmosphere. After completion of the addition, the mixture was continued to stir for 1 h. TLC monitoring showed that the reaction was almost complete and the mixture was quenched with saturated ammonium chloride solution, diluted with water and extracted with ethyl acetate (50 mL×3). The combined organic phases were washed with brine, dried over anhydrous Na$_2$SO$_4$, filtered and concentrated. The residue was purified by column chromatography (hexane/acetate, 8/1) to give intermediate 1-(6-bromopyridin-3-yl) propan-1-ol as a colorless oil (3.8 g, 66% yield).

MS (ESI), m/z, 216.1 [M+1]$^+$.

Step 2) 1-(6-bromopyridin-3-yl) propyl methanesulfonate

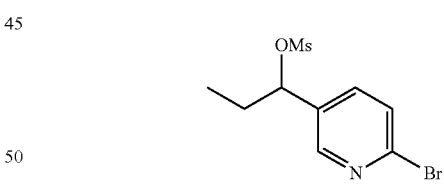

To a solution of 1-(6-bromopyridine-3-yl)propane-1-ol (3.3 g, 15.3 mmol) in dichloromethane solution (50 mL) was added triethylamine (3.1 g, 30.7 mmol) under nitrogen atmosphere, and then cooled to 0° C., methanesulfonyl chloride (2.6 g, 22.6 mmol) was added dropwise. After the completion of the addition, the mixture was continued to stir for 1 h. LCMS showed that the reaction was complete. The mixture was quenched with saturated NaHCO$_3$ solution, and extracted with dichloromethane (30 mL×3). The combined organic phases were washed with brine, dried over anhydrous Na$_2$SO$_4$, filtered, and concentrated. The residue was purified by column chromatography to give intermediate 1-(6-bromopyridin-3-yl) propyl methanesulfonate as a colorless oil (3.3 g, 69% yield).

MS (ESI), m/z, 294.1 [M+1]$^+$.

Step 3) 1-(1-(6-bromopyridin-3-yl) propyl)-4-ethylpiperazine

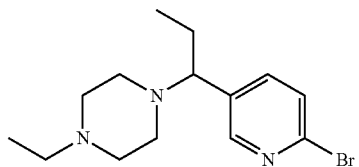 [SMILES: CCC(c1ccc(Br)nc1)N1CCN(CC)CC1]

To a solution of 1-(6-bromopyridin-3-yl) propyl methanesulfonate (4.5 g, 15.3 mmol) in DMF (50 mL) was added DIPEA (3.95 g, 30.6 mmol) and N-ethyl piperazine (3.49 g, 30.6 mmol) under nitrogen atmosphere. The mixture was heated to 80° C. and stirred for 12 h. TLC showed that the reaction was complete and the mixture was cooled to room temperature and quenched with water. The mixture was extracted with ethyl acetate (50 mL×3). The combined organic phases were washed with brine, dried over anhydrous $Na_2SO_4$, filtered, and concentrated to give intermediate 1-(1-(6-bromopyridin-3-yl) propyl)-4-ethylpiperazine as a white solid (4.5 g, 99% yield), which was used directly in the next step.

MS (ESI), m/z, 312.1 $[M+1]^+$.

$^1$H NMR (400 MHz, $CDCl_3$) δ (ppm) 8.20 (d, J=1.6 Hz, 1H), 7.48-7.34 (m, 2H), 3.18 (dd, J=9.1, 4.8 Hz, 1H), 2.89-2.17 (m, 11H), 1.91 (ddd, J=13.5, 7.4, 4.8 Hz, 1H), 1.66 (ddd, J=13.7, 9.0, 7.3 Hz, 1H), 1.05 (t, J=7.2 Hz, 3H), 0.71 (t, J=7.4 Hz, 3H).

Step 4) 5-(1-(4-ethylpiperazin-1-yl) propyl) pyridin-2-amine

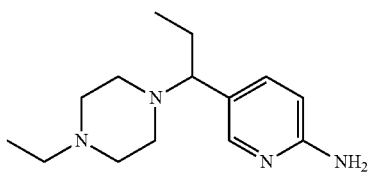 [SMILES: CCC(c1ccc(N)nc1)N1CCN(CC)CC1]

To a solution of 1-(1-(6-bromopyridin-3-yl) propyl)-4-ethylpiperazine (0.27 g, 0.91 mmol) in THF (5 mL) was added $Pd_2(dba)_3$ (82 mg, 0.09 mmol) and CyJohnPhos (63 mg, 0.18 mmol). The reaction flask was evacuated and purged with $N_2$, and heated to 50° C., LiHMDS (1.0 M in THF, 2.7 mL, 2.7 mmol) was added dropwise. After the addition, the mixture was heated to 65° C. for 4 h. TLC or LCMS showed that the reaction was complete, then the mixture was cooled to room temperature, quenched with water, concentrated, diluted with dichloromethane (20 mL), acidified to pH=1-2 with 2 N HCl, and the two layers were separated. The aqueous phase was washed with dichloromethane (10 mL×2), basified with 2 N NaOH to pH=10-12, extracted with dichloromethane (20 mL×4). The combined organic phases were washed with brine, dried over anhydrous $Na_2SO_4$, filtered, and concentrated to give intermediate 5-(1-(4-ethylpiperazin-1-yl) propyl)pyridin-2-amine as a colorless oil (0.22 g, 99% yield), which was used directly in the next step.

MS (ESI), m/z, 249.2 $[M+1]^+$.

Step 5)

N-(5-(1-(4-ethylpiperazin-1-yl)propyl)pyridin-2-yl)-5-fluoro-4-(4-fluoro-1-isopropyl-2-methyl-1H-benzo[d]imidazol-6-yl) pyrimidin-2-amine

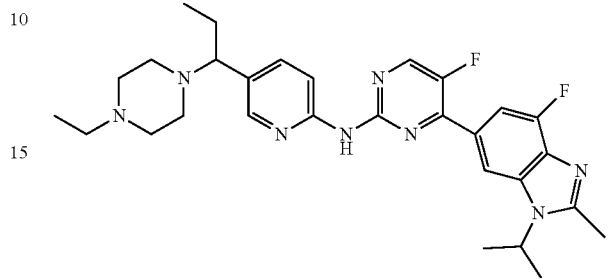

To a solution of 5-(1-(4-ethylpiperazin-1-yl) propyl) pyridin-2-amine (0.22 g, 0.89 mmol) in dioxane (10 mL) was added 6-(2-chloro-5-fluoropyrimidin-4-yl)-4-fluoro-1-isopropyl-2-methyl-1H-benzo[d]imidazole (0.29 g, 0.89 mmol), $Pd_2(dba)_3$ (81 mg, 0.09 mmol), XantPhos (103 mg, 0.18 mmol) and cesium carbonate (0.58 g, 1.78 mmol). The reaction flask was evacuated and purged with $N_2$ and heated to 110° C. for 1.5 h. TLC or LCMS showed that the reaction was complete, the mixture was cooled to room temperature, filtered with Celite, washed with dichloromethane. The filtrate was concentration and purified by Prep-TLC (DCM/MeOH=15/1) to give N-(5-(1-(4-ethylpiperazin-1-yl)propyl)pyridin-2-yl)-5-fluoro-4-(4-fluoro-1-isopropyl-2-methyl-1H-benzo[d]imidazol-6-yl)pyrimidin-2-amine as a white solid (240 mg, 98.2% HPLC purity, 51% yield).

MS (ESI), m/z, 535.3 $[M+1]^+$.

$^1$H NMR (400 MHz, $CDCl_3$) δ (ppm) 8.48-8.42 (m, 2H), 8.39 (d, J=8.6 Hz, 1H), 8.19 (d, J=0.9 Hz, 2H), 7.80 (d, J=12.3 Hz, 1H), 7.60 (dd, J=8.6, 2.2 Hz, 1H), 4.82-4.63 (m, 1H), 3.22 (dd, J=9.3, 4.6 Hz, 1H), 2.69 (s, 3H), 2.63-2.29 (m, 9H), 2.06-1.86 (m, 1H), 1.82-1.73 (m, 1H), 1.71 (d, J=7.0 Hz, 6H), 1.06 (t, J=7.2 Hz, 3H), 0.77 (t, J=7.3 Hz, 3H).

Example 2 & 3

(R or S)—N-(5-(1-(4-ethylpiperazin-1-yl)propyl) pyridin-2-yl)-5-fluoro-4-(4-fluoro-1-isopropyl-2-methyl-1H-benzo[d]imidazol-6-yl) pyrimidin-2-amine

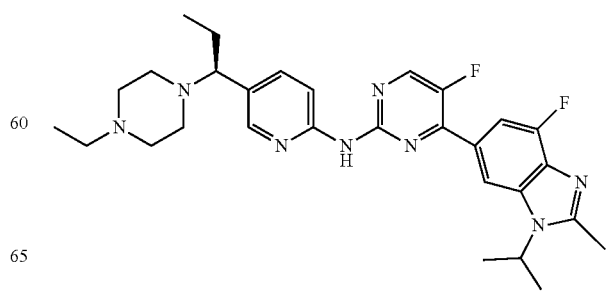

-continued

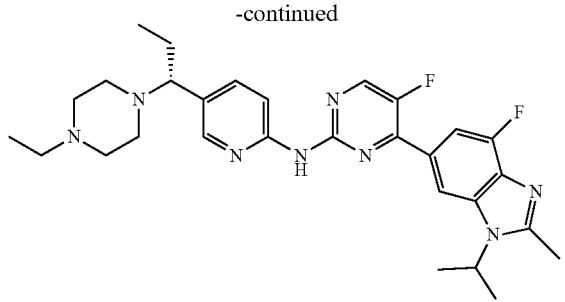

The racemic compound obtained in example 1 was separated by chiral column Chiralpak AD-H (10 mm×250 mm, 5 μm) at a column temperature of 40° C. Mobile phase A was 0.1% DEA in hexane (v/v), mobile phase B was ethanol, running time was 30 minutes, gradient was mobile phase A/mobile phase B (50/50, v/v), flow rate was 6.0 mL/min and detection wavelength was UV 210 nm. Two single-configuration compounds were separated and collected at RT of 15 minutes (compound of example 2) and 20 minutes (compound of example 3), respectively. The compounds were detected by chiral column Chiralpak AD-H (4.6 mm×250 mm) at a column temperature of 40° C. Mobile phase A was 0.1% DEA in hexane (v/v), mobile phase B was ethanol, running time was 20 minutes, gradient was mobile phase A/mobile phase B (50/50), flow rate was 1.0 mL/min, and detection wavelength was UV 210 nm. The first single configuration compound was example 2 (RT=10.4 min, 97.2% ee) and the second single configuration compound was example 3 (RT=14.2 min, 95.9% ee).

Example 4-15

The compounds of examples 4-15 in the following table were prepared according to the synthesis methods of examples 1-3 using the corresponding starting materials.

| Example | Structure | Characterization data |
|---|---|---|
| Example 4 | 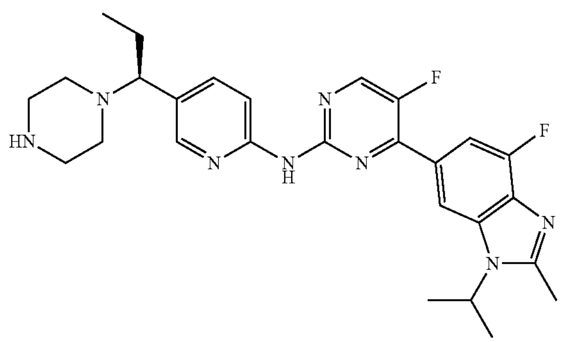 [SMILES: CC[C@@H](c1ccc(Nc2ncc(F)c(-c3cc(F)c4nc(C)n(C(C)C)c4c3)n2)nc1)N1CCNCC1] | MS-ESI, m/z: 507.2 [M + 1]$^+$ |
| Example 5 | 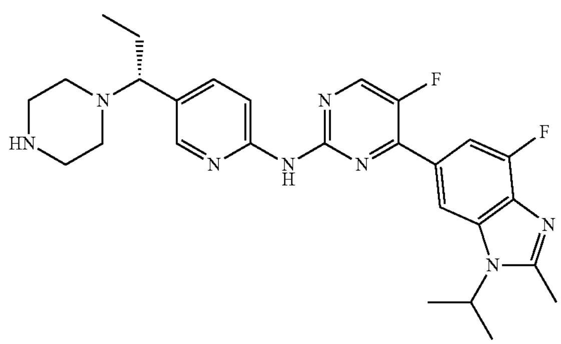 [SMILES: CC[C@H](c1ccc(Nc2ncc(F)c(-c3cc(F)c4nc(C)n(C(C)C)c4c3)n2)nc1)N1CCNCC1] | MS-ESI, m/z: 507.2 [M + 1]$^+$ |
| Example 6 | 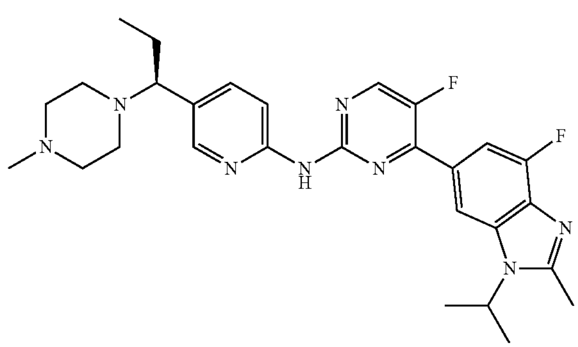 | MS-ESI, m/z: 521.3 [M + 1]$^+$ |

-continued
| Example | Structure | Characterization data |
|---|---|---|
| Example 7 | 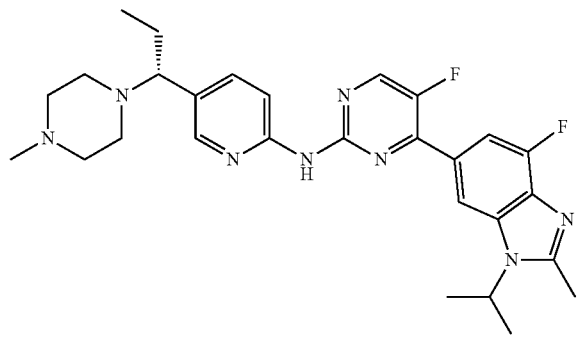 | MS-ESI, m/z: 521.3 [M + 1]$^+$ |
| Example 8 | 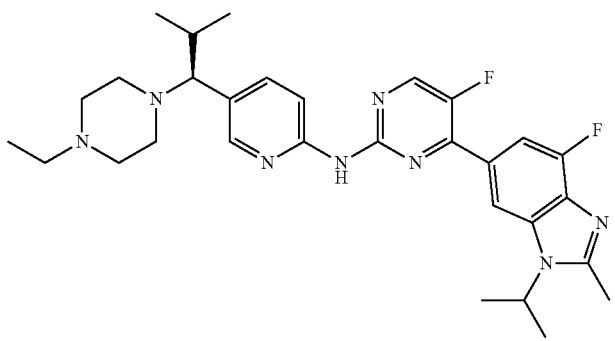 [SMILES: CCN1CCN([C@H](c2ccc(Nc3ncc(F)c(-c4cc(F)c5nc(C)n(C(C)C)c5c4)n3)nc2)C(C)C)CC1] | MS-ESI, m/z: 549.3 [M + 1]$^+$ |
| Example 9 | 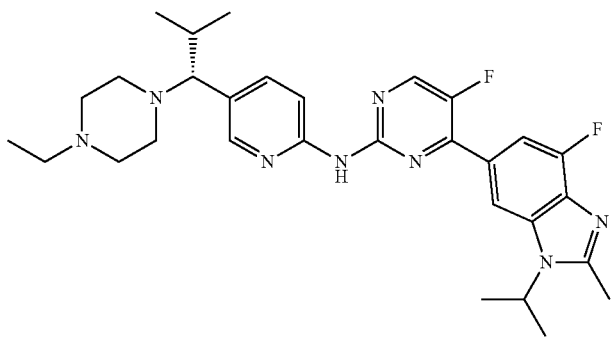 [SMILES: CCN1CCN([C@@H](c2ccc(Nc3ncc(F)c(-c4cc(F)c5nc(C)n(C(C)C)c5c4)n3)nc2)C(C)C)CC1] | MS-ESI, m/z: 549.3 [M + 1]$^+$ |
| Example 10 | 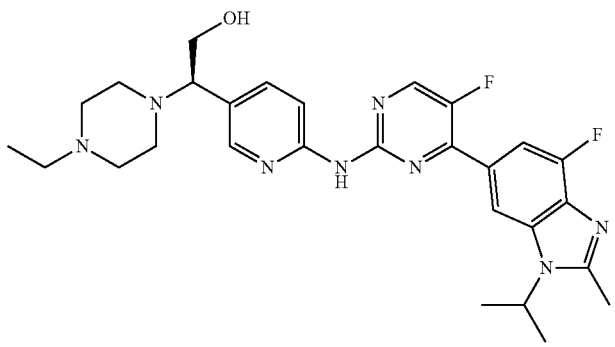 | MS-ESI, m/z: 537.2 [M + 1]$^+$ |

-continued
| Example | Structure | Characterization data |
|---|---|---|
| Example 11 | 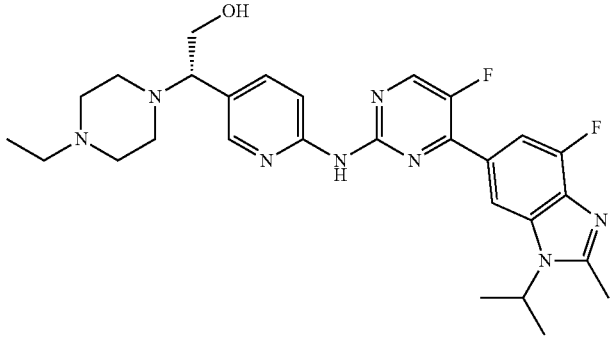 | MS-ESI, m/z: 537.2 [M + 1]+ |
| Example 12 | 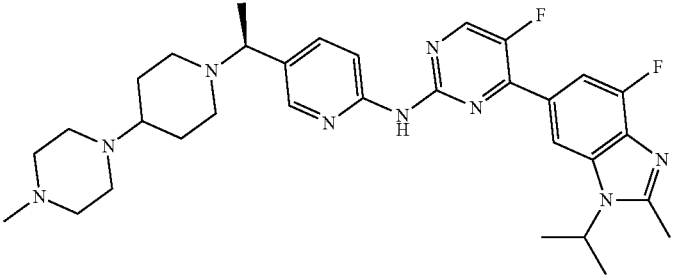 | MS-ESI, m/z: 590.3 [M + 1]+ |
| Example 13 | 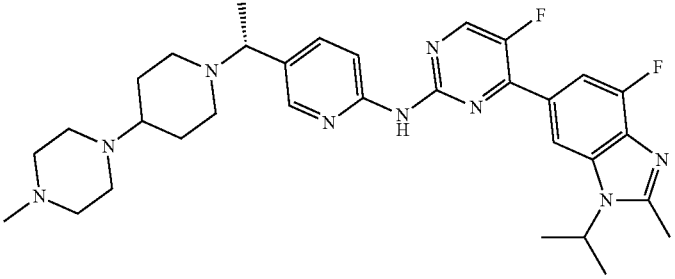 | MS-ESI, m/z: 590.3 [M + 1]+ |
| Example 14 | 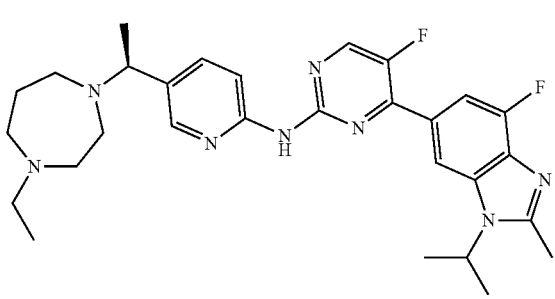 [SMILES: CCN1CCCN([C@@H](C)c2ccc(Nc3ncc(F)c(-c4cc(F)c5nc(C)n(C(C)C)c5c4)n3)nc2)CC1] | MS-ESI, m/z: 535.3 [M + 1]+ |
| Example 15 | 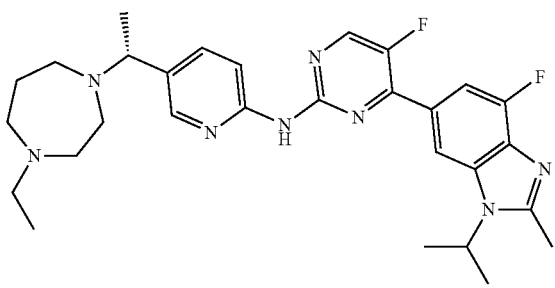 [SMILES: CCN1CCCN([C@H](C)c2ccc(Nc3ncc(F)c(-c4cc(F)c5nc(C)n(C(C)C)c5c4)n3)nc2)CC1] | MS-ESI, m/z: 535.3 [M + 1]+ |

Example 16

N-(5-(1-(1-ethylpiperidin-4-yl)ethyl)pyridin-2-yl)-5-fluoro-4-(4-fluoro-1-isopropyl-2-methyl-1H-benzo[d]imidazol-6-yl)pyrimidin-2-amine

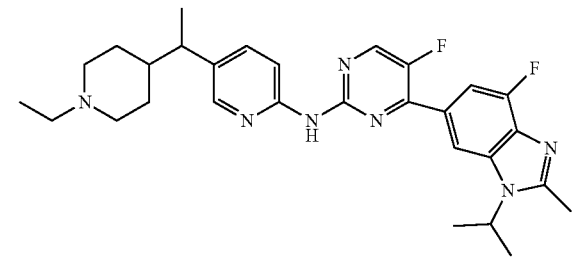

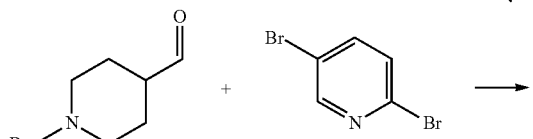

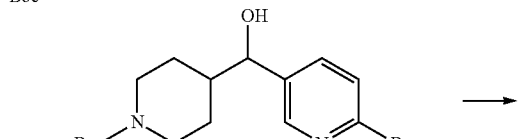

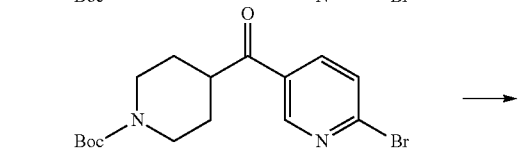

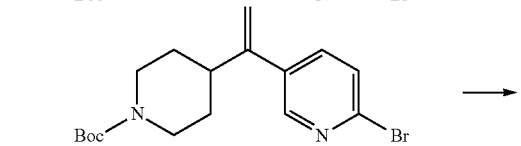

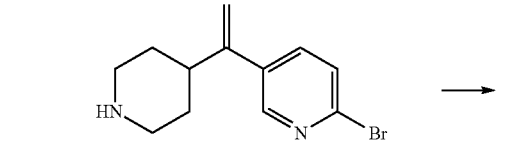

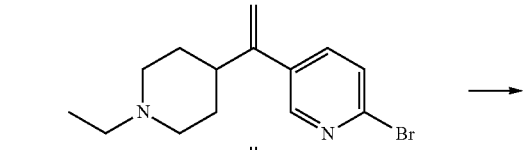

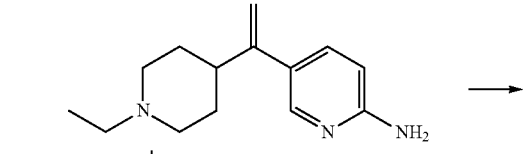

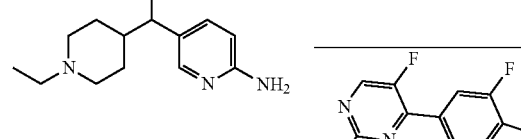

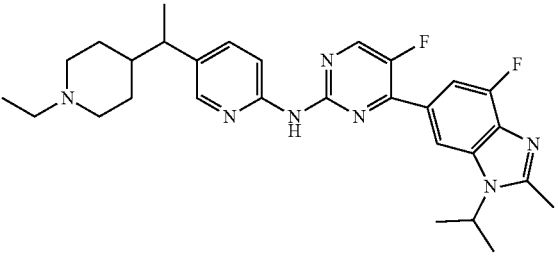 [SMILES: CCN1CCC(C(C)c2ccc(Nc3ncc(F)c(-c4cc(F)c5nc(C)n(C(C)C)c5c4)n3)nc2)CC1]

Step 1) tert-butyl 4-((6-bromopyridin-3-yl) (hydroxy)methyl) piperidine-1-carboxylate

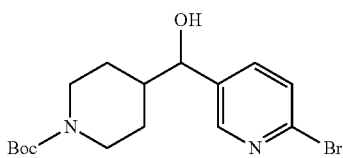 [SMILES: CC(C)(C)OC(=O)N1CCC(C(O)c2ccc(Br)nc2)CC1]

Isopropyl magnesium chloride (2.0 M in THF, 38 mL, 0.076 mol) was added dropwise to a solution of 2, 5-dibromopyridine (15.0 g, 0.063 mol) in dry THF (150 mL) at 0° C. under nitrogen atmosphere. After completion of the addition, the mixture was warmed to room temperature slowly and stirred for 2 h, and then cooled to 0° C., and a solution of 1-tert-butoxycarbonylpiperidine-4-formaldehyde (16.2 g, 0.076 mol) in THF (50 mL) was added into the above mixture. After stirring for 2 h (0-24° C.), TLC showed that the reaction was complete, and the mixture was quenched with saturated ammonium chloride solution, and extracted with ethyl acetate (50 mL×3). The combined organic phases were washed with brine, dried over anhydrous Na$_2$SO$_4$, filtered, and concentrated. The residue was purified by column chromatography to give intermediate tert-butyl 4-((6-bromopyridin-3-yl) (hydroxy)methyl) piperidine-1-carboxylate as a white solid (11.0 g, 47% yield).

MS (ESI), m/z, 315.1 [M−55]$^+$.

$^1$H NMR (400 MHz, CDCl$_3$) δ (ppm) 8.29 (d, J=2.3 Hz, 1H), 7.55 (dd, J=8.2, 2.4 Hz, 1H), 7.49 (d, J=8.1 Hz, 1H), 4.46 (d, J=6.9 Hz, 1H), 4.24-3.97 (m, 3H), 3.50 (d, J=6.2 Hz, 1H), 2.76-2.50 (m, 3H), 1.45 (d, J=5.4 Hz, 12H).

Step 2) tert-butyl 4-(6-bromonicotinoyl) piperidine-1-carboxylate

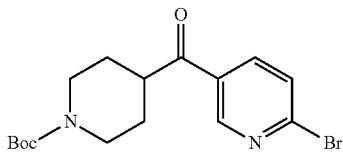 [SMILES: CC(C)(C)OC(=O)N1CCC(C(=O)c2ccc(Br)nc2)CC1]

To a solution of tert-butyl 4-((6-bromopyridin-3-yl) (hydroxy)methyl) piperidine-1-carboxylate (11.0 g, 0.030 mol) in dry dichloromethane (200 mL) at 0° C. under nitrogen atmosphere was added Dess-Martin oxidant (15.0 g, 0.036 mol) in portions, and the reaction was stirred for 1 h (0-15° C.). TLC showed that the reaction was complete, and the mixture was cooled to 0° C., then quenched with saturated Na₂S₂O₃ and saturated NaHCO₃. After stirring for 1 h, the layers were separated, and the aqueous phase was extracted with dichloromethane (50 mL×2). The combined organic phases were washed with brine, dried over anhydrous Na₂SO₄, filtered, and concentrated. The residue was purified by column chromatography (PE/EA=5/1-1/1) to give intermediate tert-butyl 4-(6-bromonicotinoyl) piperidine-1-carboxylate as a white solid (4.0 g, 68% yield).

MS (ESI), m/z, 313.1 [M−55]⁺.

Step 3) tert-butyl 4-(1-(6-bromopyridin-3-yl) vinyl) piperidine-1-carboxylate

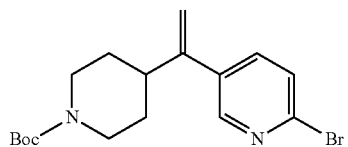 [SMILES: C=C(c1ccc(Br)nc1)C1CCN(C(=O)OC(C)(C)C)CC1]

n-BuLi (1.6 M in THF, 5.7 mL, 9.16 mmol) was added dropwise to a suspension solution of methyltriphenylphosphonium bromide (3.27 g, 9.16 mmol) in THF (20 mL) at −78° C. under nitrogen atmosphere. The reaction was stirred for 1 h, and a solution of tert-butyl 4-(6-bromonicotinoyl) piperidine-1-carboxylate (2.25 g, 6.11 mmol) in THF (10 mL) was added into the above solution, and the mixture was warmed to room temperature slowly. After stirring for 4 h, TLC or LCMS showed that the reaction was complete, and then the mixture was cooled to 0° C., quenched with saturated ammonium chloride solution, and extracted with ethyl acetate (50 mL×3). The combined organic phases were washed with brine, dried over anhydrous Na₂SO₄, filtered, and concentrated. The residue was purified by column chromatography to give intermediate tert-butyl 4-(1-(6-bromopyridin-3-yl) vinyl) piperidine-1-carboxylate as a white solid (1.2 g, 69% yield).

MS (ESI), m/z, 311.0 [M−55]⁺.
¹H NMR (400 MHz, CDCl₃) δ (ppm) 8.31 (dd, J=2.4, 0.7 Hz, 1H), 7.45 (qd, J=8.2, 1.6 Hz, 2H), 5.22 (s, 1H), 5.14 (s, 1H), 4.18 (s, 2H), 2.71 (d, J=12.3 Hz, 2H), 2.47 (t, J=11.8 Hz, 1H), 1.83-1.61 (m, 3H), 1.45 (s, 9H).

Step 4) 2-bromo-5-(1-(piperidin-4-yl) vinyl) pyridine

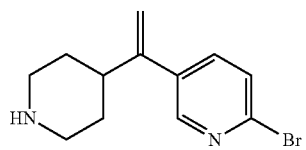

To a solution of tert-butyl 4-(1-(6-bromopyridin-3-yl) vinyl) piperidine-1-carboxylate (1.2 g, 3.28 mol) in dichloromethane (12 mL) was added TFA (3 mL). After stirring for 2 h (0-23° C.), LCMS showed that the reaction was complete, and the mixture was concentrated and diluted with dichloromethane and water (20/20 mL), neutralized with 2 N NaOH solution to pH>10. Then two layers were separated and the aqueous phase was extracted with dichloromethane (20 mL×2). The combined organic phases were washed with brine, dried over anhydrous Na₂SO₄, filtered, and concentrated to give intermediate 2-bromo-5-(1-(piperidin-4-yl) vinyl) pyridine as a colorless oil (0.86 g, 99% yield), which was used directly in next step.

MS (ESI), m/z, 267.0 [M+1]⁺.

Step 5) 2-bromo-5-(1-(1-ethylpiperidin-4-yl) vinyl) pyridine

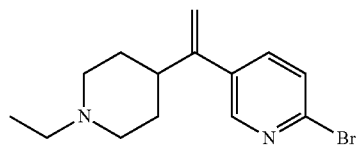 [SMILES: C=C(c1ccc(Br)nc1)C1CCN(CC)CC1]

To a solution of 2-bromo-5-(1-(piperidin-4-yl) vinyl) pyridine (0.86 g, 3.23 mmol) in dichloromethane (10 mL) was added acetaldehyde (0.43 g, 9.77 mmol). The mixture was stirred for 5 min, and then NaBH(OAc)₃ (2.05 g, 9.67 mmol) was added in portions. After stirring for 1 h (0-23° C.), LCMS showed the reaction was complete, then the mixture was cooled to 0° C., quenched with water, neutralized with 2 N NaOH solution, the two layers were separated, the aqueous phase was extracted with dichloromethane (20 mL×2). The combined organic phases was washed with brine, dried over anhydrous Na₂SO₄, filtered, and the filtrate was concentrated and purified by column chromatography (DCM)/MeOH=10/1, contained 1% NH₃.H₂O) to give intermediate 2-bromo-5-(1-(1-ethylpiperidin-4-yl) vinyl) pyridine as a colorless oil (0.58 g, 61% yield).

MS (ESI), m/z, 295.0 [M+1]⁺.

Step 6) 5-(1-(1-ethylpiperidin-4-yl) vinyl) pyridin-2-amine

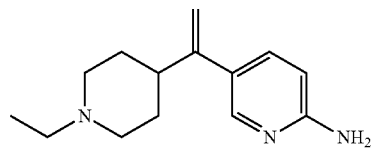 [SMILES: C=C(c1ccc(N)nc1)C1CCN(CC)CC1]

To a solution of 2-bromo-5-(1-(1-ethylpiperidin-4-yl) vinyl) pyridine (0.58 g, 1.96 mmol), in THF (10 mL) was added Pd₂(dba)₃ (180 mg, 0.20 mmol) and CyJohnPhos (140 mg, 0.39 mmol). The reaction flask was evacuated and purged with N₂ and heated to 50° C. LiHMDS (1.0 M in THF, 5.8 mL, 5.8 mmol) was added dropwise into the above mixture. After completion of the addition, the mixture was heated to 65° C. and stirred for 3 h. LCMS showed that the reaction was complete, the mixture was cooled to room temperature, quenched with water, concentrated, diluted with dichloromethane (20 mL), acidified to pH=1-2 with 2 N HCl, the two layers were separated, and the aqueous phase was washed with dichloromethane (20 mL×3). The aqueous phase was basified with 2 N NaOH to pH=10-12, extracted with dichloromethane (20 mL×3). The combined organic phases were washed with brine, dried over anhydrous Na₂SO₄, concentrated to give intermediate 5-(1-(1-ethylpiperidin-4-yl) vinyl) pyridin-2-amine as a colorless oil (0.44 g, 98% yield), which was used directly in the next step.

MS (ESI), m/z, 232.2 [M+1]⁺.

¹H NMR (400 MHz, CDCl₃) δ (ppm) 8.05 (s, 1H), 7.42 (dd, J=8.5, 2.4 Hz, 1H), 6.46 (d, J=8.5 Hz, 1H), 5.05 (d, J=49.3 Hz, 2H), 4.46 (s, 2H), 3.09 (d, J=11.7 Hz, 2H), 2.49 (q, J=7.2 Hz, 2H), 2.35 (t, J=11.9 Hz, 1H), 2.03 (t, J=11.1 Hz, 2H), 1.81 (d, J=13.3 Hz, 2H), 1.60 (ddd, J=15.7, 12.8, 3.5 Hz, 2H), 1.12 (t, J=7.2 Hz, 3H).

Step 7) 5-(1-(1-ethylpiperidin-4-yl) ethyl) pyridin-2-amine

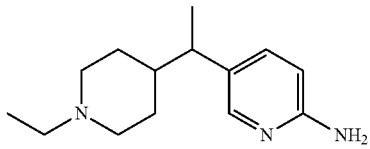

Pd/C (10%, 50 mg) was added to a solution of 5-(1-(1-ethylpiperidin-4-yl) vinyl) pyridin-2-amine (240 mg, 1.04 mmol) in methanol (10 mL). The reaction flask was evacuated and purged with H₂ and the reaction was stirred for 2 h. LCMS showed that the reaction was complete, then the mixture was filtered with Celite, washed with methanol, and the filtrate was concentrated to give intermediate 5-(1-(1-ethylpiperidin-4-yl) ethyl) pyridin-2-amine as a colorless oil (0.22 g, 91% yield), which was used directly in the next step.

MS (ESI), m/z, 234.2 [M+1]⁺.

Step 8) N-(5-(1-(1-ethylpiperidin-4-yl) ethyl) pyridin-2-yl)-5-fluoro-4-(4-fluoro-1-isopropyl-2-methyl-1H-benzo[d]imidazol-6-yl) pyrimidin-2-amine

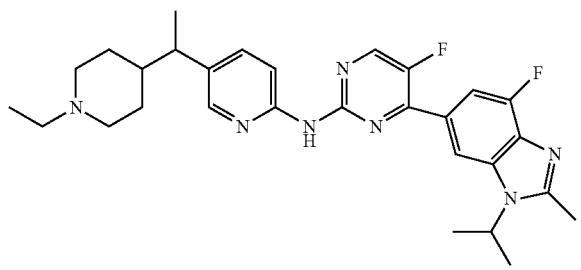 [SMILES: CCN1CCC(C(C)c2ccc(Nc3ncc(F)c(-c4cc(F)c5nc(C)n(C(C)C)c5c4)n3)nc2)CC1]

To a solution of 5-(1-(1-ethylpiperidin-4-yl)ethyl)pyridin-2-amine (220 mg, 0.94 mmol) in dioxane (10 mL) was added 6-(2-chloro-5-fluoropyrimidin-4-yl)-4-fluoro-1-isopropyl-2-methyl-1H-benzo[d]imidazole (304 mg, 0.94 mmol), Pd₂(dba)₃ (86 mg, 0.094 mmol), XantPhos (109 mg, 0.19 mmol) and cesium carbonate (613 mg, 1.89 mmol). The reaction flask was evacuated and purged with N₂ and heated to 110° C. for 2 h. LCMS showed that the reaction was complete, then the mixture was cooled to room temperature, filtered with Celite, washed with dichloromethane and the filtrate was concentrated and purified by Prep-TLC (DCM/MeOH=10/1) twice to give the racemic product N-(5-(1-(1-ethylpiperidin-4-yl) ethyl) pyridin-2-yl)-5-fluoro-4-(4-fluoro-1-isopropyl-2-methyl-1H-benzo[d]imidazol-6-yl) pyrimidin-2-amine as a white solid (0.18 g, 98.5% HPLC purity, 37% yield).

MS (ESI), m/z, 520.3 [M+1]⁺.

¹H NMR (400 MHz, CDCl₃) δ (ppm) 8.86 (s, 1H), 8.47 (d, J=3.7 Hz, 1H), 8.38 (d, J=8.6 Hz, 1H), 8.26-8.09 (m, 2H), 7.78 (d, J=11.7 Hz, 1H), 7.49 (dd, J=8.6, 2.3 Hz, 1H), 4.80-4.65 (m, 1H), 3.54 (d, J=11.6 Hz, 1H), 3.38 (d, J=11.1 Hz, 1H), 2.96 (q, J=7.2 Hz, 2H), 2.69 (s, 3H), 2.64-2.51 (m, 2H), 2.46 (t, J=11.9 Hz, 1H), 2.05 (dd, J=32.4, 13.3 Hz, 2H), 1.86 (d, J=10.1 Hz, 1H), 1.71 (dd, J=6.9, 1.8 Hz, 6H), 1.58 (d, J=12.6 Hz, 2H), 1.40 (t, J=7.3 Hz, 3H), 1.29 (d, J=7.0 Hz, 3H).

Examples 17 & 18

(R or S)—N-(5-(1-(1-ethylpiperidin-4-yl) ethyl) pyridin-2-yl)-5-fluoro-4-(4-fluoro-1-isopropyl-2-methyl-1H-benzo[d]imidazol-6-yl) pyrimidin-2-amine

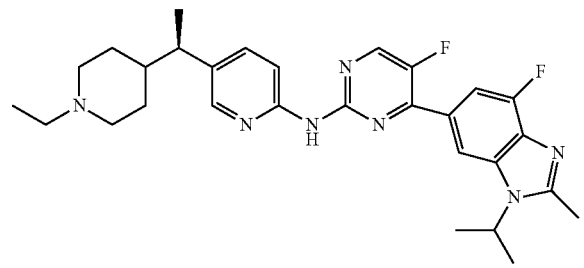

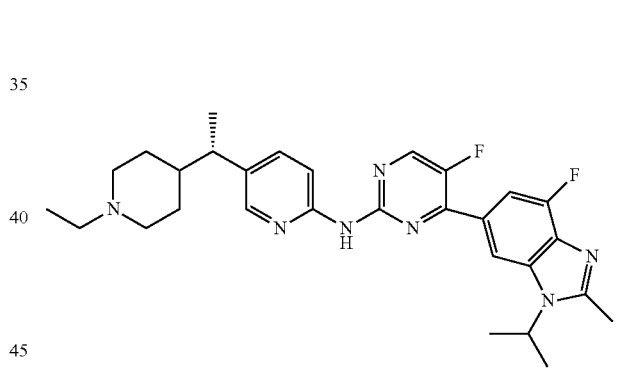

The racemic compound obtained in example 16 was separated by chiral column Chiralpak AS-H (10 mm×250 mm, 5 μm) at a column temperature of 40° C. Mobile phase was 0.1% DEA in hexane (v/v), mobile phase B was ethanol, running time was 30 minutes, gradient mobile was phase A/mobile phase B (80/20, v/v), flow rate was 3.0 mL/min and detection wavelength was UV 300 nm. Two single-configuration compounds were separated and collected at RT of 16 minutes (compound of example 17) and 22 minutes (compound of example 18), respectively. The compounds were detected by chiral column Chrialipak AS-H (4.6 mm×250 mm) at a column temperature of 40° C. Mobile phase A was 0.1% DEA in hexane (v/v), mobile phase B was ethanol, running time was 20 minutes, gradient was mobile phase A/mobile phase B (80/20), flow rate was 0.5 mL/min, and detection wavelength was UV 300 nm. The first single configuration compound was example 17 (RT=10.6 min, 99% ee), and the second single configuration compound was example 18 (RT=12.9 min, 99% ee).

Examples 19 & 20

(R or S)-5-fluoro-4-(4-fluoro-1-isopropyl-2-methyl-1H-benzo[d]imidazol-6-yl)-N-(5-(1-(piperidin-4-yl)ethyl) pyridin-2-yl) pyrimidin-2-amine

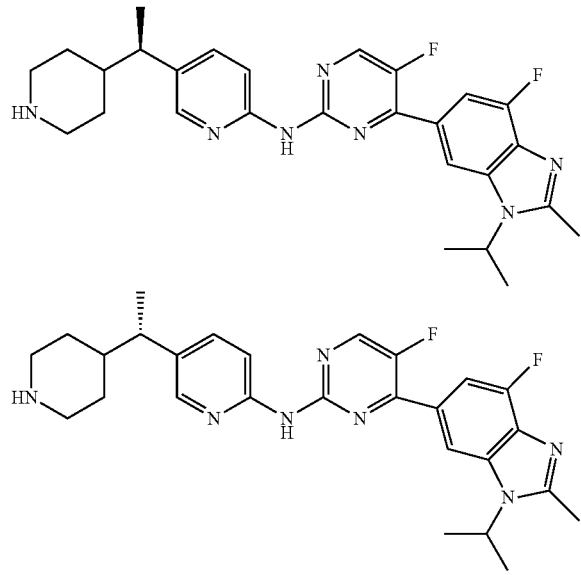

Step 1) tert-butyl 4-(1-(6-aminopyridin-3-yl) ethyl) piperidine-1-carboxylate

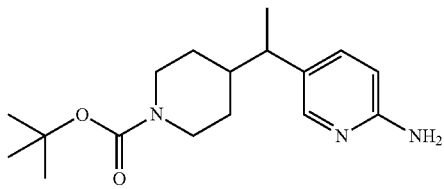 [SMILES: CC(c1ccc(N)nc1)C1CCN(C(=O)OC(C)(C)C)CC1]

The above intermediate can be obtained by a similar synthesis method to the intermediate 5-(1-(1-ethylpiperidin-4-yl) ethyl) pyridin-2-amine in example 18.
MS (ESI), m/z, 306.2 [M+1]$^+$.

Step 2) tert-butyl 4-(1-(6-((5-fluoro-4-(4-fluoro-1-isopropyl-2-methyl-1H-benzo[d]imidazol-6-yl) pyrimidin-2-yl) amino) pyridin-3-yl) ethyl) piperidine-1-carboxylate

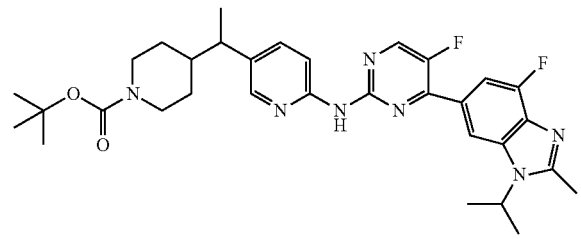 [SMILES: Cc1nc2c(F)cc(-c3nc(Nc4ccc(C(C)C5CCN(C(=O)OC(C)(C)C)CC5)cn4)ncc3F)cc2n1C(C)C]

The above intermediate can be obtained by a similar synthesis method to the intermediate in example 18.
MS (ESI), m/z, 592.3 [M+1]$^+$.

Step 3) 5-fluoro-4-(4-fluoro-1-isopropyl-2-methyl-1H-benzo[d]imidazol-6-yl)-N-(5-(1-(piperidin-4-yl) ethyl) pyridin-2-yl) pyrimidin-2-amine

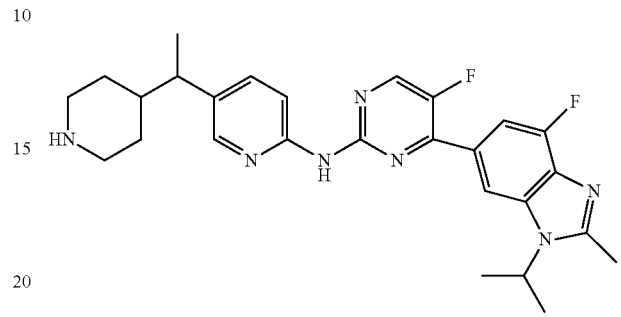

To a solution of the intermediate tert-butyl 4-(1-(6-((5-fluoro-4-(4-fluoro-1-isopropyl-2-methyl-1H-benzo[d] imidazol-6-yl) pyrimidin-2-yl) amino) pyridin-3-yl) ethyl) piperidine-1-carboxylate (329 mg, 0.56 mmol) in dichloromethane/methanol (5:1, 6 mL) was added a 6 N dioxane hydrochloride solution (3 mL) and the mixture was stirred for 12 h at room temperature. LCMS showed that the reaction was complete, and the mixture concentrated, diluted with dichloromethane, basified with 2 N NaOH and extracted with dichloromethane (30 mL×4). The combined organic phases were washed with brine, dried over anhydrous Na$_2$SO$_4$, concentrated, and purified by Prep-TLC (DCM/MeOH=8/1) to give the product 5-fluoro-4-(4-fluoro-1-isopropyl-2-methyl-1H-benzo[d]imidazol-6-yl)-N-(5-(1-(piperidin-4-yl) ethyl) pyridin-2-yl) pyrimidin-2-amine as a white solid (220 mg, 98.2% HPLC purity, 81% yield).
MS (ESI), m/z, 492.2 [M+1]$^+$.
$^1$H NMR (400 MHz, CDCl$_3$) δ 8.43 (d, J=3.7 Hz, 1H), 8.35 (d, J=8.6 Hz, 1H), 8.24 (s, 1H), 8.19 (s, 1H), 8.13 (s, 1H), 7.80 (d, J=11.6 Hz, 1H), 7.51 (dd, J=8.6, 2.0 Hz, 1H), 4.82-4.66 (m, 1H), 3.14 (d, J=12.0 Hz, 1H), 3.02 (d, J=12.2 Hz, 1H), 2.70 (s, 3H), 2.60 (dd, J=12.1, 10.0 Hz, 1H), 2.50 (dd, J=14.8, 7.9 Hz, 2H), 1.96-1.76 (m, 7H), 1.72 (d, J=6.9 Hz, 6H), 1.55-1.44 (m, 2H), 1.28 (d, J=7.0 Hz, 3H).

The racemic compound obtained in the third step was separated by chiral column Chiralpak AS-H (10 mm×250 mm, 5 μm) at a column temperature of 40° C. Mobile phase A was 0.1% DEA in hexane (v/v), mobile phase B was ethanol, running time was 30 minutes, and gradient was mobile phase A/mobile phase B (80/20, v/v), flow rate was 3.0 mL/min and detection wavelength was UV 300 nm. The two single-configuration compounds were separated and collected at RT of 13 minutes (compound of example 19) and 19 minutes (compound of example 20), respectively. The compounds were detected by chiral column Chiralpak AS-H (4.6 mm×250 mm) at a column temperature of 40° C. Mobile phase A was 0.1% DEA in hexane (v/v), mobile phase B was ethanol, running time was 20 minutes, gradient was mobile phase A/mobile phase B (80/20), flow rate was 0.5 mL/min and detection wavelength was UV 300 nm. The first single configuration compound was example 19 (RT=9.2 min, 98% ee), and the second single configuration compound was example 20 (RT=11.4 min, 97% ee).

Example 21-32

The compounds of examples 21-32 in the following table were prepared according to the synthesis methods of examples 16-20 using the corresponding starting materials.

| Example | Structure | Characterization data |
|---|---|---|
| Example 21 | 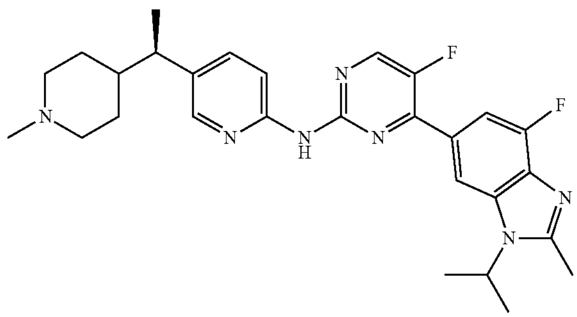 | MS-ESI, m/z: 506.2 [M + 1]$^+$<br>$^1$H NMR (400 MHz, CDCl$_3$) δ (ppm) 8.41 (d, J = 3.8 Hz, 1H), 8.33 (d, J = 8.6 Hz, 1H), 8.19 (s, 1H), 8.10 (d, J = 2.0 Hz, 1H), 7.93 (s, 1H), 7.80 (d, J = 11.6 Hz, 1H), 7.51 (dd, J = 8.6, 2.2 Hz, 1H), 4.74 (dt, J = 13.9, 7.0 Hz, 1H), 2.90 (d, J = 10.5 Hz, 1H), 2.78 (d, J = 11.0 Hz, 1H), 2.70 (s, 3H), 2.48 (t, J = 7.0 Hz, 1H), 2.23 (s, 3H), 2.08-1.96 (m, 1H), 1.94-1.74 (m, 3H), 1.71 (d, J = 6.9 Hz, 6H), 1.46-1.17 (m, 6H).<br>The compound was separated by chiral column Chiralpak AS-H, and chiral separation conditions were the same as in example 17 or 18. RT was 14.5 min. |
| Example 22 | 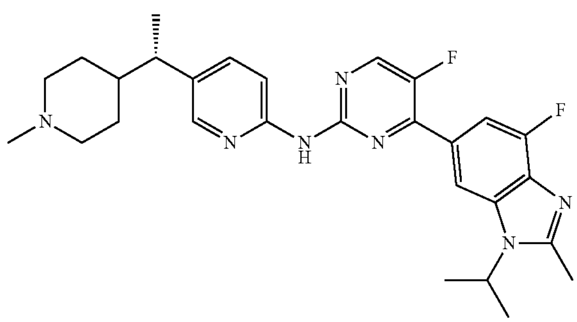 | MS-ESI, m/z: 506.2 [M + 1]$^+$<br>The compound was separated by chiral column Chiralpak AS-H, and chiral separation conditions were the same as in example 17 or 18. RT was 18 min. |
| Example 23 | 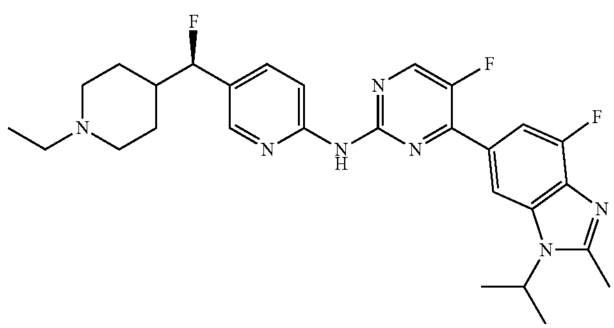 [SMILES: CCN1CCC([C@@H](F)c2ccc(Nc3ncc(F)c(-c4cc(F)c5nc(C)n(C(C)C)c5c4)n3)nc2)CC1] | MS-ESI, m/z: 524.3 [M + 1]$^+$ |
| Example 24 | 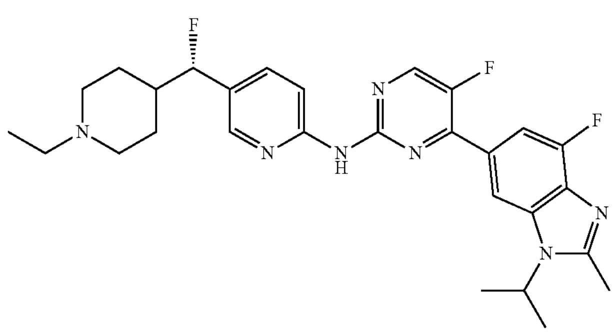 [SMILES: CCN1CCC([C@H](F)c2ccc(Nc3ncc(F)c(-c4cc(F)c5nc(C)n(C(C)C)c5c4)n3)nc2)CC1] | MS-ESI, m/z: 524.3 [M + 1]$^+$ |

| Example | Structure | Characterization data |
|---|---|---|
| Example 25 | 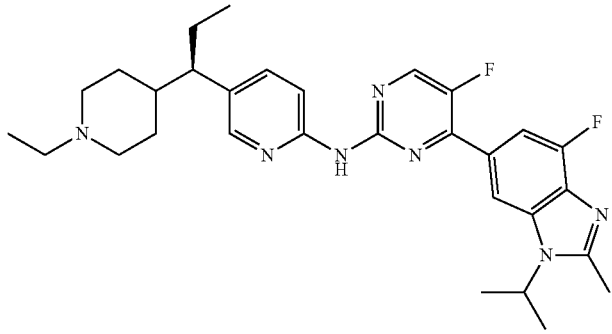 [SMILES: CC[C@@H](c1ccc(Nc2ncc(F)c(-c3cc(F)c4nc(C)n(C(C)C)c4c3)n2)nc1)C1CCN(CC)CC1] | MS-ESI, m/z: 534.3 [M + 1]+ |
| Example 26 | 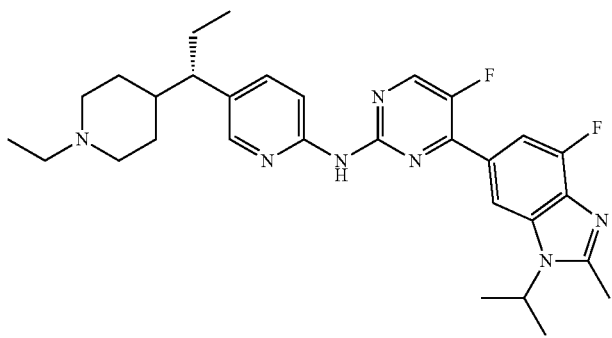 [SMILES: CC[C@H](c1ccc(Nc2ncc(F)c(-c3cc(F)c4nc(C)n(C(C)C)c4c3)n2)nc1)C1CCN(CC)CC1] | MS-ESI, m/z: 534.3 [M + 1]+ |
| Example 27 | 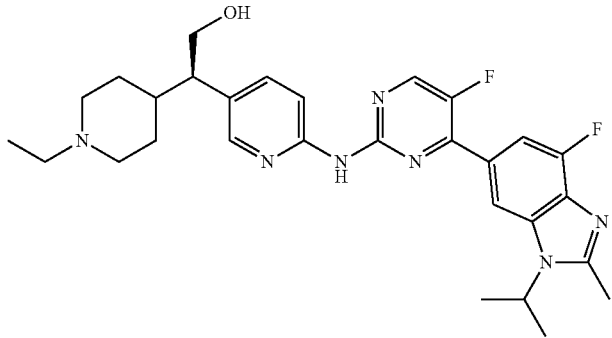 [SMILES: CCN1CCC([C@@H](CO)c2ccc(Nc3ncc(F)c(-c4cc(F)c5nc(C)n(C(C)C)c5c4)n3)nc2)CC1] | MS-ESI, m/z: 536.3 [M + 1]+ |
| Example 28 | 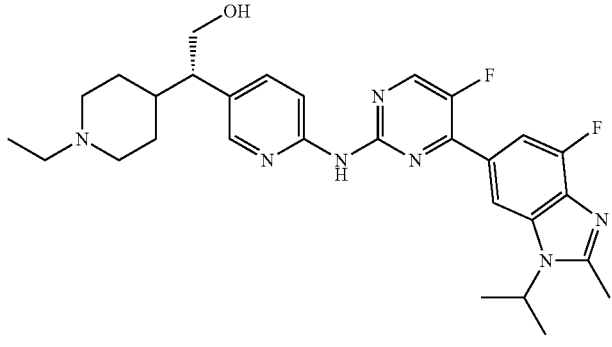 | MS-ESI, m/z: 536.2 [M + 1]+ |

-continued

| Example | Structure | Characterization data |
|---|---|---|
| Example 29 | 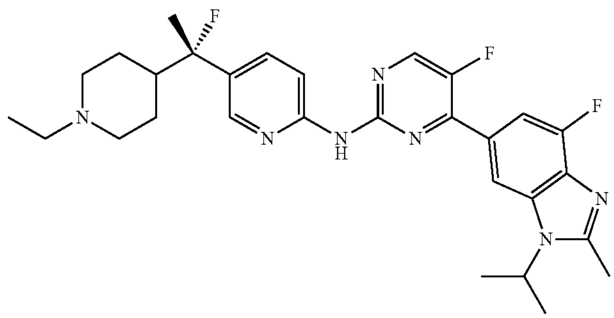 [SMILES: CCN1CCC([C@](C)(F)c2ccc(Nc3ncc(F)c(-c4cc(F)c5nc(C)n(C(C)C)c5c4)n3)nc2)CC1] | MS-ESI, m/z: 538.2 [M + 1]+ |
| Example 30 | 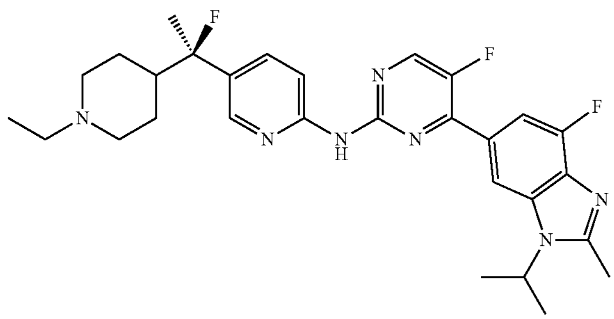 [SMILES: CCN1CCC([C@@](C)(F)c2ccc(Nc3ncc(F)c(-c4cc(F)c5nc(C)n(C(C)C)c5c4)n3)nc2)CC1] | MS-ESI, m/z: 538.2 [M + 1]+ |
| Example 31 | 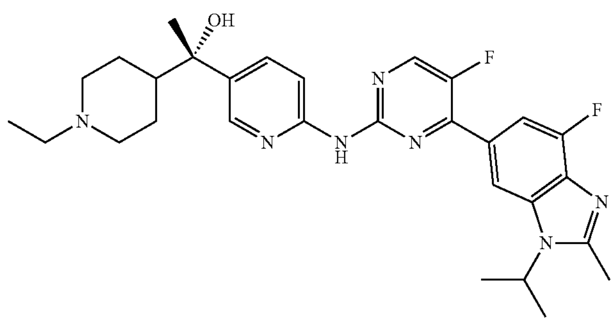 [SMILES: CCN1CCC([C@](C)(O)c2ccc(Nc3ncc(F)c(-c4cc(F)c5nc(C)n(C(C)C)c5c4)n3)nc2)CC1] | MS-ESI, m/z: 536.3 [M + 1]+ |
| Example 32 | 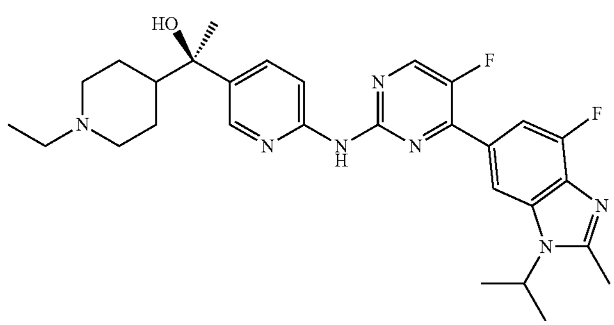 [SMILES: CCN1CCC([C@@](C)(O)c2ccc(Nc3ncc(F)c(-c4cc(F)c5nc(C)n(C(C)C)c5c4)n3)nc2)CC1] | MS-ESI, m/z: 536.3 [M + 1]+ |

Example 33

N-(5-(1-(1-ethylpiperidin-4-yl) vinyl) pyridin-2-yl)-5-fluoro-4-(4-fluoro-1-isopropyl-2-methyl-1H-benzo[d]imidazol-6-yl) pyrimidin-2-amine

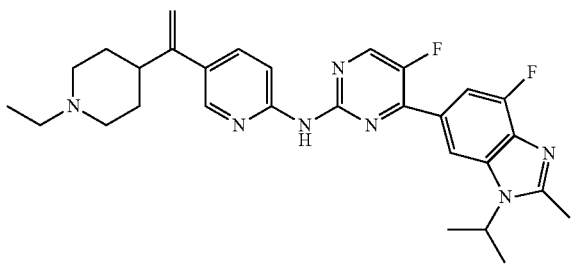 [SMILES: C=C(c1ccc(Nc2ncc(F)c(-c3cc(F)c4nc(C)n(C(C)C)c4c3)n2)nc1)C1CCN(CC)CC1]

To a solution of 5-(1-(1-ethylpiperidin-4-yl) vinyl) pyridine-2-amine (200 mg, 0.87 mmol) in dioxane (10 mL) was added 6-(2-chloro-5-fluoropyrimidin-4-yl)-4-fluoro-1-isopropyl-2-methyl-1H-benzo[d]imidazole (278 mg, 0.87 mmol), $Pd_2(dba)_3$ (79 mg, 0.086 mmol), XantPhos (100 mg, 0.17 mmol) and cesium carbonate (563 mg, 1.73 mmol). The reaction flask was evacuated and purged with $N_2$, and the mixture was heated to 110° C. for 2 h. LCMS showed that the reaction was complete, then the mixture was cooled to room temperature, filtered with Celite, washed with dichloromethane. The filtrate was concentrated, diluted with dichloromethane/water (20/10 mL), acidified with 2 N HCl to pH=1-2. The two layers were separated, and the aqueous phase was washed with dichloromethane (20 mL×2), basified with 2 N NaOH to pH=10-12 and extracted with dichloromethane (20 mL×3). The combined organic phases were washed with brine, dried over anhydrous $Na_2SO_4$, filtered, concentrated to give a crude product, which was purified by Prep-TLC (DCM/MeOH=10/1) twice to give the product N-(5-(1-(1-ethylpiperidin-4-yl) vinyl) pyridine-2-yl)-5-fluoro-4-(4-fluoro-1-isopropyl-2-methyl-1H-benzo[d]imidazole-6-yl) pyrimidine-2-amine as a white solid (0.17 g, 98.6% HPLC purity, 38% yield).

MS (ESI), m/z, 518.2 [M+1]$^+$.

$^1$H NMR (400 MHz, $CDCl_3$) δ (ppm) 8.64 (s, 1H), 8.47 (d, J=3.7 Hz, 1H), 8.43 (d, J=8.7 Hz, 1H), 8.34 (s, 1H), 8.17 (s, 1H), 7.79 (d, J=11.4 Hz, 1H), 7.66 (dd, J=8.7, 2.4 Hz, 1H), 5.25 (d, J=54.3 Hz, 2H), 4.74 (dt, J=14.0, 7.0 Hz, 1H), 3.60 (s, 2H), 3.07 (q, J=7.3 Hz, 2H), 2.70 (s, 6H), 2.29 (s, 2H), 2.05 (s, 2H), 1.71 (d, J=7.0 Hz, 6H), 1.48 (t, J=7.3 Hz, 3H).

Examples 34-38

The compounds of examples 34-38 in the following table were prepared according to the synthesis method of example 33 using the corresponding starting materials.

| Example | Structure | Characterization data |
|---|---|---|
| Example 34 | 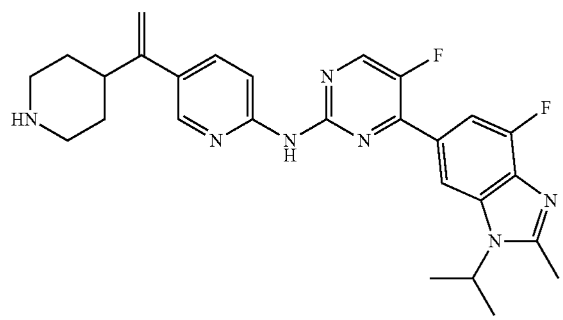 [SMILES: C=C(c1ccc(Nc2ncc(F)c(-c3cc(F)c4nc(C)n(C(C)C)c4c3)n2)nc1)C1CCNCC1] | MS-ESI, m/z: 490.2 [M + 1]$^+$ |
| Example 35 | 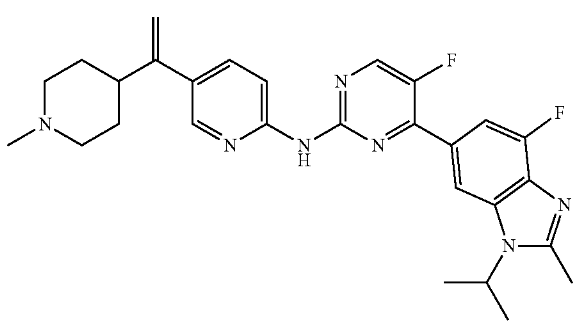 | MS-ESI, m/z: 504.2 [M + 1]$^+$ |

-continued
| Example | Structure | Characterization data |
|---|---|---|
| Example 36 | 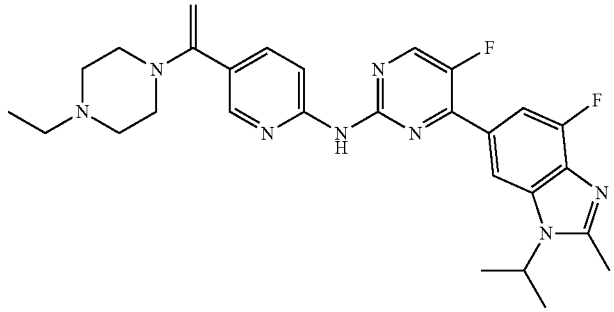 [SMILES: C=C(c1ccc(Nc2ncc(F)c(-c3cc(F)c4nc(C)n(C(C)C)c4c3)n2)nc1)N1CCN(CC)CC1] | MS-ESI, m/z: 519.2 [M + 1]⁺ |
| Example 37 | 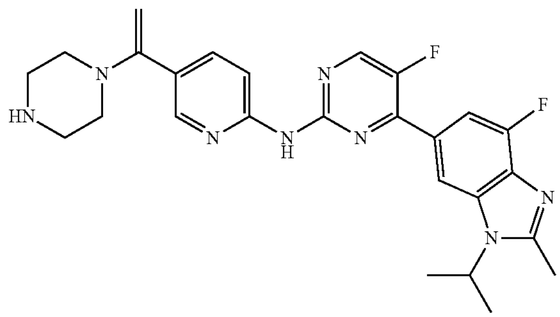 [SMILES: C=C(c1ccc(Nc2ncc(F)c(-c3cc(F)c4nc(C)n(C(C)C)c4c3)n2)nc1)N1CCNCC1] | MS-ESI, m/z: 491.2 [M + 1]⁺ |
| Example 38 | 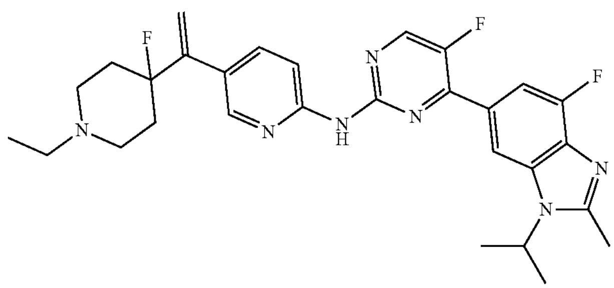 [SMILES: C=C(c1ccc(Nc2ncc(F)c(-c3cc(F)c4nc(C)n(C(C)C)c4c3)n2)nc1)C1(F)CCN(CC)CC1] | MS-ESI, m/z: 536.3 [M + 1]⁺ |
Example 39
(1-Ethylpiperidin-4-yl)(6-((5-fluoro-4-(4-fluoro-1-isopropyl-2-methyl-1H-benzo[d]imidazol-6-yl)pyrimidin-2-yl)amino)pyridin-3-yl)methanol
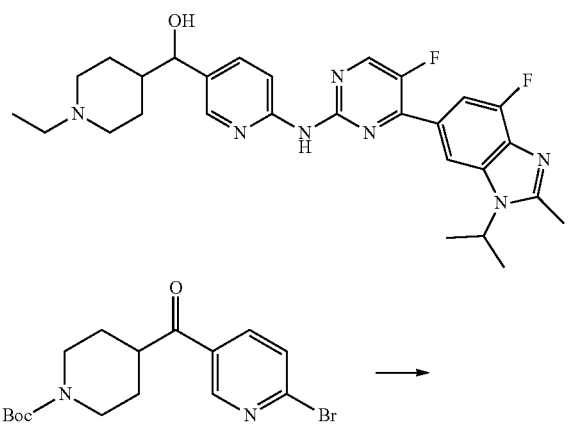
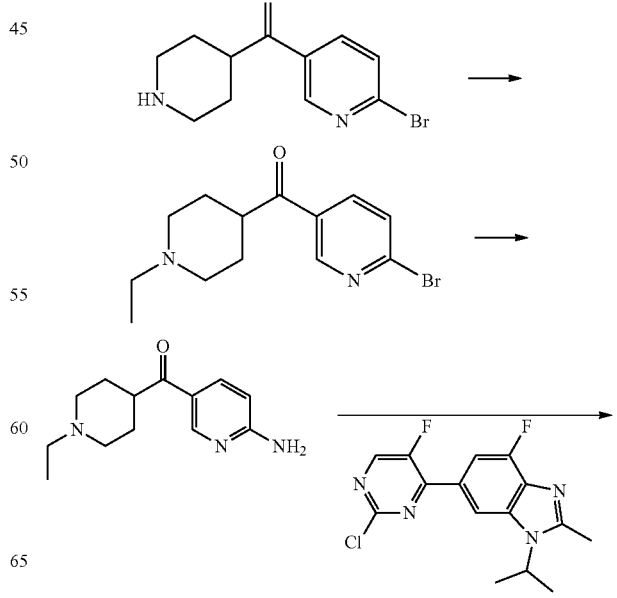

-continued

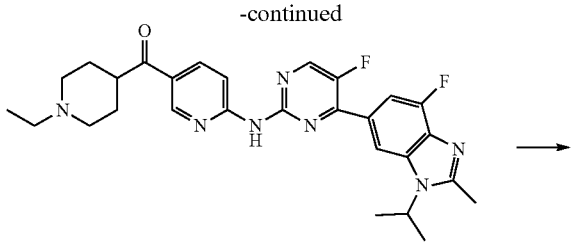

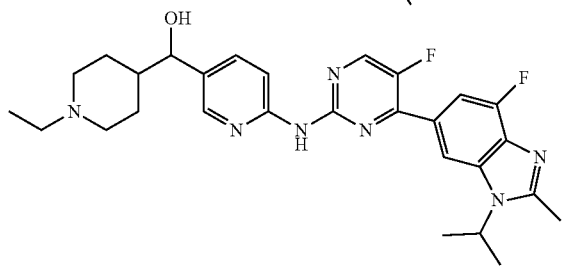

Step 1) (6-bromopyridin-3-yl) (piperidin-4-yl) methanone

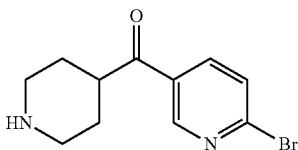 [SMILES: O=C(c1ccc(Br)nc1)C1CCNCC1]

To a solution of tert-butyl 4-(6-bromonicotinoyl)piperidine-1-carboxylate (1.0 g, 2.71 mmol) in dichloromethane (10 mL) at 0° C. was added TFA (4 mL) and stirred for 1 h (0-23° C.). TLC showed that the starting material disappeared, and the mixture was concentrated, diluted with water (10 mL), neutralized with saturated NaHCO$_3$, and extracted with dichloromethane (30 mL×4). The combined organic phases were washed with brine, dried over anhydrous Na$_2$SO$_4$, filtered and concentrated to give (6-bromopyridin-3-yl) (piperidin-4-yl) methanone as a white solid (0.64 g, 88% yield).

MS (ESI), m/z, 269.0 [M+1]$^+$.

Step 2) (6-bromopyridin-3-yl) (1-ethylpiperidin-4-yl) methanone

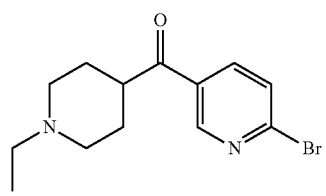 [SMILES: CCN1CCC(C(=O)c2ccc(Br)nc2)CC1]

To a solution of (6-bromopyridin-3-yl) (piperidin-4-yl) methanone (0.64 g, 2.38 mmol) in dichloromethane (10 mL) was added acetaldehyde (0.31 g, 7.14 mmol) at 0° C., and stirred for 10 min, then solid NaBH(OAc)$_3$ (1.0 g, 4.76 mmol) was added and continued to stir for 12 h (0-24° C.). TLC showed that the reaction was complete, and the mixture was quenched with water and saturated with NaHCO$_3$. The two layers were separated, and the aqueous phase was extracted with dichloromethane (15 mL×2). The combined organic phases were washed with brine, dried over anhydrous Na$_2$SO$_4$ filtered. And the filter was concentrated and purified by column chromatography (DCM/MeOH=10/1, contained 1% NH$_3$.H$_2$O) to give intermediate (6-bromopyridin-3-yl) (1-ethylpiperidin-4-yl) methanone as gum, yield (0.52 g, 74% yield).

MS (ESI), m/z, 297.0 [M+1]$^+$.

Step 3) (6-aminopyridin-3-yl)(1-ethylpiperidin-4-yl) methanone

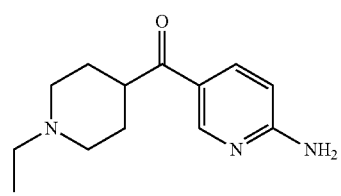 [SMILES: CCN1CCC(C(=O)c2ccc(N)nc2)CC1]

To a solution of (6-bromopyridin-3-yl) (1-ethylpiperidin-4-yl) methanone (0.52 g, 1.75 mmol) in ethylene glycol (10 mL) was added K$_2$CO$_3$ (48 mg, 0.35 mmol), DMEDA (15 mg, 0.17 mmol), Cu$_2$O (25 mg, 0.17 mmol) and 28% ammonia (10 mL). The reaction flask was evacuated and purged with N$_2$ and heated to 80° C. for 4 h. LCMS showed that the reaction was complete, and the mixture was cooled to room temperature, diluted with water and extracted with ethyl acetate (20 mL×3). The combined organic phases were washed with brine, dried over anhydrous Na$_2$SO$_4$, filtered, and concentrated to give intermediate (6-aminopyridin-3-yl) (1-ethylpiperidin-4-yl) methanone as a colorless oil (0.38 g, 95% yield), which was used directly in the next step.

MS (ESI), m/z, 234.2 [M+1]$^+$.

Step 4) (1-ethylpiperidin-4-yl)(6-((5-fluoro-4-(4-fluoro-1-isopropyl-2-methyl-1H-benzo [d]imidazol-6-yl) pyrimidin-2-yl) amino) pyridin-3-yl) methanone

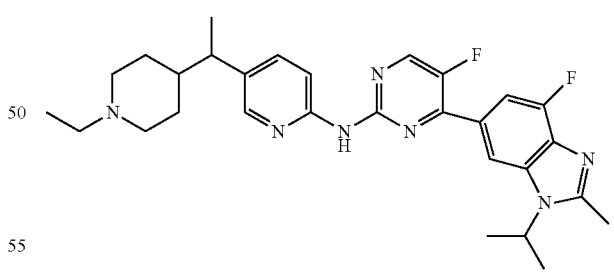

To a solution of (6-aminopyridin-3-yl)(1-ethylpiperidin-4-yl) methanone (0.38 g, 1.63 mmol) in dioxane (5 mL) was added 6-(2-chloro-5-fluoropyrimidin-4-yl)-4-fluoro-1-isopropyl-2-methyl-1H-benzo[d]imidazole (0.53 g, 1.63 mmol), Pd$_2$(dba)$_3$ (150 mg, 0.16 mmol), XantPhos (188 mg, 0.33 mmol) and cesium carbonate (1.1 g, 3.38 mmol). The reaction flask was evacuated and purged with N$_2$ and heated to 110° C. for 2 h. LCMS showed that the reaction was complete, and the mixture was cooled to room temperature, filtered with Celite, washed with dichloromethane and the filtrate was concentrated to give the residue which was purified by column chromatography (DCM/MeOH=20/1-10/1, contained 1% NH₃.H₂O) to give (1-ethylpiperidin-4-yl)(6-((5-fluoro-4-(4-fluoro-1-isopropyl-2-methyl-1H-benzo[d]imidazol-6-yl) pyrimidin-2-yl) amino) pyridin-3-yl) methanone as a white solid (0.35 g, 71% yield).

MS (ESI), m/z, 520.2 [M+1]⁺.

Step 5) (1-ethylpiperidin-4-yl)(6-((5-fluoro-4-(4-fluoro-1-isopropyl-2-methyl-1H-benzo [d]imidazol-6-yl) pyrimidin-2-yl) amino) pyridin-3-yl) methanol

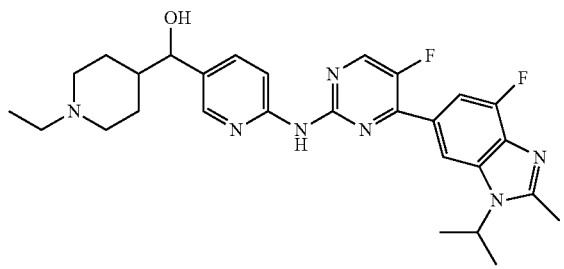

To a solution of (1-ethylpiperidin-4-yl)(6-((5-fluoro-4-(4-fluoro-1-isopropyl-2-methyl-1H-benzo[d]imidazol-6-yl) pyrimidin-2-yl) amino) pyridin-3-yl) methanone (0.15 g, 0.29 mmol) in methanol (5 mL) was added NaBH₄ (33 mg, 0.87 mmol) solid at 0° C. and stirred for 0.5 h. LCMS showed that reaction was complete, and the mixture was quenched with water, extracted with ethyl acetate (20 mg×3). The combined organic phases were washed with brine, dried over anhydrous sodium sulfate, filtered and the filture was concentrated. The residue was purified by Prep-HPLC (DCM/MeOH=10/1) twice to give racemic product (1-ethylpiperidin-4-yl) (6-((5-fluoro-4-(4-fluoro-1-isopropyl-2-methyl-1H-benzo[d]imidazol-6-yl)pyrimidin-2-yl) amino) pyridin-3-yl) methanol as a white solid (20 mg, 98.2% HPLC purity).

MS (ESI), m/z, 522.2 [M+1]⁺.
¹H NMR (400 MHz, DMSO) δ (ppm) 10.12 (s, 2H), 8.71 (d, J=3.8 Hz, 1H), 8.31 (s, 1H), 8.24 (dd, J=5.2, 3.0 Hz, 2H), 7.71 (d, J=11.5 Hz, 2H), 5.53 (d, J=4.4 Hz, 1H), 4.92-4.74 (m, 1H), 4.37 (dt, J=11.0, 5.7 Hz, 1H), 3.50-3.41 (m, 2H), 3.00 (d, J=6.7 Hz, 2H), 2.79 (s, 2H), 2.66 (s, 3H), 2.00 (d, J=15.2 Hz, 1H), 1.79 (s, 1H), 1.70-1.40 (m, 9H), 1.23 (q, J=6.9 Hz, 3H).

Examples 40 & 41

(R or S)-(1-ethylpiperidin-4-yl)(6-((5-fluoro-4-(4-fluoro-1-isopropyl-2-methyl-1H-benzo [d]imidazol-6-yl) pyrimidin-2-yl) amino) pyridin-3-yl) methanol

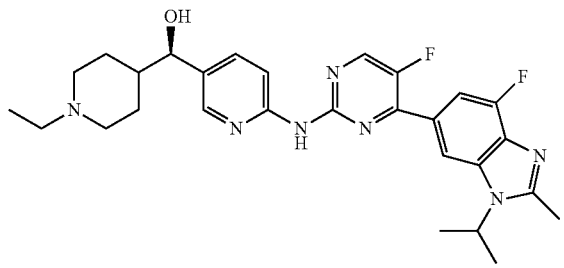

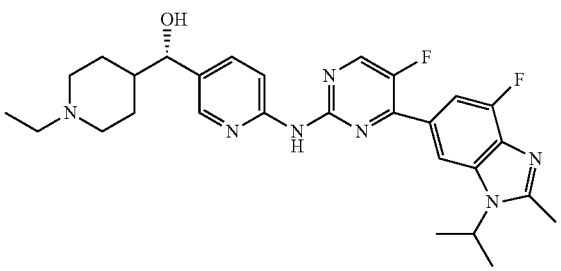 [SMILES: CCN1CCC(C(O)c2ccc(Nc3ncc(F)c(-c4cc(F)c5nc(C)n(C(C)C)c5c4)n3)nc2)CC1]

The racemic compound obtained in example 39 was separated by chiral column Chiralpak AD-H (10 mm×250 mm, 5 μm) with a column temperature of 40° C. Mobile phase A was 0.1% DEA in hexane (v/v), mobile phase B was ethanol, running time was 50 minutes, and gradient was mobile phase A/mobile phase B (50/50, v/v), flow rate was 3.0 mL/min and detection wavelength was UV 210 nm. The two single-configuration compounds were separated at the retention time of 30 minutes (compound of example 40) and 36 minutes (compound of example 41), respectively. The compounds were detected by chiral column CHRIARPAK AD-H (4.6 mm×250 mm) at a column temperature of 40° C. Mobile phase A was 0.1% DEA in hexane (v/v), mobile phase B was ethanol, running time was 30 minutes, gradient was mobile phase A/mobile phase B (50/50), flow rate was 0.5 mL/min, and detection wavelength was UV 210 nm. The first single configuration compound was example 40 (RT=25.3 min, 97% ee), and the second single configuration compound was example 41 (RT=30.0 min, 96% ee).

Example 42

(6-((5-Fluoro-4-(4-fluoro-1-isopropyl-2-methyl-1H-benzo[d]imidazol-6-yl) pyrimidin-2-yl) amino) pyridin-3-yl)(piperidin-4-yl) methanol hydrochloride

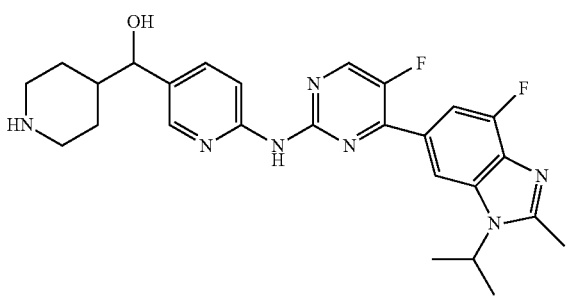

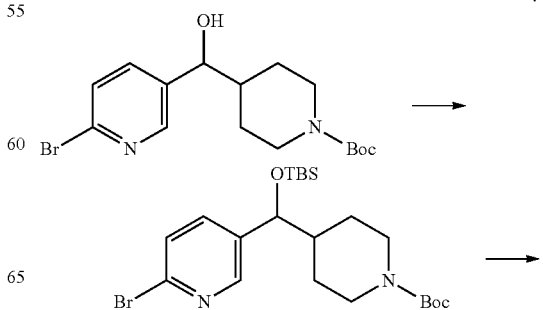

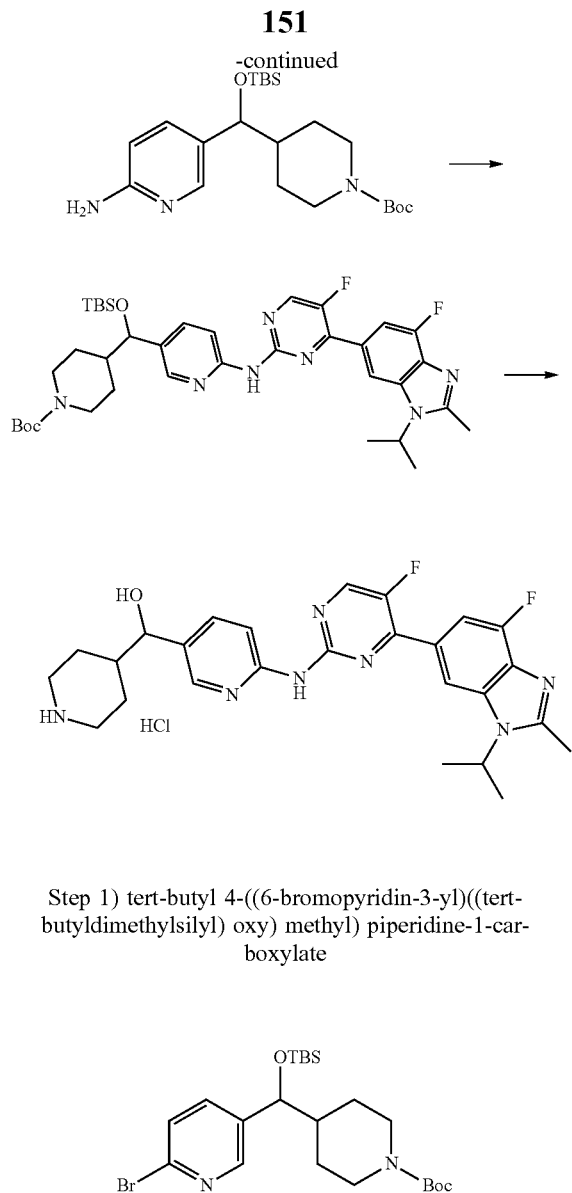

Step 1) tert-butyl 4-((6-bromopyridin-3-yl)((tert-butyldimethylsilyl) oxy) methyl) piperidine-1-carboxylate To a solution of 4-((6-bromopyridine-3-yl)(hydroxy) methyl) piperidine-1-carboxylic acid tert-butyl ester tert-butyl 4-((6-bromopyridin-3-yl)(hydroxy)methyl)piperidine-1-carboxylate (203 mg, 0.55 mmol) in DMF (5 mL) was added imidazole (186 mg, 2.74 mmol) and TBSCI (123 mg, 0.83 mmol) and the mixture was stirred at room temperature for 8 h. LCMS showed that the reaction was complete, 5.0 eq imidazole and 1.5 eq TBSCI were added into the above mixture and heated to 30° C. for 12 h. Another 5.0 eq imidazole and 1.5 eq TBSCI were added into the above mixture and stirred for 4 h. LCMS showed that the reaction was complete, and the mixture was quenched with water, extracted with ethyl acetate (20 mL×3). The combined organic phases were washed with brine, dried over anhydrous Na$_2$SO$_4$, filtered and the filtrue was concentrated and purified by Agela-HPLC (PE in EA from 0-50%) to give intermediate tert-butyl 4-((6-bromopyridin-3-yl)((tert-butyldimethylsilyl) oxy) methyl) piperidine-1-carboxylate as a colorless gum (0.26 g, 99% yield), which was used directly in the next step.

MS (ESI), m/z, 419.1 [M−55]$^+$.

Step 2) tert-butyl 4-((6-aminopyridin-3-yl) ((tert-butyldimethylsilyl) oxy) methyl) piperidine-1-carboxylate

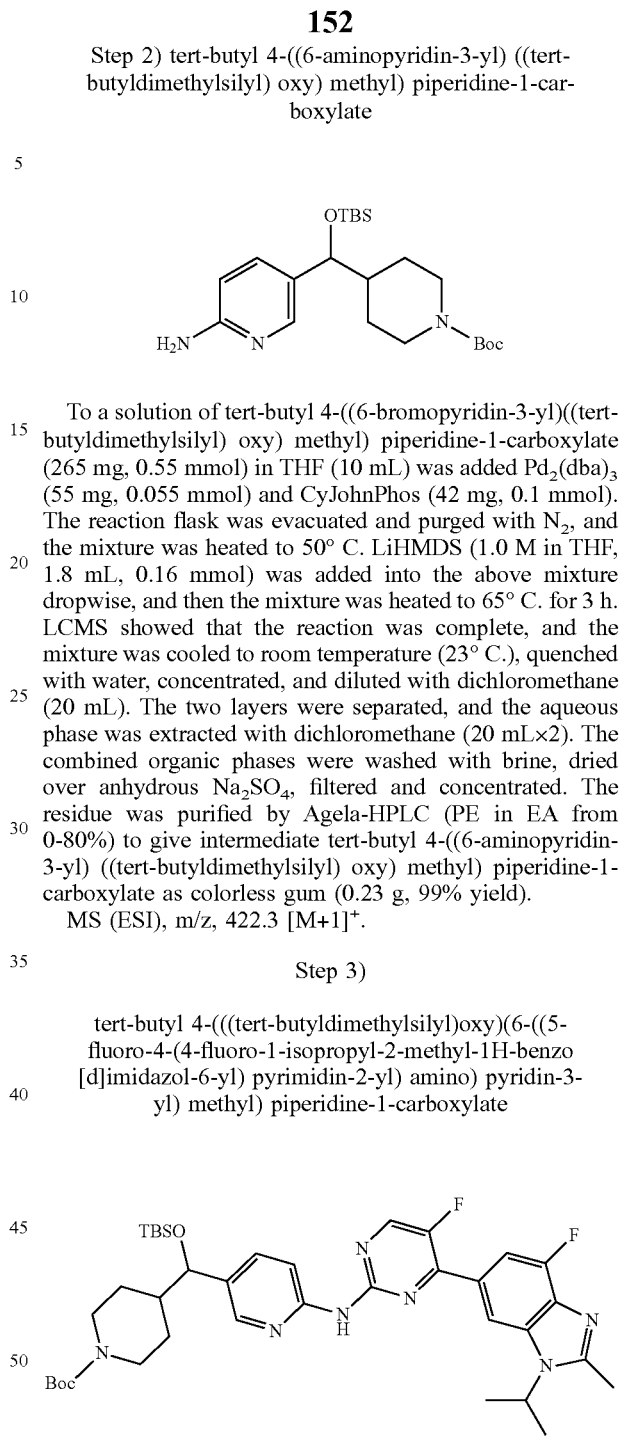

To a solution of tert-butyl 4-((6-bromopyridin-3-yl)((tert-butyldimethylsilyl) oxy) methyl) piperidine-1-carboxylate (265 mg, 0.55 mmol) in THF (10 mL) was added Pd$_2$(dba)$_3$ (55 mg, 0.055 mmol) and CyJohnPhos (42 mg, 0.1 mmol). The reaction flask was evacuated and purged with N$_2$, and the mixture was heated to 50° C. LiHMDS (1.0 M in THF, 1.8 mL, 0.16 mmol) was added into the above mixture dropwise, and then the mixture was heated to 65° C. for 3 h. LCMS showed that the reaction was complete, and the mixture was cooled to room temperature (23° C.), quenched with water, concentrated, and diluted with dichloromethane (20 mL). The two layers were separated, and the aqueous phase was extracted with dichloromethane (20 mL×2). The combined organic phases were washed with brine, dried over anhydrous Na$_2$SO$_4$, filtered and concentrated. The residue was purified by Agela-HPLC (PE in EA from 0-80%) to give intermediate tert-butyl 4-((6-aminopyridin-3-yl) ((tert-butyldimethylsilyl) oxy) methyl) piperidine-1-carboxylate as colorless gum (0.23 g, 99% yield).

MS (ESI), m/z, 422.3 [M+1]$^+$.

Step 3)

tert-butyl 4-(((tert-butyldimethylsilyl)oxy)(6-((5-fluoro-4-(4-fluoro-1-isopropyl-2-methyl-1H-benzo[d]imidazol-6-yl) pyrimidin-2-yl) amino) pyridin-3-yl) methyl) piperidine-1-carboxylate To a solution of tert-butyl 4-((6-aminopyridin-3-yl) ((tert-butyldimethylsilyl) oxy) methyl) piperidine-1-carboxylate (0.23 g, 0.55 mmol) in dioxane (10 mL) was added 6-(2-chloro-5-fluoropyrimidin-4-yl)-4-fluoro-1-isopropyl-2-methyl-1H-benzo[d]imidazole (176 mg, 0.55 mmol), Pd$_2$(dba)$_3$ (50 mg, 0.055 mmol), XantPhos (63 mg, 0.1 mmol) and cesium carbonate (355 mg, 1.1 mmol). The reaction flask was evacuated and purged with N$_2$ and the mixture was heated to 110° C. for 2 h. LCMS showed that the reaction was complete, and the mixture was cooled to room temperature, filtered with Celite, washed with dichloromethane and the filtrue was concentrated. The residue was purified by Agela-HPLC (PE in EA from 0-80%) to give intermediate tert-butyl 4-(((tert-butyldimethylsilyl)oxy) (6-((5-fluoro-4-(4-fluoro-1-isopropyl-2-methyl-1H-benzo [d] imidazol-6-yl)pyrimidin-2-yl) amino)pyridin-3-yl)methyl)piperidine-1-carboxylate as colorless gum (0.3 g, 78% yield).
MS (ESI), m/z, 708.1 [M+1]$^+$.

Step 4) (6-((5-fluoro-4-(4-fluoro-1-isopropyl-2-methyl-1H-benzo[d]imidazol-6-yl) pyrimidin-2-yl) amino) pyridin-3-yl) (piperidin-4-yl) methanol hydrochloride

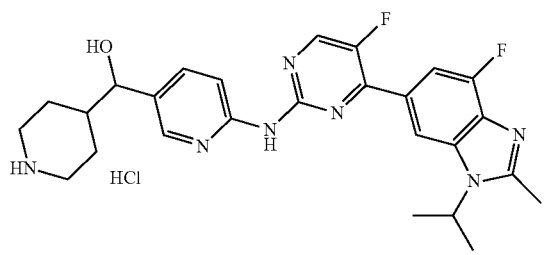 [SMILES: Cc1nc2c(F)cc(-c3nc(Nc4ccc(C(O)C5CCNCC5)cn4)ncc3F)cc2n1C(C)C ; Cl]

To a solution of tert-butyl 4-(((tert-butyldimethylsilyl) oxy) (6-((5-fluoro-4-(4-fluoro-1-isopropyl-2-methyl-1H-benzo [d] imidazol-6-yl)pyrimidin-2-yl) amino)pyridin-3-yl)methyl)piperidine-1-carboxylate (0.3 g, 0.42 mmol) in methanol (5 mL) was added HCl in dioxane (4.0 M, 2 mL) and the mixture was stirred for 12 h. LCMS showed that the reaction was complete and the mixture was concentrated to give crude product (6-((5-fluoro-4-(4-fluoro-1-isopropyl-2-methyl-1H-benzo[d]imidazol-6-yl)pyrimidin-2-yl) amino) pyridin-3-yl)(piperidin-4-yl) methanol hydrochloride as a white solid (224 mg, 99% yield).

MS (ESI), m/z, 494.2 [M+1]$^+$.

Examples 43-56

The compounds of examples 43-56 in the following table were prepared according to the synthesis method of examples 39-42 using the corresponding starting materials.

| Example | Structure | Characterization data |
| --- | --- | --- |
| Example 43 | 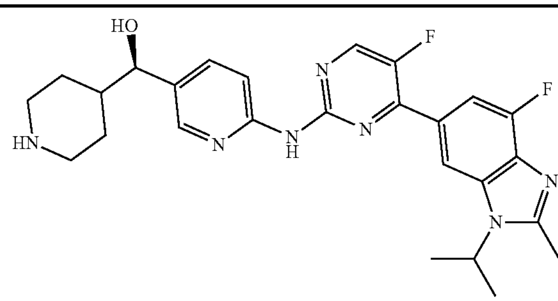 | MS-ESI, m/z: 494.2 [M + 1]$^+$ |
| Example 44 | 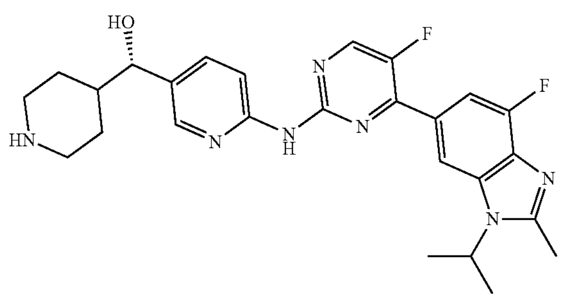 [SMILES: Cc1nc2c(F)cc(-c3nc(Nc4ccc([C@@H](O)C5CCNCC5)cn4)ncc3F)cc2n1C(C)C] | MS-ESI, m/z: 494.2 [M + 1]$^+$ |
| Example 45 | 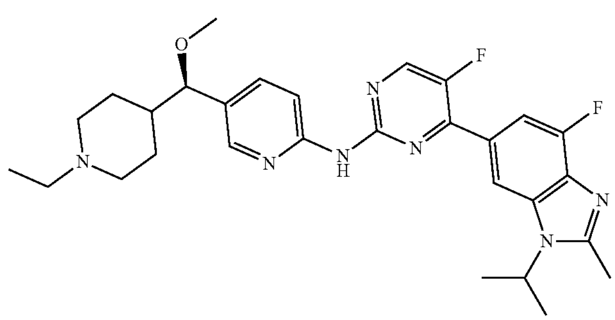 [SMILES: CCN1CCC([C@@H](OC)c2ccc(Nc3ncc(F)c(-c4cc(F)c5nc(C)n(C(C)C)c5c4)n3)nc2)CC1] | MS-ESI, m/z: 536.2 [M + 1]$^+$ <br> $^1$H NMR (400 MHz, CDCl$^3$) δ (ppm) 8.85 (d, J = 9.1 Hz, 1H), 8.62-8.45 (m, 2H), 8.10 (s, 1H), 8.00 (d, J = 9.1 Hz, 1H), 7.90 (d, J = 11.2 Hz, 1H), 4.95-4.73 (m, 1H), 3.96 (d, J = 7.0 Hz, 1H), 3.66 (dd, J = 34.5, 11.7 Hz, 2H), 3.25 (s, 3H), 3.07 (d, J = 6.7 Hz, 2H), 2.86 (s, 3H), 2.72-2.44 (m, 2H), 2.31 (d, J = 14.0 Hz, 1H), 2.02-1.81 (m, 3H), 1.78 (d, J = 6.9 Hz, 6H), 1.49 (d, J = 12.3 Hz, 1H), 1.36 (t, J = 7.3 Hz, 3H). The compound was separated with chiral column Chiralpak AD-H, and chiral separation conditions were the same as in example 40 or 41. RT was 23 min. |

| Example | Structure | Characterization data |
|---|---|---|
| Example 46 | 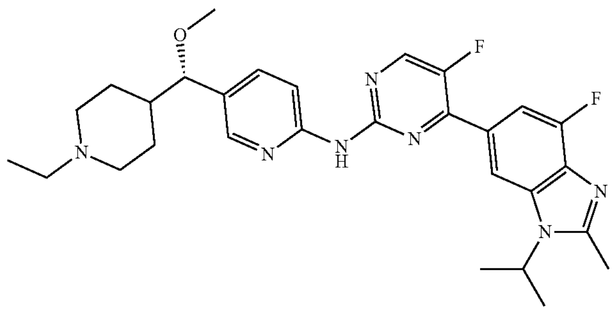 [SMILES: CCN1CCC([C@H](OC)c2ccc(Nc3ncc(F)c(-c4cc(F)c5nc(C)n(C(C)C)c5c4)n3)nc2)CC1] | MS-ESI, m/z: 436.2 [M + 1]$^+$ The compound was separated with chiral column Chiralpak AD-H, and chiral separation conditions were the same as in example 40 or 41. RT was 29 min. |
| Example 47 | 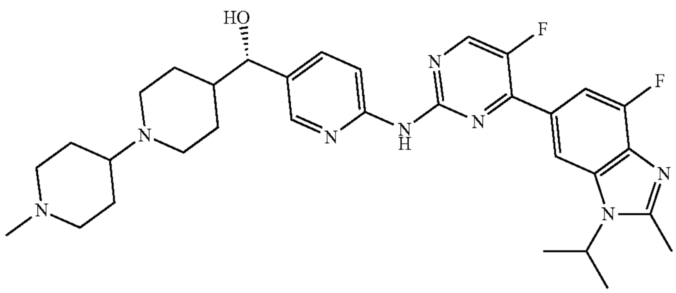 | MS-ESI, m/z: 591.3 [M + 1]$^+$ |
| Example 48 | 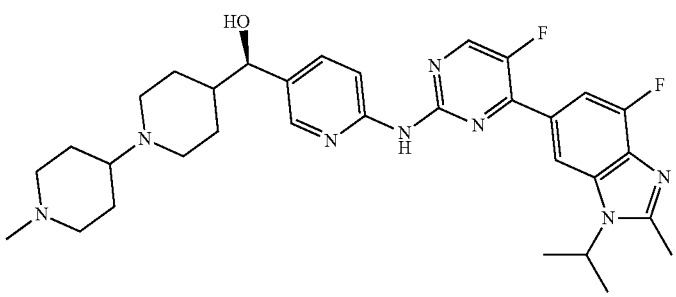 | MS-ESI, m/z: 591.3 [M + 1]$^+$ |
| Example 49 | 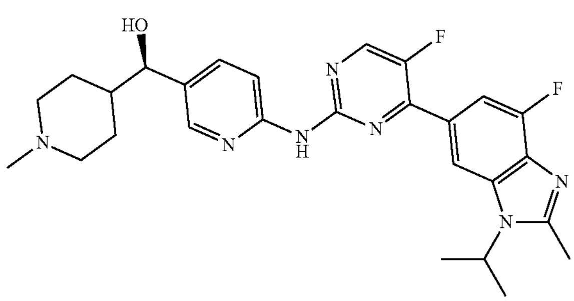 | MS-ESI, m/z: 508.2 [M + 1]$^+$ |
| Example 50 | 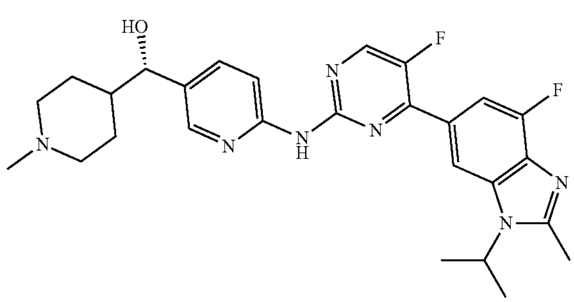 | MS-ESI, m/z: 508.2 [M + 1]$^+$ |

| Example | Structure | Characterization data |
|---|---|---|
| Example 51 | 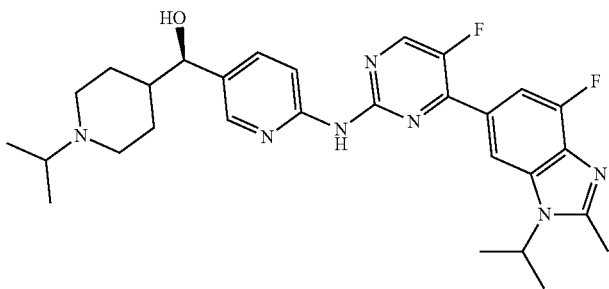 [SMILES: Cc1nc2c(F)cc(-c3nc(Nc4ccc([C@H](O)C5CCN(C(C)C)CC5)cn4)ncc3F)cc2n1C(C)C] | MS-ESI, m/z: 536.3 [M + 1]$^+$ |
| Example 52 | 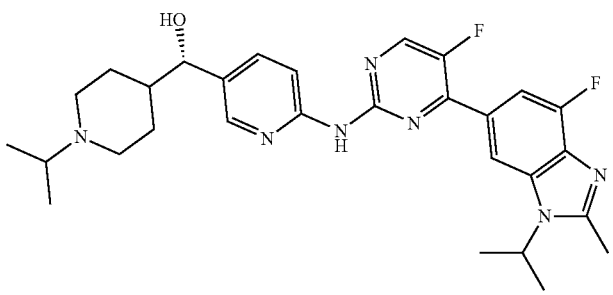 [SMILES: Cc1nc2c(F)cc(-c3nc(Nc4ccc([C@@H](O)C5CCN(C(C)C)CC5)cn4)ncc3F)cc2n1C(C)C] | MS-ESI, m/z: 536.3 [M + 1]$^+$ |
| Example 53 | 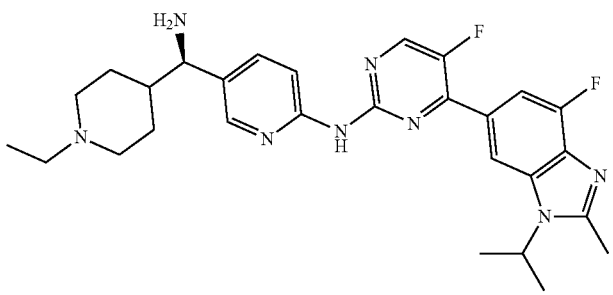 [SMILES: CCN1CCC([C@@H](N)c2ccc(Nc3ncc(F)c(-c4cc(F)c5nc(C)n(C(C)C)c5c4)n3)nc2)CC1] | MS-ESI, m/z: 520.3 [M + 1]$^+$ |
| Example 54 | 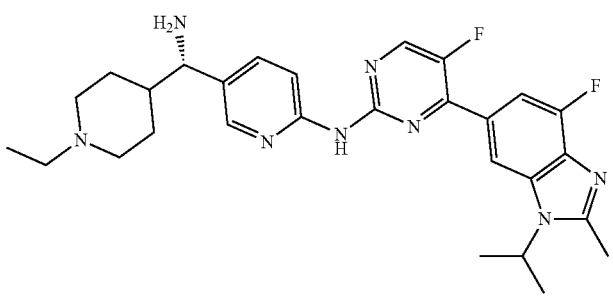 [SMILES: CCN1CCC([C@H](N)c2ccc(Nc3ncc(F)c(-c4cc(F)c5nc(C)n(C(C)C)c5c4)n3)nc2)CC1] | MS-ESI, m/z: 520.3 [M + 1]$^+$ |

Example 57

N-(5-((1-ethylpiperidin-4-ylidene)methyl)pyridin-2-yl)-5-fluoro-4-(4-fluoro-1-isopropyl-2-methyl-1H-benzo[d]imidazol-6-yl)pyrimidin-2-amine

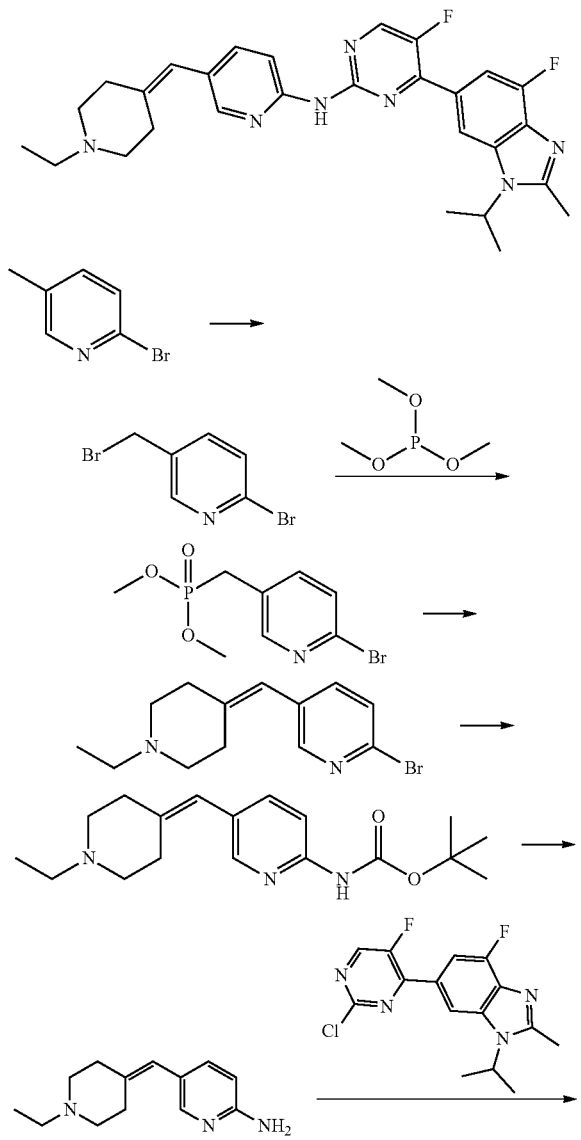

Step 1) 2-bromo-5-(bromomethyl) pyridine

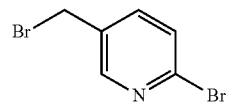

To a solution of 2-bromo-5-methylpyridine (17 g, 100 mmol) in carbon tetrabromide (250 mL) was added AIBN (164 mg, 1 mmol) and the mixture was heated to 75° C., and then NBS (26.7 g, 150 mmol) was added, and the mixture was stirred for 2 h. TLC showed that the reaction was complete, water (150 mL) was added and extracted with ethyl acetate (150 mL×3). The combined organic phases were washed with brine, dried over anhydrous $Na_2SO_4$, filtered and concentrated to give 3.0 g of the residue, which was purified by column chromatography (silica gel 200-300 mesh, PE/EA=1000:1 to 10:1) to give intermediate 2-bromo-5-(bromomethyl) pyridine (13 g, 50% yield).

MS (ESI), m/z, 250.9 [M+1]$^+$.

Step 2) dimethyl ((6-bromopyridin-3-yl) methyl) phosphonate

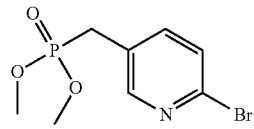

A mixture of 2-bromo-5-(bromomethyl) pyridine (13 g, 50 mmol) and trimethyl phosphite (20 mL) was heated to 80° C. and stirred for 16 h. TLC showed that the reaction was complete, and most unreacted trimethyl phosphite was removed under reduced pressure, and water (50 mL) was added, then extracted by ethyl acetate (50 mL×3). The combined organic phases were washed with brine, dried over anhydrous $Na_2SO_4$, filtered, and concentrated. The residue was purified by column chromatography (silica gel 200-300 mesh, PE/EA=1000:1 to 1:4) to give the intermediate (8 g, 57% yield).

MS (ESI), m/z, 281.1 [M+1]$^+$.

Step 3) 2-bromo-5-((1-ethylpiperidin-4-ylidene) methyl) pyridine

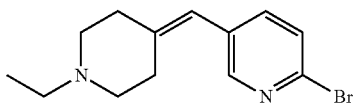 [SMILES: CCN1CCC(=Cc2ccc(Br)nc2)CC1]

To a solution of dimethyl ((6-bromopyridine-3-yl) methyl) phosphonate (2.78 g, 10 mmol) in THF (10 mL) was added NaH (60% dispersion in mineral oil, 48 mg, 12 mmol) and stirred for 10-20 min, and then N-ethylpiperidone (1.40 g, 11 mmol) was added. The mixture was warmed to 20° C. and stirred for 1-2 h. TLC showed that the reaction was complete, and the mixture was quenched with water (50 mL), and extracted with ethyl acetate (50 mL×3). The combined organic phases were washed with brine, dried over anhydrous Na₂SO₄, filtered, and concentrated. The residue was purified by column chromatography (silica gel 200-300 mesh, DCM/MeOH=1000:1 to 20:1) to give intermediate 2-bromo-5-((1-ethylpiperidin-4-ylidene) methyl) pyridine (2.0 g, 72% yield).

MS (ESI), m/z, 281.9 [M+1]⁺.

Step 4) tert-butyl (5-((1-ethylpiperidin-4-ylidene)methyl) pyridin-2-yl) carbamate

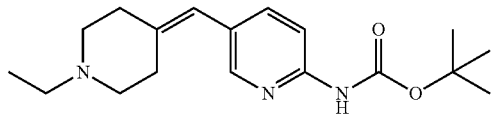 [SMILES: CCN1CCC(=Cc2ccc(NC(=O)OC(C)(C)C)nc2)CC1]

To a solution of 2-bromo-5-((1-ethylpiperidin-4-ylidene) methyl) pyridine (1.0 g, 3.6 mmol) in THF (10 mL) was added tert-butyl carbamate (0.63 g, 5.3 mmol), Pd₂(dba)₃ (91 mg, 0.01 mmol), Xantphos (32 mg, 0.01 mmol) and cesium carbonate (2.3 g, 7.2 mmol). The mixture was heated to 60° C. and stirred for 24 h. TLC showed that the reaction was complete, and the mixture was quenched with water (10 mL), and extracted with ethyl acetate (20 mL×3). The combined organic phases were washed with brine, dried over anhydrous Na₂SO₄, filtered, and concentrated. The residue was purified by column chromatography (silica gel 200-300 mesh, DCM/MeOH=1000:1 to 20:1) to give tert-butyl (5-((1-ethylpiperidin-4-ylidene) methyl) pyridin-2-yl) carbamate (0.8 g, 74% yield).

MS (ESI), m/z, 318.1 [M+1]⁺.

Step 5) 5-((1-ethylpiperidin-4-ylidene) methyl) pyridin-2-amine hydrochloride

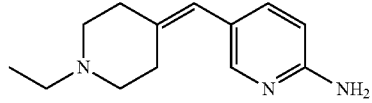

To a solution of tert-butyl (5-((1-ethylpiperidin-4-ylidene) methyl) pyridin-2-yl) carbamate (0.30 g, 1 mmol) in ethyl acetate (3 mL) was added HCl ethyl acetate solution (4 mol/L, 2 mL). The reaction mixture was heated to 60° C. and stirred for 3 h. TLC showed that the reaction was complete, and the mixture was filtered and dried to give intermediate 5-((1-ethylpiperidin-4-ylidene) methyl) pyridin-2-amine hydrochloride (100 mg, 47% yield).

MS (ESI), m/z, 218.1 [M+1]⁺.

Step 6)

N-(5-((1-ethylpiperidin-4-ylidene)methyl)pyridin-2-yl)-5-fluoro-4-(4-fluoro-1-isopropyl-2-methyl-1H-benzo[d]imidazol-6-yl) pyrimidin-2-amine

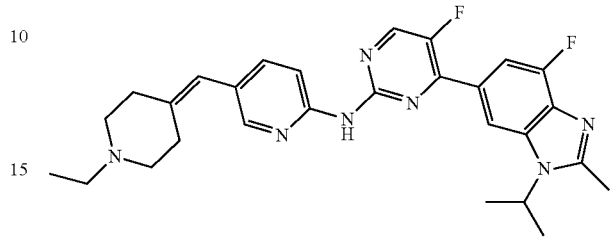

To a solution of 5-((1-ethylpiperidin-4-ylidene) methyl) pyridin-2-amine hydrochloride in NMP (3 mL) was added 6-(2-chloro-5-fluoropyrimidin-4-yl)-7-fluoro-1-isopropyl-2-methyl-1H-benzo[d]imidazole (0.16 g, 0.5 mmol), Pd₂(dba)₃ (91 mg, 0.01 mmol) and XantPhos (63 mg, 0.01 mmol) and cesium carbonate (0.32 g, 1 mmol). The reaction mixture was heated to 100° C. and stirred for 3 h. TLC showed that the reaction was complete, the mixture was filtered and concentrated. The crude product was purified by Prep-HPLC to give 50 mg of the product.

MS (ESI), m/z, 504.5 [M+1]⁺.

¹H NMR (400 MHz, DMSO) δ (ppm) 9.56 (s, 1H), 8.79 (d, J=3.6 Hz, 1H), 8.30-8.25 (m, 2H), 8.13 (s 8.5 Hz, 1H), 7.89 (s, 1H), 7.76 (s, 1H), 7.35 (s, 1H), 6.49 (s, 1H), 4.90-4.86 (m, 1H), 3.60-3.52 (m, 3H), 3.50-3.42 (m, 2H), 2.97-2.91 (m, 3H), 2.84 (s, 3H), 2.69-2.62 (m, 2H), 1.64 (d, J=6.9 Hz, 6H), 1.26-1.25 (m, 3H).

Example 58

N-(5-(1-(1-ethylpiperidin-4-ylidene)ethyl)pyridin-2-yl)-5-fluoro-4-(4-fluoro-1-isopropyl-2-methyl-1H-benzo[d]imidazol-6-yl)pyrimidin-2-amine

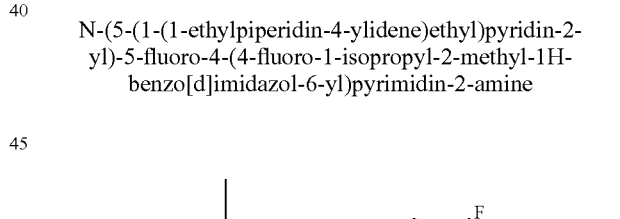

-continued

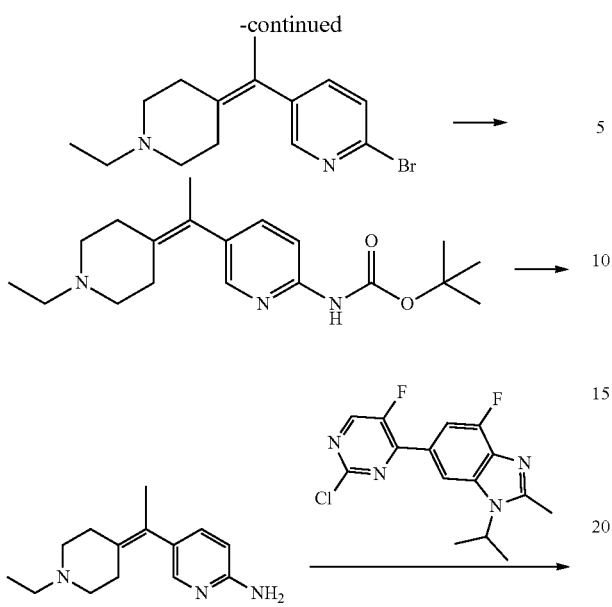

Step 1) diethyl (1-(6-bromopyridin-3-yl) ethyl) phosphonate

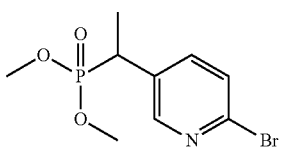

To a solution of dimethyl ((6-bromopyridine-3-yl) methyl) phosphonate (1.4 g, 5 mmol) in THF (10 mL) was added LDA (6 mL, 1.2 mmol) at −78° C. and stirred for 30 min, methyl iodide (0.75 g, 0.55 mmol) was added and continued to stir for 1-2 h. TLC showed that the reaction was complete, and the mixture was quenched with water (15 mL) and extracted with ethyl acetate (15 mL×3). The combined organic phases were washed with brine, dried over anhydrous Na$_2$SO$_4$, filtered and concentrated. The residue was purified by column chromatography (silica gel 200-300 mesh, PE/EA=1000:1 to 10:1) to give the intermediate diethyl (1-(6-bromopyridin-3-yl) ethyl) phosphonate as colorless oil (0.8 g, 56% yield).

MS (ESI), m/z, 295.1 [M+1]$^+$.

Step 2) 2-bromo-5-(1-(1-ethylpiperidin-4-ylidene) ethyl) pyridine

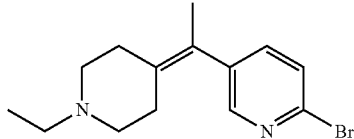 [SMILES: CCN1CCC(=C(C)c2ccc(Br)nc2)CC1]

To a solution (5 mL) of diethyl (1-(6-bromopyridin-3-yl) ethyl) phosphonate (0.8 g, 2.7 mmol) in THF (5 mL) was added NaH (60% dispersion in mineral oil, 126 mg, 3.2 mmol) and stirred for 10-20 min. Then N-ethylpiperidone (0.41 g, 3.2 mmol) was added, and the reaction mixture was warmed to 20° C. and stirred for 1-2 h. TLC showed that the reaction was complete, quenched with water (50 mL), and extracted with ethyl acetate (50 mL×3). The combined organic phases were washed with brine, dried over anhydrous Na$_2$SO$_4$, filtered and concentrated to give 2.30 g of crude product, which was purified by column chromatography (Silica gel 200-300 mesh, DCM/MeOH=1000:1 to 20:1) to give intermediate 2-bromo-5-(1-(1-ethylpiperidin-4-ylidene) ethyl) pyridine (0.57 g, yield 72%).

MS (ESI), m/z, 296.1 [M+1]$^+$.

Step 3) tert-butyl (5-(1-(1-ethylpiperidin-4-ylidene) ethyl) pyridin-2-yl) carbamate

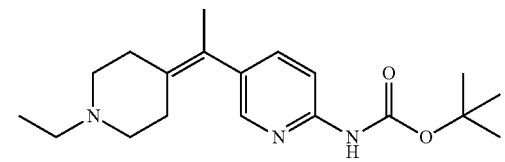 [SMILES: CCN1CCC(=C(C)c2ccc(NC(=O)OC(C)(C)C)nc2)CC1]

To a solution of 2-bromo-5-(1-(1-ethylpiperidin-4-ylidene) ethyl) pyridine (0.53 g, 1.8 mmol) in THF (10 mL) was added tert-butyl carbamate (0.33 g, 2.6 mmol), Pd$_2$(dba)$_3$ (45 mg, 0.005 mmol), Xantphos (16 mg, 0.005 mmol) and cesium carbonate (1.2 g, 3.6 mmol). The reaction was heated to 60° C. and stirred for 24 h. TLC showed that the product was formed, and after completion of the reaction, the mixture was quenched with water (10 mL), and extracted with ethyl acetate (20 mL×3). The combined organic phases were washed with brine, dried over anhydrous Na$_2$SO$_4$, filtered and concentrated to give 0.50 g of the crude product, which was purified by Prep-TLC to give tert-butyl (5-(1-(1-ethylpiperidin-4-ylidene) ethyl) pyridin-2-yl) carbamate (0.33 g, 55% yield).

MS (ESI), m/z, 318.1 [M+1]$^+$.

Step 4) 5-(1-(1-ethylpiperidin-4-ylidene) ethyl) pyridin-2-amine

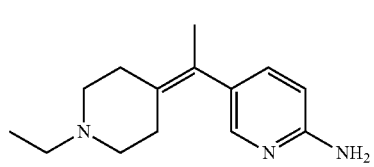 [SMILES: CCN1CCC(=C(C)c2ccc(N)nc2)CC1]

To a solution of tert-butyl (5-(1-(1-ethylpiperidin-4-ylidene) ethyl) pyridin-2-yl) carbamate (0.30 g, 1 mmol) in ethyl acetate (3 mL) was added HCl ethyl acetate solution (4 mol/L, 2 mL). The reaction mixture was heated to 50-60° C. and stirred for 2-3 h. TLC showed that the reaction was complete, and the mixture was filtered and dried to give 5-(1-(1-ethylpiperidin-4-ylidene) ethyl) pyridin-2-amine (100 mg, 47% yield).

MS (ESI), m/z, 218.1 [M+1]$^+$.

Step 5) 5-(1-(1-ethylpiperidin-4-ylidene) ethyl) pyridin-2-amine

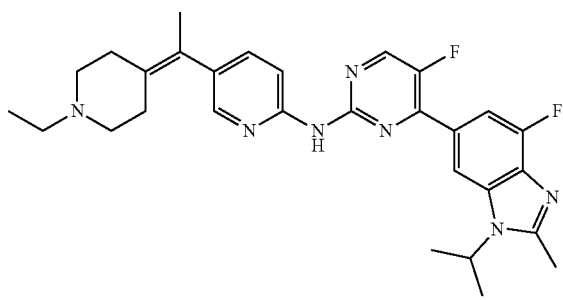 [SMILES: CCN1CCC(=C(C)c2ccc(Nc3ncc(F)c(-c4cc(F)c5nc(C)n(C(C)C)c5c4)n3)nc2)CC1]

To a solution of 5-(1-(1-ethylpiperidin-4-ylidene) ethyl) pyridin-2-amine (0.10 g, 0.47 mmol) in NMP (3 mL) was added 6-(2-chloro-5-fluoropyrimidin-4-yl)-7-fluoro-1-isopropyl-2-methyl-1H-benzo[d]imidazole (0.16 g, 0.5 mmol), Pd$_2$(dba)$_3$ (91 mg, 0.01 mmol), Xantphos (60 mg, 0.01 mmol) and cesium carbonate (0.32 g, 1 mmol). The reaction mixture was heated to 100° C. and stirred for 2-3 h. TLC showed that the reaction was complete, and the mixture was concentrated to give a crude product, which was purified by Prep-HPLC to give the product (40 mg, 99.54% purity).

MS (ESI), m/z, 518.1 [M+1]$^+$.

$^1$H NMR (400 MHz, DMSO) δ (ppm) 10.64 (s, 1H), 9.51 (s, 1H), 8.78 (s, 1H), 8.15 (s, 1H), 7.75-7.72 (m, 1H), 4.87-4.86 (m, 1H), 3.63-3.6 (m, 2H), 3.16-3.12 (m, 2H), 2.98-2.90 (m, 3H), 2.89 (s, 3H), 2.51-2.34 (m, 2H), 2.27 (s, 3H), 2.06 (d, J=6.9 Hz, 6H), 1.64 (m, 3H).

Example 59-70

The compounds of examples 59-70 in the following table were prepared according to the synthesis method of examples 57-58 using the corresponding starting materials.

| Example | Structure | Characterization data |
|---|---|---|
| Example 59 | 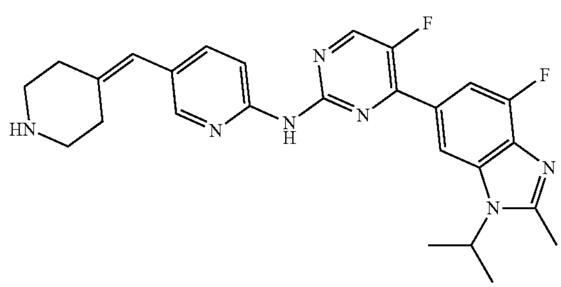 [SMILES: Cc1nc2c(F)cc(-c3nc(Nc4ccc(C=C5CCNCC5)cn4)ncc3F)cc2n1C(C)C] | MS-ESI, m/z: 476.2 [M + 1]+<br>$^1$H NMR (400 MHz, DMSO) TFA salt δ (ppm) 10.49 (s, 1H), 8.76 (s, 1H), 8.64 (s, 2H), 8.28-8.17 (m, 3H), 7.76-7.71 (m, 2H), 6.43 (s, 1H), 4.88-4.85 (m, 1H), 3.19-3.13 (m, 4H), 3.54-3.42 (m, 3H), 2.67-2.61 (m, 8H), 1.64 (d, J = 6.9 Hz, 6H). |
| Example 60 | 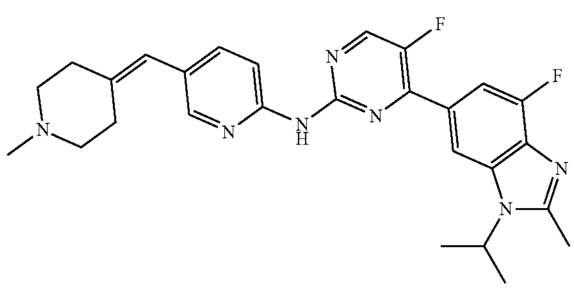 | MS-ESI, m/z: 490.2 [M + 1]$^+$<br>$^1$H NMR (400 MHz, DMSO) TFA salt δ (ppm) 10.78 (s, 1H), 9.87 (s, 1H), 8.78 (d, J = 3.6 Hz, 1H), 8.36-8.21 (m, 2H), 8.14 (d, J = 8.8 Hz, 1H), 7.82 (dd, J = 8.8, 2.0 Hz, 1H), 7.74 (d, J = 11.9 Hz, 1H), 6.46 (s, 1H), 4.98-4.77 (m, 1H), 2.99 (ddd, J = 37.6, 21.1, 12.2 Hz, 3H), 2.82 (d, J = 4.2 Hz, 3H), 2.69 (s, 3H), 1.64 (d, J = 6.9 Hz, 6H). |
| Example 61 | 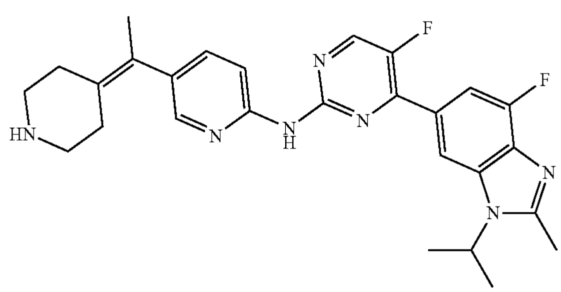 [SMILES: CC(=C1CCNCC1)c1ccc(Nc2ncc(F)c(-c3cc(F)c4nc(C)n(C(C)C)c4c3)n2)nc1] | MS-ESI, m/z: 490.2 [M + 1]$^+$ |

-continued
| Example | Structure | Characterization data |
|---|---|---|
| Example 62 | 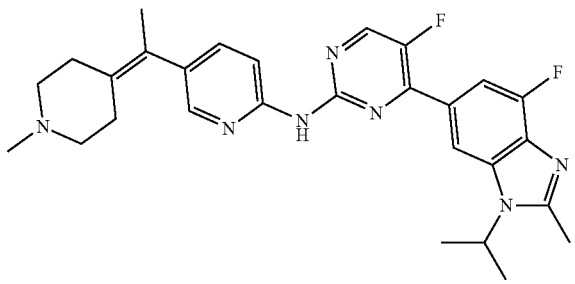 | MS-ESI, m/z: 504.2 [M + 1]$^+$ |
| Example 63 | 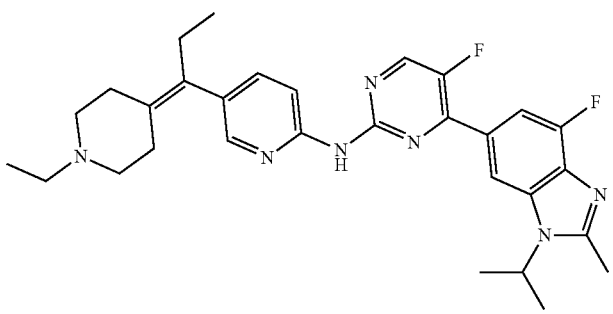 [SMILES: CCC(=C1CCN(CC)CC1)c1ccc(Nc2ncc(F)c(-c3cc(F)c4nc(C)n(C(C)C)c4c3)n2)nc1] | MS-ESI, m/z: 532.3 [M + 1]$^+$ |
| Example 64 | 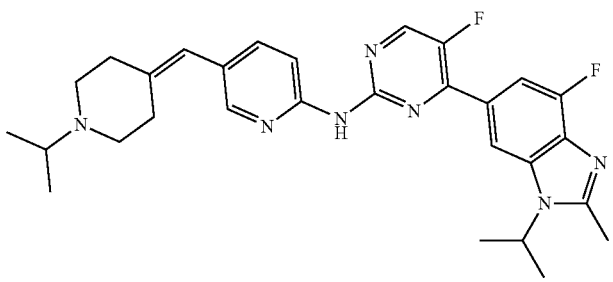 [SMILES: Cc1nc2c(F)cc(-c3nc(Nc4ccc(C=C5CCN(C(C)C)CC5)cn4)ncc3F)cc2n1C(C)C] | MS-ESI, m/z: 518.3 [M + 1]$^+$<br>$^1$H NMR (400 MHz, DMSO) δ (ppm) TFA salt 10.06 (s, 1H), 9.51 (s, 1H), 8.30-8.25 (m, 2H), 8.26-8.17 (m, 3H), 7.82-7.77 (m, 2H), 6.45 (s, 1H), 4.89-4.86 (m, 1H), 3.60-3.52 (m, 3H), 3.54-3.42 (m, 3H), 3.30-2.91 (m, 3H), 2.84 (s, 3H), 2.69-2.50 (m, 5H), 1.64 (d, J = 6.9 Hz, 6H), 1.26-1.25 (m, 6H). |
| Example 65 | 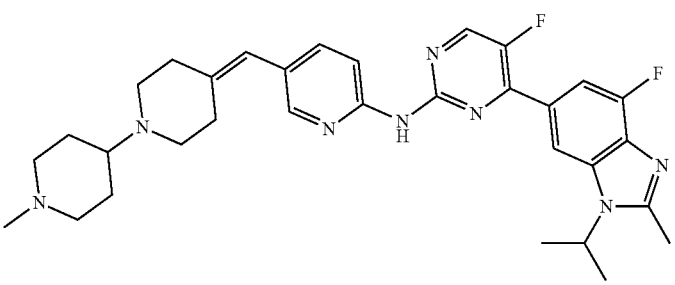 | MS-ESI, m/z: 573.3 [M + 1]$^+$ |
| Example 66 | 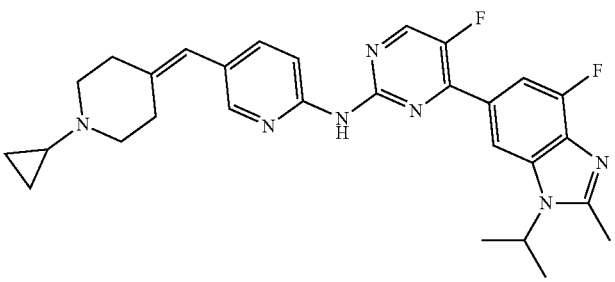 [SMILES: Cc1nc2c(F)cc(-c3nc(Nc4ccc(C=C5CCN(C6CC6)CC5)cn4)ncc3F)cc2n1C(C)C] | MS-ESI, m/z: 516.2 [M + 1]$^+$<br>$^1$H NMR (400 MHz, DMSO) δ (ppm) TFA salt 10.48 (s, 1H), 9.12 (s, 1H), 8.74 (s, 1H), 8.25-8.20 (m, 3H), 7.76-7.71 (m, 2H), 6.48 (s, 1H), 4.88-4.85 (m, 1H), 3.60-3.54 (m, 4H), 3.26-3.19 (m, 2H), 2.95-2.88 (m, 3H), 2.67-2.62 (m, 5H), 1.64 (d, J = 6.9 Hz, 6H), 0.97-0.85 (m, 4H). |

-continued

| Example | Structure | Characterization data |
|---|---|---|
| Example 67 | 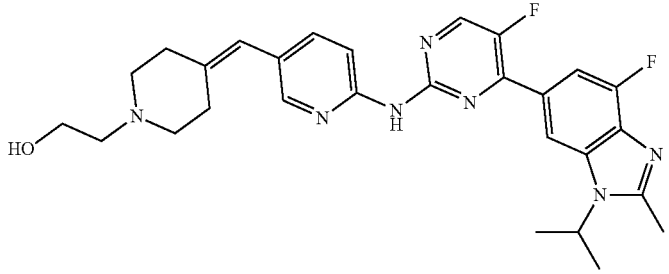 [SMILES: Cc1nc2c(F)cc(-c3nc(Nc4ccc(C=C5CCN(CCO)CC5)cn4)ncc3F)cc2n1C(C)C] | MS-ESI, m/z: 520.2 [M + 1]$^+$<br>$^1$H NMR (400 MHz, DMSO) δ (ppm) TFA salt 10.46 (s, 1H), 9.52 (s, 1H), 8.76 (s, 1H), 8.28-8.21 (m, 3H), 7.76-7.71 (m, 2H), 6.45 (s, 1H), 4.88-4.86 (m, 1H), 3.85-3.71 (m, 6H), 3.21-3.02 (m, 4H), 2.67-2.58 (m, 7H), 1.64 (d, J = 6.9 Hz, 6H). |
| Example 68 | 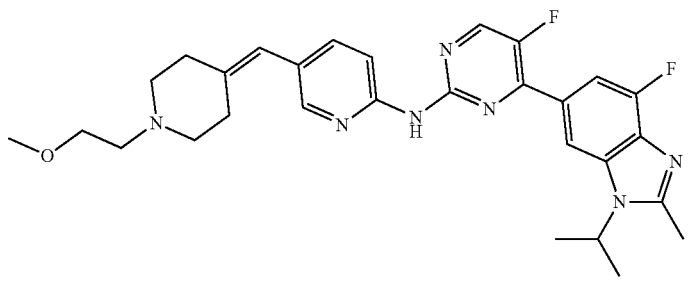 | MS-ESI, m/z: 534.2 [M + 1]$^+$<br>$^1$H NMR (400 MHz, DMSO) δ (ppm) TFA salt 10.48 (s, 1H), 9.61 (s, 1H), 8.76 (s, 1H), 8.28-8.19 (m, 3H), 7.76-7.71 (m, 2H), 6.47 (s, 1H), 4.88-4.83 (m, 1H), 3.68-3.34 (m, 6H), 3.452 (s, 3H), 3.07-2.37 (m, 4H), 2.67-2.60 (m, 5H), 1.64 (d, J = 6.9 Hz, 6H). |
| Example 69 | 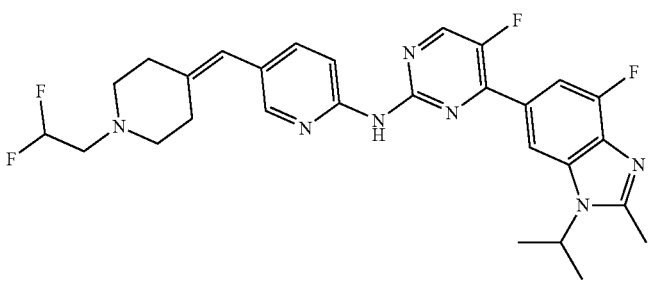 [SMILES: Cc1nc2c(F)cc(-c3nc(Nc4ccc(C=C5CCN(CC(F)F)CC5)cn4)ncc3F)cc2n1C(C)C] | MS-ESI, m/z: 540.2 [M + 1]$^+$<br>$^1$H NMR (400 MHz, DMSO) δ (ppm) TFA salt 10.50 (s, 1H), 8.76 (d, J = 3.6 Hz, 1H), 8.29 (s, 1H), 8.23 (d, J = 1.8 Hz, 1H), 8.20 (d, J = 8.8 Hz, 1H), 7.74 (t, J = 10.6 Hz, 2H), 6.60 (d, J = 55.2 Hz, 1H), 6.43 (s, 1H), 4.87 (dt, J = 13.8, 6.7 Hz, 1H), 3.31-2.95 (m, 4H), 2.64 (d, J = 21.7 Hz, 7H), 2.00 (dd, J = 14.7, 7.1 Hz, 2H), 1.64 (d, J = 6.9 Hz, 6H). |
| Example 70 | 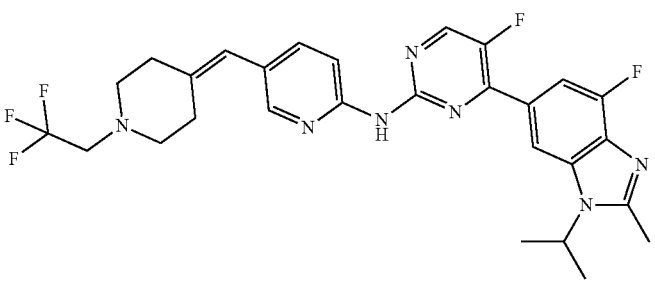 [SMILES: Cc1nc2c(F)cc(-c3nc(Nc4ccc(C=C5CCN(CC(F)(F)F)CC5)cn4)ncc3F)cc2n1C(C)C] | MS-ESI, m/z: 558.2 [M + 1]$^+$<br>$^1$H NMR (400 MHz, DMSO) δ (ppm) TFA salt 11.02 (s, 1H), 8.81 (d, J = 2.5 Hz, 1H), 8.29 (s, 1H), 8.21 (s, 1H), 8.02 (d, J = 8.6 Hz, 1H), 7.88 (s, 1H), 7.74 (d, J = 12.0 Hz, 1H), 6.30 (s, 1H), 4.93-4.78 (m, 1H), 3.32 (d, J = 9.9 Hz, 2H), 2.80 (s, 2H), 2.72 (s, 2H), 2.68 (s, 3H), 2.39 (s, 2H), 2.00 (dd, J = 14.5, 6.9 Hz, 2H), 1.64 (d, J = 6.9 Hz, 6H). |

Examples 71 & 72

(R or S)-(1-ethylpiperidin-4-yl) (6-((5-fluoro-4-(4-fluoro-1-isopropyl-2-methyl-1H-benzo[d]imidazol-6-yl) pyrimidin-2-yl) amino) pyridin-3-yl) methyl acetate

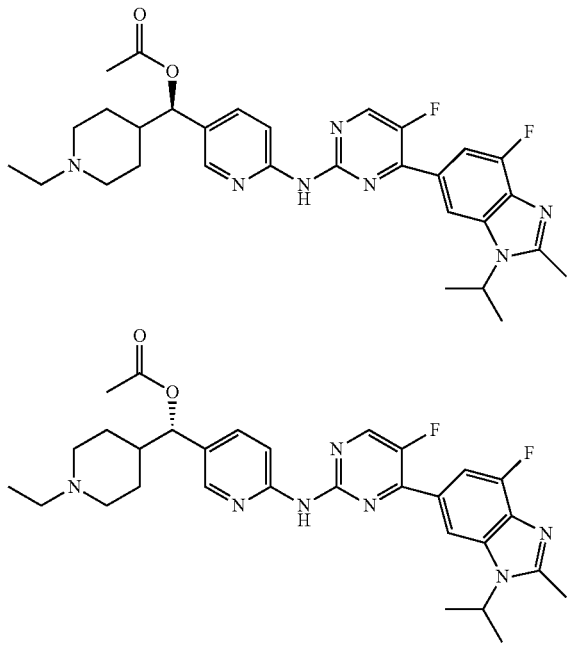

To a solution of example 39 (60 mg, 0.11 mmol) in dichloromethane (5 mL) was added triethylamine (17 mg, 0.17 mmol) and 4-dimethylaminopyridine (2.8 mg, 0.023 mmol), followed by dropwise addition of a solution of acetic anhydride (17.6 mg, 0.17 mmol) in dichloromethane (0.5 mL). After stirring for 2 hours, LCMS showed that the reaction was complete, purified by Prep-HPLC and basified to a salt-free form.

MS (ESI), m/z, 564.2 [M+1]+.

$^1$H NMR (400 MHz, CDCl$_3$) δ (ppm) 8.43 (dd, J=12.0, 6.2 Hz, 2H), 8.32-8.22 (m, 2H), 8.19 (d, J=1.1 Hz, 1H), 7.80 (d, J=11.9 Hz, 1H), 7.65 (dd, J=8.7, 2.2 Hz, 1H), 5.52 (d, J=7.9 Hz, 1H), 4.75 (dt, J=13.8, 6.9 Hz, 1H), 2.98 (dd, J=32.6, 11.1 Hz, 2H), 2.70 (s, 3H), 2.39 (dd, J=14.2, 7.1 Hz, 2H), 2.09 (s, 3H), 1.94-1.77 (m, 4H), 1.72 (d, J=7.0 Hz, 6H), 1.08 (t, J=7.2 Hz, 3H).

The racemic compound was separated by chiral column Chiralpak AD-H (10 mm×250 mm, 5 μm) at a column temperature of 40 OC. Mobile phase A was 0.1% DEA in hexane (v/v), mobile phase B was ethanol, running time was 30 minutes, gradient was mobile phase A/mobile phase B (50/50, v/v), flow rate was 6.0 mL/min and detection wavelength was UV 210 nm. The two single-configuration compounds were separated in the retention time of 25 minutes (compound of example 71) and 31 minutes (compound of example 72) respectively. The compound was detected by chiral column CHRIARPAK AD-H (4.6 mm×250 mm) at a column temperature of 40° C., and mobile phase A was 0.1% DEA in hex (V/V), mobile phase B was ethanol, running time was 30 minutes, gradient was mobile phase A/mobile phase B (50/50), flow rate was 0.5 mL/min, and detection wavelength was UV 210 nm. The first single configuration compound was example 71 (RT=21.3 min, 98% ee), and the second single configuration compound was example 72 (RT 28.6 min, 97% ee).

Example 73-86

The compounds of examples 73-86 in the following table were prepared according to the synthesis method of examples 16-19 using the corresponding starting materials.

| Example | Structure | Characterization data |
|---|---|---|
| Example 73 | 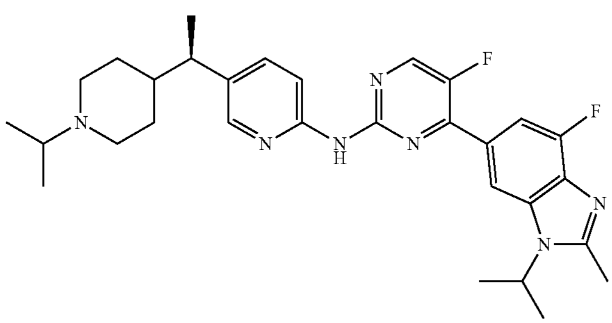 [SMILES: Cc1nc2c(F)cc(-c3nc(Nc4ccc([C@H](C)C5CCN(C(C)C)CC5)cn4)ncc3F)cc2n1C(C)C] | MS-ESI, m/z: 534.3 [M + 1]+<br>$^1$H NMR (400 MHz, CDCl$_3$) δ (ppm) 8.54 (s, 1H), 8.46 (d, J = 3.5 Hz, 1H), 8.35 (d, J = 8.6 Hz, 1H), 8.20 (s, 1H), 8.16 (d, J = 2.3 Hz, 1H), 7.80 (d, J = 11.6 Hz, 1H), 7.55-7.46 (m, 1H), 4.79-4.69 (m, 1H), 2.94 (d, J = 11.2 Hz, 1H), 2.81 (d, J = 11.1 Hz, 1H), 2.70 (s, 3H), 2.65 (dd, J = 13.0, 6.5 Hz, 1H), 2.49 (p, J = 7.1 Hz, 1H), 2.09 (dd, J = 16.0, 6.8 Hz, 1H), 2.03-1.80 (m, 4H), 1.72 (d, J = 6.9 Hz, 6H), 1.50-1.41 (m, 1H), 1.36 (ddd, J = 16.3, 9.5, 3.3 Hz, 1H), 1.28 (d, J = 7.0 Hz, 3H), 1.18 (ddd, J = 15.0, 11.9, 3.5 Hz, 1H), 1.01 (d, J = 6.5 Hz, 6H).<br>The compound was separated with chiral column Chiralpak AS-H, and chiral separation conditions were the same as in example 17 or 18. RT was 17.5 min. |

-continued

| Example | Structure | Characterization data |
|---|---|---|
| Example 74 | 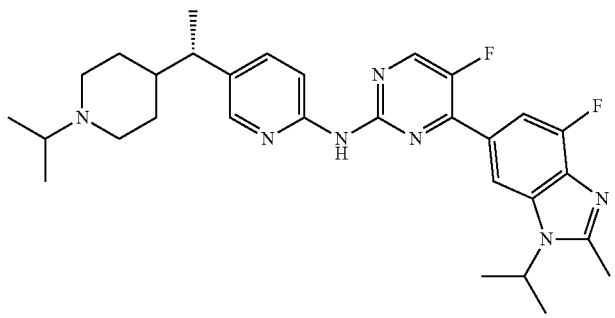 [SMILES: Cc1nc2c(F)cc(-c3nc(Nc4ccc([C@@H](C)C5CCN(C(C)C)CC5)cn4)ncc3F)cc2n1C(C)C] | MS-ESI, m/z: 534.3 [M + 1]+<br>The compound was separated with chiral column Chiralpak AS-H, and chiral separation conditions were the same as in example 17 or 18. RT was 24 min. |
| Example 75 | 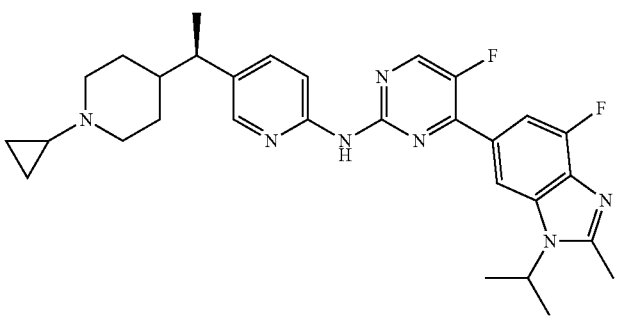 [SMILES: Cc1nc2c(F)cc(-c3nc(Nc4ccc([C@H](C)C5CCN(C6CC6)CC5)cn4)ncc3F)cc2n1C(C)C] | MS-ESI, m/z: 532.3 [M + 1]+<br>$^1$H NMR (400 MHz, CDCl$_3$) δ (ppm) 8.43 (d, J = 3.7 Hz, 1H), 8.34 (d, J = 8.6 Hz, 1H), 8.20 (s, 2H), 8.12 (s, 1H), 7.80 (d, J = 11.6 Hz, 1H), 7.50 (dd, J = 8.6, 1.9 Hz, 1H), 4.83-4.65 (m, 1H), 3.08 (d, J = 11.2 Hz, 1H), 2.96 (d, J = 11.1 Hz, 1H), 2.96 (d, J = 11.1 Hz, 1H), 2.70 (s, 3H), 2.57-2.39 (m, 1H), 2.13 (t, J = 10.7 Hz, 1H), 2.03 (t, J = 10.8 Hz, 1H), 1.85 (d, J = 12.8 Hz, 1H), 1.71 (d, J = 6.9 Hz, 6H), 1.56-1.47 (m, 1H), 1.47-1.35 (m, 2H), 1.35-1.20 (m, 4H), 1.13 (dt, J = 22.4, 11.0 Hz, 1H), 0.53-0.30 (m, 4H).<br>The compound was separated with chiral column Chiralpak AS-H, and chiral separation conditions were the same as in example 17 or 18. RT was 18.4 min. |
| Example 76 | 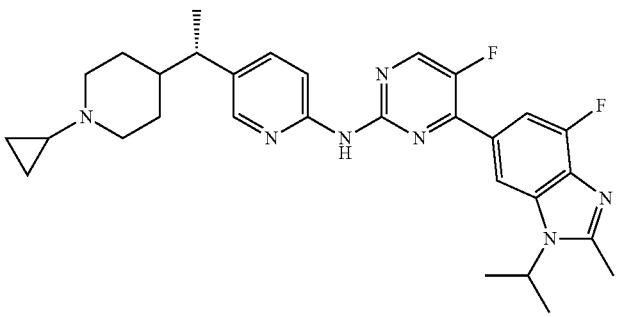 [SMILES: Cc1nc2c(F)cc(-c3nc(Nc4ccc([C@@H](C)C5CCN(C6CC6)CC5)cn4)ncc3F)cc2n1C(C)C] | MS-ESI, m/z: 532.3 [M + 1]+<br>The compound was separated with chiral column Chiralpak AS-H, and chiral separation conditions were the same as in example 17 or 18. RT was 25 min. |
| Example 77 | 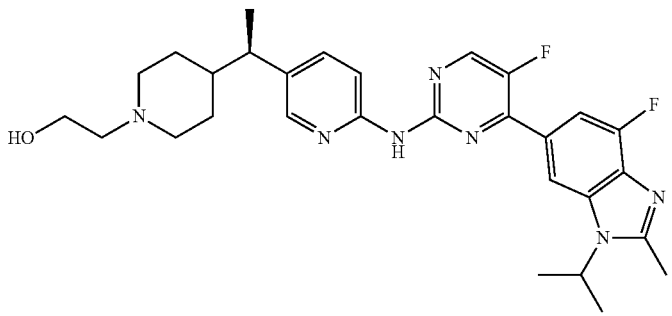 [SMILES: Cc1nc2c(F)cc(-c3nc(Nc4ccc([C@H](C)C5CCN(CCO)CC5)cn4)ncc3F)cc2n1C(C)C] | MS-ESI, m/z: 536.3 [M + 1]+<br>$^1$H NMR (400 MHz, CDCl$_3$) δ (ppm) 8.42 (d, J = 3.7 Hz, 1H), 8.35 (d, J = 8.6 Hz, 1H), 8.19 (s, 1H), 8.15-8.09 (m, 2H), 7.80 (d, J = 11.6 Hz, 1H), 7.51 (dd, J = 8.6, 2.1 Hz, 1H), 4.74 (dt, J = 13.8, 6.9 Hz, 1H), 3.57 (t, J = 5.4 Hz, 2H), 2.96 (d, J = 11.7 Hz, 1H), 2.83 (d, J = 11.3 Hz, 1H), 2.69 (s, 3H), 2.48 ((m, 3H), 2.03 (dd, J = 11.5, 9.4 Hz, 1H), 1.98-1.83 (m, 3H), 1.71 (d, J = 6.9 Hz, 6H), 1.47-1.30 (m, 3H), 1.28 (d, J = 7.0 Hz, 3H).<br>The compound was separated with chiral column Chiralpak AS-H, and chiral separation conditions were the same as in example 17 or 18. RT was 14.6 min. |

-continued

| Example | Structure | Characterization data |
| --- | --- | --- |
| Example 78 | 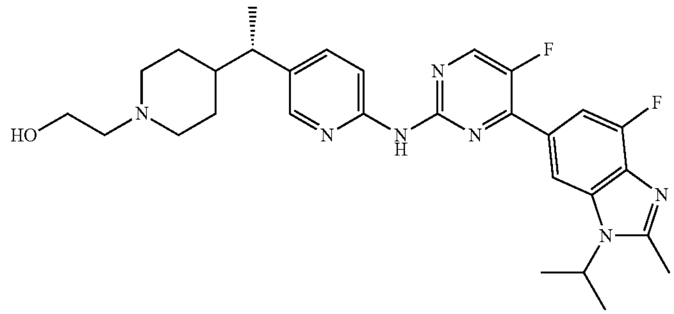 [SMILES: Cc1nc2c(F)cc(-c3nc(Nc4ccc([C@@H](C)C5CCN(CCO)CC5)cn4)ncc3F)cc2n1C(C)C] | MS-ESI, m/z: 536.3 [M + 1]+<br>The compound was separated with chiral column Chiralpak AS-H, and chiral separation conditions were the same as in example 17 or 18. RT was 18.4 min. |
| Example 79 | 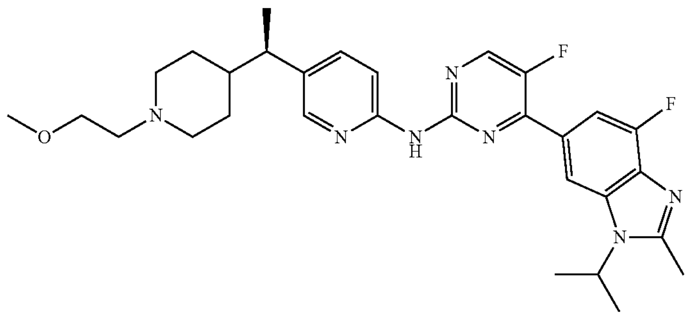 | MS-ESI, m/z: 550.3 [M + 1]+<br>$^1$H NMR (400 MHz, CDCl$_3$) δ (ppm) 8.42 (d, J = 3.7 Hz, 1H), 8.33 (d, J = 8.6 Hz, 1H), 8.19 (s, 1H), 8.10 (d, J = 2.0 Hz, 1H), 8.08 (s, 1H), 7.80 (d, J = 11.6 Hz, 1H), 7.50 (dd, J = 8.6, 2.1 Hz, 1H), 4.74 (dt, J = 13.9, 6.9 Hz, 1H), 3.48 (t, J = 5.7 Hz, 2H), 3.33 (s, 3H), 3.01 (d, J = 10.4 Hz, 1H), 2.88 (d, J = 11.1 Hz, 1H), 2.69 (s, 3H), 2.57-2.42 (m, 3H), 2.04-1.89 (m, 1H), 1.84 (t, J = 10.5 Hz, 2H), 1.71 (d, J = 6.9 Hz, 6H), 1.40 (d, J = 14.3 Hz, 3H), 1.27 (d, J = 7.1 Hz, 4H).<br>The compound was separated with chiral column Chiralpak AS-H, and chiral separation conditions were the same as in example 17 or 18. RT was 15.7 min. |
| Example 80 | 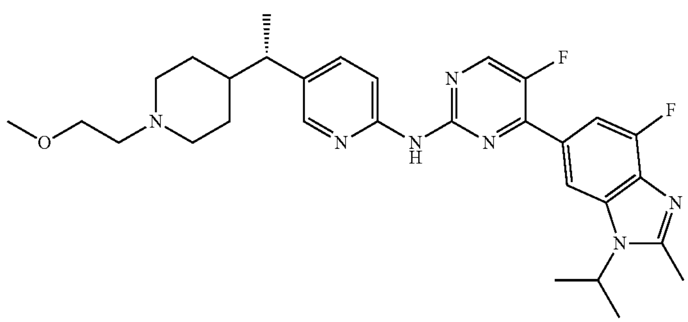 | MS-ESI, m/z: 550.3 [M + 1]+<br>The compound was separated with chiral column Chiralpak AS-H, and chiral separation conditions were the same as in example 17 or 18. RT was 21.3 min. |
| Example 81 | 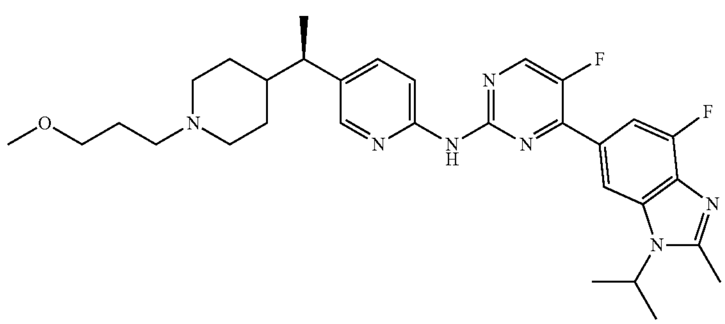 | MS-ESI, m/z: 564.3 [M + 1]+<br>$^1$H NMR (400 MHz, CDCl$_3$) δ 8.35 (d, J = 3.7 Hz, 1H), 8.27 (d, J = 8.6 Hz, 1H), 8.13 (s, 1H), 8.04 (d, J = 1.9 Hz, 1H), 7.99 (s, 1H), 7.73 (d, J = 11.6 Hz, 1H), 7.43 (dd, J = 8.6, 2.1 Hz, 1H), 4.73-4.59 (m, 1H), 3.33 (t, J = 6.4 Hz, 2H), 3.24 (s, 3H), 2.98-2.86 (m, 1H), 2.85-2.73 (m, 1H), 2.63 (s, 3H), 2.48-2.37 (m, 1H), 2.30 (s, 2H), 1.90-1.75 (m, 2H), 1.76-1.67 (m, 2H), 1.63 (t, J = 8.7 Hz, 6H), 1.57 (s, 1H), 1.31 (dt, J = 10.3, 9.1 Hz, 3H), 1.25-1.08 (m, 4H).<br>The compound was separated with chiral column Chiralpak AS-H, and chiral separation conditions were the same as in example 17 or 18. RT was 14.9 min. |

| Example | Structure | Characterization data |
|---|---|---|
| Example 82 | 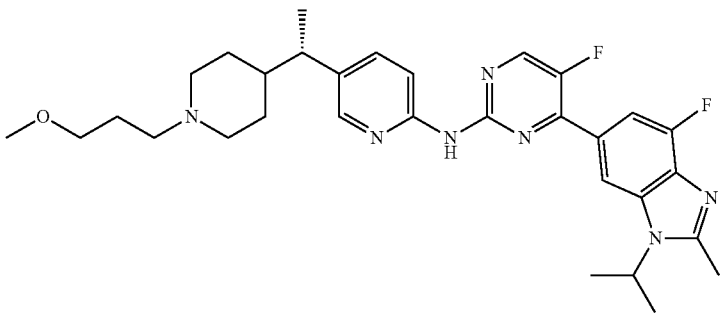 | MS-ESI, m/z: 564.3 [M + 1]+<br>The compound was separated with chiral column Chiralpak AS-H, and chiral separation conditions were the same as in example 17 or 18. RT was 19.7 min. |
| Example 83 | 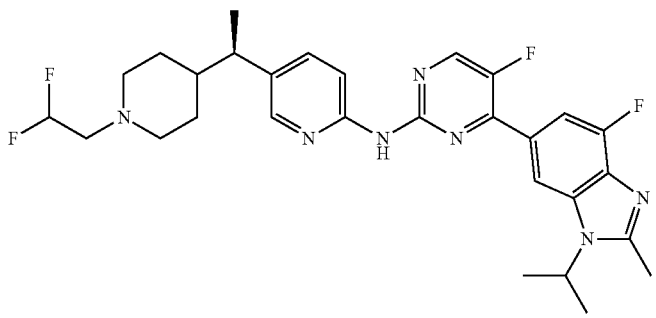 [SMILES: Cc1nc2c(F)cc(-c3nc(Nc4ccc([C@H](C)C5CCN(CC(F)F)CC5)cn4)ncc3F)cc2n1C(C)C] | MS-ESI, m/z: 556.3 [M + 1]+<br>$^1$H NMR (400 MHz, CDCl$_3$) δ 8.44 (d, J = 3.7 Hz, 1H), 8.36 (d, J = 8.1 Hz, 2H), 8.19 (s, 1H), 8.14 (d, J = 1.6 Hz, 1H), 7.80 (d, J = 11.6 Hz, 1H), 7.50 (dd, J = 8.6, 1.9 Hz, 1H), 5.85 (tt, J = 56.0, 4.3 Hz, 1H), 4.88-4.63 (m, 1H), 2.99 (d, J = 11.2 Hz, 1H), 2.87 (d, J = 11.0 Hz, 1H), 2.80-2.59 (m, 5H), 2.56-2.40 (m, 1H), 2.16 (t, J = 11.3 Hz, 1H), 2.05 (t, J = 11.0 Hz, 1H), 1.85 (d, J = 11.1 Hz, 1H), 1.72 (s, 6H), 1.46-1.31 (m, 3H), 1.31-1.17 (m, 5H).<br>The compound was separated with chiral column Chiralpak AS-H, and chiral separation conditions were the same as in example 17 or 18. RT was 18.3 min. |
| Example 84 | 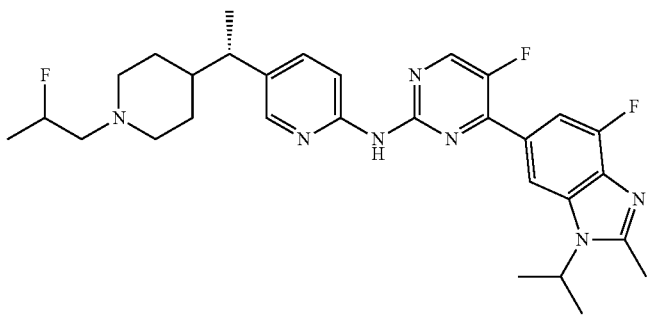 | MS-ESI, m/z: 556.3 [M + 1]+<br>The compound was separated with chiral column Chiralpak AS-H, and chiral separation conditions were the same as in example 17 or 18. RT was 24.8 min. |
| Example 85 | 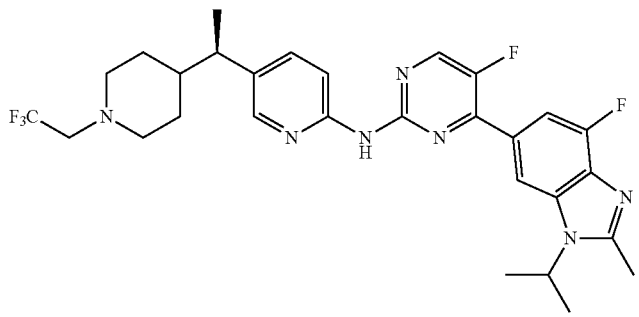 [SMILES: Cc1nc2c(F)cc(-c3nc(Nc4ccc([C@H](C)C5CCN(CC(F)(F)F)CC5)cn4)ncc3F)cc2n1C(C)C] | MS-ESI, m/z: 574.3 [M + 1]+<br>$^1$H NMR (400 MHz, CDCl$_3$) δ 8.44 (d, J = 3.7 Hz, 1H), 8.41-8.31 (m, 2H), 8.19 (s, 1H), 8.14 (d, J = 2.0 Hz, 1H), 7.80 (d, J = 11.6 Hz, 1H), 7.50 (dd, J = 8.6, 2.1 Hz, 1H), 4.74 (hept, J = 6.8 Hz, 1H), 3.02 (d, J = 10.8 Hz, 1H), 2.98-2.84 (m, 3H), 2.70 (s, 3H), 2.55-2.42 (m, 1H), 2.31 (t, J = 11.1 Hz, 1H), 2.21 (t, J = 11.2 Hz, 1H), 1.84 (d, J = 10.8 Hz, 1H), 1.72 (s, 6H), 1.47-1.31 (m, 2H), 1.34-1.16 (m, 5H).<br>The compound was separated with chiral column Chiralpak AS-H, and chiral separation conditions were the same as in example 17 or 18. RT was 19.7 min. |

| Example | Structure | Characterization data |
|---|---|---|
| Example 86 | 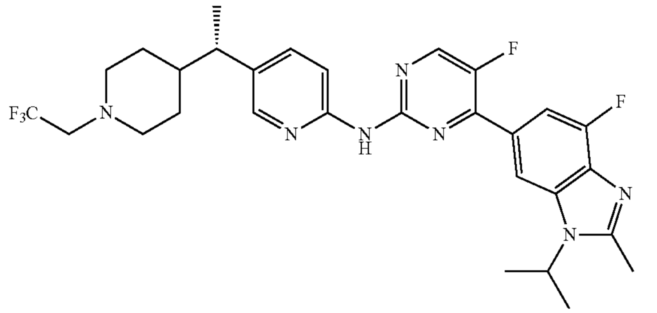 [SMILES: Cc1nc2c(F)cc(-c3nc(Nc4ccc([C@@H](C)C5CCN(CC(F)(F)F)CC5)cn4)ncc3F)cc2n1C(C)C] | MS-ESI, m/z: 574.3 [M + 1]+<br>The compound was separated with chiral column Chiralpak AS-H, and chiral separation conditions were the same as in example 17 or 18. RT was 25.1 min. |

Biological Example 1: Determination of CDK Activity

In vitro, CDK (CDK4, CDK6, CDK1, CDK2, CDK7, and CDK9) kinase activity was tested by the following method.

CDK and raw materials used here: CDK4/CycD3 (Carna, Cat. No 04-105, Lot. No 10CBS-0429 C, GST-CDK4(1-303end)/GST-CycD3(1-292end)); CDK6/cycD3 (Carna, Cat. No 04-107, Lot. No 09CBS-0622K, GST-CDK6(1-326(end))); CDK1/CyclinB (Millipore, Cat. 14-450k, Lot. No 25729U, His-CDK1+GST-cyclinB); CDK2/CycA2 (Carna, Cat. No 04-103, Lot. No 06CBS-3024, GST-CDK2 (1-298 (end))); CDK7/CyclinH/MAT1 (Millipore, Cat. No 14-476M, Lot. No WAB0365-A, His-CDK7+GST-MAT1+cyclinH); CDK9/cyclinTl (Millipore, Cat. No 14-685K, Lot. No. 2476163-A, His-CDK9+cyclinTl); Peptide FAM-P8 (GL Biochem, Cat. No. 112396, Lot. No. P100804-XZ112396); ATP (Sigma, Cat. No. A7699-1G, CAS No. 987-65-5); DMSO (Sigma, Cat. No. D2650, Lot. No. 474382); EDTA (Sigma, Cat. No. E5134, CAS No. 60-00-4); 96-well plate (Corning, Cat. No. 3365, Lot. No. 22008026); 384-well plate (Corning, Cat. No. 3573, Lot. No. 12608008); Staurosporine (Sigma, Cat. No. S4400-1MG, Lot. No. 046K4080).

Experimental Methods:
1. Prepared 1× Kinase Buffer and Stop Buffer for the Test
  1) 1× Kinase Base Buffer (CDK1, 2, and 6).
  50 mM HEPES, pH 7.5
  0.0015% Brij-35
  10 mM $MgCl_2$
  2 mM DTT
  2) 1× Kinase Base Buffer (CDK4).
  50 mM HEPES, pH 7.5
  0.01% Triton X-100
  10 mM $MgCl_2$
  2 mM DTT
  3) 1× Kinase Base Buffer (CDK7 and 9).
  20 mM HEPES, pH 7.5
  0.01% Triton X-100
  10 mM $MgCl_2$
  2 mM DTT
  4) Stop Buffer.
  100 mM HEPES, pH 7.5
  0.015% Brij-35
  0.2% Coating Reagent #3
  50 mM EDTA
2. Compound Preparation
  1) Diluted the compound to 50 times of the maximum concentration with 100% DMSO. For example, if the desired maximum inhibitory concentration is 10 µM, then a DMSO solution of 500 µM concentration is required.
  2) Transferred the compound to a 96-well plate and serially diluted the compound from a 100% DMSO solution at a ratio of 30 µm to 60 µm for a total of 10 concentrations gradients. 3) Transferred 100 µm of 100% DMSO to two empty wells as a no compound control and a no enzyme control.
  4) Prepared intermediate plate and transferred the compound of 10 µm concentration from the original plate to the intermediate plate, and then 90 µm of 1× kinase buffer was added and mixed by shaking for 10 min.
  4) Preparing intermediate plate and transferred the compound of 10 µm concentration from the original plate to the intermediate plate, and then 90 µm of 1× kinase buffer was added and mixed by shaking for 10 min.
3. Prepared Assay Plate
  1) Transferred 5 µm of each compound from the 96-well intermediate plate to a 384-well plate. For example, A1 of the 96-well plate was transferred to A1 and A2 of the 384-well plate. A2 of the 96-well plate was transferred to A3 and A4 of the 384-well plate, and so on.
4. Kinase Reaction
  1) Prepared a 2.5× enzyme solution: added kinase into 1× kinase base buffer.
  2) Prepared a 2.5× peptide solution: added FAM-labeled peptide and ATP into the 1× kinase base buffer.
  3) Transferred the 2.5× enzyme solution to the assay plate: Assay plate already contained 5 µm of 10% DMSO and transferred 10 µm of 2.5× enzyme solution to each well.
  4) Incubated at room temperature for 10 min.
  5) Transferred the 2.5× peptide solution to the assay plate: added 10 µm of 2.5× peptide solution to each well of the 384-well assay plate.
  6) Kinase reaction and termination: incubated at 28° C. for a specified period and added 25 µm of stop buffer to stop the reaction.
5. Caliper Reading: Collect Data on Caliper.
6. Curve Fitting
  1) Copied conversion data from Caliper program and Converted conversion values to inhibition values:

Inhibition rate (%)=(1−OD value of the compound−OD value of the control well)/(OD value of the control empty−OD value of the control well) *100%.

2) Fitted the data in XLFit excel add-in version 4.3.1 to give the corresponding $IC_{50}$ values.

The CDK (CDK4, CDK6, CDK1, CDK2, CDK7, and CDK9) inhibitory activities of the compounds of the present invention were determined by the above experimental method, and the enzymatic inhibitory activity ($IC_{50}$) of the compounds were shown in Table 1 below: "+" represents 10-100 μm, "++" represents 1-10 μm, "+++" represents 0.5-1p, "++++" represents 0.1-0.5 μm, "+++++" represents less than 0.1 μm.

TABLE 1

Inhibition of CDK by the compounds of the invention

| Example | CDK4 | CDK6 | CDK1 | CDK2 | CDK7 | CDK9 |
|---|---|---|---|---|---|---|
| Abemaciclib | +++++ | +++++ | ++++ | +++++ | ++ | ++++ |
| 1 | +++++ | ++ | + | ++ | ++ | ++ |
| 2 | +++++ | ++++ | + | ++ | ++ | ++ |
| 3 | +++++ | ++++ | + | + | ++ | + |
| 4 | +++++ | +++ | + | ++ | ++ | ++ |
| 5 | +++++ | ++ | + | + | ++ | + |
| 6 | +++++ | ++++ | + | ++ | ++ | ++ |
| 7 | +++++ | ++ | + | + | ++ | + |
| 16 | +++++ | +++++ | ++++ | +++++ | ++ | ++++ |
| 17 | +++++ | +++++ | ++++ | +++++ | ++ | ++++ |
| 18 | +++++ | ++++ | +++ | ++++ | ++ | +++ |
| 19 | ++++ | +++++ | ++++ | ++++ | ++ | ++++ |
| 20 | +++++ | ++++ | +++ | ++++ | ++ | +++ |
| 21 | +++++ | +++++ | ++++ | +++++ | ++ | ++++ |
| 22 | +++++ | ++++ | +++ | ++++ | ++ | +++ |
| 25 | ++++ | ++++ | +++ | ++++ | ++ | +++ |
| 26 | ++++ | ++++ | +++ | +++ | ++ | +++ |
| 33 | +++++ | +++++ | ++++ | +++++ | ++ | +++++ |
| 34 | ++++ | ++++ | +++ | ++++ | ++ | ++++ |
| 35 | +++++ | ++++ | ++++ | +++++ | ++ | +++++ |
| 36 | ++++ | ++++ | +++ | +++ | ++ | +++ |
| 39 | +++++ | +++++ | +++++ | +++++ | ++++ | +++++ |
| 40 | +++++ | +++++ | +++++ | +++++ | +++ | +++++ |
| 41 | +++++ | +++++ | ++++ | +++++ | +++ | ++++ |
| 42 | ++++ | ++++ | ++++ | +++++ | ++++ | ++++ |
| 43 | +++++ | ++++ | ++++ | ++++ | +++ | ++++ |
| 44 | ++++ | ++++ | ++++ | ++++ | ++++ | +++ |
| 45 | +++++ | ++++ | ++++ | +++++ | ++ | ++++ |
| 46 | +++++ | ++++ | ++++ | +++++ | ++ | ++++ |
| 49 | +++++ | +++++ | ++++ | ++++ | ++++ | ++++ |
| 50 | +++++ | ++++ | +++++ | +++++ | ++++ | ++++ |
| 57 | +++++ | +++++ | ++++ | +++++ | ++ | +++++ |
| 58 | +++++ | ++++ | +++ | ++++ | ++ | ++++ |
| 59 | +++++ | +++ | +++ | ++++ | ++ | ++++ |
| 60 | +++++ | ++++ | +++ | ++++ | ++ | ++++ |
| 61 | +++++ | +++ | +++ | ++++ | ++ | ++++ |
| 62 | +++++ | +++ | +++ | ++++ | ++ | +++ |
| 64 | +++++ | ++++ | ++ | ++++ | + | ++++ |
| 66 | +++++ | +++++ | ++++ | +++++ | ++ | ++++ |
| 67 | +++++ | +++++ | ++++ | +++++ | ++ | ++++ |
| 68 | +++++ | +++++ | ++++ | +++++ | ++ | ++++ |
| 69 | +++++ | +++++ | ++++ | +++++ | ++ | ++++ |
| 70 | +++++ | +++++ | ++++ | +++++ | ++ | ++++ |
| 71 | +++++ | +++++ | ++++ | +++++ | ++ | ++++ |
| 72 | +++++ | +++++ | ++++ | +++++ | ++ | ++++ |
| 73 | +++++ | +++++ | ++++ | +++++ | ++ | +++ |
| 74 | +++++ | ++++ | +++ | ++++ | ++ | ++++ |
| 75 | +++++ | +++++ | ++++ | +++++ | ++ | ++++ |
| 76 | +++++ | ++++ | +++ | ++++ | ++ | ++++ |
| 77 | +++++ | +++++ | ++++ | +++++ | ++ | ++++ |
| 79 | +++++ | +++++ | ++++ | +++++ | ++ | ++++ |
| 80 | +++++ | ++++ | +++ | ++++ | ++ | ++++ |
| 81 | +++++ | +++++ | ++++ | +++++ | ++ | ++++ |
| 83 | +++++ | +++++ | ++++ | +++++ | ++ | ++++ |
| 85 | +++++ | +++++ | ++++ | +++++ | ++ | ++++ |
| 86 | +++++ | ++++ | +++ | ++++ | ++ | ++++ |

Conclusion: The compounds of the present invention showed high inhibitory activity against CDK, especially CDK4 and CDK6.

Biological Example 2: Pharmacokinetic Study in Rats 2.1 Experimental Animal

Healthy adult Sprague-Dawley rats, male, 7-10 weeks old, weighing 240-270 g, provided by Beijing Vital River Laboratory Animal Technology Co., Ltd., with an animal certificate number of 1140070278736.

2.2 Sample Preparation

Test compounds of the invention: example 17, 33, 40, and 57.

Intravenous administration solvent system of compounds: 10% (V/V) NMP and 90% (20% (V/V)) SBE-β-CD in 16.667 mM PBS with a concentration of 1.0 mg/mL.

Oral administration solvent system of compounds: pure water system containing 0.1% hydroxyethyl cellulose and 0.5% Tween-80, with a concentration of 1 mg/mL.

2.3 Drug Administration

Intravenous administration: 3 male Sprague-Dawley rats of each test compound were injected intravenously after fasting overnight, with a dose of 2 mg/kg, and the dosing volume was 2 mL/kg.

Oral administration: 3 male Sprague-Dawley rats of each test compound were taken orally after fasting overnight, with a dose of 5 mg/kg, and the dosing volume was 5 mL/kg.

2.4 Experimental Method

Before the administration, and after administration of 0.0833 (iv), 0.25, 0.5, 1, 2, 4, 8, 12, and 24 h, the jugular vein puncture (approximately 0.15 mL per time point) of each animal was performed by collecting blood from polypropylene tubes. All blood samples were transferred to pre-cooled EDTA-K2 test tubes or pre-cooled plastic microcentrifuge tubes containing 3 μL of 0.5 M EDTA-K2 as anticoagulant and placed on wet ice until centrifugation. Each collected blood was centrifuged at 4° C. for 15 minutes, and plasma was collected. All plasma would be stored in a freezer at about −80° C. until LCMS/MS detection.

2.5 Pharmacokinetic Results

The rat pharmacokinetic parameters of the compounds of the invention were shown in Table 2 below.

TABLE 2

Pharmacokinetic parameters of compounds in rats

| Example | $C_{max}$ (ng/mL) | Tmax (h) | $T_{1/2}$ (h) | $AUC_{0-24\,h}$ (ng · h/mL) | Cl (mL/min/kg) | F (%) |
|---|---|---|---|---|---|---|
| 17 | 225 | 8.0 | 9.38 | 3582 | 14.1 | 66.9 |
| 33 | 161 | 8.0 | 8.19 | 2570 | 12.1 | 43.7 |
| 40 | 12.9 | 4.0 | 11.9 | 132 | 72.8 | 13.3 |
| 57 | 205 | 8.0 | 11.7 | 3077 | 14.8 | 57.6 |

2.6 Experimental Conclusion

As shown in the table, at the dose of 10 mg/kg, the compounds of examples 17, 33, and 57 have lower clearance, longer half-life and a high level of exposure at 24 h in rat plasma.

Biological Example 3: Pharmacodynamic Study of Example 17, 57 and Abemaciclib on Mouse MCF-7 Model 3.1 Experimental Animals BALB/c nude mice, 6-8 weeks old, weighing 18-20 g, female, provided by Shanghai Lab Animal Research Center (Shanghai Xipuer-Beikai) with an animal certificate No: 2008001681946.

3.2 Feeding Conditions

The experiment was started after 3-7 days in the experimental environment when the animals arrived. Animals were housed in IVC (independent air supply system) cages (four animals per cage) in SPF grade experimental animal facilities. Each cage animal information card contained the number of animals in the cage, sex, strain, receiving date, dosing schedule, experiment number, group and start date of the experiment. All cages, bedding, and drinking water were sterilized before use and were updated twice a week.

3.3 Tumor Cell Inoculation Method

Human breast cancer MCF-7 cells (ECACC, Cat. No. 86012803) were cultured in vitro in monolayer under the conditions of EMEM (EBSS)+2 mM glutamine+1% non-essential amino acids (NEAA) medium with 10% fetal bovine serum, 100 U/mL penicillin and 100 pig/mL streptomycin, and 37° C. 5% $CO_2$ incubator. The passage was routinely digested with trypsin-EDTA twice a week. When the cell saturation was up to 80%-90% and reached the requirement, the cells were collected, counted and inoculated. 0.2 mL ($1\times10^7$) MCF-7 cells (with matrix gel, volume ratio 1:1) were subcutaneously inoculated into the right back of each mouse, and mice were randomly grouped and dosed when the average tumor volume reached 209 $mm^3$.

3.4 Sample Preparation 4.14 mL of lactic acid was added to a large beaker containing 800 mL of deionized water, the pH was adjusted to 4.0 with 5 N NaOH, and then the volume was fixed to 1,000 mL to obtain 50 mmol/L sodium lactate buffer. An appropriate amount of mesylate of example 17, mesylate of example 57 and mesylate of Abemaciclib (made in the laboratory) were weighted, and an appropriate amount of the above sodium lactate buffer was added, vortexed and sonicated for several seconds to give a clear solution.

3.5 Drug Administration.

Dosage and administration schedule were showed in Table 3. The subcutaneous tumor volume of nude mice was measured 2-3 times a week, and the mice were weighed, and the data were recorded.

TABLE 3

| No. | Group | dose (mg/kg) | Route | Number of animals | Drug delivery cycle |
|---|---|---|---|---|---|
| 1 | Vehicle | — | PO | 8 | PO × 14 days |
| 2 | Example 17 | 30 | PO | 8 | PO × 14 days |
| 3 | Example 57 | 30 | PO | 8 | PO × 14 days |
| 4 | Abemaciclib | 30 | PO | 8 | PO × 14 days |

Note:
Dose volume was 10 mg/mL.

3.6 Analysis and Evaluation

Experimental evaluation index: the tumor growth inhibition rate TGI (%) or the relative tumor proliferation rate T/C (%) was used for evaluation, wherein T was the experimental group, and C was the vehicle group.

Calculation of the relative tumor proliferation rate T/C (%): If $T>T_0$, then T/C (%)=$(T-T_0)/(C-C_0)\times100\%$, if $T<T_0$, then T/C (%)=$(T-T_0)/T_0\times100\%$, wherein T and C were tumor volumes at the end of the experiment; $T_0$ and $C_0$ were tumor volumes at the beginning of the experiment.

Calculation of percent tumor growth inhibition rate
TGI (%):TGI (%)=$(1-T/C)\times100\%$.

Evaluation criteria: T/C (%)>40 (i.e. TGI (%)<60%) means invalid; T/C (%)≤40 (i.e. TGI (%)≥60%) means valid and statistical significance value P<0.05 was effective.

3.7 Results of Pharmacodynamics Experiment

The inhibitory effects of the vehicle, examples 17, 57, and Abemaciclib on tumor volume of MCF-7 cells were shown in FIG. 1 and Table 4.

TABLE 4

Effects of examples 17, 57 and Abemaciclib on tumor volumes of MCF-7 cells

| Group | Route | Tumor volume ($mm^3$) (day 0) | Tumor volume ($mm^3$) (day 14) | T/C (%) | TGI (%) | P value |
|---|---|---|---|---|---|---|
| Vehicle | PO | 210 | 857 | — | — | — |
| Example 17 | PO | 210 | 216 | 0.9 | 99.1 | 0.006 |
| Example 57 | PO | 209 | 290 | 12.5 | 87.5 | 0.010 |
| Abemaciclib | PO | 209 | 365 | 24.1 | 75.9 | 0.024 |

The results indicated that the compound of example 17, 57, and the positive control Abemaciclib had a strong inhibitory effect on the tumor growth of the MCF-7 nude mouse model at a dose of 30 mg/kg and continuous PO administration for 14 days. Example 17 and example 57 had better antitumor effects than positive control compound Abemaciclib in the same dosage.

Biological Example 4: Pharmacodynamic Study of Example 17 on Mouse Colo-205 Model 4.1 Experimental Animals BALB/c nude mice, 6-8 weeks old, weighing 12-14 g, female, provided by Shanghai Lab Animal Research Center (Shanghai Xipuer-Beikai) with an animal certificate No: 2008001682093.

4.2 Feeding Conditions

The experiment was started after 3-7 days in the experimental environment when the animals arrived. Animals were housed in IVC (independent air supply system) cages (Four animals per cage) in SPF grade experimental animal facilities. Each cage animal information card contained the number of animals in the cage, sex, strain, receiving date, dosing schedule, experiment number, group and start date of the experiment. All cages, bedding, and drinking water were sterilized before use and were updated twice a week.

4.3 Tumor Cell Inoculation Method

Human colorectal cancer Colo-205 cells (ATCC-CCL-222) were cultured in vitro in monolayer under the conditions of RPMI 1640 medium with 10% fetal bovine serum, 100 U/mL penicillin and 100 μg/mL streptomycin, and 37° C. 5% $CO_2$ incubator. The passage was routinely digested with trypsin-EDTA twice a week. When the cell saturation was up to 80%-90% and reached the requirement, the cells were collected, counted and inoculated. 0.2 mL ($5\times10^6$) Colo-205 cells were subcutaneously inoculated on the right back of each mouse, and mice were randomly grouped and dosed when the average tumor volume reached 163 $mm^3$.

4.4 Sample Preparation 4.14 mL of lactic acid was added to a large beaker containing 800 mL of deionized water, and the pH was adjusted to 4.0 with 5 N NaOH. Then the volume was fixed to 1,000 mL to obtain 50 mmol/L sodium lactate buffer. An appropriate amount of mesylate of example 17 and mesylate of Abemaciclib (made in the laboratory) were weighted, and an appropriate amount of the above sodium lactate buffer was added, vortexed and sonicated for several seconds to give a clear solution.

4.5 Drug administration.

Dosage and administration schedule were showed in Table 5. The subcutaneous tumor volume of nude mice was measured 2-3 times a week, and the mice were weighed, and the data were recorded.

TABLE 5

| No. | Group | dose (mg/kg) | Route | Number of animals | Drug delivery cycle |
|---|---|---|---|---|---|
| 1 | Vehicle | — | PO | 6 | PO × 28 days |
| 2 | Example 17 | 50 | PO | 6 | PO × 28 days |
| 3 | Abemaciclib | 50 | PO | 6 | PO × 28 days |

Note:
Dose volume was 10 mg/mL.

4.6 Analysis and Evaluation

Experimental evaluation index: the tumor growth inhibition rate TGI (%) or the relative tumor proliferation rate T/C (%) was used for evaluation, wherein T was the experimental group, and C was the vehicle group.

Calculation of relative tumor proliferation rate TGI (%): If $T>T_0$, then T/C (%)=$(T-T_0)/(C-C_0)\times 100\%$, if $T<T_0$, then T/C (%)=$(T-T_0)/T_0 \times 100\%$, wherein T and C were tumor volumes at the end of the experiment; $T_0$ and $C_0$ were tumor volumes at the beginning of the experiment.

Calculation of percent tumor growth inhibition rate
TGI (%):TGI (%)=$(1-T/C)\times 100\%$.

Evaluation criteria: T/C (%)>40 (i.e. TGI (%)<60%) means invalid; T/C (%)≤40 (i.e. TGI (%)≥60%) means valid and statistical significance value P<0.05 was effective.

4.7 Results of Pharmacodynamics Experiment

Figure 2:
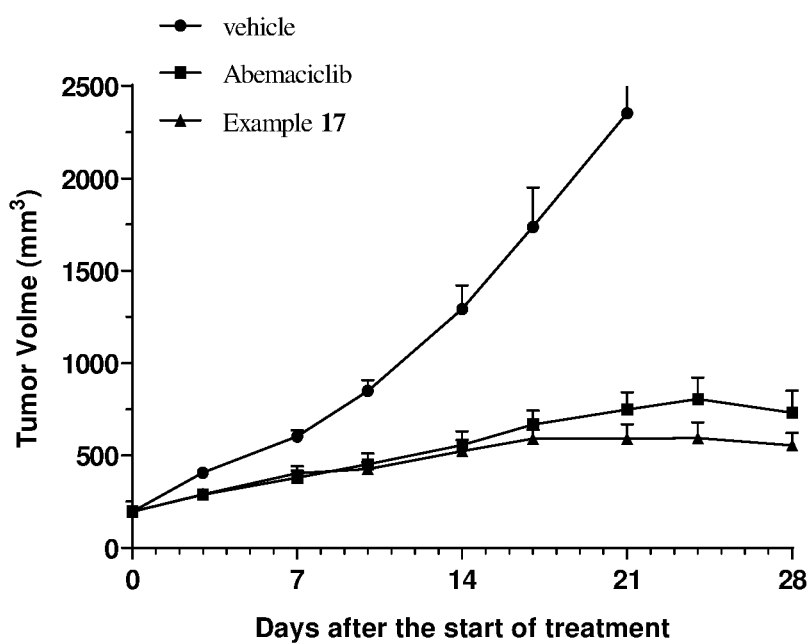
FIG. 2 shows the inhibitory effects on tumor volumes in Colo-205 cancer cells of vehicle, example 17 and Abemaciclib.

The inhibitory effects of the vehicle, examples 17 and Abemaciclib on tumor volume of Colo-205 cells were shown in FIG. 2 and Table 6.

TABLE 6

Effects of examples 17 and Abemaciclib on tumor volumes of Colo-205 cells

| Group | Route | Tumor volume (mm³) (day 0) | Tumor volume (mm³) (day 28) | T/C (%) | TGI (%) | P value |
|---|---|---|---|---|---|---|
| Vehicle | PO | 198 | 2352 | — | — | — |
| Example 17 | PO | 198 | 591 | 18.2 | 81.8 | 0.011 |
| Abemaciclib | PO | 198 | 749 | 25.5 | 74.5 | 0.007 |

The results indicated that the compound of example 17 and the positive control Abemaciclib had a strong inhibitory effect on the tumor growth of the Colo-205 nude mouse model at a dose of 50 mg/kg and continuous PO administration for 28 days. Example 17 had better antitumor effect than positive control compound Abemaciclib in the same dosage.

Biological Example 5: Pharmacodynamic Study of Example 17, 57 and Abemaciclib on Mouse MV4-11 Model 5.1 Experimental Animals BALB/c nude mice, 6-8 weeks old, weighing 18-22 g, female, provided by Shanghai Lab Animal Research Center (Shanghai Xipuer-Beikai) with an animal certificate No: 212212121210000.

5.2 Feeding Conditions

The experiment was started after 3-7 days in the experimental environment when the animals arrived. Animals were housed in IVC (independent air supply system) cages (four animals per cage) in SPF grade experimental animal facilities. Each cage animal information card contained the number of animals in the cage, sex, strain, receiving date, dosing schedule, experiment number, group and start date of the experiment. All cages, bedding, and drinking water were sterilized before use and were updated twice a week.

5.3 Tumor Cell Inoculation Method

Human leukemia MV4-11 cells (ATCC-CRL-9591) were cultured in vitro in suspension under the conditions of RPMI 1640 medium with 10% fetal bovine serum, 100 U/mL penicillin and 100 µg/mL streptomycin and 37° C. 5% $CO_2$ incubator. Regular passages were performed twice a week. When the cell saturation was up to 80%-90% and reached the requirement, the cells were collected, counted, and inoculated. 0.2 mL ($1\times10^7$) MV4-11 cells (added with matrix gel, volume ratio 1:1) were subcutaneously inoculated into the right back of each mouse, and mice were randomly grouped and dosed when the average tumor volume reached 158 mm³.

5.4 Sample Preparation 4.14 mL of lactic acid was added to a large beaker containing 800 mL of deionized water, and the pH was adjusted to 4.0 with 5 N NaOH, and then the volume was fixed to 1,000 mL to obtain 50 mmol/L sodium lactate buffer. An appropriate amount of mesylate of example 17, mesylate of example 57 and mesylate of Abemaciclib (made in the laboratory) were weighted, and an appropriate amount of the above sodium lactate buffer was added, vortexed and sonicated for several seconds to give a clear solution.

5.5 Drug Administration.

Dosage and administration schedule were showed in Table 7. The subcutaneous tumor volume of nude mice was measured 2-3 times a week, and the mice were weighed, and the data were recorded.

TABLE 7

| No. | Group | dose (mg/kg) | Route | Number of animals | Drug delivery cycle |
|---|---|---|---|---|---|
| 1 | Vehicle | — | PO | 8 | PO × 21 days |
| 2 | Example 17 | 50 | PO | 8 | PO × 21 days |
| 3 | Example 57 | 50 | PO | 8 | PO × 21 days |
| 4 | Abemaciclib | 50 | PO | 8 | PO × 21 days |

Note:
Dose volume was 10 mg/mL.

5.6 Analysis and Evaluation

Experimental evaluation index: the tumor growth inhibition rate TGI (%) or the relative tumor proliferation rate T/C (%) was used for evaluation, wherein T was the experimental group, and C was the vehicle group.

Calculation of relative tumor proliferation rate TGI (%): If $T>T_0$, T/C (%)=$(T-T_0)/(C-C_0)\times 100\%$, if $T<T_0$, T/C (%)=$(T-T_0)/T_0 \times 100\%$, wherein T and C were tumor volumes at the end of the experiment; $T_0$ and $C_0$ were tumor volumes at the beginning of the experiment.

Calculation of percent tumor growth inhibition rate
TGI (%):TGI (%)=$(1-T/C)\times 100\%$.

Evaluation criteria: T/C (%)>40 (i.e. TGI (%)<60%) means invalid; T/C (%)≤40 (i.e. TGI (%)≥60%) means valid and statistical significance value P<0.05 was effective.

5.7 Results of Pharmacodynamics Experiment

Figure 3:
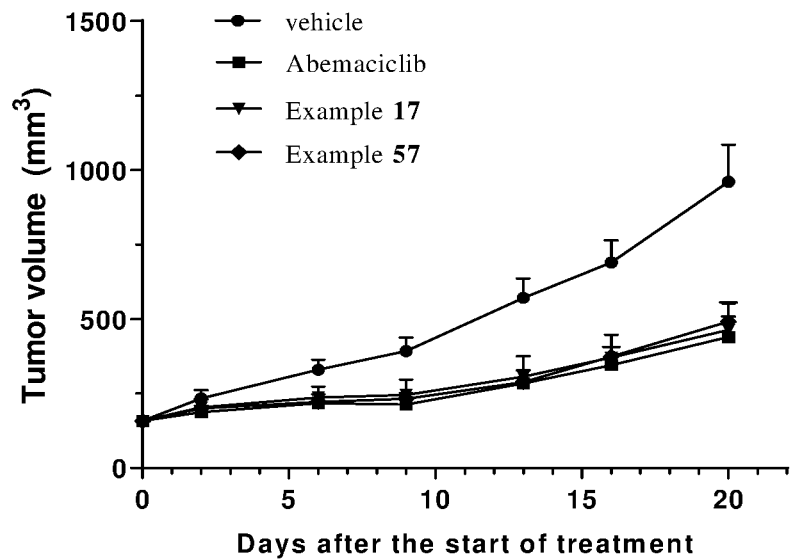
FIG. 3 shows the inhibitory effects on tumor volumes in MV4-11 cancer cells of vehicle, examples 17, 57 and Abemaciclib.

The inhibitory effects of the vehicle, examples 17, 57, and Abemaciclib on tumor volume of MV4-11 cells were shown in FIG. 3 and Table 8.

TABLE 8

Effects of examples 17,57 and Abemaciclib on tumor volumes of MV4-11 cells

| Group | Route | Tumor volume (mm$^3$) (day 0) | Tumor volume (mm$^3$) (day 21) | T/C (%) | TGI (%) | P value |
|---|---|---|---|---|---|---|
| Vehicle | PO | 158 | 961 | — | — | — |
| Example 17 | PO | 158 | 463 | 38 | 62 | 0.018 |
| Example 57 | PO | 158 | 491 | 41 | 59 | 0.021 |
| Abemaciclib | PO | 158 | 440 | 35 | 65 | 0.005 |

The results showed that the compound of example 17, 57, and the positive control Abemaciclib had a good inhibitory effect on the tumor growth of the MV4-11 nude mouse model at a dose of 50 mg/kg and continuous PO administration for 21 days. The tumor inhibition effect of example 17 and example 57 were equivalent to that of positive control compound Abemaciclib on the MV4-11 model.

Effect Example 6 Pharmacodynamic Study of Compounds of the Present Invention Example 17, Example 57 and Abemaciclib on Mouse MDA-MB-361 Model

6.1 Experimental Animals

SCID Beige mice, 6-8 weeks old, weighing 18-22 g, female, provided by Beijing Vital River Laboratory Animal Technology Co., Ltd., with the animal certificate number of 11400700253449.

6.2 Feeding Conditions

The experiment was started after 3-7 days when the animal arrived. Animals were housed in IVC (independent air supply system) cages (four animals per cage) in SPF grade experimental animal facilities. Each cage animal information card contained the number of animals in the cage, sex, strain, receiving date, dosing schedule, experiment number, group, and start date of the experiment. All cages, bedding and drinking water were sterilized before use and were updated twice a week.

6.3 Tumor Cell Inoculation Method

Human breast cancer MDA-MB-361 cells (ATCC-HTB-27) were cultured in vitro in monolayer under the conditions of RPMI 1640 medium with 10% fetal bovine serum, 100 U/mL penicillin and 100 g/mL streptomycin, and 37° C. 5% $CO_2$ incubator. The passage was routinely digested with trypsin-EDTA twice a week. When the cell saturation was up to 80%-90% and reached the requirement, the cells were collected, counted and inoculated. 0.2 mL ($1\times10^7$) MDA-MB-361 cells (added with matrix gel, volume ratio 1:1) were subcutaneously inoculated into the right back of each mouse, and mice were randomly grouped and dosed when the average tumor volume reached 175 mm$^3$.

6.4 Sample Preparation 4.14 mL of lactic acid was added to a large beaker containing 800 mL of deionized water, and the pH was adjusted to 4.0 with 5 N NaOH. Then the volume was fixed to 1,000 mL to obtain 50 mmol/L sodium lactate buffer. An appropriate amount of methanesulfonic acid salt of example 17, methanesulfonic acid salt of example 57 and methanesulfonic acid salt of Abemaciclib (made in the laboratory) were weighted, and an appropriate amount of the above sodium lactate buffer solution was added, vortexed and sonicated for several seconds to give a clear solution.

6.5 Drug Administration.

Dosage and schedule were showed in Table 9. The subcutaneous tumor volume of nude mice was measured 2-3 times a week, and the mice were weighed, and the data were recorded.

TABLE 9

| Number | Group | dose (mg/kg) | Route | Number of animals | Drug delivery cycle |
|---|---|---|---|---|---|
| 1 | Vehicle | — | PO | 8 | PO × 28 days |
| 2 | Example 17 | 15 | PO | 8 | PO × 28 days |
| 3 | Example 57 | 15 | PO | 8 | PO × 28 days |
| 4 | Abemaciclib | 15 | PO | 8 | PO × 28 days |

Note:
Dose volume was 10 mg/mL.

6.6 Analysis and Evaluation

Experimental evaluation index: Percent tumor growth inhibition TGI (%) or relative tumor proliferation rate T/C (%) was used for evaluation, wherein T was the experimental group, and C was the control group.

Calculation of relative tumor proliferation rate: If $T>T_0$, T/C (%)=(T−$T_0$)/(C−$C_0$)×100%, if $T<T_0$, T/C (%)=(T−$T_0$)/$T_0$×100%, wherein T and C were tumor volumes at the end of the experiment; $T_0$ and $C_0$ were tumor volumes at the beginning of the experiment.

Calculation of percent tumor growth inhibition TGI (%):TGI (%)=(1−T/C)×100%.

Evaluation criteria: T/C (%)>40 (i.e. TGI (%)<60%) means invalid; T/C (%)≤40 (i.e. TGI (%)≥60%) means valid and statistical significance value P<0.05 was effective.

6.7 Results of Pharmacodynamics Experiment

Figure 4:
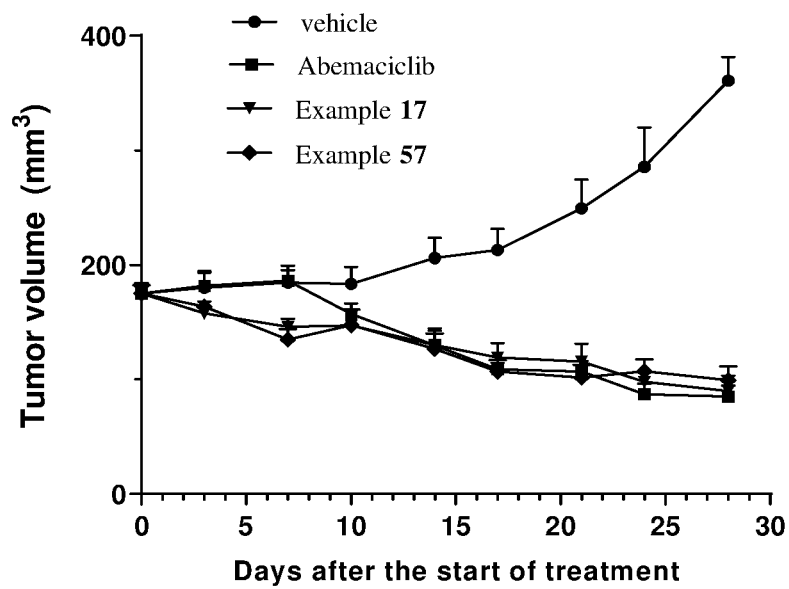
FIG. 4 shows the inhibitory effects on tumor volumes in MDA-MB-361 cancer cells of vehicle, examples 17, 57 and Abemaciclib.

The inhibitory effects of the vehicle, examples 17, 57, and Abemaciclib on tumor volume of MDA-MB-361 cells were shown in FIG. 4 and Table 10.

TABLE 10

Effects of examples 17, 57 and Abemaciclib on tumor volumes of MDA-MB-361 cells

| Group | Route | Tumor volume (mm$^3$) (day 0) | Tumor volume (mm$^3$) (day 28) | T/C (%) | TGI (%) | P value |
|---|---|---|---|---|---|---|
| Vehicle | PO | 175 | 361 | — | — | — |
| Example 17 | PO | 175 | 90 | −49 | 149 | <0.001 |
| Example 57 | PO | 175 | 99 | −43 | 143 | <0.001 |
| Abemaciclib | PO | 175 | 85 | −51 | 151 | <0.001 |

The results showed that the compound of example 17, example 57, and the positive control Abemaciclib exhibited a very strong inhibitory effect on the tumor growth of the MDA-MB-361 nude mouse model at a dose of 15 mg/kg and continuous PO administration for 28 days.

Although specific embodiments of the present invention have been described and illustrated herein, those skilled in the art should understand that these embodiments are merely examples and can be varied or modified without departing from the principles and essence of the present invention. Therefore, the scope of the present invention is limited only by the appended claims.

What is claimed is:

1. A compound represented by general formula (I-2), a pharmaceutically acceptable salt thereof, a stereoisomer thereof or a mixture of the stereoisomers, a solvate thereof, or a stable isotope derivative thereof;

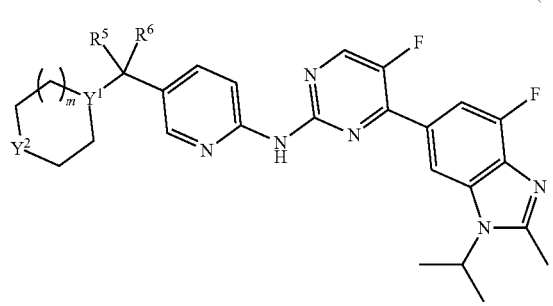

(I-2)

wherein,
R⁵ is hydrogen;
R⁶ is hydroxyl;
m is 1;
Y¹ is CH;
Y² is NCH₂CH₃.

2. The compound, the pharmaceutically acceptable salt thereof, the stereoisomer thereof or a mixture of the stereoisomers, the solvate thereof, or the stable isotope derivative thereof as defined in claim 1, wherein the compound is

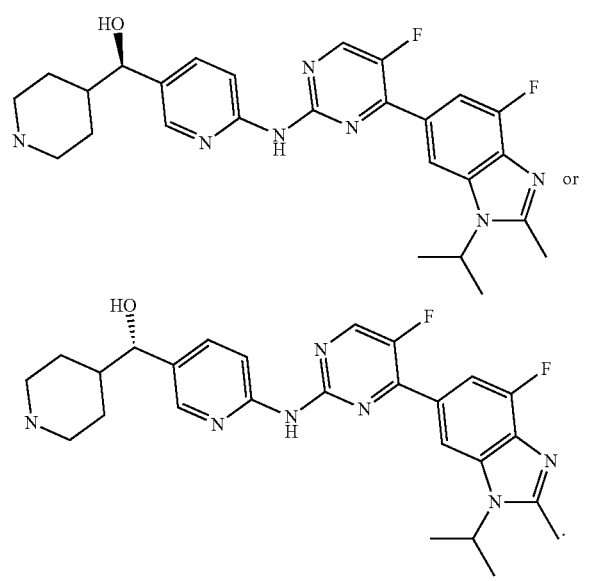

3. A process for preparing the compound represented by the general formula (I-2) as defined in claim 1, comprising the following steps:

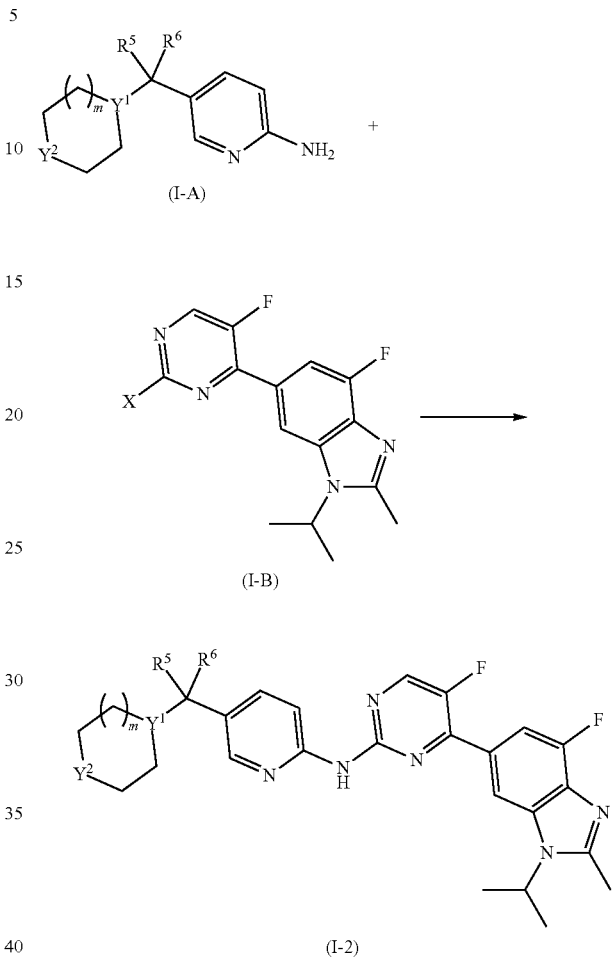

coupling the compound of the general formula (I-A) with the compound represented by the general formula (I-B) under basic and catalyst conditions to obtain the compound represented by the general formula (I-2);
wherein X is halogen; the definitions of R⁵, R⁶, Y¹, Y², and m are defined as in claim 1.

4. A pharmaceutical composition comprising a therapeutically effective amount of the compound, the pharmaceutically acceptable salt thereof, the stereoisomer thereof or a mixture of the stereoisomers, the solvate thereof, or the stable isotope derivative thereof as defined in claim 1, and a pharmaceutically acceptable carrier, diluent or excipient.

* * * * *